US008093363B2

(12) United States Patent
Yu et al.

(10) Patent No.: US 8,093,363 B2
(45) Date of Patent: Jan. 10, 2012

(54) TUMOR NECROSIS FACTOR-GAMMA

(75) Inventors: Guo-Liang Yu, Berkeley, CA (US); Jian Ni, Germantown, MD (US); Craig A. Rosen, Laytonsville, MD (US); Jun Zhang, San Diego, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 12/879,210

(22) Filed: Sep. 10, 2010

(65) Prior Publication Data

US 2011/0003399 A1 Jan. 6, 2011

Related U.S. Application Data

(60) Division of application No. 11/837,082, filed on Aug. 10, 2007, now Pat. No. 7,820,798, which is a continuation of application No. 10/226,294, filed on Aug. 23, 2002, now abandoned, which is a continuation-in-part of application No. 09/899,059, filed on Jul. 6, 2001, now Pat. No. 7,597,886, said application No. 11/837,082 is a continuation-in-part of application No. 09/899,059, which is a continuation-in-part of application No. PCT/US00/11689, filed on Apr. 28, 2000, and a continuation-in-part of application No. 09/246,129, filed on Feb. 8, 1999, now Pat. No. 6,824,767, which is a continuation-in-part of application No. 09/131,237, filed on Aug. 7, 1998, now Pat. No. 6,599,719, said application No. 09/899,059 is a continuation-in-part of application No. 09/131,237, which is a continuation-in-part of application No. 09/005,020, filed on Jan. 9, 1998, now abandoned, which is a continuation-in-part of application No. 08/461,246, filed on Jun. 5, 1995, now abandoned, which is a continuation-in-part of application No. PCT/US94/12880, filed on Nov. 7, 1994.

(60) Provisional application No. 60/314,381, filed on Aug. 24, 2001, provisional application No. 60/278,449, filed on Mar. 26, 2001, provisional application No. 60/216,879, filed on Jul. 7, 2000, provisional application No. 60/180,908, filed on Feb. 8, 2000, provisional application No. 60/134,067, filed on May 13, 1999, provisional application No. 60/132,227, filed on May 3, 1999, provisional application No. 60/131,963, filed on Apr. 30, 2009, provisional application No. 60/074,047, filed on Feb. 9, 1998.

(51) Int. Cl.
*C07K 16/28* (2006.01)
*C07K 16/18* (2006.01)
*C07K 16/22* (2006.01)
*C07K 16/46* (2006.01)
*C07K 14/525* (2006.01)
*C12N 5/00* (2006.01)
*G01N 33/53* (2006.01)

(52) U.S. Cl. ............ 530/388.23; 530/387.1; 530/388.1; 530/389.2; 435/7.1; 435/326; 930/144

(58) Field of Classification Search ........................ None
See application file for complete search history.

(56) References Cited

U.S. PATENT DOCUMENTS

| 4,002,531 | A | 1/1977 | Royer |
| 4,179,337 | A | 12/1979 | Davis et al. |
| 4,433,092 | A | 2/1984 | Nemeth |
| 4,444,887 | A | 4/1984 | Hoffmann |
| 4,474,893 | A | 10/1984 | Reading |
| 4,631,211 | A | 12/1986 | Houghten |
| 4,676,980 | A | 6/1987 | Segal et al. |
| 4,708,781 | A | 11/1987 | Poorten |
| 4,714,681 | A | 12/1987 | Reading |
| 4,716,111 | A | 12/1987 | Osband et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,873,191 | A | 10/1989 | Wagner et al. |
| 4,925,648 | A | 5/1990 | Hansen et al. |
| 4,946,778 | A | 8/1990 | Ladner et al. |
| 4,980,286 | A | 12/1990 | Morgan et al. |
| 4,994,560 | A | 2/1991 | Kruper et al. |
| 5,112,946 | A | 5/1992 | Maione |

(Continued)

FOREIGN PATENT DOCUMENTS

DE 196 39 601 A1 9/1997

(Continued)

OTHER PUBLICATIONS

Peerlinck et al. Antifactor VIII antibody inhibiting allogeneic but not autologous factor VIII in patients with mild hemophilia A. Blood. Apr. 1, 1999;93(7):2267-73.*

(Continued)

*Primary Examiner* — David Romeo

(57) ABSTRACT

Human TNF-gamma-alpha and TNF-gamma-beta polypeptides and DNA (RNA) encoding such polypeptides and a procedure for producing such polypeptides by recombinant techniques are disclosed. Also disclosed are methods for utilizing such polypeptides to inhibit cellular growth, for example in a tumor or cancer, for facilitating wound-healing, to provide resistance against infection, induce inflammatory activities, and stimulating the growth of certain cell types to treat diseases, for example restenosis. Also disclosed are diagnostic methods for detecting a mutation in the TNF-gamma-alpha and TNF-gamma-beta nucleic acid sequences or overexpression of the TNF-gamma-alpha and/or TNF-gamma-beta polypeptides. Antagonists against such polypeptides and their use as a therapeutic to treat cachexia, septic shock, cerebral malaria, inflammation, arthritis and graft-rejection are also disclosed.

20 Claims, 33 Drawing Sheets

U.S. PATENT DOCUMENTS

| | | | |
|---|---|---|---|
| 5,122,464 A | 6/1992 | Wilson et al. |
| 5,194,392 A | 3/1993 | Geysen |
| 5,223,409 A | 6/1993 | Ladner et al. |
| 5,225,539 A | 7/1993 | Winter |
| 5,258,498 A | 11/1993 | Huston et al. |
| 5,274,119 A | 12/1993 | Frazier et al. |
| 5,314,995 A | 5/1994 | Fell, Jr. et al. |
| 5,336,603 A | 8/1994 | Capon et al. |
| 5,342,604 A | 8/1994 | Wilson et al. |
| 5,349,052 A | 9/1994 | Delgado et al. |
| 5,349,053 A | 9/1994 | Landolfi |
| 5,359,046 A | 10/1994 | Capon et al. |
| 5,399,349 A | 3/1995 | Paunescu et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,139 A | 6/1995 | Kiefer et al. |
| 5,435,990 A | 7/1995 | Cheng et al. |
| 5,436,146 A | 7/1995 | Shenk et al. |
| 5,441,050 A | 8/1995 | Thurston et al. |
| 5,447,851 A | 9/1995 | Beutler et al. |
| 5,460,959 A | 10/1995 | Mulligan et al. |
| 5,463,575 A | 10/1995 | White |
| 5,474,981 A | 12/1995 | Leder et al. |
| 5,478,925 A | 12/1995 | Wallach et al. |
| 5,480,971 A | 1/1996 | Houghten et al. |
| 5,489,425 A | 2/1996 | Kruper et al. |
| 5,505,931 A | 4/1996 | Pribish |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,573,920 A | 11/1996 | Randle |
| 5,580,717 A | 12/1996 | Dower et al. |
| 5,580,859 A | 12/1996 | Felgner et al. |
| 5,585,089 A | 12/1996 | Queen et al. |
| 5,601,819 A | 2/1997 | Wong et al. |
| 5,605,793 A | 2/1997 | Stemmer |
| 5,612,460 A | 3/1997 | Zalipsky |
| 5,622,929 A | 4/1997 | Willner et al. |
| 5,625,126 A | 4/1997 | Lonberg et al. |
| 5,633,425 A | 5/1997 | Lonberg et al. |
| 5,641,670 A | 6/1997 | Treco et al. |
| 5,643,575 A | 7/1997 | Martinez et al. |
| 5,652,361 A | 7/1997 | Simon et al. |
| 5,658,727 A | 8/1997 | Barbas et al. |
| 5,661,016 A | 8/1997 | Lonberg et al. |
| 5,693,622 A | 12/1997 | Wolff et al. |
| 5,696,239 A | 12/1997 | Wilson et al. |
| 5,698,426 A | 12/1997 | Huse |
| 5,705,151 A | 1/1998 | Dow et al. |
| 5,714,631 A | 2/1998 | Wilson et al. |
| 5,733,743 A | 3/1998 | Johnson et al. |
| 5,750,753 A | 5/1998 | Kimae et al. |
| 5,756,065 A | 5/1998 | Wilson et al. |
| 5,766,883 A | 6/1998 | Ballance et al. |
| 5,780,225 A | 7/1998 | Wigler et al. |
| 5,807,715 A | 9/1998 | Morrison et al. |
| 5,808,003 A | 9/1998 | Subramanian et al. |
| 5,811,097 A | 9/1998 | Allison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,830,721 A | 11/1998 | Stemmer et al. |
| 5,834,252 A | 11/1998 | Stemmer et al. |
| 5,837,458 A | 11/1998 | Minshull et al. |
| 5,876,969 A | 3/1999 | Fleer et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 5,985,660 A | 11/1999 | Galy |
| 6,075,181 A | 6/2000 | Kucherlapati et al. |
| 6,114,598 A | 9/2000 | Kucherlapati et al. |
| 6,599,719 B2 | 7/2003 | Yu et al. |
| 6,824,767 B2 | 11/2004 | Yu et al. |
| 7,597,886 B2 | 10/2009 | Yu et al. |
| 2002/0111325 A1 | 8/2002 | Li et al. |
| 2003/0129189 A1 | 7/2003 | Yu et al. |
| 2005/0214305 A1 | 9/2005 | Li et al. |
| 2007/0297977 A1 | 12/2007 | Yu et al. |

FOREIGN PATENT DOCUMENTS

| | | |
|---|---|---|
| EP | 0 173 494 A2 | 3/1986 |
| EP | 0 239 400 B1 | 9/1987 |
| EP | 0 282 317 A2 | 9/1988 |
| EP | 0 307 434 B2 | 3/1989 |
| EP | 0 367 166 A1 | 5/1990 |
| EP | 0 394 827 A1 | 10/1990 |
| EP | 0 396 387 B1 | 11/1990 |
| EP | 0 401 384 A1 | 12/1990 |
| EP | 0 413 622 B1 | 2/1991 |
| EP | 0 439 095 A2 | 7/1991 |
| EP | 0 322 094 B1 | 2/1992 |
| EP | 0 506 477 B1 | 9/1992 |
| EP | 0 519 596 A1 | 12/1992 |
| EP | 0 171 496 B1 | 5/1993 |
| EP | 0 592 106 B1 | 4/1994 |
| EP | 0 682 110 A1 | 11/1995 |
| EP | 0 399 816 B1 | 12/1995 |
| WO | WO-86/01533 A1 | 3/1986 |
| WO | WO-86/05807 A1 | 10/1986 |
| WO | WO-87/01130 A1 | 2/1987 |
| WO | WO-87/02671 A1 | 5/1987 |
| WO | WO-87/04462 A1 | 7/1987 |
| WO | WO-89/01036 A1 | 2/1989 |
| WO | WO-89/02036 A1 | 3/1989 |
| WO | WO-89/10404 A1 | 11/1989 |
| WO | WO-89/12624 A1 | 12/1989 |
| WO | WO-90/02809 A1 | 3/1990 |
| WO | WO-90/11092 A1 | 10/1990 |
| WO | WO-90/13649 A1 | 11/1990 |
| WO | WO-91/00360 A1 | 1/1991 |
| WO | WO-91/06570 A1 | 5/1991 |
| WO | WO-91/06657 A1 | 5/1991 |
| WO | WO-91/09967 A1 | 7/1991 |
| WO | WO-91/10737 A1 | 7/1991 |
| WO | WO-91/10741 A1 | 7/1991 |
| WO | WO-91/14438 A1 | 10/1991 |
| WO | WO-92/01047 A1 | 1/1992 |
| WO | WO-92/05793 A1 | 4/1992 |
| WO | WO-92/06180 A1 | 4/1992 |
| WO | WO-92/06194 A1 | 4/1992 |
| WO | WO-92/08495 A1 | 5/1992 |
| WO | WO-92/08802 A1 | 5/1992 |
| WO | WO-92/18619 A1 | 10/1992 |
| WO | WO-92/22324 A1 | 12/1992 |
| WO | WO-92/22635 A1 | 12/1992 |
| WO | WO-93/11236 A1 | 6/1993 |
| WO | WO-93/14188 A1 | 7/1993 |
| WO | WO-93/17715 A1 | 9/1993 |
| WO | WO-93/20221 A1 | 10/1993 |
| WO | WO-93/21232 A1 | 10/1993 |
| WO | WO-93/25788 A1 | 12/1993 |
| WO | WO-94/08598 A1 | 4/1994 |
| WO | WO-94/12649 A2 | 6/1994 |
| WO | WO-94/12650 A2 | 6/1994 |
| WO | WO-95/06058 A1 | 3/1995 |
| WO | WO-95/15982 A2 | 6/1995 |
| WO | WO-95/20401 A1 | 8/1995 |
| WO | WO-96/04388 A1 | 2/1996 |
| WO | WO-96/26736 A1 | 9/1996 |
| WO | WO-96/29411 A1 | 9/1996 |
| WO | WO-96/33735 A1 | 10/1996 |
| WO | WO-96/34095 A1 | 10/1996 |
| WO | WO-96/34096 A1 | 10/1996 |
| WO | WO-96/39515 A1 | 12/1996 |
| WO | WO-97/03394 A1 | 1/1997 |
| WO | WO-97/33899 A1 | 9/1997 |
| WO | WO-97/33904 A1 | 9/1997 |
| WO | WO-97/34911 A1 | 9/1997 |
| WO | WO-98/02543 A1 | 1/1998 |
| WO | WO-98/06842 A1 | 2/1998 |
| WO | WO-98/07832 A1 | 2/1998 |
| WO | WO-98/07880 A1 | 2/1998 |

| WO | WO-98/11779 A1 | 3/1998 |
| WO | WO-98/16654 A1 | 4/1998 |
| WO | WO-98/18921 A1 | 5/1998 |
| WO | WO-98/24893 A1 | 6/1998 |
| WO | WO-98/30693 A2 | 7/1998 |
| WO | WO-98/30694 | 7/1998 |
| WO | WO-98/32466 A1 | 7/1998 |
| WO | WO-98/32856 A1 | 7/1998 |
| WO | WO-98/41629 A1 | 9/1998 |
| WO | WO-98/46645 A1 | 10/1998 |
| WO | WO-98/49305 A1 | 11/1998 |
| WO | WO-98/50433 A1 | 11/1998 |
| WO | WO-98/54202 A1 | 12/1998 |
| WO | WO-98/56892 A1 | 12/1998 |
| WO | WO-99/04813 A1 | 2/1999 |
| WO | WO-99/23105 A1 | 5/1999 |
| WO | WO-00/52028 A1 | 9/2000 |
| WO | WO-00/64465 A1 | 11/2000 |

OTHER PUBLICATIONS

Deregt et al. Mapping of a type 1-specific and a type-common epitope on the E2 (gp53) protein of bovine viral diarrhea virus with neutralization escape mutants. Virus Res. Jan. 1998;53(1):81-90.*

McGuinness et al. Class 1 outer membrane protein of Neisseria meningitidis: epitope analysis of the antigenic diversity between strains, implications for subtype definition and molecular epidemiology. Mol Microbiol. Feb. 1993;7(4):505-14.*

Abatangelo et al. The frequent mutation Gly/Asp in CDR1H may determine a cross-reactive idiotope in anti-I cold agglutinins. Clin Exp Immunol. Apr. 1996;104(1):185-90.*

Ciarlet et al. Single point mutations may affect the serotype reactivity of serotype G11 porcine rotavirus strains: a widening spectrum? J Virol. Nov. 1997;71(11):8213-20.*

"Production of Antibody-Producing Hybridomas in Rodent Systems," pp. 563-587 (1978).

A. Ashkenazi et al., "Protection against endotoxic shock by a tumor necrosis factor receptor immunoadhesin," *Proc. Natl. Acad. Sci. USA*, vol. 88, Dec. 1991, pp. 10535-10539.

A. Bout et al., "Lung Gene Therapy: in Vivo Adenovirus-Mediated Gene Transfer to Rhesus Monkey Airway Epithelium," *Human Gene Therapy*, vol. 5, (1994), pp. 3-10.

A. Creasey et al., "Biological Effects of Recombinant Human Tumor Necrosis Factor and its Novel Muteins on Tumor and Normal Cell Lines," *Cancer Research*, vol. 47, Jan. 1, 1987, pp. 145-149.

A. Cuenda et al., "SB 203580 is a specific inhibitor of a MAP kinase homologue which is stimulated by cellular stresses and interleukin-1," *FEBS Letters*, vol. 364, (1995), pp. 229-233.

A. D. Miller et al., "Improved Retroviral Vectors for Gene Transfer and Expression," *Bio Techniques*, vol. 7, No. 9, (1989), pp. 980-990.

A. D. Miller et al., "Use of Retroviral Vectors for Gene Transfer and Expression," *Methods in Enzymology*, vol. 217, pp. 580-599 (1993).

A. D. Miller, "Retrovirus Packaging Cells," *Human Gene Therapy*, vol. 1, (1990), pp. 5-14.

A. Joliot et al., "Antennapedia homeobox peptide regulates neural morphogenesis," *Proc. Natl. Acad. Sci. USA*, vol. 88, Mar. 1991, pp. 1864-1868.

A. Karsan, "Tumor Necrosis Factor and Endothelial Cell Death," *TCM*, vol. 8, No. 1, (1998), pp. 19-24.

A. Mastrangeli et al., "Diversity of Airway Epithelial Cell Targets for In Vivo Recombinant Adenovirus-mediated Gene Transfer," *The Journal of Clinical Investigation*, vol. 91, Jan. 1993, pp. 225-234.

A. Nisonoff, "Idiotypes: Concepts and applications," *Journal of Immunology*, vol. 147, No. 8, Oct. 5, 1991, pp. 2429-2438.

A. Patz, "Clinical and Experimental Studies on Retinal Neovascularization," *American Journal of Ophthalmology*, vol. 94, No. 6, Dec. 1982, pp. 715-743.

A. S. Carver et al., "Transgenic Livestock as Bioreactors: Stable Expression of Human alpha-1-Antitrypsin by a Flock of Sheep," *Bio/Technology*, vol. 11, Nov. 1993, pp. 1263-1270.

A. Skerra et al., "Assembly of a Functional Immunoglobulin Fv Fragment in *Escherichia coli*," Science, vol. 240, (1988), pp. 1038-1041.

A. Traunecker et al., "Soluble CD4 molecules neutralize human immunodeficiency virus type 1," Nature, vol. 331, Jan. 7, 1988, pp. 84-86.

A. Tutt et al., "Trispecific F(ab')3 Derivatives that use Cooperative Signaling via the TCR/CD3 Complex and CD2 to Activate and Redirect Resting Cytotoxic T Cells," The Journal of Immunology, vol. 147, No. 1, Jul. 1, 1991, pp. 60-69.

B. A. Jameson et al., "The antigenic index: a novel algorithm for predicting antigenic determinants," Cabios, vol. 4, No. 1, (1988), pp. 181-186.

B. Abdallah et al., "Non-viral gene transfer: Applications in developmental biology and gene therapy," *Biol. Cell*, vol. 85, (1995), pp. 1-7.

B. Beutler et al., "The Biology of Cachectin/TNF-A Primary Mediator of the Host Response," *Ann. Rev. Immunol.*, vol. 7, (1989), pp. 625-655.

B. C. Cunningham et al., "High-Resolution Epitope Mapping of hGH-Receptor Interactions by Alanine-Scanning Mutagenesis," *Science*, vol. 244, (1989), pp. 1081-1085.

B. Deng et al., "An Agonist Murine Monoclonal Antibody to the Human c-Mpl Receptor Stimulates Megakaryocytopoiesis," *Blood*, vol. 92, No. 6, Sep. 1998, pp. 1981-1988.

B. Dérijard et al., "JNK1: A Protein Kinase Stimulated by UV Light and Ha-Ras that Binds and Phosphorylates the c-Jun Activation Domain," *Cell*, vol. 76, Mar. 25, 1994, pp. 1025-1037.

B. H. Koller et al., "Inactivating the Beta-2-microglobulin locus in mouse embryonic stem cells by homologous recombination," *Proc. Natl. Acad. Sci. USA*, vol. 86, Nov. 1989, pp. 8932-8935.

B. Lewin, Genes, second edition, John Wiley & Sons, (1985).

B. Salmons et al., "Targeting of Retroviral Vectors for Gene Therapy," *Human Gene Therapy*, vol. 4, (1993), pp. 129-141.

B. Schwartz et al., "Gene transfer by naked DNA into adult mouse brain," *Gene Therapy*, vol. 3, No. 4. (1996), pp. 405-411.

B. Terman et al., "Identification of the KDR Tyrosine Kinase as a Receptor for Vascular Endothelial Cell Growth Factor," *Biochemical and Biohphysical Research Communications*, vol. 187, No. 3, Sep. 30, 1992, pp. 1579-1586.

B. W. Zanke et al., "The stress-activated protein kinase pathway mediates cell death following injury induced by cis-platinum, UV irradiation or heat," *Current Biology*, vol. 6, No. 5, (1996), pp. 606-613.

C. A. Kettleborough et al., "Isolation of tumor cell-specific single-chain Fv from immunized mice using phage-antibody libraries and the re-construction of whole antibodies from these antibody fragments," *Eur. J. Immunol.*, vol. 24 (1994), pp. 952-958.

C. Chothia et al., "Structural Determinants in the Sequences of Immunoglobulin Variable Domain," *J. Mol. Biol.*, vol. 278 (1998), pp. 457-479.

C. D. Saudek et al., "A Preliminary Trial of the Programmable Implantable Medication System for Insulin Delivery," *The New England Journal of Medicine*, vol. 321, No. 9, Aug. 1989, pp. 574-579.

C. Delgado et al., "The uses and properties of PEG-linked proteins," *Critical Reviews in Therapeutic Drug Carrier Systems*, vol. 9, Issue 1, (1992), pp. 249-304.

C. E. Walsh et al., "Gene Therapy for Human Hemoglobinopathies," *Proceedings of the Society for Experimental Biology and Medicine*, vol. 204, No. 3, Dec. 1993, pp. 289-300.

C. M. Pearson et al., "Experimental Production of Arthritis in Rats," *Ann. Rheum. Dis.*, vol. 15, (1956), pp. 379-380.

C. M. Pearson et al., "Studies of Polyarthritis and Other Lesions Induced in Rats by Injection of Mycobacterial Adjuvant. I. General Clinical and Pathologic Characteristics and Some Modifying Factors," *Arthritis Rheum.*, vol. 2, (1959), pp. 440-459.

C. R. Bebbington et al., "High-level expression of a recombinant antibody from myeloma cells using a glutamine synthetase gene as an amplifiable selectable marker," *Bio/Technology*, vol. 10, Feb. 1992, pp. 169-175.

C. Reinhard et al., "Tumor necrosis factor alpha-induced activation of c-jun N-terminal kinase is mediated by TRAF2," *The EMBO Journal*, vol. 16, No. 5, (1997), pp. 1080-1092.

C. V. Johnson et al., "A Simple, Rapid Technique for Precise Mapping of Multiple Sequences in Two Colors Using a Single Optical Filter Set," *GATA*, vol. 8, No. 2, (1991), pp. 75-76.

C. V. Johnson et al., "Fluorescent Detection of Nuclear RNA and DNA: Implications for Genome Organization," *Methods in Cell Biology*, vol. 35, (1991), pp. 73-99.

C. W. Lo, "Transformation by Iontrophoretic Microinjection of DNA: Multiple Integrations Without Tandem Insertions," *Molecular and Cellular Biology*, vol. 3, No. 10, Oct. 1983, pp. 1803-1814.

*Clinical Pharmacy*, vol. 12, No. 7, Jul. 1993, pp. 488-505.

Current Protocols in Human Genetics, "Vectors for Gene Therapy," Chapter 12, (2007), pp. 12.0.1-13.10.06.

Current Protocols in Immunology, "Cytokines and Their Cellular Receptors," Chapter 6, (1991), pp. 6.0.1-6.30.8.

D. B. Smith et al., "Single-step purification of polypeptides expressed in *Escherichia coli* as fusions with glutathione S-transferase," *Gene*, vol. 67, (1988), pp. 31-40.

D. Bennett et al., "Kinetic Characterization of the Interaction of Biotinylated Human Interleukin 5 with an Fc Chimera of its Receptor alpha Subunit and Development of an ELISA Screening Assay using Real-Time Interaction Biosensor Analysis," *Journal of Molecular Recognition*, vol. 8, (1995), pp. 52-58.

D. Brutlag et al., "Improved sensitivity of biological sequence data base searches," *CABIOS*, vol. 6, No. 3, 1990, pp. 237-245.

D. Bryant et al., "Cardiac Failure in Transgenic Mice with Myocardial Expression of Tumor Necrosis Factor-alpha," *Basic Science Reports*, Apr. 14, 1998, pp. 1375-1381.

D. C. Robbins et al., "Antibodies to Covalent Aggregates of Insulin in Blood of Insulin-Using Diabetic Patients," *Diabetes*, vol. 36, Jul. 1987, pp. 838-841.

D. D. Waltman et al., "Choroidal Neovascularization Associated with Choroidal Nevi," *American Journal of Ophthalmology*, vol. 85, No. 5, (1978), pp. 704-710.

D. Goeddel et al., "Synthesis of human fibroblast interferon by *E. coli*," *Nucleic Acids Research*, vol. 8, No. 18, (1980), pp. 4057-4074.

D. Good et al., "A tumor suppressor-dependent inhibitor of angiogenesis is immunologically and functionally indistinguishable from a fragment of thrombospondin," *Proc. Natl. Acad. Sci. USA*, Vol. 87, Sep. 1990, pP. 6624-6628.

D. L. Stemple et al., "Isolation of a Stem Cell for Neurons and Glia from the Mammalian Neural Crest," *Cell*, vol. 71, Dec. 1992, pp. 973-985.

D. R. Burton et al., "Human Antibodies from Combinatorial Libraries," *Advances in Immunology*, vol. 57 (1994), pp. 191-280.

D. R. Thomsen et al., "Promoter-regulatory region of the major immediate early gene of human cytomegalovirus," *Proc. Natl. Acad. Sci. USA*, vol. 81, Feb. 1984, pp. 659-663.

D. Ron et al., "Expression of Biologically Active Recombinant Keratinocyte Growth Factor," *The Journal of Biological Chemistry*, vol. 268, No. 4, Feb. 5, 1993, pp. 2984-2988.

D. Sidransky et al., "Identification of P53 Gene Mutations in Bladder Cancers and Urine Samples," *Science*, vol. 252, May 3, 1991, pp. 706-709.

D. W. Leung et al., "Vascular Endothelial Growth Factor is a Secreted Angiogenic Mitogen," *Science*, vol. 246, Dec. 8, 1989, pp. 1306-1309.

D. W. Nicholson et al., "Identification and inhibition of the ICE/CED-3 protease necessary for mammalian apoptosis," *Nature*, vol. 367, Jul. 6, 1995, pp. 37-43.

D. Wilson et al., "JNK, but not MAPK, activation is associated with Fas-mediated apoptosis in human T cells," *Eur. J. Immunol.*, vol. 26, (1996), pp. 989-994.

D.Y. Yoon et al., "Antibodies to Domains II and III of the IL-1 Receptor Accessory Protein Inhibit IL-1-Beta Activity But Not Binding: Regulation of IL-1 Responses is Via Type I Receptor, Not the Accessory Protein," *The Journal of Immunology*, vol. 160, (1998), pp. 3170-3179.

E. A. Padlan, "A Possible Procedure for Reducing the Immunogenicity of Antibody Variable Domains While Preserving Their Ligand-Binding Properties," Molecular Immunology, vol. 28, No. 4/5, (1991), pp. 489-498.

E. H. Szybalska et al., "Genetics of Human Cell Lines, IV. DNA-Medicated Heritable Transformation of a Biochemical Trait," *Proc. Natl. Acad. Sci.*, vol. 48 (1962), pp. 2026-2034.

E. Hochuli et al., "New Metal Chelate Adsorbent Selective for Proteins and Peptides Containing Neighbouring Histidine Residues," *Journal of Chromatography*, vol. 411, (1987), pp. 177-184.

E. S. Ward et al., "Binding activities of a repertoire of single immunoglobulin variable domains secreted from *Escherichia coli*," *Nature*, vol. 341, Oct. 1989, pp. 544-546.

F. Arenzana-Seisdedos et al., "HIV blocked by chemokine antagonist," *Nature*, vol. 383, Oct. 1996, p. 400.

F. Cocchi et al., "Identification of RANTES, MIP-alpha, and MIP-1-beta as the Major HIV-Suppressive Factors Produced by CD8+ T Cells," *Science*, vol. 270, Dec. 15, 1995, pp. 1811-1815.

F. Golbere-Garapin et al., "A New Dominant Hybrid Selective Marker for Higher Eukaryotic Cells," *J. Mol. Biol.*, vol. 150, (1981), pp. 1-14.

F. L. Graham et al., "A New Technique for the Assay of Infectivity of Human Adenovirus 5 DNA," *Virology*, vol. 52, No. 2, Apr. 1973, pp. 456-467.

F. M. Ausubel et al., "Current Protocols in Molecular Biology," vol. 1, (1999).

F. M. Ausubel, "Current Protocols in Molecular Biology," (2008).

F. Malik et al., "Polyethylene Glycol (PEG)-modified Granulocyte-Macrophage Colony-stimulating Factor (GM-CSF) with Conserved Biological Activity," *Experimental Hematology*, vol. 20, No. 8, Sep. 1992, pp. 1028-1035.

F. Rastinejad et al., "Regulation of the Activity of a New Inhibitor of Angiogenesis by a Cancer Suppressor Gene," *Cell*, vol. 56, Feb. 10, 1989, pp. 345-355.

F.M. Ausubel et al., "Current Protocols in Molecular Biology," vol. 1, 1998 edition.

G. A. Bitter et al., "Expression and Secretion Vectors for Yeast," *Methods in Enzymology— Recombinant DNA*, vol. 153, Part D, (1987), pp. 516-545.

G. E. Francis et al., "PEGylation of cytokines and other therapeutic proteins and peptides: the importance of biological optimisation of coupling techniques," *International Journal of Hematology*, vol. 68 (1998), pp. 1-18.

G. F. Crouse et al., "Expression and Amplification of Engineered Mouse Dihydrofolate Reductase Minigenes," *Molecular and Cellular Biology*, vol. 3, No. 2, Feb. 1983, pp. 257-266.

G. Gimenez-Gallego et al., "Brain-Derived Acidic Fibroblast Growth Factor: Complete Amino Acid Sequence and Homologies," *Science*, vol. 230, Dec. 20, 1985, pp. 1385-1388.

G. Köhler et al., "Continuous cultures of fused cells secreting antibody of predefined specificity," *Nature*, vol. 256, Aug. 7, 1975, pp. 495-497.

G. Köhler et al., "Derivation of specific antibody-producing tissue culture and tumor lines by cell fusion," *Eur. J. Immunol.*, vol. 6, (1976), pp. 511-519.

G. Köhler et al., "Fusion between immunoglobulin-secreting and nonsecreting myeloma cell lines," *Eur. J. Immunol.*, vol. 6, (1976), pp. 292-295.

G. Köhler, "Immunoglobulin chain loss in hybridoma lines," *Proc. Natl. Acad. Sci. USA*, vol. 77, No. 4, Apr. 1980, pp. 2197-2199.

G. Kütemeier et al., "Assembly of Humanized Antibody Genes from Synthetic Oligonucleotides Using a Single-Round PCR," *BioTechniques*, vol. 17, No. 2, (1994), pp. 242-246.

G. L. Boulianne et al., "Production of functional chimaeric mouse/human antibody," *Nature*, vol. 312, Dec. 13, 1984, pp. 643-646.

G. L. Denardo et al., "Comparison of 1,4,7,10-Tetraazacyclododecane-N,N',N'',N'''—tetraacetic cid (DOTA)-Peptide-ChL6, a Novel Immunoconjugate with Catabolizable Linker, to 2-Iminothiolane-2[p-(Bromoacetamido)benzyl]-DOTA-ChL6 in Breast Cancer Xenografts," *Clinical Cancer Research*, vol. 4, Oct. 1998, pp. 2483-2490.

G. Lopez-Berestein, "Treatment of systemic Fungal Infections with Liposomal-Amphotericin B," *Liposomes in the Therapy of Infectious Diseases and Cancer*, (1989), pp. 317-327.

G. M. Studnicka et al., "Human-engineered monoclonal antibodies retain full specific binding activity by preserving non-CDR complementarity-modulating residues," *Protein Engineering*, vol. 7, No. 6, (1994), pp. 805-814.

G. Petersen et al., "Mapping of linear epitopes recognized by monoclonal antibodies with gene-fragment phage display libraries," *Mol. Gen. Genet.*, vol. 249, (1995), pp. 425-431.

G. Simmons et al., "Potent Inhibition of HIV-1 Infectivity in Macrophages and Lymphocytes by a Novel CCR5 Antagonist," *Science*, vol. 276, Apr. 11, 1997, pp. 276-279.

G. Van Heeke et al., "Expression of Human Asparagine Synthetase in *Escherichia coli*," *The Journal of Biological Chemistry*, vol. 264, No. 10, Apr. 1989, p. 5503-5509.

G. Wright et al., "High Level Expression of Active Human Alpha-1-Antitrypsin in the Milk of Transgenic Sheep," *Bio/Technology*, vol. 9, Sep. 1991, pp. 830-834.

G. Y. Wu et al., "Delivery systems for gene therapy," *Biotherapy*, vol. 3, No. 1, (1991), pp. 87-95.

G. Y. Wu et al., "Receptor-mediated in Vitro Gene Transformation by a Soluble DNA Carrier System," *The Journal of Biological Chemistry*, vol. 262, No. 10, Apr. 1987, pp. 4429-4432.

H. Buchwald et al., "Long-term continuous intravenous heparin administration by an implantable infusion pump in ambulatory patients with recurrent venous thrombosis," *Surgery*, vol. 88, No. 4, Oct. 1980, pp. 507-516.

H. Dobeli et al., "Role of the carboxy-terminal sequence on the biological activity of human immune interferon (IFN-y)," Journal of Biotechnology, vol. 7 (1988), pp. 199-216.

H. Gu et al., "Deletion of a DNA Polymerase Beta Gene Segment in T Cells using Cell Type-Specific Gene Targeting," *Science*, vol. 265, Jul. 1, 1994, pp. 103-106.

H. Hohmann et al., "Two Different Cell Types Have Different Major Receptors for Human Tumor Necrosis Factor (TNF alpha)," *The Journal of Biological Chemistry*, vol. 264, No. 25, Sep. 5, 1989, pp. 14927-14934.

H. K. Sluss et al., "Signal Transduction by Tumor Necrosis Factor Mediated by JNK Protein Kinases," *Molecular and Cellular Biology*, vol. 14, No. 12, Dec. 1994, pp. 8376-8384.

H. Kiem et al., "Retrovirus-Mediated Gene Transduction into Canine Peripheral Blood Repopulating Cells," *Blood*, vol. 83, No. 6, Mar. 1994, pp. 1467-1473.

H. Loetscher et al., "Molecular Cloning and Expression of the Human 55 kd Tumor Necrosis Factor Receptor," *Cell*, vol. 61, Apr. 20, 1990, pp. 351-359.

H. M Geysen et al., "Use of peptide synthesis to probe viral antigens for epitopes to a resolution of a single amino acid," *Proc. Natl. Acad. Sci. USA*, vol. 81, Jul. 1984, pp. 3998-4002.

H. Nishiyama et al., "Homozygous Deletion at the 9q32-33 Candidate Tumor Suppressor Locus in Primary Human Bladder Cancer," *Genes, Chromosomes & Cancer*, vol. 26 (1999), pp. 171-175.

H. Okano et al., "Myelin Basic Protein Gene and the Function of Antisense RNA and its Repression in Myelin-Deficient Mutant Mouse," *Journal of Neurochemistry*, vol. 56, No. 2, (1991), pp. 560-567.

H. P. Fell et al., "Genetic Construction and Characterization of a Fusion Protein Consisting of a Chimeric F(ab') with Specificity for Carcinomas and Human IL-2," *The Journal of Immunology*, vol. 146, No. 7, Apr. 1991, pp. 2446-2452.

H. Sawai et al., "Direct Production of the Fab Fragment Derived from the Sperm Immobilizing Antibody Using Polymerase Chain Reaction and cDNA Expression Vectors," *American Journal of Reproductive Immunology*, vol. 34, (1995), pp. 26-34.

H. Tabata et al., "Arterial gene transfer of acidic fibroblast growth factor for therapeutic angiogenesis in vivo: critical role of secretion signal in use of naked DNA," *Cardiovascular Research*, vol. 35, (1997), pp. 470-479.

H. Van Der Putten et al., "Efficient insertion of genes into the mouse germ line via retroviral vectors," *Proc. Natl. Acad. Sci. USA*, vol. 82, Sep. 1985, pp. 6148-6152.

H. Vie et al., "Human fusion proteins between interleukin 2 and IgM heavy chain are cytotoxic for cells expressing the interleukin 2 receptor," *Proc. Natl. Acad. Sci. USA*, vol. 89, Dec. 1992, pp. 11337-11341.

I. Lowy et al., "Isolation of Transforming DNA: Cloning the Hamster aprt Gene," *Cell*, vol. 22, Dec. 1980, pp. 817-823.

I. Wilmut et al., "Viable offspring derived from fetal and adult mammalian cells," *Nature*, vol. 385, Feb. 27, 1997, pp. 810-813.

I. Wilson et al., "The Structure of an Antigenic Determinant in a Protein," *Cell*, vol. 37, Jul. 1984, pp. 767-778.

J .J. B. Boesen et al., "Circumvention of chemotherapy-induced myelosuppression by transfer of the mdrl gene," *Biotherapy*, vol. 6, (1994), pp. 291-302.

J. A. Carlino et al., "Use of a Sensitive Receptor Binding Assay to Discriminate Between Full-length and Truncated Human Recombinant Tumor Necrosis Factor Proteins," *The Journal of Biological Chemistry*, vol. 262, No. 3, Jan. 25, 1987, pp. 958-961.

J. A. Harrop et al., "Antibodies to TR2 (Herpesvirus Entry Mediator), a New Member of the TNF Receptor Superfamily, Block T Cell Proliferation, Expression of Activation Markers, and Production of Cytokines," *Journal of Immunology*, vol. 161, No. 4, (1998), pp. 1786-1794.

J. A. Wells et al., "Cassette mutagenesis: an efficient method for generation of multiple mutations at defined sites," *Gene*, vol. 34 (1985), pp. 315-323.

J. A. Wells et al., "Importance of hydrogen-bond formation in stabilizing the transition state of subtilisin," *Phil. Tran. R. Soc. Lond. A*, vol. 317 (1986), pps. 415-423.

J. B. Ulmer et al., "Heterologous Protection Against Influenza by Injection of DNA Encoding a Viral Protein," *Science*, vol. 259, Mar. 19, 1993, pp. 1745-1749.

J. Bowie et al., "Deciphering the Message in Protein Sequences: Tolerance to Amino Acid Substitutions," *Science*, vol. 247, Mar. 16, 1990, pp. 1306-1310.

J. Chao et al., "Experimental Kallikrein Gene Therapy in Hypertension, Cardiovascular and Renal Diseases," *Pharmacological Research*, vol. 35, No. 6, (1997), pp. 517-522.

J. Coligan et al., "Isolation of T Cells Using Rosetting Procedures," Chapter 7.22 of Current Protocols in Immunology, vol. 2, 1994 edition, pp. 7.2.1-7.2.4.

J. D. Taurog et al., "Synergy Between Adjuvent Arthritis and Collagen-Induced Arthritis in Rats," *J. Exp. Med.*, vol. 162, Sep. 1985, pp. 962-978.

J. Denekamp, "Vascular attack as a therapeutic strategy for cancer," *Cancer and Metastasis Reviews*, vol. 9, (1990), pp. 267-282.

J. Folkman, "Angiogenesis in cancer, vascular, rheumatoid and other disease," *Nature Medicine*, vol. 1, No. 1, (1995), pp. 27-31.

J. Folkman et al., "Angiogenesis Inhibition and Tumor Regression Caused by Heparin or a Heparin Fragment in the Presence of Cortisone," *Science*, vol. 221, Aug. 19, 1983, pp. 719-725.

J. Folkman et al., "Angiogenesis Regulation of Angiogenesis in Health & Disease," *The Journal of Biological Chemistry*, vol. 267, No. 16, Jun. 5, 1992, pp. 10931-10934.

J. Folkman et al., "Angiogenic Factors," *Science*, vol. 235, Jan. 23, 1987, pp. 442-447.

J. Folkman, "Clinical Applications of Research on Angiogenesis," *New England Journal of Medicine*, vol. 333, No. 26, (1995), pp. 1757-1763.

J. G. Sutcliffe et al., "Antibodies that React with Predetermined Sites on Proteins," *Science*, vol. 219, (1983), pp. 660-666.

J. J. Peterson et al., "Enzymatic Cleavage of Peptide-Linked Radiolabels from Immunoconjugates," *Bioconjugate Chemistry*, vol. 10, No. 4, Jul./Aug. 1999, pp. 553-557.

J. L. Cleland et al., "The Development of Stable Protein Formulations: A Close Look at Protein Aggregation, Deamidation, and Oxidation," *Critical Reviews in Therapeutic Drug Carrier Systems*, vol. 10, No. 4, (1993), pp. 307-377.

J. Liautard et al., "Specific Inhibition of IL-6 Signalling with Monoclonal Antibodies Against the gp130 Receptor," *Cytokine*, vol. 9, No. 4, Apr. 1997, pp. 223-241.

J. Loeffler et al., "Gene Transfer into Primary and Established Mammalian Cell Lines with Lipopolyamine-Coated DNA," *Methods in Enzymology*, vol. 217, (1993), pp. 598-619.

J. Logan et al., "Adenovirus tripartite leader sequence enhances translation of mRNAs late after infection," *Proc. Natl. Acad. Sci. USA*, vol. 81, Jun. 1984, pp. 3655-3659.

J. M. Goodson, "Dental Applications," *Medical Applications of Controlled Release*, vol. II, (1984), pp. 115-138.

J. Ni et al., "Cystatin E is a Novel Human Cysteine Proteinase Inhibitor with Structural Resemblance to Family 2 Cystatins," *The Journal of Biological Chemistry*, vol. 272, No. 16, Apr. 18, 1997, pp. 10853-10858.

J. R. Wands et al., "High Afinity Monoclonal Antibodies to Hepatitis B Surface Antigen (HBsAg) Produced by Somatic Cell Hybrids," *Gastroenterology*, vol. 80, No. 2, (1981), pp. 225-232.

J. Rheinwald, "Serial Cultivation of Normal Human Epidermal Keratinocytes," *Methods in Cell Biology*, vol. 21A, Chapter 15, (1980), pp. 229-253.

J. S. Huston et al., "Protein engineering of antibody binding sites: Recovery of specific activity in an anti-digoxin single-chain Fv analogue produced in *Escherichia coli*," *Proc. Natl. Acad. Sci. USA*, vol. 85, Aug. 1988, pp. 5879-5883.

J. S. Huston et al., "Protein Engineering of Single-Chain Fv Analogs and Fusion Proteins," *Methods in Enzymology*, vol. 203, (1991), pp. 46-88.

J. S. Lee et al., "Complexes formed by (pyrimidine)n—(purine)nDNAs on lowering the pH are three-stranded," *Nucleic Acids Research*, vol. 6, No. 9, (1979), pp. 3073-3091.

J. Sambrook et al., "Molecular Cloning—A Laboratory Manual," second edition, 1990.

J. Treat et al., "Liposome Encapsulated Doxorubicin Preliminary Results of Phase 1 and Phase II Trials," Liposomes in the Therapy of Infectious Diseases and Cancer, Proceedings of a Ciba-Geigy-Squibb-UCLA Colloquium, Feb. 16-20, 1988, pp. 353-365.

K. E. Hellstrom et al., "Antibodies for Drug Delivery," Controlled Drug Delivery Fundamentals and Applications, second edition, (1987), pp. 624-653.

K. F. Kozarsky et al., "Gene therapy: adenovirus vectors," *Current Opinion in Genetics and Development*, vol. 3, (1993), pp. 499-503.

K. Gase et al., "Critical role of the C-terminus in the biological activities of human tumour necrosis factor-alpha," *Immunology*, vol. 71, (1990), pp. 368-371.

K. H. S. Campbell et al., "Sheep cloned by nuclear transfer from a cultured cell line," *Nature*, vol. 380, Mar. 7, 1996, pp. 64-66.

K. Miura et al., "Detailed Deletion Mapping in Squamous Cell Carcinomas of the Esophagus Narrows a Region Containing a Putative Tumor Suppressor Gene to about 200 Kilobases on Distal Chromosomes 9q1," *Cancer Research*, vol. 56, Apr. 1, 1996, pp. 1629-1634.

K. O'Hare et al., "Transformation of mouse fibroblasts to methotrexate resistance by a recombinant plasmid expressing a prokaryotic dihydrofolate reductase," *Proc. Natl. Acad. Sci. USA*, vol. 78, No. 3, Mar. 1981, pp. 1527-1531.

K. Thomas et al., "Site-Directed Mutagenesis by Gene Targeting in Mouse Embryo-Derived Stem Cells," *Cell*, vol. 51, Nov. 6, 1987, pp. 503-512.

K. Zimmermann et al., "A Triglycine Linker Improves Tumor Uptake and Biodistributions of 67-Cu-Labeled Anti-Neuroblastoma MAb chCE7 F(ab')2 Fragments," *Nuclear Medicine & Biology*, vol. 26, 1999, pp. 943-950.

L. G. Davis et al., "Methods in Molecular Biology," (1986).

L. M. Martins et al., "Activation of Multiple Interleukin-1beta Converting Enzyme Homologues in Cytosol and Nuclei of HL-60 Cells during Etoposide-induced Apoptosis," *The Journal of Biological Chemistry*, vol. 272, No. 11, Mar. 14, 1997, pp. 7421-7430.

L. O. Hansson et al., "Evolution of Differential Substrate Specificities in Mu Class Glutathione Transferases Probed by DNA Shuffling," *J. Mol. Biol.*, vol. 287 (1999), pp. 265-276.

L. Persic et al., "An integrated vector system for the eukaryotic expression of antibodies or their fragments after selection from phage display libraries," *Gene*, vol. 187 (1997), pp. 9-18.

L. Riechmann et al., "Reshaping human antibodies for therapy," *Nature*, vol. 332, Mar. 1988, pp. 323-327.

L. S. Jespers et al., "Guiding the Selection of Human Antibodies from Phage Display Repertoires to a Single Epitope of an Antigen," *Bio/Technology*, vol. 12, Sep. 1994, pp. 899-903.

L. Schweigerer et al., "Capillary endothelial cells express basic fibroblast growth factor, a mitogen that promotes their own growth," *Nature*, vol. 325, Jan. 15, 1987, pp. 257-259.

L. Shu et al., "Secretion of a single-gene-encoded immunoglobulin from myeloma cells," *Proc. Natl. Acad. Sci. USA*, vol. 90, Sep. 1993, pp. 7995-7999.

L. W. Burrus et al., "Isolation of a Receptor for Acidic and Basic Fibroblast Growth Factor from Embryonic Chick," *The Journal of Biological Chemistry*, vol. 264, No. 31, Nov. 5, 1989, pp. 18647-18653.

L. Wu et al., "CCR5 Levels and Expression Pattern Correlate with Infectability by Macrophage-tropic HIV-1, in Vitro," *J. Exp. Med.*, vol. 185, No. 9, May 5, 1997, pp. 1681-1691.

L. Zurfluh et al., "Auxin-induced changes in the patterns of protein synthesis in soybean hypocotyl," *Proc. Natl. Acad. Sci. USA*, vol. 77, No. 1, Jan. 1980, pp. 357-361.

M. A. Howard et al., "Interacerebral drug delivery in rats with lesion-induced memory deficits," *J. Neurosurg*, vol. 71, Jul. 1989, pp. 105-112.

M. A. Moses et al., "Inhibitors of Angiogenesis," *Bio/Technology*, vol. 9, Jul. 1991, pp. 630-634.

M. A. Roguska et al., "Humanization of murine monoclonal antibodies through variable domain resurfacing," *Proc. Natl. Acad. Sci. USA*, vol. 91, Feb. 1994, pp. 969-973.

M. A. Rosenfeld et al., "Adenovirus-Mediated Transfer of a Recombinant alpha-1-Antitrypsin Gene to the Lung Epithelium in Vivo," *Science*, vol. 252, Apr. 1991, pp. 431-434.

M. A. Rosenfeld et al., "In Vivo Transfer of the Human Cystic Fibrosis Transmembrane Conductance Regulator Gene to the Airway Epithelium," *Cell*, vol. 68, Jan. 1992, pp. 143-155.

M. Better et al., "*Escherichia coli* Secretion of an Active Chimeric Antibody Fragment," *Science*, vol. 240, May 1988, pp. 1041-1043.

M. C. Fishman et al., Medicine, 2d Ed. J. B. Lippincott Co. (1985).

M. Chow et al., "Synthetic peptides from four separate regions of the poliovirus type 1 capsid protein VP1 induce neutralizing antibodies," *Proc. Natl. Acad. Sci. USA*, vol. 82, Feb. 1985, pp. 910-914.

M. Cooney et al., "Site-Specific Oligonucleotide Binding Represses Transcription of the Human c-myc Gene in Vitro," Cooney *Science*, vol. 241, Jul. 22, 1988, pp. 456-459.

M. Cotten et al., "Receptor-Mediated Transport of DNA into Eukaryotic Cells," *Methods in Enzymology*, vol. 217, (1993), pp. 618-645.

M. D. Jacobson et al., "Role of Ced-3/ICE-Family Proteases in Staurosporine-induced Programmed Cell Death," *The Journal of Cell Biology*, vol. 133, No. 5, Jun. 1996, pp. 1041-1051.

M. D. Summers et al., "A Manual of Methods for Baculovirus Vectors and Insect Cell Culture Procedures," May, 1987, pp. 1-56.

M. del Mar Lorenzo et al., "PCR-Based Method for the Introduction of Mutations in Genes Cloned and Expressed in Vaccinia Virus," *Bio Techniques*, vol. 24, No. 2 (1998), pp. 308-313.

M. Fountoulakis et al., "Interferon γ Receptor Extracellular Domain Expressed as IgG Fusion Protein in Chinese Hamster Ovary Cells," *The Journal of Biological Chemistry*, vol. 270, No. 8, Feb. 24, 1995, pp. 3958-3964.

M. Grossman et al., "Retroviruses: delivery vehicle to the liver," *Current Opinion in Genetics and Development*, vol. 3, (1993), pp. 110-114.

M. Hahne et al., "April, A New Ligand of the Tumor Necrosis Factor Family, Stimulates Tumor Cell Growth," *J. Exp. Med.*, vol. 188, No. 6, Sep. 21, 1988, pp. 1185-1190.

M. I. Cockett et al., "High Level Expression of Tissue Inhibitor of Metalloproteinases in Chinese Hamster Ovary Cells using Glutamine Synthetase Gene Amplification," *Bio/Technology*, vol. 8, Jul. 1990, pp. 662-667.

M. J. During et al., "Controlled Release of Dopamine from a Polymeric Brain Implant: in Vivo Characterization," *Annals of Neurology*, vol. 25, No. 4, Apr. 1989, pp. 351-356.

M. J. Francis et al., "Immunological Priming with Synthetic Peptides of Foot-and-Mouth Disease Virus," *J. Gen. Virol.*, vol. 66 (1985), pp. 2347-2354.

M. J. Zoller et al., "Oligonucleotide-directed mutagenesis using M13-derived vectors: an efficient and general procedure for the production of point mutations in any fragment of DNA," *Nucleic Acids Research*, vol. 10, No. 20, (1982), pp. 6487-6500.

M. Jalkanen et al., "Cell Surface Proteoglycan of Mouse Mammary Epithelial Cells is Shed by Cleavage of its Matrix-binding Ectodomain from its Membrane-associated Domain," *The Journal of Cell Biology*, vol. 105, (No. 6, Pt. 2), Dec. 1987, pp. 3087-3096.

M. Jalkanen et al., "Heparan Sulfate Proteoglycans from Mouse Mammary Epithelial Cells: Localization on the Cell Surface with a Monoclonal Antibody," *The Journal of Cell Biology*, vol. 101, Sep. 1985, pp. 976-984.

M. K. Foecking et al., "Powerful and versatile enhancer-promoter unit for mammalian expression vectors," *Gene*, vol. 45 (1986), pp. 101-105.

M. Kozak, "Point mutations close to the AUG initiator codon affect the efficiency of translation of rat preproinsulin in vivo," *Nature*, vol. 308, Mar. 15, 1984, pp. 241-246.

M. Kriegler, "Gene Transfer and Expression—A Laboratory Manual," (1990).

M. L. Iruela-Arispe et al., "Angiogenesis: a Dynamic Balance of Stimulators and Inhibitors," *Thrombosis and Haemostasis*, (1997), pp. 672-677.

M. Lakso et al., "Targeted oncogene activation by site-specific recombination in transgenic mice," *Proc. Natl. Acad. Sci. USA*, vol. 89, Jul. 1992, pp. 6232-6236.

M. Lavitrano et al., "Sperm Cells as Vectors for Introducing Foreign DNA into Eggs: Genetic Transformation of Mice," *Cell*, vol. 57, Jun. 2, 1989, pp. 717-723.

M. M. Clowes et al., "Long-Term Biological Response of Injured Rat Carotid Artery Seeded with Smooth Muscle Cells Expressing Retrovirally Introduced Human Genes," *J. Clin. Invest.*, vol. 93, Feb. 1994, pp. 644-651.

M. Morpurgo et al., "Covalent Modification of Mushroom Tyrosinase with Different Amphiphic Polymers for Pharmaceutical and Biocatalysis Applications," *Applied Biochemistry and Biotechnology*, vol. 56, (1996), pp. 59-72.

M. Naramura et al., "Mechanisms of cellular cytotoxicity mediated by a recombinant antibody-IL2 fusion protein against human melanoma cells," *Immunology Letters*, vol. 39, (1994), pp. 91-99.

M. Nguyen et al., "Quantitation of Angiogenesis and Antiangiogenesis in the Chick Embryo Chorioallantoic Membrane," *Microvascular Research*, vol. 47, (1994), pp. 31-40.

M. O'Reilly et al., "Endostatin: An Endogenous Inhibitor of Angiogenesis and Tumor Growth," *Cell*, vol. 88, Jan. 24, 1997, pp. 277-285.

M. Prat et al., "Agonistic monoclonal antibodies against the Met receptor dissect the biological responses to HGF," *Journal of Cell Science*, vol. 111 (1998), pp. 237-247.

M. R. Pittelkow et al., "New Techniques for the in Vitro Culture of Human Skin Keratinocytes and Perspectives on Their Use for Grafting of Patients with Extensive Burns," *Mayo Clin. Proc.*, vol. 61, (1986), pp. 771-777.

M. S. Neuberger et al., "A hapten-specific chimaeric IgE antibody with human physiological effector function," *Nature*, vol. 314, Mar. 21, 1985, pp. 268-270.

M. S. Neuberger et al., "Recombinant antibodies possessing novel effector functions," *Nature*, vol. 312, Dec. 1984, pp. 604-608.

M. S. O'Reilly et al., "Angiostatin: a Novel Angiogenesis Inhibitor That Mediates the Suppression of Metastases by a Lewis Lung Carcinoma," *Cell*, vol. 79, Oct. 21, 1994, pp. 315-328.

M. V. Sefton, "Implantable Pumps," *Critical Reviews in Biomedical Engineering*, vol. 14, Issue 3, (1987), pp. 201-240.

M. Verheij et al., "Requirement for ceramide-initiated SAPK/JNK signalling in stress-induced apoptosis," *Nature*, vol. 380, Mar. 7, 1996, pp. 75-79.

M. Wigler et al., "Transfer of Purified Herpes Virus Tymidine Kinase Gene to Cultured Mouse Cells," *Cell*, vol. 11, May 1977, pp. 223-232.

M. Woo et al., "Essential contribution of caspase 3/CPP32 to apoptosis and its associated nuclear changes," *Genes & Development*, vol. 12, (1998), pp. 806-819.

Zijlstra et al., "Germ-line transmission of a disrupted Beta-2-microglobulin gene produced by homologous recombination in embryonic stem cells," *Nature*, vol. 342, Nov. 23, 1989, pp. 435-438.

A. Thornberry et al., "A novel heterodimeric cysteine protease is required for interleukin-1beta processing in monocytes," *Nature*, vol. 356, Apr. 30, 1992, pp. 768-774.

N. Carlson et al., "Identification of Amino Acids in the Glutamate Receptor, GluR3, Important for Antibody-binding and Receptor-specific Activation," *The Journal of Biological Chemistry*, vol. 272, No. 17, Apr. 25, 1997, pp. 11295-11301.

N. J. Proudfoot, "Transcriptional interference and termination between duplicated alpha-globin gene constructs suggests a novel mechanism for gene regulation," *Nature*, vol. 322, Aug. 1986, pp. 562-565.

N. Lonberg et al., "Human Antibodies from Transgenic Mice," *Intern. Rev. Immunol.*, vol. 13, (1995), pp. 65-93.

N. S. Greenspan et al., "Idiotypes: Structure and immunogenicity," *The FASEB Journal*, vol. 7, Mar. 1993, pp. 437-444.

O. Smithies et al., "Insertion of DNA sequences into the human chromosomal Beta-globin locus by homologous recombination," *Nature*, vol. 317, Sep. 19, 1985, pp. 230-234.

P. A. Patten et al., "Applications of DNA shuffling to pharmaceuticals and vaccines," Pharmaceutical Biotechnology, Vol. 8 (1997), pp. 724-733.

P. Bartunvek et al., "Avian Stem Cell Factor (SCF): Production and Characterization of the Recombinant HIS-Tagged SCF of Chicken and its Neutralizing Antibody," *Cytokine*, vol. 8, No. 1, Jan. 1996, pp. 14-20.

P. C. Brooks et al., "Integrin alpha-v-beta-3 Antagonists Promote Tumor Regression by Inducing Apoptosis of Angiogenic Blood Vessels," *Cell*, vol. 79, Dec. 30, 1994, pp. 1157-1164.

P. Caliceti et al., "Biopharmaceutical Properties of Uricase Conjugated to Neutral and Amphiphilic Polymers," *Bioconjugate Chem.*, No. 10 (1999), pp. 638-646.

P. Carter et al., "Improved oligonucleotide site-directed mutagenesis using M13 vectors," *Nucleic Acids Research*, vol. 13, No. 12, (1985), pp. 4431-4443.

P. Chomczynski et al., "Single-Step Method of RNA Isolation by Acid Guanidinium Thiocyanate-Phenol-Chloroform Extraction," *Analytical Biochemistry*, vol. 162, (1987), pp. 156-159.

P. E. Thorpe et al., "The Preparation and Cytotoxic Properties of Antibody-Toxin Conjugates," *Immunological Rev.*, vol. 62, (1982), pp. 119-158.

P. E. Vorobjev et al., "Oligonucleotide conjugated to linear and branched high molecular weight polyethylene glycol as substrates for RNase H.," *Nucleosides and Nucleotides*, vol. 18 (1999), pp. 2745-2750.

P. Felgner et al., "Improved Cationic Lipid formulations for In Vivo Gene Therapy," *Annals NY Academy of Sciences*, vol. 772, (1995), pp. 126-139.

P. Forrer et al., "Enzyme-Linked Immunosorbent Assay for Measurement of JNK, ERK, and p38 Kinase Activities," *Biol. Chem.*, vol. 379, Aug./Sep. 1998, pp. 1101-1111.

P. Juo et al., "Fas Activation of the p38 Mitogen-Activated Protein Kinase Signalling Pathway Requires ICE/CED-3 Family Proteases," *Molecular and Cellular Biology*, vol. 17, No. 1, Jan. 1997, pp. 24-35.

P. Kirschmeier et al., "Laboratory Methods—Construction and Characterization of a Retroviral Vector Demonstrating Efficient Expression of Cloned cDNA Sequences," *DNA*, vol. 7, No. 3, (1988), pp. 219-225.

P. L. Felgner et al., "Lipofection: A highly efficient, lipid-mediated DNA-transfection procedure," *Proc. Natl. Acad. Sci. USA*, vol. 84, Nov. 1987, pp. 7413-7417.

P. Tolstoshev, "Gene Therapy, Concepts, Current Trials and Future Directions," *Ann. Rev. Pharmacol. Toxicol.*, vol. 32, (1993), pp. 573-596.

Q. Wang et al., "A packaging cell line for propagation of recombinant adenovirus vectors containing two lethal gene-region deletions," *Gene Therapy*, vol. 2, (1995), pp. 775-783.

R. A. Houghten, "General method for the rapid solid-phase synthesis of large numbers of peptides: Specificity of antigen-antibody interaction at the level of individual amino acids," *Proc. Natl. Acad. Sci. USA*, vol. 82, Aug. 1985, pp. 5131-5135.

R. A. Morgan et al., "Human Gene Therapy," *Annu. Rev. Biochem.*, vol. 62, (1993), pp. 191-217.

R. Arnon et al., "Monoclonal Antibodies for Immunotargeting of Drugs in Cancer Therapy," *Monoclonal Antibodies and Cancer Therapy*, (1985), pp. 243-256.

R. C. Mulligan et al., "Selection for animal cells that express the *Escherichia coli* gene coding for xanthine-guanine phosphoribosyltransferase," *Proc. Natl. Acad. Sci. USA*, vol. 78, No. 4, Apr. 1981, pp. 2072-2076.

R. C. Mulligan, "The Basic Science of Gene Therapy," *Science*, vol. 260, May 1993, pp. 926-932.

R. Cotton et al., "Reactivity of cytosine and thymine in single-base-pair mismatches with hydroxylamine and osmium tetroxide and its application to the study mutations," *Proc. Natl. Acad. Sci. USA*, vol. 85, Jun. 1988, pp. 4397-4401.

R. E. Bird et al., "Single-Chain Antigen-Binding Proteins," *Science*, vol. 242, Oct. 1988, pp. 423-426.

R. F. Santerre et al., "Expression of prokaryotic genes for hygromycin B and G418 resistance as dominant-selection markers in mouse L cells," *Gene*, vol. 30 (1984), pp. 147-156.

R. Gentz et al., "Bioassay for trans-activation using purified human immunodeficiency virus tat-encoded protein: Trans-activation requires mRNA synthesis," *Proc. Natl. Acad. Sci. USA*, vol. 86, Feb. 1989, pp. 821-824.

R. Janknecht et al., "Rapid and efficient purification of native histidine-tagged protein expressed by recombinant vaccinia virus," *Proc. Natl. Acad. Sci. USA*, vol. 88, Oct. 1991, pp. 8972-8976.

R. Kamijo et al., "Induction of Differentiation of Human Monoblastic and Myeloblastic Leukemia Cell Lines by TNF Muteins," *Biochemical and Biophysical Research Commuinications*, vol. 160, No. 2, 1989, pp. 820-827.

R. L. Mullinax et al., "Expression of a Heterodimeric Fab Antibody Protein in One Cloning Step," *Biotechniques*, vol. 12, No. 6, (1992), pp. 864-869.

R. Langer et al., "Chemical and Physical Structure of Polymers as Carriers for Controlled Release of Bioactive Agents: A Review," *Rev. Macromol. Chem. Phys.*, vol. C23, No. 1, (1983), pp. 61-126.

R. Langer, "New Methods of Drug Delivery," *Science*, vol. 249, Sep. 1990, pp. 1527-1533.

R. Levy et al., "Inhibition of Calcification of Bioprosthetic Heart Valves by Local Controlled-Release Diphosphonate," *Science*, vol. 228, Apr. 1985, pp. 190-192.

R. Myers et al., "Detection of Single Base Substitutions by Ribonuclease Cleavage at Mismatches in RNA:DNA Duplexes," *Science*, vol. 230, Dec. 13, 1985, pp. 1242-1246.

R. N. Pinckard et al., "Factors Influencing the Immune Response," *Clin. Exp. Immunol.*, vol. 2 (1967), pp. 331-341.

R. S. Ames et al., "Conversion of murine Fabs isolated from a combinatorial phage display library to full length immunoglobulins," *Journal of Immunological Methods*, vol. 184 (1995), pp. 177-186.

R. S. Langer et al., "Medical Applications of Controlled Release," CRC Press, Boca Raton, FL (1974).

R. S. Sidhu et al., "Tumor Necrosis Factor Analogs: Identification of Functional Domains," *Anticancer Research*, vol. 9, No. 6, Nov.-Dec. 1989, pp. 1569-1576.

R. S. Verma et al., "Human Chromosomes, Manual of Basic Technique," (1988).

R. Saiki et al., "Analysis of enzymatically amplified Beta-globin and HLA-DQ-alpha DNA with allele-specific oligonucleotide probes," *Nature*, vol. 324, Nov. 13, 1986, pp. 163-166.

R. Twyman et al., "Glutamate Receptor Antibodies Activate a Subset of Receptors and Reveal an Agonist Binding Site," *Neuron*, vol. 14, Apr. 1995, pp. 755-762.

R. V. Talanian et al., "Substrate specificities of Caspase Family Proteases," *The Journal of Biological Chemistry*, vol. 272, No. 15, Apr. 11, 1997, pp. 9677-9682.

S. A. Kostelny et al., "Formation of a Bispecific Antibody by the use of Leucine Zippers," *The Journal of Immunology*, vol. 148, No. 5, Mar. 1, 1992, pp. 1547-1553.

S. Anderson et al., "Cloning, Structure, and Expression of the Mitochondrial Cytochrome P-450 Sterol 26-Hydroxylase, a Bile Acid Biosynthetic Enzyme," *The Journal of Biological Chemistry*, vol. 264, No. 14, May 15, 1989, pp. 8222-8229.

S. Burchiel et al., "Immunopharmacokinetics of Radiolabeled Antibodies and Their Fragments," Tumor Imaging—the Radioimmunochemical Detection of Cancer, Chapter 13, (1982), pp. 125-139.

S. D. Gillies et al., "Antibody-targeted interleukin 2 stimulates T-cell killing of autologous tumor cells," *Proc. Natl. Acad. Sci. USA*, vol. 89, Feb. 1992, pp. 1428-1432.

S. E. Order, "Analysis, Results, and Future Prospective of the Therapeutic Use of Radiolabeled Antibody in Cancer Therapy," Monoclonal Antibodies for Cancer Detection and Therapy, Academic Press, (1982), pp. 303-316.

S. Gartner et al., "Neovascularization of the Iris (*Rubeosis iridis*)," *Survey of Ophthalmology*, vol. 22, No. 5, Mar.-Apr. 1978, pp. 291-312.

S. Hauser et al., "A Heparin-Binding Form of Placenta Growth Factor (P1GF-2) is Expressed in Human Umbilical Vein Endothelial Cells and in Placenta," *Growth Factors*, vol. 9, (1993), pp. 259-268.

S. Inouye et al., "Up-promoter mutations in the Ipp gene of *Escherichia coli*," *Nucleic Acids Research*, vol. 13, No. 9, (1985), pp. 3101-3110.

S. J. Morrison et al., "Prospective Identification, Isolation by Flow Cytometry, and In Vivo Self-Renewal of Multipotent Mammalian Neural Crest Stem Cells," *Cell*, vol. 96, Mar. 1999, pp. 737-749.

S. J. Pollack et al., "Introduction of Nucleophiles and Spectroscopic Probes into Antibody Combining Sites," *Science*, vol. 242, Nov. 1988, pp. 1038-1040.

S. Kumar et al., "Activation of the HIV-1 Long Terminal Repeat by Cytokines and Environmental Stress Requires an Active CSBP/p38 MAP Kinase," *The Journal of Biological Chemistry*, vol. 271, No. 48, Nov. 29, 1996, pp. 30864-30869.

S. L. Morrison et al., "Chimeric human antibody molecules: Mouse antigen-binding domains with human constant region domains," *Proc. Natl. Acad. Sci. USA*, vol. 81, Nov. 1984, pp. 6851-6855.

S. L. Morrison, "Transfectomas Provide Novel Chimeric Antibodies," *Science*, vol. 229, Sep. 1985, pp. 1202-1207.

S. Nagata et al., "The Fas Death Factor," *Science*, vol. 267, Mar. 10, 1995, pp. 1449-1456.

S. Singh et al., "Activation of Transcription of Factor NF-kB is Suppressed by Curcumin (Diferulolylmethane)," *The Journal of Biological Chemistry*, vol. 270, No. 42, Oct. 1995, pp. 24995-25000.

S. Singh et al., "Protein-tyrosine Phosphatase Inhibitors Block Tumor nNecrosis Factor-dependent Activation of the Nuclear Transcription Factor NF-kB," *The Journal of Biological Chemistry*, vol. 270, No. 18, May 1995, pp. 10631-10639.

S. Takeda et al., "Construction of chimaeric processed immunoglobulin genes containing mouse variable and human constant region sequences," *Nature*, vol. 314, Apr. 1985, pp. 452-454.

S. Thompson et al., "Germ Line Transmission and Expression of a Corrected HPRT Gene Produced by Gene Targeting in Embryonic Stem Cells," *Cell*, vol. 56, Jan. 27, 1989, pp. 313-321.

S. Wennström et al., "cDNA Cloning and Expression of a Human FGF Receptor which Binds Acidic and Basic FGF," *Growth Factors*, vol. 4, (1991), pp. 197-208.

T. A. Bibila et al., "In Pursuit of the Optimal Fed-Batch Process for Monoclonal Antibody Production," *Biotechnol. Prog.*, vol. 11, No. 1, (1995), pp. 1-13.

T. A. Holton et al., "A simple and efficient method for direct cloning of PCR products using ddT-tailed vectors," *Nucleic Acids Research*, vol. 19, No. 5, (1991), p. 1156.

T. Habuchi et al., "A novel candidate tumor suppressor locus at 9q32-33 in bladder cancer: localization of the candidate region within a single 840 kb YAC," *Human Molecular Genetics*, vol. 6, No. 6, (1997), pp. 913-919.

T. Habuchi et al., "Structure and Methylation-Based Silencing of a Gene (DBCCR1) within a Candidate Bladder Cancer Tumor Suppressor Region at 9q32-q33," *Genomics*, vol. 48, (1998), pp. 277-288.

T. Hirano et al., "Complementary DNA for a novel human interleukin (BSF-2) that induces B lymphocytes to produce immunoglobulin," *Nature*, vol. 324, Nov. 1986, pp. 73-76.

T. Maione et al., "Inhibition of Angiogenesis by Recombinant Human Platelet Factor—4 and Related Peptides," *Science*, vol. 247, Jan. 5, 1990, pp. 77-79.

T. Nishiwaki et al., "Isolation and Mutational Analysis of a Novel Human cDNA, DECI (Deleted in Esophageal Cancer I), Derived from the Tumor Suppressor Locus in 9q32," *Genes, Chromosomes & Cancer*, vol. 27, (2000), pp. 169-176.

T. Paterson et al., "Approaches to maximizing stable expression of alpba-1-antitrypsin in transformed CHO cells," *Appl. Microbiol. Biotechnol.*, vol. 40, (1994), pp. 691-698.

T. Smith et al., "Comparison of Biosequences," *Advances in Applied Mathematics*, vol. 2, (1981), pp. 482-489.

T. Yue et al., "2-Methoxyestradiol, an Endogenous Estrogen Metabolite, Induces Apoptosis in Endothelial Cells and Inhibits Angiogenesis: Possible Role for Stress-Activated Protein Kinase Signaling Pathway and Fas Expression," *Molecular Pharmacology*, vol. 51, (1997), pp. 951-962.

T. Yue et al., "Straurosporine-induced Apoptosis in Cardiomyocytes: A Potential Role of Caspase-3," *J. Mol. Cell Cardiol.*, vol. 30, (1998), pp. 495-507.

U. Brinkmann et al., "Phage display of disulfide-stabilized Fv fragments," *Journal of Immunological Methods*, vol. 182 (1995), pp. 41-50.

U. Rüther et al., "Easy identification of cDNA clones," *The EMBO Journal*, vol. 2, No. 10, (1983), pp. 1791-1794.

V. A. Polunovsky et al., "Induction of Endotheilial Cell Apoptosis by TNF-alpha: Modulation by Inhibitors of Protein Synthesis," *Experimental Cell Research*, vol. 214, (1994), pp. 584-594.

V. F. Smolen et al, "Controlled Drug Bioavailability," *Drug Product Design and Performance*, vol. 1, John Wiley & Sons, (1984).

V. McKusick et al., "Mendelian Inheritance of Man," A Catalog of Human Genes and Genetic Disorders, The Johns Hopkins University, vol. 3, (1998).

V. Pitard et al., "Production and characterization of monoclonal antibodies against the leukemia inhibitory factor low affinity receptor, gp190," *Journal of Immunological Methods*, vol. 205 (1997), pp. 177-190.

V. T. Oi et al., "Chimeric Antibodies", *BioTechniques*, vol. 4, No. 3 (1986), pp. 214-221.

X. Wang et al., "Cleavage of sterol regulatory element binding proteins (SREBPs) by CPP32 during apoptosis," *The EMBO Journal*, vol. 15, No. 5, (1996), pp. 1012-1020.

X. X. Zheng et al., "Administration of Noncytolytic IL-10/Fc in Murine Models of Lipopolysaccharide-Induced Septic Shock and Allogeneic Islet Transplantation," *The Journal of Immunology*, vol. 154, (1995), pp. 5590-5600.

Y. Gluzman, "SV40-Transformed Simian Cells Support the Replication of Early SV40 Mutants," *Cell*, vol. 23, Jan. 1981, pp. 175-182.

Y. Li et al., "Use of Green Fluorescent Protein in Studies of Apoptosis of Transfected Cells," *BioTechniques*, vol. 23, No. 6, (1997), pp. 1026-1028.

Y. Tsurumi et al., "Direct Intramuscular Gene Transfer of Naked DNA Encoding Vascular Endothelial Growth Factor Augments Collateral Development and Tissue Perfusion," *Circulation*, vol. 94, No. 12, Dec. 15, 1996, pp. 3281-3290.

Y.A. Muller et al., "VEGF and the Fab fragment of a humanized neutralizing antibody: crystal structure of the complex at 2.4 Å resolution and mutational analysis of the interface," *Structure*, vol. 6, No. 9, (1998), pp. 1153-1167.

Z. Chen et al., "Effects of Interleukin-1alpha, Interleukin-1 Receptor Antagonist, and Neutralizing Antibody on Proinflammatory Cytokine Expression by Human Squamous Cell Carcinoma Lines," *Cancer Research*, vol. 58, Aug. 15, 1998, pp. 3668-3676.

Z. Xia et al., "Opposing Effects of ERK and JNK-p38 MAP Kinases on Apoptosis," *Science*, vol. 270, Nov. 24, 1995, pp. 1326-1331.

Z. Zhu et al., "Inhibition of Vascular Endothelial Growth Factor-induced Receptor Activation with Anti-Kinase Insert Domain-containing Receptor Single-Chain Antibodies from a Phage Display Library," *Cancer Research*, vol. 58, Aug. 1998, pp. 3209-3214.

Colitis, from Wikipedia [online], Nov. 16, 2008 [retrieved on Nov. 21, 2008], Retrieved from the Internet.<URL:http://en.wikipedia.org/wiki/Colitis>.

Bamias et al., "Role of TL1A and its receptor DR3 in two models of chronic murine ileitis," *Proc. Nat'l Acad. Sci. USA*, 103(22):8441-8446 (May 30, 2006).

Zhang et al., "Modulation of T-cell responses to alloantigens by TR6/DcR3," *J. Clin. Invest.* 107(11):1459-1468 (Jun. 2001).

Feldman et al., "Anti-TNF alpha therapy is useful in rheumatoid arthritis and Crohn's disease: analysis of the mechanism of action predicts utility in other diseases," *Transplant Proc.* 30(8):4126-4127 (Dec. 1998).

Kelly et al., "Intercellular adhesion molecule-1-deficient mice are protected against ischemic renal injury," *J. Clin. Invest.* 97(4):1056-1063 (Feb. 15, 1996).

Tang et al., "The type 1-stimulating activity of lung macrophages inhibits Th2-mediated allergic airway inflammation by an IFN-gamma-dependent mechanism," *J. Immunol.* 166(3):1471-1481 (Feb. 1, 2001).

Charlton et al., "The Th1/Th2 balance in autoimmunity," *Curr. Opin. Immunol.* 7(6):793-798 (Dec. 1995).

Migone et al., "TL1A is a TNF-like ligand for DR3 and TR6/DcR3 and functions as a T cell costimulator," *Immunity* 16(3):479-492 (Mar. 2002).

Zhai et al., "Inhibition of angiogenesis and breast cancer xenograft tumor growth by VEGI, a novel cytokine of the TNF superfamily," *Int'l J. Cancer*, 82(1):131-136 (Jul. 2, 1999).

Marks et al., "By-passing immunization. Human antibodies from V-gene libraries displayed on phage," *J. Mol. Biol.*, 222(3):581-597 (Dec. 5, 1991).

\* cited by examiner

TNF-gamma

```
  1  CCCAATCAAGAGAAATTCCATACTATCACCAGTTGGCCGACTTTCCAAGTCTAGTGCAGA   60
 61  AATCCAAGGCACCTCACACCTAGAGTTCCTATACCTCTGAGACTCCAGAGGAAAGAACAA  120
121  GACAGTGCAGAAGGATATGTTAGAACCCACTGAAAACCTAGAACGTTGAAAAGGAACCAT  180
181  ACCCTCCTGACCTATAAGAAAATTTTCAGTCTGCAGGGGGATATCCTTGTGGCCCAAGAC  240
241  ATTGGTGTTATCATTTGACTAAGAGGAAATTATTTGTGGTGAGCTCTGAGTGAGGATTAG  300
301  GACCAGGGAGATGCCAAGTTTCTATCACTTACCTCATGCCTGTAAGACAAGTGTTTTGTT  360
361  CCAATTGATGAATGGGAGAAAACAGTTCAGCCAATCACTTATGGGCACAGAATGGAATT   420
421  TGAAGCGTCTGGTGCCTGCCCTTGTCATACGTAAACAAGAGAGGCATCGATGAGTTTTAT  480
481  CTGAGTCATTTGGGAAAGGATAATTCTTGCACCAAGCCATTTTCCTAAACACAGAAGAAT  540
541  AGGGGGATTCCTTAACCTTCATTGTTCTCCAGGATCATAGGTCTCAGGATAAATTAAAAA  600
601  TTTTCAGGTCAGACCACTCAGTCTCAGAAAGGCAAAGTAATTTGCCCCAGGTCACTAGTC  660
661  CAAGATGTTATTCTCTTTGAACAAATGTGTATGTCCAGTCACATATTCTTCATTCATTCC  720
721  TCCCCAAAGCAGTTTTTAGCTGTTACGTATATTCGATCACTTTAGTCTATTTTGAAAATG  780
781  ATATGAGACGCTTTTTAAGCAAAGTCTACAGTTTCCCAATGAGAAAATTAATCCTCTTTC  840
  1      M R R F L S K V Y S F P M R K L I L F L            20
841  TTGTCTTTCCAGTTGTGAGACAAACTCCCACACAGCACTTTAAAAATCAGTTCCCAGCTC  900
 21      V F P V V R Q T P T Q H F K N Q F P A L            40
901  TGCACTGGGAACATGAACTAGGCCTGGCCTTCACCAAGAACCGAATGAACTATACCAACA  960
 41      H W E H E L G L A F T K N R M N Y T N K            60
961  AATTCCTGCTCATCCCAGAGTCGGGAGACTACTTCATTTACTCCCAGGTCACATTCCGTG 1020
 61      F L L I P E S G D Y F I Y S Q V T F R G            80
```

FIG. 1A

TNF-gamma

```
1021 GGATGACCTCTGAGTGCAGTGAAATCAGACAAGCAGGCCGACCAAACAAGCCCAGACTCCA 1080
  81    M  T  S  E  C  S  E  I  R  Q  A  G  R  P  N  K  P  D  S  I   100

1081 TCACTGTGGTCATCACCAAGGTAACAGACAGCTACCCTGAGCCAACCCAGCTCCTCATGG 1140
 101    T  V  V  I  T  K  V  T  D  S  Y  P  E  P  T  Q  L  L  M  G   120

1141 GGACCAAGTCTGTATGCGAAGTAGGTAGCAACTGGTTCCAGCCCATCTACCTCGGAGCCA 1200
 121    T  K  S  V  C  E  V  G  S  N  W  F  Q  P  I  Y  L  G  A  M   140

1201 TGTTCTCCTTGCAAGAAGGCGACAAGCTAATGGTGAACGTCAGTGACATCTCTTTGGTGG 1260
 141    F  S  L  Q  E  G  D  K  L  M  V  N  V  S  D  I  S  L  V  D   160

1261 ATTACACAAAAGAAGATAAAAACCTTCTTTGGAGCCTTCTTACTATAGGAGCAGAGCAAAT 1320
 161    Y  T  K  E  D  K  T  F  F  G  A  F  L  L                     175

1321 ATCATTATATGAAAGTCCTCTGCCACCGAGTTCCTAATTTTCTTTGTTCAAATGTAATTA 1380

1381 TAACCAGGGGTTTTCTTGGGGCCGCGAGTAGGGGGCATTCCACAGGGACAACGGTTTAGC 1440

1441 TATGAAATTTGGGGCCAAAATTTCACACTTCATGTGCCTTACTGATGAGAGTACTAACTG 1500

1501 GAAAAACGCTGAAGAGAGCAAATATATTATTAAGATGGGTTGGAGGATTGGCGAGTTTCT 1560

1561 AAATATTAAGACACTGATCACTAAATGAATGGATGATCTACTCGGGTCAGGATTGAAAGA 1620

1621 GAAATATTTCAACACCTCCCTGCTATACAATGGTCACCAGTGGTCCAGTTATTGTTCAAT 1680

1681 TTGATCATAAATTTGCTTCAATTCAGGAGCTTTGAAGGAAGTCCAAGCAAAGCTCTAGAA 1740

1741 AACAGTATAAACTTTCAGAGGCAAAATCCTTCACCAATTTTTCCACATACTTTCATGCCT 1800

1801 TGCCTAAAAAAAATGAAAAGAGAGTTGGTATGTCTCATGAATGTTCACACAGAAGGAGTT 1860

1861 GGTTTTCATGTCATCTACAGCATATGAGAAAAGCTACCTTTCTTTTGATTATGTACACAG 1920

1921 ATATCTAAATAAGGAAGTTTGAGTTTCACATGTATATCCCAAATACAACAGTTGCTTGTA 1980

1981 TTCAGTAGAGTTTTCTTGCCCACCTATTTTGTCCTGGGTTCTACCTTAACCCAGAAGACA 2040
```

FIG. 1B

TNF-gamma

```
2041  CTATGAAAAACAAGACAGACTCCACTCAAAATTTATATGAACACCACTAGATACTTCCTG  2100

2101  ATCAAACATCAGTCAACATACTCTAAAGAATAACTCCAAGTCTTGGCCAGGCGCAGTGGC  2160

2161  TCACACCTGTAATCCCAACACTTTGGGAGGCCAAGGTGGGTGGATCATCTAAGGCCGGGA  2220

2221  GTTCAAGACCAGCCTGACCAACGTGGAGAAACCCCATCTCTACTNAAAATACNAAATTAG  2280

2281  CCGGGCGTGGTAGCGCATGGCTGTAANCCTGGCTACTCAGGAGGCCGAGGCAGAANAATT  2340

2341  NCTTGAACTGGGGAGGCAGAGGTTGCGGTGAGCCCAGANCGCGCCATTGCACTCCAGCCT  2400

2401  GGGTAACAAGAGCAAAACTCTGTCCAAAAAAAAAAAAAAAAAA  2442
```

MATCH WITH FIG. 2B

```
119 M G T K S V C E - - - - - - - - V G S N W F Q P I Y L G A   TNFgamma
171 A I A R S P C Q R E T P E G - - - - A E A K P W Y E P I Y L G G   TNFalpha
150 S Q K M V Y P - - - - - - - - G L Q E P W L H S M Y H G A   TNFbeta
180 E G A E T Y P - V L D P A R R Q - - G Y G P L W Y T S V G F G G   LTbeta
223 E E K K E L N Y - - - - C - - - T T G Q L W A H S S Y L G A   FASL 140 M F S H Q E G D K M V N V E D T S S H L D Y T K E D K I F F P   TNFgamma
199 V F Q L E K G D R L S A E I N R P D Y L D F A E S G Q V Y F   TNFalpha
172 A F Q L T Q G D Q L S T H T D G I P H L V L S - P S T V F   TNFbeta
210 L V Q R E R Y A B H H Y N D F A R - I E E S K T F F   LTbeta
245 V Y N T S I G L S Q L H I N E - E E S K T P F   FASL 170 G A E L L L I H Q   TNFgamma
229 G I I A L L   TNFalpha
201 G A E A L   TNFbeta
239 G V M V G   LTbeta
274 G L Y K L   FASL
```

FIG.2C

Tissue distribution of TNFgamma mRNA

Expression of TNFgamma in HUVEC

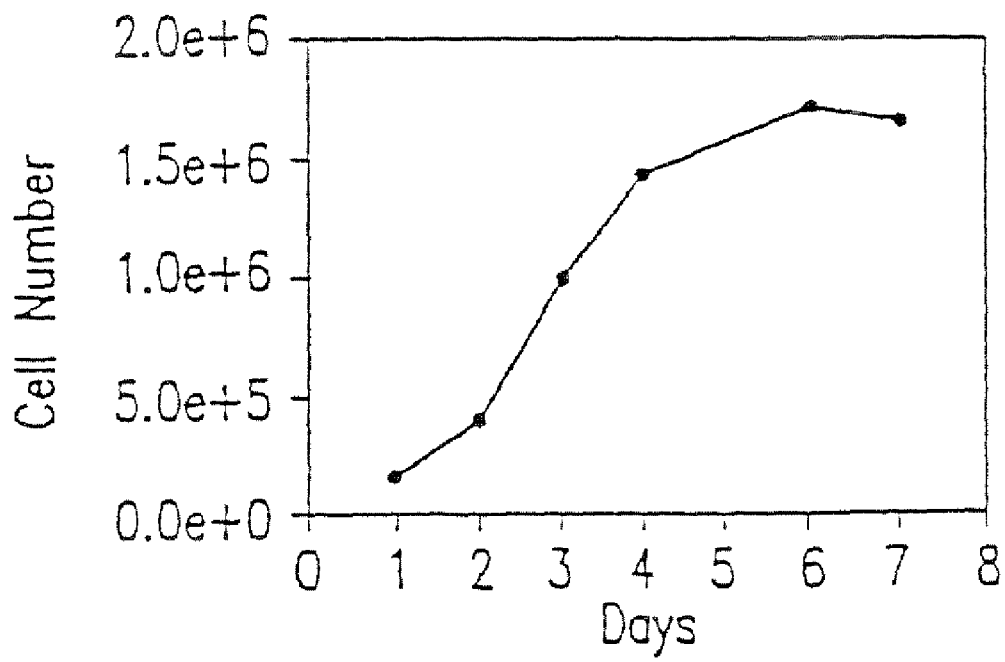
FIG.4

Expression of TNFγ in baculovirus system 1  2  3  4

TNFγ

FIG.6

TNF-gamma-alpha vs. TNF-gamma-beta

| | | |
|---|---|---|
| TNF-gamma-alpha | 1 CCCAATCAAGAGAAATTCCATACTATCACCAGTTGGCCGACTTTCCAAG | 49 |
| TNF-gamma-alpha | 50 TCTAGTGCAGAAATCCAAGGCACCTCACACCTAGAGTTCCTATACCTCTG | 99 |
| TNF-gamma-alpha | 100 ACACTCCAGAGGAAAGAACAAGACAGTGCAGAAGGATATGTTAGAACCCA | 149 |
| TNF-gamma-alpha | 150 CTGAAAACCTAGAACGTTGAAAAGGAAGCATACCCTCCTGACCTATAAGA | 199 |
| TNF-gamma-alpha | 200 AAATTTTCAGTCTGCAGGGGGATATCCTTGTGGCCCAAGACATTGGTGTT | 249 |
| TNF-gamma-alpha | 250 ATCATTTGACTAAGAGGAAATTATTTGTGGTGAGCTCTGACTGAGGATTA | 299 |
| TNF-gamma-alpha | 300 GGACCAGGGACATGCCAAGTTTCTATCACTTACCTCATGCCTGTAAGACA | 349 |
| TNF-gamma-alpha | 350 AGTGTTTTGTTCCAATTGATGAATGGGGAGAAAACAGTTCAGCCAATCAC | 399 |
| TNF-gamma-alpha | 400 TTATGGGCACAGAATGGAATTTCAAGCGTCTGGTGCCTGCCCTTGTCATA | 449 |
| TNF-gamma-alpha | 450 CGTAAACAAGAGAGGCATCGATCAGTTTTATCTGAGTCATTTGGGAAAGG | 499 |
| TNF-gamma-alpha | 500 ATAATTCTTGCACCAAGCCATTTTCCTAAACACAGAAGAATAGGGGGATT | 549 |
| TNF-gamma-alpha | 550 CCTTAACCTTCATTGTTCTCCACGATCATAGGTCTCAGGATAAATTAAAA | 599 |
| |           \| \|\|   \| \|   \| \|   \| \|\|   \| \|   \| \|\| | |
| TNF-gamma-beta | 1 ATGGCCGAGGATCTGGGACTGAGCCTTTGGGGAAACAGCCAGTGTGGAA | 48 |
| TNF-gamma-alpha | 600 ATTTTCAGGTCAGACCACTCAGTCTCAGAAAGGCAAAGTAATTTGCCCCA | 649 |
| |       \|\| \|     \|\| \|    \| \|   \| \|\|   \| | |
| TNF-gamma-beta | 49 ATGCTGCCAGAGCACGGCAGCTGCAGGCCCAAGGCCAGGACCAGCAGCGC | 98 |
| TNF-gamma-alpha | 650 GGTCACTAGTCCAAGATGTTATTCTCTTTGAACAAATGTGTATGTCCAGT | 699 |
| |     \|  \|\| \| \|\|\|    \|\| \|     \|     \| | |
| TNF-gamma-beta | 99 ACGCTGGGCTCTCACCTGCTGCCTGGTGTTGCTCCCCTTCCTTGCAGGAC | 148 |
| TNF-gamma-alpha | 700 CACATATTCTTCATTCATTCCTCCCCAAAGCAGTTTTTAGCTGTTAGGTA | 749 |
| |     \|    \|    \|  \|\|   \|    \| | |
| TNF-gamma-beta | 149 TCACCACATACCTGCTTGTCAGCCAGCTCCGGGCCCAGGGAGAGGCCTGT | 198 |
| TNF-gamma-alpha | 750 TATTCGATCACTTTAGTCTATTTTGAAAATGATATGAGACGCTTTTTAAG | 799 |
| |   \|\|\|       \|\|\|     \|\|\|     \| | |
| TNF-gamma-beta | 199 GTGCAGTTCCAGGCTCTAAAAGGACAGGAGTTTGCACCTTCACATCAGCA | 248 |

FIG. 18A

TNF-gamma-alpha vs. TNF-gamma-beta

```
TNF-gamma-alpha   800 CAAAGTCTACAGTTTCCCAATGAGAAAATTAATCCTCTTTCTTGTCTTTC  849
                      | |   |   |   | |   |           | |
TNF-gamma-beta    249 AGTTTATGCACCTCTTAGAGCAGACGGAGATAAGCCAAGGGCACACCTGA  298

TNF-gamma-alpha   850 CAGTTGTGAGACAAACTCCCACACAGCACTTTAAAAATCAGTTCCCAGCT  899
                      ||||||||| ||||||||||||||||||||||||||||||||||||||||
TNF-gamma-beta    299 CAGTTGTGACACAAACTCCCACACAGCACTTTAAAAATCAGTTCCCAGCT  348

TNF-gamma-alpha   900 CTGCACTGGGAACATGAACTAGGCCTGGCCTTCACCAAGAACCGAATGAA  949
                      ||||||||||||||||||||||||||||||||||||||||||||||||||
TNF-gamma-beta    349 CTGCACTGGGAACATGAACTAGGCCTGGCCTTCACCAAGAACCGAATGAA  398

TNF-gamma-alpha   950 CTATACCAACAAATTCCTGCTGATCCCAGAGTCGGGACACTACTTCATTT  999
                      ||||||||||||||||||||||||||||||||||||||||||||||||||
TNF-gamma-beta    399 CTATACCAACAAATTCCTGCTGATCCCAGAGTCGGGACACTACTTCATTT  448

TNF-gamma-alpha  1000 ACTCCCAGGTCACATTCCGTGGGATGACCTCTGAGTGCACTGAAATCAGA 1049
                      ||||||||||||||||||||||||||||||||||||||||||||||||||
TNF-gamma-beta    449 ACTCCCAGGTCACATTCCGTGGGATGACCTCTGAGTGCACTGAAATCAGA  498

TNF-gamma-alpha  1050 CAAGCACGCCGACCAAACAAGCCAGACTCCATCACTGTGGTCATCACCAA 1099
                      ||||||||||||||||||||||||||||||||||||||||||||||||||
TNF-gamma-beta    499 CAAGCACGCCGACCAAACAAGCCAGACTCCATCACTGTGGTCATCACCAA  548

TNF-gamma-alpha  1100 GGTAACAGACAGCTACCCTGAGCCAACCCAGCTCCTCATGGGGACCAAGT 1149
                      ||||||||||||||||||||||||||||||||||||||||||||||||||
TNF-gamma-beta    549 GGTAACAGACAGCTACCCTGAGCCAACCCAGCTCCTCATGGGGACCAAGT  598

TNF-gamma-alpha  1150 CTGTATGCGAAGTAGGTAGCAACTGGTTCCAGCCCATCTACCTCGGAGCC 1199
                      ||||||||||||||||||||||||||||||||||||||||||||||||||
TNF-gamma-beta    599 CTGTATGCGAAGTAGGTAGCAACTGGTTCCAGCCCATCTACCTCGGAGCC  648

TNF-gamma-alpha  1200 ATGTTCTCCTTGCAAGAAGGGGACAAGCTAATGGTGAACGTCAGTGACAT 1249
                      ||||||||||||||||||||||||||||||||||||||||||||||||||
TNF-gamma-beta    649 ATGTTCTCCTTGCAAGAAGGGGACAAGCTAATGGTGAACGTCAGTGACAT  698

TNF-gamma-alpha  1250 CTCTTTGGTGGATTACACAAAAGAAGATAAAACCTTCTTTGGAGCCTTCT 1299
                      ||||||||||||||||||||||||||||||||||||||||||||||||||
TNF-gamma-beta    699 CTCTTTGGTGGATTACACAAAAGAAGATAAAACCTTCTTTGGAGCCTTCT  748

TNF-gamma-alpha  1300 TACTATAGGAGGACAGCAAATATCATTATATGAAAGTCCTCTGCCACCGA 1349
                      ||||||||||||||||||||||||||||||||||||||||||||||||||
TNF-gamma-beta    749 TACTATAGGAGGACAGCAAATATCATTATATGAAAGTCCTCTGCCACCGA  798

TNF-gamma-alpha  1350 GTTCCTAATTTTCTTTGTTCAAATGTAATTATAACCACGGGTTTTCTTGG 1399
                      ||||||||||||||||||||||||||||||||||||||||||||||||||
TNF-gamma-beta    799 GTTCCTAATTTTCTTTGTTCAAATGTAATTATAACCACGGGTTTTCTTGG  848

TNF-gamma-alpha  1400 GGCCGGGAGTAGGGGGCATTCCACAGGGACAACGGTTTAGCTATGAAATT 1449
                      ||||||||||| ||||||||||||||||||||||||||||||||||||||
TNF-gamma-beta    849 GGCCGGGAGTA.GGGGCATTCCACAGGGACAACGGTTTAGCTATGAAATT  897
```

FIG. 18B

TNF-gamma-alpha vs. TNF-gamma-beta

```
TNF-gamma-alpha 1450 TGGGG CCAAAATTTCACACTTCATGTGCCTTACTGATGAGAGTACTAAC 1498
                    |||||  |||||||||||||||||||||||||||||||||||||||||||
TNF-gamma-beta   898 TGGGGCCCAAAATTTCACACTTCATGTGCCTTACTGATGAGAGTACTAAC 947

TNF-gamma-alpha 1499 TGGAAAAAGGCTGAACAGAGCAAATATATTATTAAGATGGGTTGGAGGAT 1548
                    ||||||||||||||||||||||||||||||||||||||||||||||||||
TNF-gamma-beta   948 TGGAAAAAGGCTGAACAGAGCAAATATATTATTAAGATGGGTTGGACGAT 997

TNF-gamma-alpha 1549 TGGCGAGTTTCTAAATATTAAGACACTGATCACTAAATGAATGGATGATC 1598
                    ||||||||||||||||||||||||||||||||||||||||||||||||||
TNF-gamma-beta   998 TGGCGAGTTTCTAAATATTAAGACACTGATCACTAAATGAATGGATGATC 1047

TNF-gamma-alpha 1599 TACTCGGGTCAGGATTGAAAGAGAAATATTTCAACACCTCCCTGCTATAC 1648
                    |||||||||||||||||||||||||||||||||||||||| |||||||||
TNF-gamma-beta  1048 TACTCGGGTCAGGATTGAAAGAGAAATATTTCAACACCTTCCTGCTATAC 1097

TNF-gamma-alpha 1649 AATGGTCACCAGTGGTCCAGTTATTGTTCAATTTGATCATAAATTTGCTT 1698
                    ||||||||||||||||||||
TNF-gamma-beta  1098 AATGGTCACCAGTGGTCCA 1116

TNF-gamma-alpha 1699 CAATTCAGGAGCTTTGAAGGAAGTCCAAGGAAAGCTCTAGAAAACAGTAT 1748

TNF-gamma-alpha 1749 AAACTTTCAGAGGCAAAATCCTTCACCAATTTTTCCACATACTTTCATGC 1798

TNF-gamma-alpha 1799 CTTGCCTAAAAAAAATGAAAAGAGAGTTGGTATGTCTCATGAATGTTCAC 1848

TNF-gamma-alpha 1849 ACAGAAGGAGTTGGTTTTCATGTCATCTACAGCATATGAGAAAAGCTACC 1898

TNF-gamma-alpha 1899 TTTCTTTTGATTATGTACACAGATATCTAAATAAGGAAGTTTGACTTTCA 1948

TNF-gamma-alpha 1949 CATGTATATCCCAAATACAACAGTTGCTTGTATTCAGTAGAGTTTTCTTG 1998

TNF-gamma-alpha 1999 CCCACCTATTTTGTGCTGGGTTCTACCTTAACCCAGAAGACACTATGAAA 2048

TNF-gamma-alpha 2049 AACAAGACAGACTCCACTCAAAATTTATATGAACACCACTAGATACTTCC 2098

TNF-gamma-alpha 2099 TGATCAAACATCAGTCAACATACTCTAAAGAATAACTCCAAGTCTTGGCC 2148

TNF-gamma-alpha 2149 AGGCGCAGTGGCTCACACCTGTAATCCCAACACTTTGGGAGGCCAAGGTG 2198

TNF-gamma-alpha 2199 GGTGGATCATCTAAGGCCGGGAGTTCAAGACCAGCCTGACCAACGTGGAG 2248
```

FIG. 18C

TNF-gamma-alpha vs. TNF-gamma-beta

TNF-gamma-alpha  2249  AAACCCCATCTCTACTNAAAATACNAAATTAGCCGGGCGTGGTAGCGCAT  2298

TNF-gamma-alpha  2299  GGCTGTAANCCTGGCTACTCAGGAGGCCCAGGCAGAANAATTNCTTGAAC  2348

TNF-gamma-alpha  2349  TGGGCAGGCAGAGGTTGCGGTGAGCCCAGANCGCGCCATTGCACTCCAGC  2398

TNF-gamma-alpha  2399  CTGCGTAACAAGAGCAAAACTCTGTCCAAAAAAAAAAAAAAAAA        2442

FIG. 18D

TNF-gamma-alpha vs. TNF-gamma-beta

```
TNF-gamma-beta    1 MAEDLGLSFGETASVEMLPEHCSCRPKARSSSARWALTCCLVLLPFLAGL 50

TNF-gamma-alpha   1                           MRRFLSKVYSFPMRKLILFLVFP 23

TNF-gamma-beta   51 TTYLLVSQLRACGEACVQFQALKGQEFAPSHQQVYAPLRADCDKPRAHLT 100

TNF-gamma-alpha  24 WRQTPTQHFKNQFPALHWEHELGLAFTKNRMNYTNKFLLIPESGDYFIY 73
                    |||||||||||||||||||||||||||||||||||||||||||||||||
TNF-gamma-beta  101 WRQTPTQHFKNQFPALHWEHELGLAFTKNRMNYTNKFLLIPESGDYFIY 150

TNF-gamma-alpha  74 SQVTFRCMTSECSEIRQAGRPNKPDSITVVITKVTDSYPEPTQLLMGTKS 123
                    |||||||||||||||||||||||||||||||||||||||||||||||||
TNF-gamma-beta  151 SQVTFRCMTSECSEIRQAGRPNKPDSITVVITKVTDSYPEPTQLLMGTKS 200

TNF-gamma-alpha 124 VCEVGSNWFQPIYLGAMFSLQEGDKLMVNVSDISLVDYTKEDKTFFGAFL 173
                    |||||||||||||||||||||||||||||||||||||||||||||||||
TNF-gamma-beta  201 VCEVGSNWFQPIYLGAMFSLQEGDKLMVNVSDISLVDYTKEDKTFFGAFL 250

TNF-gamma-alpha 174 L 174
                    |
TNF-gamma-beta  251 L 251
```

FIG. 19

TNF-gamma-beta

```
  1 ATGGCCGAGGATCTGGGACTGAGCTTTGGGGAAACAGCCAGTGTGGAAATGCTGCCAGAG  60
  1  M  A  E  D  L  G  L  S  F  G  E  T  A  S  V  E  M  L  P  E   20

61 CACGGCAGCTGCAGGCCCAAGGCCAGGAGCAGCAGCGCACGCTGGGCTCTCACCTGCTGC 120
 21  H  G  S  C  R  P  K  A  R  S  S  S  A  R  W  A  L  T  C  C   40

121 CTGGTGTTGCTCCCCTTCCTTGCAGGACTCACCACATACCTGCTTGTCAGCCAGCTCCGG 180
 41  L  V  L  L  P  F  L  A  G  L  T  T  Y  L  L  V  S  Q  L  R   60

181 GCCCAGGGAGAGGCCTGTGTGCAGTTCCAGGCTCTAAAAGGACAGGAGTTTGCACCTTCA 240
 61  A  Q  G  E  A  C  V  Q  F  Q  A  L  K  G  Q  E  F  A  P  S   80

241 CATCAGCAAGTTTATGCACCTCTTAGAGCAGACGGAGATAAGCCAAGGGCACACCTGACA 300
 81  H  Q  Q  V  Y  A  P  L  R  A  D  G  D  K  P  R  A  H  L  T  100

301 GTTGTGAGACAAACTCCCACACAGCACTTTAAAAATCAGTTCCCAGCTCTGCACTGGGAA 360
101  V  V  R  Q  T  P  T  Q  H  F  K  N  Q  F  P  A  L  H  W  E  120

361 CATGAACTAGGCCTGGCCTTCACCAAGAACCGAATGAACTATACCAACAAATTCCTGCTG 420
121  H  E  L  G  L  A  F  T  K  N  R  M  N  Y  T  N  K  F  L  L  140

421 ATCCCAGAGTCGGGAGACTACTTCATTTACTCCCAGGTCACATTCCGTGGGATGACCTCT 480
141  I  P  E  S  G  D  Y  F  I  Y  S  Q  V  T  F  R  G  M  T  S  160

481 GAGTGCAGTGAAATCAGACAAGCAGGCCGACCAAACAAGCCAGACTCCATCACTGTGGTC 540
161  E  C  S  E  I  R  Q  A  G  R  P  N  K  P  D  S  I  T  V  V  180

541 ATCACCAAGGTAACAGACAGCTACCCTGAGCCAACCCAGCTCCTCATGGGGACCAACTCT 600
181  I  T  K  V  T  D  S  Y  P  E  P  T  Q  L  L  M  G  T  K  S  200

601 GTATGCGAAGTAGGTAGCAACTGGTTCCAGCCCATCTACCTCGGAGCCATGTTCTCCTTG 660
201  V  C  E  V  G  S  N  W  F  Q  P  I  Y  L  G  A  M  F  S  L  220

661 CAAGAAGGGGACAAGCTAATGGTGAACGTCAGTGACATCTCTTTGGTGGATTACACAAAA 720
221  Q  E  G  D  K  L  M  V  N  V  S  D  I  S  L  V  D  Y  T  K  240

721 GAAGATAAAACCTTCTTTGGAGCCTTCTTACTATAGGAGGAGAGCAAATATCATTATATG 780
241  E  D  K  T  F  F  G  A  F  L  L                             251

781 AAAGTCCTCTGCCACCGAGTTCCTAATTTTCTTTGTTCAAATGTAATTATAACCAGGGCT 840

841 TTTCTTGGGGCCGGGAGTAGGGGCATTCCACAGGGACAACGGTTTAGCTATGAAATTTGG 900
```

FIG. 20A

TNF-gamma-beta

```
 901 GGCCCAAAATTTCACACTTCATGTGCCTTACTGATGAGAGTACTAACTGGAAAAAGGCTG  960
 961 AAGAGAGCAAATATATTATTAAGATGGGTTGGAGGATTGGCGAGTTTCTAAATATTAAGA 1020
1021 CACTGATCACTAAATGAATGCATGATCTACTCGGTCAGGATTGAAAGAGAAATATTTCA 1080
1081 ACACCTTCCTGCTATACAATGGTCACCAGTGGTCCA                         1116
```

FIG. 20B

TUMOR NECROSIS FACTOR-GAMMA

CROSS REFERENCE TO RELATED APPLICATIONS

This application is a divisional of U.S. application Ser. No. 11/837,082, filed Aug. 10, 2007, which is a continuation of U.S. application Ser. No. 10/226,294, filed Aug. 23, 2002, now abandoned, which claims benefit under 35 U.S.C. §119(e) based on U.S. Prov. App. No. 60/314,381, filed Aug. 24, 2001, and is a continuation-in-part of U.S. application Ser. No. 09/899,059, filed Jul. 6, 2001 (now U.S. Pat. No. 7,597,886, issued Oct. 6, 2009). U.S. application Ser. No. 11/837,082 is also a continuation-in-part of U.S. application Ser. No. 09/899,059, filed Jul. 6, 2001, which claims benefit under 35 U.S.C. §119(e) based on U.S. Prov. App. Nos. 60/278,449, filed Mar. 26, 2001, and 60/216,879, filed Jul. 7, 2000; U.S. application Ser. No. 09/899,059 is also a continuation-in-part of Int'l. App. No. PCT/US00/11689, filed Apr. 28, 2000, which claims benefit under 35 U.S.C. §119(e) based on U.S. Prov. App. Nos. 60/180,908, filed Feb. 8, 2000, 60/134,067, filed May 13, 1999, 60/132,227, filed May 3, 1999, and 60/131,963, filed Apr. 30, 1999; U.S. application Ser. No. 09/899,059 is also a continuation-in-part of U.S. patent application Ser. No. 09/246,129, filed Feb. 8, 1999 (now U.S. Pat. No. 6,824,767, issued Nov. 30, 2004), which claims benefit under 35 U.S.C. §119(e) based on U.S. Prov. App. No. 60/074,047, filed Feb. 9, 1998, and is a continuation-in-part of U.S. application Ser. No. 09/131,237, filed Aug. 7, 1998 (now U.S. Pat. No. 6,599,719, issued Jul. 29, 2003), which claims benefit under 35 U.S.C. §119(e) based on U.S. Prov. App. No. 60/074,047, filed Feb. 9, 1998; U.S. application Ser. No. 09/899,059 is also a continuation-in-part of U.S. application Ser. No. 09/131,237, filed Aug. 7, 1998, which is a continuation-in-part of U.S. application Ser. No. 09/005,020, filed Jan. 9, 1998, now abandoned, which is a continuation-in-part of U.S. application Ser. No. 08/461,246, filed Jun. 5, 1995, now abandoned, which is a continuation-in-part of Int'l. App. No. PCT/US94/12880 filed Nov. 7, 1994. The contents of each of the above-identified applications and their associated sequence listings are hereby incorporated by reference in their entireties.

STATEMENT UNDER 37 C.F.R. §1.77(b)(5)

This application refers to a "Sequence Listing" listed below, which is provided as a text document. The document is entitled "PF141P8C1D1-SequenceListing.txt" (49,739 bytes, created Sep. 8, 2010), and is hereby incorporated by reference herein in its entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been identified as a new member of the tumor necrosis factor family and is hereinafter referred to as "TNF-gamma-alpha". The invention also relates to a protein encoded by a splice variant of the gene encoding TNF-gamma-alpha which is hereinafter referred to as "TNF-gamma-beta". The invention also relates to inhibiting the action of such polypeptides.

BACKGROUND OF THE INVENTION

Human tumor necrosis factors-alpha (TNF-alpha) and beta (TNF-beta or lymphotoxin) are related members of a broad class of polypeptide mediators, which includes the interferons, interleukins and growth factors, collectively called cytokines (Beutler, B. and Cerami, A., Annu. Rev. Immunol., 7:625-655 (1989)).

Tumor necrosis factor (TNF-alpha and TNF-beta) was originally discovered as a result of its anti-tumor activity, however, now it is recognized as a pleiotropic cytokine playing important roles in immune regulation and inflammation. To date, there are eight known members of the TNF-related cytokine family, TNF-alpha, TNF-beta (lymphotoxin (LT)-alpha), LT-beta, and ligands for the Fas, CD30, CD27, CD40 and 4-1BB receptors. These proteins have conserved C-terminal sequences and variable N-terminal sequences which are often used as membrane anchors, with the exception of TNF-beta. Both TNF-alpha and TNF-beta function as homotrimers when they bind to TNF receptors.

TNF is produced by a number of cell types, including monocytes, fibroblasts, T-cells, natural killer (NK) cells and predominately by activated machrophages. TNF-alpha has been reported to have a role in the rapid necrosis of tumors, immunostimulation, autoimmune disease, graft rejection, resistance to parasites, producing an anti-viral response, septic shock, growth regulation, vascular endothelium effects and metabolic effects. TNF-alpha also triggers endothelial cells to secrete various factors, including PAI-1, IL-1, GM-CSF and IL-6 to promote cell proliferation. In addition, TNF-alpha up-regulates various cell adhesion molecules such as E-Selectin, ICAM-1 and VCAM-1. TNF-alpha and Fas ligand have also been shown to induce programmed cell death.

The first step in the induction of the various cellular responses mediated by TNF or LT is their binding to specific cell surface receptors. Two distinct TNF receptors of approximately 55-KDa (TNF-R1) and 75-KDa (TNF-R2) have been identified (Hohman, H. P. et al., J. Biol. Chem., 264:14927-14934 (1989)), and human and mouse cDNAs corresponding to both receptor types have been isolated and characterized (Loetscher, H. et al., Cell, 61:351 (1990)). Both TNF-Rs share the typical structure of cell surface receptors including extracellular, transmembrane and intracellular regions.

The endothelium, which under physiological conditions is mostly a quiescent tissue (Denekamp, J. Cancer Metas. Rev. 9:267-282 (1990)), plays an essential role in the maintenance of vascular homeostasis and permeability. Endothelial cells are actively involved in inflammation, cell adhesion, coagulation, thrombosis, fibrinolysis, and angiogenesis. During angiogenesis, endothelial cells proliferate, invade into stroma, migrate toward the source of an angiogenesis stimulus, such as cancer cells, interact with perivascular cells and stromal cells, and eventually, form capillary vessels linking the tumor tissue to the circulatory system (Folkman, J. Nature Med. 1:27-31 (1995)). Although the complex mechanism that regulates angiogenesis is yet to be fully understood, it is becoming clear that the initiation or termination of the process is a result of a balance between positive and negative factors.

A number of angiogenic factors, often markedly upregulated in tumor tissues, have been described. These include several members of the fibroblast growth factor (FGF) family, such as FGF-1, FGF-2, and those of the vascular endothelial cell growth factor (VEGF) family and the receptors for all of these molecules (Gimenez-Gallego, G, et al., Science 230: 1385-1388 (1985); Schweigerer, L., et al., Nature 325:257-259 (1987); Leung, D. W., et al., Science 246:1306-1309 (1989); Burrus, L. W. and Olwin, B. B. J. Biol. Chem. 264: 18647-18653 (1989); Wennstrom, S., et al., Growth Factors 4:197-208 (1991); Terman, B. I., et al., Biochem. Biophys.

Res. Comm. 187:1579-1586 (1992); de Vries, C., et al., *Science* 255:989-991 (1992)). Likewise, several inhibitors of angiogenesis have also been reported, including thrombospondin, angiostatin, endostatin, and platelet factor-4 (Good, D. J., et al., *Proc. Natl. Acad. Sci. USA* 87:6623-6628 (1990); O'Reilly, M. S., et al., *Cell* 79:315-328 (1994); O'Reilly, M. S., et al., *Cell* 88:277-285 (1997); Maione, T. E., et al., *Science* 247:77-79 (1990)). It is apparent that normal angiogenesis is promptly activated when needed, and swiftly terminated when no longer required. However, pathological angiogenesis, once initiated, is often prolonged and often difficult to stop. This may indicate that a negative regulatory mechanism normally functioning is missing or suppressed in a pathological angiogenic process. It is conceivable that endothelial cells may produce autocrine factors to suppress an angiogenesis process or maintain the quiescence of a mature vasculature.

The polypeptide of the present invention has been identified as a novel member of the TNF family based on structural, amino acid sequence homology, and functional similarities, for example, TNF-gamma is a pro-inflammatory protein. Further, the TNF-gamma polypeptide of the present invention is a negative regulator of angiogenesis and of endothelial cell growth. There is a need for polypeptides that function in this manner, since disturbances of such regulation may be involved in disorders relating to angiogenesis, hemostasis, tumor metastasis, cellular migration, and cancers of many systems. Therefore, there is a need for identification and characterization of such human polypeptides which can play a role in detecting, preventing, ameliorating or correcting such disorders.

SUMMARY OF THE INVENTION

In accordance with one aspect of the present invention, there is provided a novel mature polypeptide which is TNF-gamma-alpha, and a novel mature polypeptide which is TNF-gamma-beta, as well as biologically active and diagnostically or therapeutically useful fragments, analogs and derivatives thereof.

In accordance with another aspect of the present invention, there are provided isolated nucleic acid molecules encoding human TNF-gamma-alpha or TNF-gamma-beta, including mRNAs, DNAs, cDNAs, genomic DNAs as well as analogs and biologically active and diagnostically or therapeutically useful fragments and derivatives thereof.

The present invention provides isolated nucleic acid molecules comprising a polynucleotide encoding at least a portion of the TNF-gamma-alpha polypeptide having the complete amino acid sequence shown in SEQ ID NO:2 or the complete amino acid sequence encoded by the cDNA clone HUVEO91 deposited as plasmid DNA as ATCC™ Deposit Number 75927 at the American Type Culture Collection ("ATCC™") on Oct. 26, 1994. The ATCC™ is located at 10801 University Boulevard, Manassas, Va. 20110-2209, USA. The nucleotide sequence determined by sequencing the deposited TNF-gamma-alpha clone, which is shown in FIGS. 1A-1C (SEQ ID NO:1), contains an open reading frame encoding a complete polypeptide of 174 amino acid residues, including an initiation codon encoding an N-terminal methionine at nucleotide positions 783-785, and a predicted molecular weight of about 20,132 Da.

The present invention also provides isolated nucleic acid molecules comprising a polynucleotide encoding at least a portion of the TNF-gamma-beta polypeptide having the complete amino acid sequence shown in SEQ ID NO:20 or the complete amino acid sequence encoded by the cDNA clone HEMCZ56 deposited as plasmid DNA as ATCC™ Deposit Number 203055 on Jul. 9, 1998. The nucleotide sequence determined by sequencing the deposited TNF-gamma-beta clone, which is shown in FIGS. 20A and B (SEQ ID NO:20), contains an open reading frame encoding a complete polypeptide of 251 amino acid residues, including an initiation codon encoding an N-terminal methionine at nucleotide positions 1-3, and a predicted molecular weight of about 28,089 Da.

Thus, in one embodiment the invention provides an isolated nucleic acid molecule comprising a polynucleotide having a nucleotide sequence selected from the group consisting of: (a) a nucleotide sequence encoding the TNF-gamma-alpha polypeptide having the complete amino acid sequence in SEQ ID NO:2 (i.e., positions −27 to 147 of SEQ ID NO:2, (b) a nucleotide sequence encoding the TNF-gamma-alpha polypeptide having the complete amino acid sequence in SEQ ID NO:2 excepting the N-terminal methionine (i.e., positions −26 to 147 of SEQ ID NO:2); (c) a nucleotide sequence encoding the mature TNF-gamma-alpha polypeptide having the amino acid sequence in SEQ ID NO:2 shown as positions 1 to 147 of SEQ ID NO:2; (d) a nucleotide sequence encoding the TNF-gamma-alpha polypeptide having the complete amino acid sequence encoded by the cDNA clone HUVEO91 contained in ATCC™ Deposit No. 75927; (e) a nucleotide sequence encoding the TNF-gamma-alpha polypeptide having the complete amino acid sequence excepting the N-terminal methionine encoded by the cDNA clone HUVEO91 contained in ATCC™ Deposit No. 75927; (f) a nucleotide sequence encoding the mature TNF-gamma-alpha polypeptide having the amino acid sequence encoded by the cDNA clone HUVEO91 contained in ATCC™ Deposit No. 75927; and (g) a nucleotide sequence complementary to any of the nucleotide sequences in (a), (b), (c), (d), (e) or (f), above.

In another embodiment, the invention provides an isolated nucleic acid molecule comprising a polynucleotide having a nucleotide sequence selected from the group consisting of (a) a nucleotide sequence encoding the TNF-gamma-beta polypeptide having the complete amino acid sequence in SEQ ID NO:20 (i.e., positions 1 to 251 of SEQ ID NO:20); (b) a nucleotide sequence encoding the TNF-gamma-beta polypeptide having the complete amino acid sequence in SEQ ID NO:20 excepting the N-terminal methionine (i.e., positions 2 to 251 of SEQ ID NO:20); (c) a nucleotide sequence encoding the mature TNF-gamma-beta polypeptide having the amino acid sequence in SEQ ID NO:20 shown as positions 60 to 251 of SEQ ID NO:20; (d) a nucleotide sequence encoding the mature TNF-gamma-beta polypeptide having the amino acid sequence in SEQ ID NO:20 shown as positions 62 to 251 of SEQ ID NO:20; (e) a nucleotide sequence encoding the mature TNF-gamma-beta polypeptide having the amino acid sequence in SEQ ID NO:20 shown as positions 72 to 251 of SEQ ID NO:20; (f) a nucleotide sequence encoding the TNF-gamma-beta polypeptide having the complete amino acid encoded by the cDNA clone HEMCZ56 contained in ATCC™ Deposit No. 203055; (g) a nucleotide sequence encoding the TNF-gamma-beta polypeptide having the complete amino acid sequence excepting the N-terminal methionine encoded by the cDNA clone HEMCZ56 contained in ATCC™ Deposit No. 203055; (h) a nucleotide sequence encoding the mature TNF-gamma-beta polypeptide having the amino acid sequence encoded by the cDNA clone HEMCZ56 contained in ATCC™ Deposit No. 203055; and (i) a nucleotide sequence complementary to any of the nucleotide sequences in (a), (b), (c), (d), (e), (f), (g) or (h), above.

In accordance with all aspects of the invention, the term "TNF-gamma" refers to TNF-gamma-alpha and/or TNF-gamma-beta.

Further embodiments of the invention include isolated nucleic acid molecules that comprise a polynucleotide having a nucleotide sequence at least 80%, 85% or 90% identical, and more preferably at least 92%, 94%, 95%, 96%, 97%, 98% or 99% identical, to any of the TNF-gamma-alpha or TNF-gamma-beta nucleotide sequences in (a), (b), (c), (d), (e), (f), (g), (h) or (i), above, or a polynucleotide which hybridizes under stringent hybridization conditions to a TNF-gamma-alpha or TNF-gamma-beta polynucleotide in (a), (b), (c), (d), (e), (f), (g) or (h), above, a fragment thereof (such as, for example, fragments described herein), or the complementary strand thereto. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion (i.e., a fragment) of a TNF-gamma-alpha or TNF-gamma-beta polypeptide having an amino acid sequence in (a), (b), (c), (d), (e), (f), (g) or (h), above. A further embodiment of the invention relates to an isolated nucleic acid molecule comprising a polynucleotide which encodes the amino acid sequence of a TNF-gamma polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a TNF-gamma polypeptide to have an amino acid sequence which contains not more than 10, 9, 8, 7, 6, 5, 4, 3, 2 or 1 amino acid substitutions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of TNF-gamma polypeptides or peptides by recombinant techniques.

In accordance with a further aspect of the present invention, there is provided a process for producing such polypeptide by recombinant techniques comprising culturing recombinant prokaryotic and/or eukaryotic host cells, containing a human TNF-gamma nucleic acid sequence, under conditions promoting expression of said protein and subsequent recovery of said protein.

The invention further provides an isolated TNF-gamma polypeptide comprising an amino acid sequence selected from the group consisting of: (a) the amino acid sequence of the full-length TNF-gamma-alpha polypeptide having the complete amino acid sequence shown in SEQ ID NO:2 (i.e., positions −27 to 147 of SEQ ID NO:2); (b) the amino acid sequence of the full-length TNF-gamma-alpha polypeptide having the complete amino acid sequence shown in SEQ ID NO:2 excepting the N-terminal methionine (i.e., positions −26 to 147 of SEQ ID NO:2); (c) the amino acid sequence of the predicted mature TNF-gamma-alpha polypeptide having the amino acid sequence at positions 1-147 in SEQ ID NO:2; (d) the complete amino acid sequence encoded by the cDNA clone HUVEO91 contained in the ATCC™ Deposit No. 75927; (e) the complete amino acid sequence excepting the N-terminal methionine encoded by the cDNA clone HUVEO91 contained in the ATCC™ Deposit No. 75927; (f) the complete amino acid sequence of the predicted mature TNF-gamma polypeptide encoded by the cDNA clone HUVEO91 contained in the ATCC™ Deposit No. 75927; and (g) fragments of the polypeptide of (a), (b), (c), (d), (e), or (f). The polypeptides of the present invention also include polypeptides having an amino acid sequence at least 80% or 85% identical, more preferably at least 90%, 92% or 94% identical, and still more preferably 95%, 96%, 97%, 98% or 99% identical to those described in (a), (b), (c), (d), (e) (f), or (g) above, as well as polypeptides having an amino acid sequence with at least 90% similarity, and more preferably at least 95% similarity, to those above. Additional embodiments of the invention relates to a polypeptide which comprises the amino acid sequence of an epitope-bearing portion of a TNF-gamma-alpha polypeptide having an amino acid sequence described in (a), (b), (c), (d), (e), (f), or (g) above. Peptides or polypeptides having the amino acid sequence of an epitope-bearing portion of a TNF-gamma-alpha polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

The invention further provides an isolated TNF-gamma polypeptide comprising an amino acid sequence selected from the group consisting of: (a) the amino acid sequence of the full-length TNF-gamma-beta polypeptide having the complete amino acid sequence shown in SEQ ID NO:20 (i.e., positions 1 to 251 of SEQ ID NO:20); (b) the amino acid sequence of the full-length TNF-gamma-beta polypeptide having the complete amino acid sequence shown in SEQ ID NO:20 excepting the N-terminal methionine (i.e., positions 2 to 251 of SEQ ID NO:20); (c) the amino acid sequence of the predicted mature TNF-gamma-beta polypeptide having the amino acid sequence at positions 60-251 in SEQ ID NO:20; (d) the amino acid sequence of the predicted mature TNF-gamma-beta polypeptide having the amino acid sequence at positions 62-251 in SEQ ID NO:20; (e) the amino acid sequence of the predicted mature TNF-gamma-beta polypeptide having the amino acid sequence at positions 72-251 in SEQ ID NO:20; (f) the complete amino acid sequence encoded by the cDNA clone HEMCZ56 contained in the ATCC™ Deposit No. 203055; (g) the complete amino acid sequence excepting the N-terminal methionine encoded by the cDNA clone HEMCZ56 contained in the ATCC™ Deposit No. 203055; (h) the complete amino acid sequence of the predicted mature TNF-gamma polypeptide encoded by the cDNA clone contained in the ATCC™ Deposit No. 203055; and (i) fragments of the polypeptide of (a), (b), (c), (d), (e), (f), (g) or (h), above. The polypeptides of the present invention also include polypeptides having an amino acid sequence at least 80% or 85% identical, more preferably at least 90%, 92% or 94% identical, and still more preferably 95%, 96%, 97%, 98% or 99% identical to those described in (a), (b), (c), (d), (e) (f), (g) or (h), above, as well as polypeptides having an amino acid sequence with at least 90% similarity, and more preferably at least 95% similarity, to those above. Additional embodiments of the invention relates to a polypeptide which comprises the amino acid sequence of an epitope-bearing portion of a TNF-gamma-beta polypeptide having an amino acid sequence described in (a), (b), (c), (d), (e), (f), (g) or (h), above. Peptides or polypeptides having the amino acid sequence of an epitope-bearing portion of a TNF-gamma-beta polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises the amino acid sequence of a TNF-gamma polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a TNF-gamma polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A and 1B, FIGS. 20A and B, or fragments thereof (e.g., the extracellular domain and/or other fragments described herein), is 1-5, 5-10, 5-25, 5-50, 10-50 or 50-150, conservative amino acid substitutions are preferable.

In another embodiment, the invention provides an isolated antibody that binds specifically to a TNF-gamma polypeptide having an amino acid sequence described above. The invention further provides methods for isolating antibodies that bind specifically to a TNF-gamma polypeptide having an amino acid sequence as described herein. Such antibodies are useful diagnostically or therapeutically as described below. In preferred embodiments, neutralizing or antagonistic anti-TNF-gamma-alpha and/or TNF-gamma-beta antibodies may be used to treat, prevent or diagnose, inflammatory diseases (e.g., inflammatory bowel disease, encephalitis) and immune disorders, especially T-cell mediated immune disorders, including but not limited to autoimmune diseases (e.g., systemic lupus erythematosus, arthritis, multiple sclerosis).

In accordance with yet a further aspect of the present invention, there is provided a process for utilizing polynucleotides and/or polypeptides of the invention as well as agonists and antagonists thereof, and for therapeutic purposes, which include, but are not limited to, wound healing, to inhibit tumor proliferation, to provide resistance to parasites, bacteria and viruses, to induce inflammatory activities, to induce proliferation of endothelial cells and certain hematopoietic cells, to treat, prevent, diagnose, and/or detect restenosis and to prevent certain autoimmune diseases.

In accordance with yet a further aspect of the present invention, there are also provided nucleic acid probes comprising nucleic acid molecules of sufficient length to specifically hybridize to human TNF-gamma sequences.

In accordance with another aspect of the present invention, there are provided TNF-gamma agonists which mimic TNF-gamma and binds to the TNF-gamma receptors to elicit TNF-gamma type responses.

In accordance with yet another aspect of the present invention, there are provided antagonists to such polypeptides, which may be used to inhibit the action of such polypeptides, for example, to prevent septic shock, inflammation, cerebral malaria, activation of the HIV virus, graft rejection, bone resorption and cachexia.

In accordance with still another aspect of the present invention, there are provided diagnostic assays for detecting diseases related to the under-expression and over-expression of the TNF-gamma polypeptide and nucleic acid sequences encoding such polypeptide.

In a further aspect of the invention, TNF-gamma may be used to treat, prevent, diagnose, and/or detect rheumatoid arthritis (RA) by inhibiting the increase in angiogensis or the increase in endothelial cell proliferation required to sustain an invading pannus in bone and cartilage as is often observed in RA.

In a further aspect of the invention, TNF-gamma may be used to treat, prevent, diagnose, and/or detect diseases or conditions including, but not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In yet another aspect, the TNF-gamma may bind to a cell surface protein which also functions as a viral receptor or coreceptor. Thus, TNF-gamma, or agonists or antagonists thereof, may be used to regulate viral infectivity at the level of viral binding or interaction with the TNF-gamma receptor or coreceptor or during the process of viral internalization or entry into the cell.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A-1C illustrate the cDNA (SEQ ID NO:1) and corresponding deduced amino acid sequence (SEQ ID NO:2) of the polypeptide of TNF-gamma-alpha of the present invention. The initial 27 amino acids (underlined) are the putative leader sequence. The standard one-letter abbreviations for amino acids are used. Potential asparagine-linked glycosylation sites are marked in FIGS. 1A and 1B with a bolded asparagine symbol (N) in the TNF-gamma-alpha amino acid sequence and a bolded pound sign (#) above the first nucleotide encoding that asparagine residue in the TNF-gamma-alpha nucleotide sequence. Potential N-linked glycosylation sequences are found at the following locations in the TNF-gamma-alpha amino acid sequence: N-29 through N-32 (N-29, Y-30, T-31, N-32) and N-125 through D-128 (N-125, V-126, S-127, D-128). Potential Protein Kinase C (PKC) phosphorylation sites are also marked in FIGS. 1A and 1B with a bolded threonine symbol (T) in the TNF-gamma-alpha amino acid sequence and an asterisk (*) above the first nucleotide encoding that threonine residue in the TNF-gamma-alpha nucleotide sequence. Potential PKC phosphorylation sequences are found at the following locations in the TNF-gamma-alpha amino acid sequence: T-32 through K-34 (T-32, N-33, K-34) and T-50 through R-52 (T-50, F-51, R-52). Potential Casein Kinase II (CK2) phosphorylation sites are also marked in FIGS. 1A and 1B with a bolded serine or threonine symbol (S or T) in the TNF-gamma-alpha amino acid sequence and an asterisk (*) above the first nucleotide encoding the appropriate serine or threonine residue in the TNF-gamma-alpha nucleotide sequence. Potential CK2 phosphorylation sequences are found at the following locations in the TNF-gamma-alpha amino acid sequence: S-83 through E-86 (S-83, Y-84, P-85, E-86); S-96 through E-99 (S-96, V-97, C-98, E-99); S-115 through E-118 (S-115, L-116, Q-117, E-118); S-130 through D-133 (S-130, L-I31, V-132, D-133); and T-135 through D-138 (T-135, K-136, E-137, D-138). Potential myristylation sites are also marked in FIGS. 1A and 1B with a double underline in the TNF-gamma-alpha amino acid sequence. Potential myristylation sequences are found at the following locations in the TNF-gamma-alpha amino acid sequence: G-20 through K-25 (G-20, L-21, A-22, F-23, T-24, K-25) and G-111 through L-116 (G-111, A-112, M-113, F-114, S-115, L-116).

FIGS. 2A, 2B, and 2C illustrate an amino acid sequence alignment between TNF-gamma-alpha (SEQ ID NO:2) and other members of the TNF family including human TNF-alpha (GenBank No. Z15026; SEQ ID NO:3), human TNF-beta (GenBank No. Z15026; SEQ ID NO:4), human lymphotoxin-beta (LTbeta; GenBank No. L11016; SEQ ID NO:5), and rat Fas Ligand (FASL: GenBank No. U034070; SEQ ID NO:6). TNF-gamma contains the conserved amino acid residues of the TNF family as shown by the boxed and shaded areas. The aligned molecules are presented in their entirety as FIGS. 2A, 2B, and 2C.

FIG. 3A shows a distinct band. Other lanes seem to show strong hybridization, however, these are actually non-specific smears.

FIG. 4 illustrates the relative expression of TNF-gamma in proliferating or quiescent endothelial cells. The TNF-gamma mRNA levels in cultured HUVEC cells were determined by Northern blotting analysis. Identical amounts of total RNA (15 µg) were loaded on each lane, as indicated by the intensity of b-actin. The signal which corresponds to TNF-gamma is designated "VEGI". Total RNA was prepared at the indicated time point (days post-seeding). The number of cells in each culture flask was determined simultaneously. The experiment was carried out in duplicate. Cells were seeded at 125,00 cells per flask (T-25).

FIG. 6 is a photograph of a gel showing the relative purity and mobility of baculovirus-expressed TNF-gamma. The expression and purification of TNF-gamma using the baculovirus system is described in Example 2.

FIGS. 18A, 18B, 18C, and 18D show an alignment of the nucleotide sequences of TNF-gamma-alpha (SEQ ID NO:1) and TNF-gamma-beta (SEQ ID NO:19) constructed by using the computer program BESTFIT set at default parameters.

FIG. 19 shows an alignment of the amino acid sequences of TNF-gamma-alpha (SEQ ID NO:2) and TNF-gamma-beta (SEQ ID NO:20) constructed using the default parameters of the computer program BESTFIT.

FIGS. 20A and 20B illustrate the cDNA (SEQ ID NO:19) and corresponding deduced amino acid sequence (SEQ ID NO:20) of the polypeptide of the TNF-gamma-beta of the present invention. The standard one-letter abbreviations for amino acids are used. In one embodiment, amino acids methionine-1 to tryptophan-35 comprise the predicted intracellular domain. Amino acid residues alanine-36 through alanine-61 (underlined) comprise the putative transmembrane sequence. Amino acid residues glutamine-62 through leucine-251 (underlined) comprise the putative extracellular domain. In another embodiment, amino acids methionine-1 to tryptophan-35 comprise the predicted intracellular domain; amino acid residues alanine-36 through leucine-59 comprise the putative transmembrane sequence; and amino acid residues arginine-60 through leucine-251 comprise the putative extracellular domain. Potential asparagine-linked glycosylation sites are marked in FIGS. 20A and B with a bolded asparagine symbol (N) in the TNF-gamma-beta amino acid sequence and a bolded pound sign (#) above the first nucleotide encoding that asparagine residue in the TNF-gamma-alpha nucleotide sequence. Potential N-linked glycosylation sequences are found at the following locations in the TNF-gamma-beta amino acid sequence: N-133 through N-136 (N-133, Y-134, T-135, N-136) and N-229 through D-232 (N-229, V-230, S-231, D-232). Potential Protein Kinase C (PKC) phosphorylation sites are also marked in FIGS. 20A and B with a bolded serine or threonine symbol (S or T) in the TNF-gamma-beta amino acid sequence and an asterisk (*) above the first nucleotide encoding that threonine residue in the TNF-gamma-beta nucleotide sequence. Potential PKC phosphorylation sequences are found at the following locations in the TNF-gamma-beta amino acid sequence: S-23 through R-25 (S-23, C-24, R-25); S-32 through R-34 (S-32, A-33, R-34); T-135 through K-137 (T-135, N-136, K-137); and T-154 through R-156 (T-154, F-155, R-156). Potential Casein Kinase II (CK2) phosphorylation sites are also marked in FIGS. 20A and B with a bolded serine or threonine symbol (S or T) in the TNF-gamma-beta amino acid sequence and an asterisk (*) above the first nucleotide encoding the appropriate serine or threonine residue in the TNF-gamma-beta nucleotide sequence. Potential CK2 phosphorylation sequences are found at the following locations in the TNF-gamma-beta amino acid sequence: S-8 through E-11 (S-8, F-9, G-10, E-11); S-187 through E-190 (S-187, Y-188, P-189, E-190); S-200 through E-203 (S-200, V-201, C-202, E-203); S-219 through E-222 (S-219, L-220, Q-221, E-222); S-234 through D-237 (S-234, L-235, V-236, D-237); and T-239 through D-242 (T-239, K-240, E-241, D-242). Potential myristylation sites are also marked in FIGS. 20A and B with a double underline in the TNF-gamma-beta amino acid sequence. Potential myristylation sequences are found at the following locations in the TNF-gamma-beta amino acid sequence: G-6 through E-11 (G-6, L-7, S-8, F-9, G-10, E-11); G-124 through G-129 (G-124, L-125, A-126, F-127, T-128, K-129); and G-215 through L-220 (G-215, A-216, M-217, F-218, S-219, L-220).

DETAILED DESCRIPTION

Figure 2A:
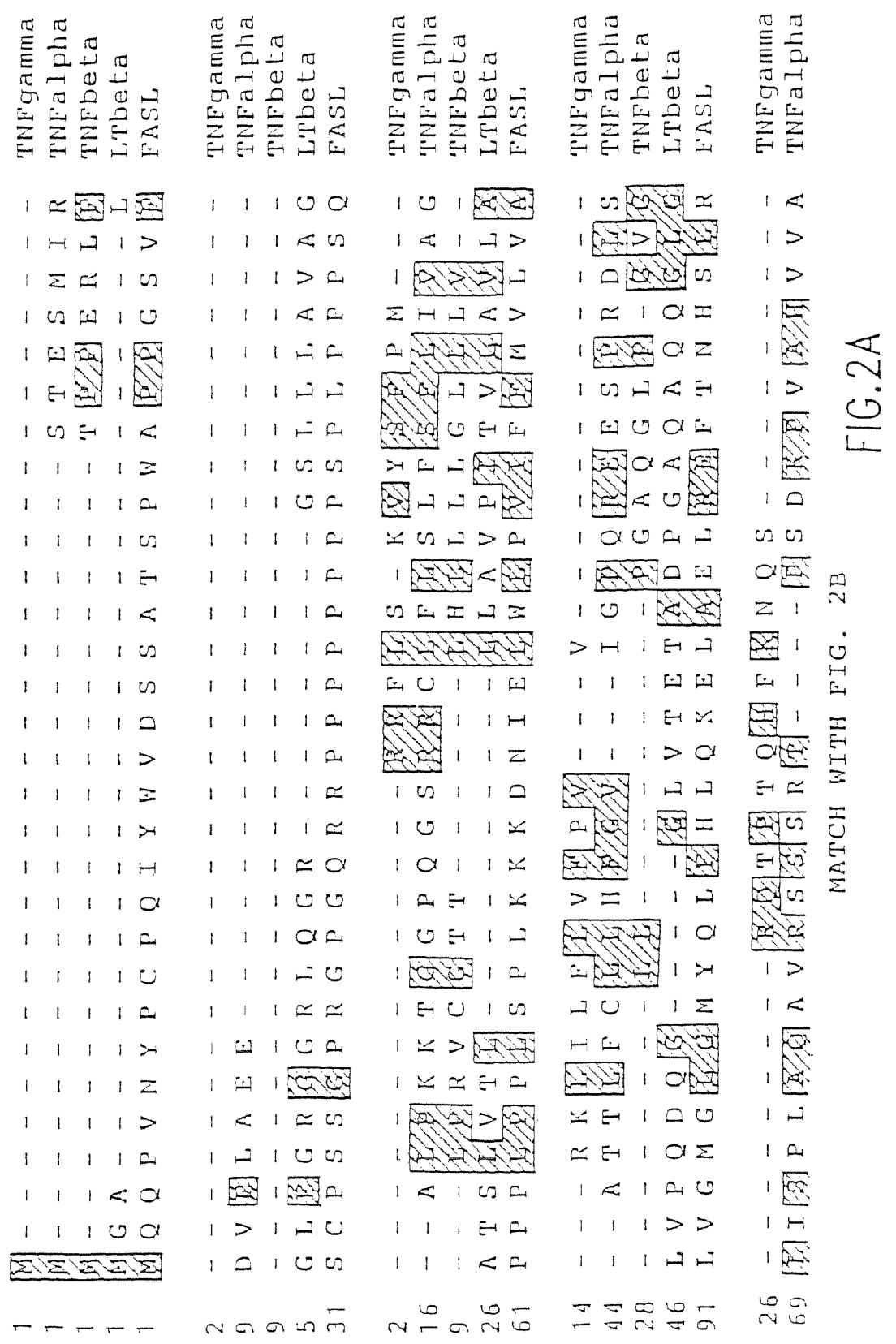
Figure 2B:
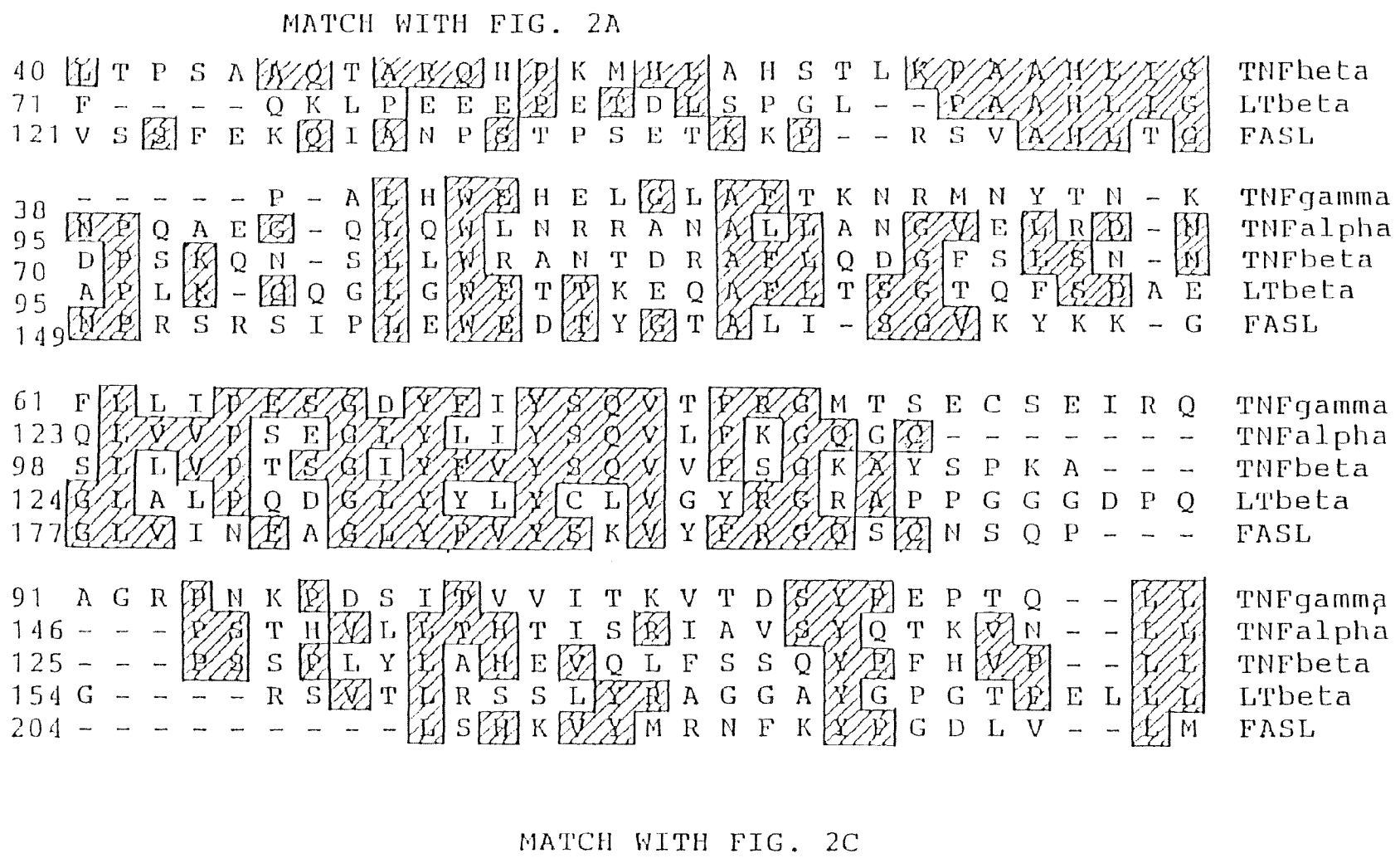
Figure 3A:
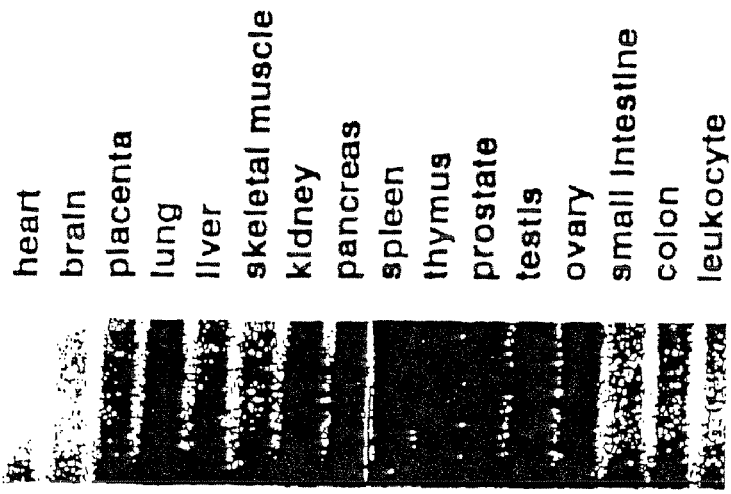
FIG. 3A is an RNA blot analysis showing the human tissues where TNF-gamma is expressed. RNA from the tissues indicated were probed with labeled TNF-gamma cDNA. TNF-gamma-alpha mRNA exists predominantly in the kidney since

The present invention provides isolated nucleic acid molecules comprising a polynucleotide encoding a TNF-gamma-alpha polypeptide having the amino acid sequence shown in FIGS. 1A and B (SEQ ID NO:2), which was determined by sequencing a cloned cDNA (HUVE091). As shown in FIGS. 2A-2C, the TNF-gamma-alpha polypeptide of the present invention shares sequence homology with human TNF-alpha (SEQ ID NO:3), TNF-beta (SEQ ID NO:4), human lymphotoxin-beta (SEQ ID NO:5) and FAS ligand (SEQ ID NO:6). The TNF-gamma-alpha of the invention functions at least in the inhibition of angiogenesis, as an anti-tumor cytokine-like molecule, as a treatment for arthritis by the inhibition of angiogenesis and/or endothelial cell proliferation associated with invading pannus in bone and cartilage, as an inducer of NF-kappaB and c-Jun kinase (JNK), an inducer of cell adhesion, and as an inducer of apoptosis (See Examples, particularly Examples 12-15). The nucleotide sequence shown in SEQ ID NO:1 was obtained by sequencing a cDNA clone (HUVE091), which was deposited on Oct. 26, 1994 at the American Type Culture Collection, 10801 University Boulevard, Manassas, Va. 20110-2209, and given accession number 75927. The deposited plasmid is contained in pBluescript SK(−) plasmid (Stratagene, La Jolla, Calif.). Further characterization of the protein encoded by clone HUVEO91 is presented in copending U.S. Provisional Application Ser. No. 60/074,047, filed Feb. 9, 1998; the entire disclosure of which is hereby incorporated by reference.

The present invention also provides isolated nucleic acid molecules comprising a polynucleotide (SEQ ID NO:19) encoding a TNF-gamma-beta polypeptide having the amino acid sequence shown in FIGS. 20A and B (SEQ ID NO:20), which was determined by sequencing a cloned cDNA (HEMCZ56). The TNF-gamma-beta polypeptide is a splice variant of the TNF-gamma-alpha polypeptide disclosed herein. The nucleotide sequence shown in SEQ ID NO:19 was obtained by sequencing a cDNA clone (HEMCZ56), which was deposited on Jul. 9, 1998 at the American Type Culture Collection, 10801 University Boulevard, Manassas, Va. 20110-2209, and given accession number 203055. The deposited plasmid is contained in pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A-1C (SEQ ID NO:1), or the nucleotide sequence in FIGS. 20A and B (SEQ ID NO:19) a nucleic acid molecule (i.e., polynucleotide) of the present invention encoding a TNF-gamma-alpha or TNF-gamma-beta polypeptide may be obtained using standard cloning and screening procedures, such as, for example, those for cloning cDNAs using mRNA as the starting material. For example, polynucleotides encoding TNF-gamma-alpha polypeptides may routinely be obtained from any cell or tissue source that expresses TNF-gamma-alpha, such as, for example, human kidney and umbilical vein endothelial cells. Illustrative of the invention, the nucleic acid molecule described in FIGS. 1A-1C (SEQ ID NO:1) was discovered in a cDNA library derived from human umbilical vein endothelial cells. The cDNA clone corresponding to TNF-gamma-alpha (clone HUVEO91) contains an open reading frame encoding a protein of 174 amino acid residues of which approximately the first 27 amino acids residues are the putative leader sequence such that the mature protein comprises 147 amino acids. The protein exhibits the highest degree of homology at the C-terminus to Rabbit TNF-alpha (Ito, H., et al., DNA 5:157-165 (1986); GenBank Accession No. M12846; SEQ ID NO:7) with 38% identity and 58% similarity over a 111 amino acid stretch. Sequences conserved throughout the members of the TNF family are also conserved in TNF-gamma (see FIGS. 2A-2C). The shaded letters indicate conserved amino acid residues. The TNF-gamma mRNA is specifically expressed in human umbilical vein endothelial cells as shown in the RNA blot analysis of FIG. 3B.

Further, polynucleotides encoding a TNF-gamma-beta polypeptide may routinely be obtained from induced and resting endothelial cells, umbilical vein, tonsils, and several other cell and tissue types. Illustrative of the invention, the nucleic acid molecules described in FIGS. 20A and B (SEQ ID NO:19) was discovered in a cDNA library derived from induced endothelial cells. The cDNA clone corresponding to TNF-gamma-beta (HEMCZ56) contains an open reading frame encoding a protein of 251 amino acid residues of which approximately the first 35 amino acid residues are the putative intracellular domain and amino acids 36-61 are a putative transmembrane domain and amino acid residues 62-251 are a putative extracellular domain. In specific embodiments, the mature form of TNF-gamma-beta is amino acid residues 72-251 of the protein encoded by the cDNA clone HEMCZ56.

In another embodiment, the cDNA clone corresponding to TNF-gamma-beta (HEMCZ56) contains an open reading frame encoding a protein of 251 amino acid residues of which approximately the first 35 amino acid residues are the putative intracellular domain and amino acids 36-59 are a putative transmembrane domain and amino acid residues 60-251 are a putative extracellular domain.

In one embodiment, the polynucleotides of the invention comprise, or alternatively consist of, the sequence shown in SEQ ID NO:25. A polynucleotide comprising the nucleotide sequence provided as SEQ ID NO:25 was constructed by PCR amplification of the TNF-gamma-beta polynucleotide shown as SEQ ID NO:19 in a two-step process. The first PCR reaction used the following primer pair.

Nde 1-169 (Nde I site with 1-169 bp):

```
                                          (SEQ ID NO: 27)
5'-GGA ATT CCA TAT GCT GAA AGG TCA AGA ATT

CGC ACC GTC CCA CCA GCA GGT TT ACG CAC CGC

TGC GTG CAG ACG GTG ATA AGC CGC GTG CAC ACC

TGA CCG TTG TGC GCC AGA CCC CGA CCC AGC ACT

TCA AAA ACC AGT TCC CGG CTC TGC ACT GGG AGC

ACG AAC TGG GCC TGG CCT TCA-3'
```

151-329 BstXI (151-329 bp which contains BstXI site at 3'):

```
                                          (SEQ ID NO: 28)
5'-ATC ACC ACG GTG ATG GAG TCC GGC TTG TTC

GGA CGG CCT GCC TGA CGG ATT TCG GAG CAC TCA

GAG GTC ATA CCA CGG AAG GTC ACC TGG GAG TAG
```

-continued

```
ATG AAG TAG TCA CCA GAC TCC GGG ATC AGC AGG

AAT TTG TTG GTG TAG TTC ATG CGG TTC TTG GTG

AAG GCC AGG CCC AGT TC-3'
```

A second PCR reaction used the following primer pair:
BstXI 311-441 (311-441 bp which contains BstXI site at 5'):

```
                                    (SEQ ID NO: 29)
5'-ACT CCA TCA CCG TGG TGA TCA CCA AAG TGA

CCG ACT CTT ACC CGG AGC CGA CCC AGC TGC TGA

TGG GTA CCA AGT CTG TTT GCG AAG TTG GTT CCA

ACT GGT TCC AGC CGA TCT ACC TCG GTG CCA TGT

TC-3'
```

521-546 Xba (521-546 bp+Xba site):

```
                                    (SEQ ID NO: 30)
5'-CGC TCT AGA TTA TTA CAG CAG GAA GGC ACC

GAA GAA GGT TTT ATC TTC CTT GGT GTA ATC CAC

CAG AGA GAT GTC GGA CAC GTT CAC CAT CAG TTT

GTC GCC CTC TTG CAG GGA GAA CAT GGC ACC GAG

GTA GAT-3'
```

A codon-optimized form of TNF-gamma-beta resulted from restricting the PCR products with Nde I and BstXI (first pair), BstXI and Xba (second pair), and then ligating the restricted products together into precut pHE4b vector (Nde and Xba). The amino acid sequence resulting from the translation of SEQ ID NO:25 is provided as SEQ ID NO:26. Fragments, variants, and derivatives of the sequences provided as SEQ ID NO:25 and SEQ ID NO:26 are also encompassed by the invention. In certain embodiments, polynucleotides of the invention comprise, or alternatively consist of, a polynucleotide sequence at least 90%, 91%, 92%, 93%, 94%, 95%, 96%, 97%, 98% or 99% identical to the polynucleotide of SEQ ID NO:25. The present invention also encompasses the above polynucleotide sequences fused to a heterologous polynucleotide sequences as described herein and as are well known in the art. Polypeptides encoded by these nucleic acids and/or polynucleotide sequences are also encompassed by the invention.

The amino acid residues constituting the extracellular, transmembrane, and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

In accordance with an aspect of the present invention, there is provided an isolated nucleic acid (polynucleotide) which encodes for the mature polypeptide having the deduced amino acid sequence of FIGS. 1A and B (SEQ ID NO:2), or for the mature polypeptide encoded by the cDNA of the clone designated HUVEO91 deposited as ATCC™ Deposit No. 75927 on Oct. 26, 1994.

In addition, in accordance with another aspect of the present invention, there is provided an isolated nucleic acid (polynucleotide) which encodes for the mature polypeptide having the deduced amino acid sequence of FIGS. 20A and B (SEQ ID NO:20), or for the mature polypeptide encoded by the cDNA of the clone designated HEMCZ56 deposited as ATCC™ Deposit No. 203055 on Jul. 9, 1998.

By "isolated" nucleic acid molecule(s) or polynucleotide is intended a molecule, DNA or RNA, which has been removed form its native environment. For example, recombinant DNA molecules (polynucleotides) contained in a vector are considered isolated for the purposes of the present invention. Further examples of isolated DNA molecules (polynucleotides) include recombinant DNA molecules maintained in heterologous host cells or purified (partially or substantially) DNA molecules in solution. Isolated RNA molecules (polynucleotides) include in vivo or in vitro RNA transcripts of the DNA molecules (polynucleotides) of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread", as in a karyotype), or a genomic DNA preparation (either intact, or mechanically and/or enzymatically sheared) is not "isolated" for the purposes of this invention. Isolated nucleic acid molecules or polynucleotides according to the present invention further include such molecules produced synthetically.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

Isolated nucleic acid molecules of the present invention include the polynucleotide sequence depicted in FIGS. 1A-1C (SEQ ID NO:1) encoding the full-length and/or mature TNF-gamma-alpha polypeptide, the polynucleotide sequence depicted in FIGS. 20A and B (SEQ ID NO:19) encoding the full-length and/or mature TNF-gamma-beta polypeptide, the polynucleotide sequences contained in deposited clone (HUVE091) deposited as ATCC™ Deposit No. 75927 encoding the full-length and/or mature TNF-gamma-alpha polypeptide, the polynucleotide sequences contained in deposited clone (HEMCZ56) deposited as ATCC™ Deposit No. 203055 encoding the full-length and/or mature TNF-gamma-beta polypeptide, and polynucleotide sequences which comprise a sequence different from those described above, but which due to the degeneracy of the genetic code, encode the same full-length and/or mature polypeptide as the DNA of FIGS. 1A-1C, FIGS. 20A and B, or the deposited cDNAs. Of course, the genetic code is well known in the art. Thus, it would be routine for one skilled in the art to generate such degenerate variants.

The amino acid sequence of the complete TNF-gamma-alpha protein includes a leader sequence and a mature protein, as shown in FIGS. 1A and B (SEQ ID NO:2). The amino acid sequence of the complete TNF-gamma-beta protein includes a leader sequence and a mature protein, as shown in FIGS. 20A and B (SEQ ID NO:20). More in particular, the present invention provides nucleic acid molecules encoding a mature form of the TNF-gamma-alpha protein. The present invention also provides nucleic acid molecules encoding a mature form of the TNF-gamma-beta protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TNF-gamma-alpha polypeptide having the amino acid sequence encoded by the cDNA clone contained in ATCC™ Deposit No. 75927. The present invention also provides a nucleotide sequence encoding the mature TNF-gamma-beta polypeptide having the amino acid sequence encoded by the cDNA clone contained in ATCC™ Deposit No. 203055. By the "mature TNF-gamma-alpha polypeptide having the amino acid sequence encoded by the cDNA clone in ATCC™ Deposit No. 75927" is meant the mature form(s) of the TNF-gamma-alpha protein produced by expression in a mammalian cell (e.g., COS cells, as described below) of the complete open reading frame encoded by the human DNA sequence of the deposited clone. Likewise, by the "mature TNF-gamma-beta polypeptide having the amino acid sequence encoded by the cDNA clone in ATCC™ Deposit No. 203055" is meant the mature form(s) of the TNF-gamma-beta protein produced by expression in a mammalian cell (e.g., COS cells, as described below) of the complete open reading frame encoded by the human DNA sequence of the deposited clone.

The polynucleotide which encodes for the mature polypeptide of FIGS. 20A and B or for the mature polypeptide encoded by the deposited cDNA (HEMCZ56) may include, but is not limited to: only the coding sequence for the mature polypeptide; the coding sequence for the mature polypeptide and additional coding sequence such as a leader or secretory sequence or a transmembrane sequence or a proprotein sequence; the coding sequence for an extracellular domain; the coding sequence for the mature polypeptide (and optionally additional coding sequence) and non-coding sequence, such as introns or non-coding sequence 5' and/or 3' of the coding sequence for the mature polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments (i.e., portions), analogs and derivatives of the polypeptide having the deduced amino acid sequence of FIGS. 1A and B, FIGS. 20A and B, and the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A and B, or the mature polypeptide encoded by the cDNA of the deposited clone HUVEO91 as well as variants of such polynucleotides which variants encode for a fragment, derivative or analog of the polypeptide of FIGS. 1A and B, or the polypeptide encoded by the cDNA of the deposited clone HUVEO91. Such nucleotide variants include deletion variants, substitution variants and addition or insertion variants.

Additionally, the present invention includes polynucleotides encoding the mature polypeptide as shown in FIGS. 20A and B, as described herein, or the mature polypeptide encoded by the cDNA of the deposited clone HEMCZ56 as well as variants of such polynucleotides which variants encode for a fragment, derivative or analog of the polypeptide of FIGS. 20A and B, the polypeptide as described herein, or the polypeptide encoded by the cDNA of the deposited clone HEMCZ56. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A-1C or of the coding sequence of the deposited clone HUVEO91. Alternatively, the polynucleotide may have a coding sequence which is a naturally occurring allelic variant of the coding sequence shown in FIGS. 20A and B or of the coding sequence of the deposited clone HEMCZ56. As known in the art, an allelic variant is an alternate form of a polynucleotide sequence which may have a substitution, deletion, or addition of one or more nucleotides, which does not substantially alter the function of the encoded polypeptide.

The present invention is further directed to fragments of the isolated nucleic acid molecules described herein. By a fragment of an isolated nucleic acid molecule having the nucleotide sequence of the deposited cDNAs (HUVEO91 and HEMCZ56), or the nucleotide sequence shown in FIGS. 1A-1C (SEQ ID NO:1), FIGS. 20A and B (SEQ ID NO:19), or the complementary strand thereto, is intended fragments at least 15 nt, and more preferably at least 20 nt, still more preferably at least 30 nt, and even more preferably, at least 40, 50, 100, 150, 200, 250, 300, 400, or 500 nt in length. These fragments have numerous uses which include, but are not limited to, diagnostic probes and primers as discussed herein. Of course, larger fragments 50-1500 nt in length are also useful according to the present invention as are fragments corresponding to most, if not all, of the nucleotide sequence of the deposited cDNA clone HUVEO91, the deposited cDNA clone HEMCZ56, the nucleotide sequence depicted in FIGS. 1A-1C (SEQ ID NO:1), or the nucleotide sequence depicted in FIGS. 20A and B (SEQ ID NO 20). By a fragment at least 20 nt in length, for example, is intended fragments which include 20 or more contiguous bases from the nucleotide sequence of the deposited cDNA clones (HUVEO91 and HEMCZ56), the nucleotide sequence as shown in FIGS. 1A-1C (SEQ ID NO:1), or the nucleotide sequence as shown in FIGS. 20A and B.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete or mature TNF-gamma polypeptide. Such functional activities include, but are not limited to, biological activity ((e.g., inhibition of angiogenesis, inhibition of endothelial cell proliferation, induction of NF-kappaB and c-Jun kinase (JNK), induction of cell adhesion, and induction of apoptosis (See Examples, particularly Examples 12-15) induction of T cell proliferation and secretion of interferon-gamma and/or GM-CSF by T cells, exacerbation of an in-vivo mixed-lymphocyte reaction (see Examples 35-37), antigenicity [ability to bind (or compete with a TNF-gamma polypeptide for binding) to an anti-TNF-gamma antibody], immunogenicity (ability to generate antibody which binds to a TNF-gamma polypeptide), the ability to form polymers with other TNF-gamma polypeptides, and ability to bind to a receptor or ligand for a TNF-gamma polypeptide (e.g. DR3 (International Publication Numbers WO97/33904 and WO00/64465 and TR6 (International Publication Numbers WO98/30694 and WO00/52028).

The invention also provides nucleic acid molecules having nucleotide sequences related to extensive fragments of SEQ ID NO:1 which have been determined from the following related cDNA clones: HUVEO91 (SEQ ID NO:8), HMPAP05 (SEQ ID NO:9), HSXCA44 (SEQ ID NO:10), HEMFG66 (SEQ ID NO:11), and HELAM93 (SEQ ID NO:12).

The invention also provides nucleic acid molecules having nucleotide sequences related to extensive fragments of SEQ ID NO:19 which have been determined from the following related cDNA clones: HUVEO91P01 (SEQ ID NO:21), HMPTI24R (SEQ ID NO:22), HELAM93R (SEQ ID NO:23), and HEMFG66R (SEQ ID NO:24).

In specific embodiments, the polynucleotide fragments of the invention comprise, or alternatively, consist of, a polynucleotide comprising any portion of at least 30 nucleotides, preferably at least 50 nucleotides, of SEQ ID NO:1 from nucleotide residue 1 to 2442, preferably excluding the nucleotide sequences determined from the above listed cDNA clones. Representative examples of the TNF-gamma-alpha polynucleotide fragments of the invention, include fragments that comprise, or alternatively, consist of, a member selected from the group consisting of nucleotides: 783-1304, 800-1300, 850-1300, 900-1300, 950-1300, 1000-1300, 1050-1300, 1100-1300, 1150-1300, 1200-1300, 1250-1300, 783-1250, 800-1250, 850-1250, 900-1250, 950-1250, 1000-1250, 1050-1250, 1100-1250, 1150-1250, 1200-1250, 783-1200, 800-1200, 850-1200, 900-1200, 950-1200, 1000-1200, 1050-1200, 1100-1200, 1150-1200, 783-1150, 800-1150, 850-1150, 900-1150, 950-1150, 1000-1150, 1050-1150, 1100-1150, 783-1100, 800-1100, 850-1100, 900-1100, 950-1100, 1000-1100, 1050-1100, 783-1050, 800-1050, 850-1050, 900-1050, 950-1050, 1000-1050, 783-1000, 800-1000, 850-1000, 900-1000, 950-1000, 783-950, 800-950, 850-950, 900-950, 783-900, 800-900, and 850-900 of SEQ ID NO:1, or the complementary polynucleotide strand thereto, or the cDNA contained in the deposited clone HUVEO91. Polypeptides encoded by these polynucleotide fragments are also encompassed by the invention. In certain embodiments, polynucleotides of the invention comprise, or alternatively consist of, a polynucleotide sequence at least 90%, 91%, 92%, 93%, 94%, 95%, 96%, 97%, 98% or 99% identical to a polynucleotide sequence described above. The present invention also encompasses the above polynucleotide sequences fused to a heterologous polynucleotide sequences as described herein and as are well known in the art. Polypeptides encoded by these nucleic acids and/or polynucleotide sequences are also encompassed by the invention.

In additional specific embodiments, the polynucleotide fragments of the invention comprise, or alternatively, consist of, a polynucleotide comprising any portion of at least 30 nucleotides, preferably at least 50 nucleotides, of SEQ ID NO:19 from nucleotide residue 1 to 1116, preferably excluding the nucleotide sequences determined from the above listed cDNA clones (i.e., list from p. 25).

Preferred embodiments of the invention encompass polynucleotides encoding polypeptides comprising, or alternatively consisting of, a member selected from the group consisting of the amino acid sequence of residues –1-147 (i.e., –1 to 147), 1-147 (i.e., +1 to 147), 2-147, 3-147, 4-147, 5-147, 6-147, 7-147, 8-147, 9-147, 10-147, 11-147, 12-147, and 13-147 of SEQ ID NO:2. Polynucleotides encoding these polypeptides are also provided.

Representative examples of the TNF-gamma-beta polynucleotide fragments of the invention, include fragments that comprise, or alternatively, consist of, a member selected from the group consisting of nucleotides 1-1116, 50-1116, 100-1116, 150-1116, 200-1116, 250-1116, 300-1116, 350-1116, 400-1116, 450-1116, 500-1116, 550-1116, 600-1116, 650-1116, 700-1116, 750-1116, 800-1116, 850-1116, 900-1116, 950-1116, 1000-1116, 1050-1116, 1-1100, 50-1100, 100-1100, 150-1100, 200-1100, 250-1100, 300-1100, 350-1100, 400-1100, 450-1100, 500-1100, 550-1100, 600-1100, 650-1100, 700-1100, 750-1100, 800-1100, 850-1100, 900-1100, 950-1100, 1000-1100, 1050-1100, 1-1050, 50-1050, 100-1050, 150-1050, 200-1050, 250-1050, 300-1050, 350-1050, 400-1050, 450-1050, 500-1050, 550-1050, 600-1050, 650-1050, 700-1050, 750-1050, 800-1050, 850-1050, 900-1050, 950-1050, 1000-1050, 1-1000, 50-1000, 100-1000, 150-1000, 200-1000, 250-1000, 300-1000, 350-1000, 400-1000, 450-1000, 500-1000, 550-1000, 600-1000, 650-1000, 700-1000, 750-1000, 800-1000, 850-1000, 900-1000, 950-1000, 1-950, 50-950, 100-950, 150-950, 200-950, 250-950, 300-950, 350-950, 400-950, 450-950, 500-950, 550-950, 600-950, 650-950, 700-950, 750-950, 800-950, 850-950, 900-950, 1-900, 50-900, 100-900, 150-900, 200-900, 250-900, 300-900, 350-900, 400-900, 450-900, 500-900, 550-900, 600-900, 650-900, 700-900, 750-900, 800-900, 850-900, 1-850, 50-850, 100-850, 150-850, 200-850, 250-850, 300-850, 350-850, 400-850, 450-850, 500-850, 550-850, 600-850, 650-850, 700-850, 750-850, 800-850, 1-800, 50-800, 100-800, 150-800, 200-800, 250-800, 300-800, 350-800, 400-800, 450-800, 500-800, 550-800, 600-800, 650-800, 700-800, 750-800, 1-750, 50-750, 100-750, 150-750, 200-750, 250-750, 300-750, 350-750, 400-750, 450-750, 500-750, 550-750, 600-750, 650-750, 700-750, 1-700, 50-700, 100-700, 150-700, 200-700, 250-700, 300-700, 350-700, 400-700, 450-700, 500-700, 550-700, 600-700, 650-700, 1-650, 50-650, 100-650, 150-650, 200-650, 250-650, 300-650, 350-650, 400-650, 450-650, 500-650, 550-650, 600-650, 1-600, 50-600, 100-600, 150-600, 200-600, 250-600, 300-600, 350-600, 400-600, 450-600, 500-600, 550-600, 1-550, 50-550, 100-550, 150-550, 200-550, 250-550, 300-550, 350-550, 400-550, 450-550, 500-550, 1-500, 50-500, 100-500, 150-500, 200-500, 250-500, 300-500, 350-500, 400-500, 450-500, 1-450, 50-450, 100-450, 150-450, 200-450, 250-450, 300-450, 350-450, 400-450, 1-400, 50-400, 100-400, 150-400, 200-400, 250-400, 300-400, 350-400, 1-350, 50-350, 100-350, 150-350, 200-350, 250-350, 300-350, 1-300, 50-300, 100-300, 150-300, 200-300, 250-300, 1-250, 50-250, 100-250, 150-250, 200-250, 1-200, 50-200, 100-200, 150-200, 1-150, 50-150, 100-150, 1-100, 50-100, and 1-50 of SEQ ID NO:19 or the complementary polynucleotide strand thereto, or the cDNA contained in the deposited clone HEMCZ56. Polypeptides encoded by these polynucleotide fragments are also encompassed by the invention. In certain embodiments, polynucleotides of the invention comprise, or alternatively consist of, a polynucleotide sequence at least 90%, 91%, 92%, 93%, 94%, 95%, 96%, 97%, 98% or 99% identical to a polynucleotide sequence described above. The present invention also encompasses the above polynucleotide sequences fused to a heterologous polynucleotide sequences as described herein and as are well known in the art. Polypeptides encoded by these nucleic acids and/or polynucleotide sequences are also encompassed by the invention.

Preferred nucleic acid fragments of the present invention also include nucleic acid molecules encoding one or more of the following domains of TNF-gamma-alpha (e.g., as described also in the legend to FIGS. 1A and 1B): potential asparagine-linked glycosylation sites N-29 through N-32 (N-29, Y-30, T-31, N-32) and N-125 through D-128 (N-125, V-126, S-127, D-128); potential Protein Kinase C (PKC) phosphorylation sites T-32 through K-34 (T-32, N-33, K-34) and T-50 through R-52 (T-50, F-51, R-52); potential Casein Kinase II (CK2) phosphorylation sites S-83 through E-86 (S-83, Y-84, P-85, E-86); S-96 through E-99 (S-96, V-97, C-98, E-99); S-115 through E-118 (S-115, L-116, Q-117, E-118); S-130 through D-133 (S-130, L-131, V-132, D-133); and T-135 through D-138 (T-135, K-136, E-137, D-138); and potential myristylation sites G-20 through K-25 (G-20, L-21, A-22, F-23, T-24, K-25) and G-111 through L-116 (G-111, A-112, M-113, F-114, S-115, L-116) of SEQ ID NO:2.

Among the especially preferred polynucleotides of the invention are those characterized by encoding structural or functional attributes of TNF-gamma. Such polynucleotides encode amino acid residues that comprise alpha-helix and alpha-helix forming regions ("alpha-regions"), beta-sheet and beta-sheet forming regions ("beta regions"), turn and turn-forming regions ("turn-regions"), coil and coil-forming regions ("coil regions"), hydrophilic regions, hydrophobic regions, alpha amphipathic regions, beta amphipathic regions, surface forming regions, and high antigenic index regions (i.e., having an antigenic regions of three or more contiguous amino acid residues each of which having an antigenic index of greater than or equal to 1.5) of TNF-gamma. Certain preferred regions are those set out in FIG. 17, and include, but are not limited to, regions of the aforementioned types identified by analysis of the amino acid sequence depicted in FIG. 1 (SEQ ID NO:2) using the default parameters of the identified computer programs, such preferred regions include; Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Data which represent TNF-gamma-beta in a fashion as described above for TNF-gamma-alpha (see FIG. 17) may easily be prepared using the amino acid sequence shown in FIGS. 20A and 20B and in SEQ ID NO:20. As such, each of the above listed structural or functional attributes of TNF-gamma listed above (i.e. Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index, etc.) apply equally well to TNF-gamma-alpha and TNF-gamma-beta.

Certain preferred regions in these regards are set out in FIG. 17, but may also be represented or identified by using a tabular representation of the data presented in FIG. 17. The DNA*STAR computer algorithm used to generate FIG. 17 (set on the original default parameters) will easily present the data in FIG. 17 in such a tabular format. A tabular format of the data in FIG. 17 may be used to easily determine specific boundaries of a preferred region.

The above-mentioned preferred regions set out in FIG. 17 include, but are not limited to, regions of the aforementioned types identified by analysis of the amino acid sequence set out in FIGS. 1A and 1B. As set out in FIG. 17, such preferred regions include Gamier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Among highly preferred fragments in this regard are those that comprise regions of TNF-gamma-alpha and/or TNF-gamma-beta that combine several structural features, such as several (e.g., 1, 2, 3 or 4) of the features set out above.

Additional preferred nucleic acid fragments of the present invention include nucleic acid molecules encoding one or more epitope-bearing portions of the TNF-gamma polypeptide. In particular, such nucleic acid fragments of the present invention include nucleic acid molecules encoding a member selected from the group consisting of: a polypeptide comprising amino acid residues from about Thr-24 to about Asn-32 in SEQ ID NO:2; a polypeptide comprising amino acid residues from about Ile-37 to about Ile-45 in SEQ ID NO:2; a polypeptide comprising amino acid residues from about Met-54 to about Arg-62 in SEQ ID NO:2; a polypeptide comprising amino acid residues from about Gln-63 to about Asp-71 in SEQ ID NO:2; a polypeptide comprising amino acid residues from about Glu-57 to about Gly-65 in SEQ ID NO:2; a polypeptide comprising amino acid residues from about Val-80 to about Thr-88 in SEQ ID NO:2; a polypeptide comprising amino acid residues from about Leu-116 to about Val-124 in SEQ ID NO:2; and a polypeptide comprising amino acid residues from about Asp-133 to about Phe-141 in SEQ ID NO:2. These polypeptide fragments have been determined to bear antigenic epitopes of the TNF-gamma protein by the analysis of the Jameson-Wolf antigenic index, as shown in FIG. 17, above. Methods for determining other such epitope-bearing portions of TNF-gamma are described in detail below.

Polypeptide fragments which bear antigenic epitopes of the TNF-gamma-beta protein may be easily determined by one of skill in the art using the above-described analysis of the Jameson-Wolf antigenic index, as shown in FIG. 17. Methods for determining other such epitope-bearing portions of TNF-gamma-beta are described in detail below.

Another embodiment of the invention is directed to polynucleotides that hybridize, preferably under stringent hybridization conditions, to a portion of the polynucleotide sequence of a polynucleotide of the invention such as, for instance, the cDNA clone contained in ATCC™ Deposit No.

75927, the cDNA clone contained in ATCC™ Deposit 203055 or a TNF-gamma polynucleotide fragment as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 micrograms/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30-70, or 80-150 nt, or the entire length of the reference polynucleotide. These are useful as diagnostic probes and primers as discussed above and in more detail below. Of course, a polynucleotide which hybridizes only to a poly A sequence (such as the 3' terminal poly tract of the TNF-gamma cDNA shown in SEQ ID NO:1 or SEQ ID NO:19), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In preferred embodiments, polynucleotides which hybridize to the reference polynucleotides disclosed herein encode polypeptides which either retain substantially the same biological function or activity as the mature polypeptide encoded by the polynucleotide sequences depicted in FIGS. 1A-1C (SEQ ID NO:1) and/or FIGS. 20A and B (SEQ ID NO:19), or the cDNAs contained in the deposit.

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotide of SEQ ID NO:1, for recovery of the polynucleotide, as diagnostic probes, and as PCR primers.

The present invention further relates to variants of the nucleic acid molecules of the present invention, which encode portions, analogs or derivatives of the TNF-gamma protein. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions of the polynucleotide sequences described herein (including fragments). The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TNF-gamma protein or portions thereof. Also especially preferred in this regard are conservative substitutions.

Further embodiments of the invention are directed to isolated nucleic acid molecules comprising a polynucleotide sequence at least 70% or at least 80% or 85% identical, more preferably at least 90%, 92% or 94% identical, and still more preferably at least 95%, 96%, 97%, 98% or 99% identical to a polynucleotide having a nucleotide sequence selected from the group consisting of (a) a nucleotide sequence encoding the TNF-gamma-alpha polypeptide having the complete amino acid sequence in SEQ ID NO:2 (i.e., positions –27 to 147 of SEQ ID NO:2); (b) a nucleotide sequence encoding the TNF-gamma-alpha polypeptide having the complete amino acid sequence in SEQ ID NO:2 excepting the N-terminal methionine (i.e., positions –26 to 147 of SEQ ID NO:2); (c) a nucleotide sequence encoding the mature TNF-gamma-alpha polypeptide having the amino acid sequence in SEQ ID NO:2 shown as positions 1 to 147 of SEQ ID NO:2; (d) a nucleotide sequence encoding the extracellular domain of the TNF-gamma-alpha polypeptide having the amino acid sequence in SEQ ID NO:2 shown as positions 1 to 147 of SEQ ID NO:2; (e) a nucleotide sequence encoding the TNF-gamma-alpha polypeptide having the complete amino acid sequence encoded by the cDNA clone HUVEO91 contained in ATCC™ Deposit No. 75927; (f) a nucleotide sequence encoding the TNF-gamma-alpha polypeptide having the complete amino acid sequence excepting the N-terminal methionine encoded by the cDNA clone HUVEO91 contained in ATCC™ Deposit No. 75927; (g) a nucleotide sequence encoding the mature TNF-gamma-alpha polypeptide having the amino acid sequence encoded by the cDNA clone HUVEO91 contained in ATCC™ Deposit No. 75927; (h) a nucleotide sequence encoding the extracellular domain of the TNF-gamma-alpha polypeptide having the amino acid sequence encoded by the cDNA clone HUVEO91 contained in ATCC™ Deposit No. 75927; (i) a nucleotide sequence encoding a polypeptide fragment described herein; and (j) a nucleotide sequence complementary to any of the nucleotide sequences in (a), (b), (c), (d), (e), (f), (g), (h) or (i), above. The polypeptides of the present invention also include polypeptides having an amino acid sequence at least 80% or 85% identical, more preferably at least 90%, 92% or 94% identical, and still more preferably 95%, 96%, 97%, 98% or 99% identical to those described in (a), (b), (c), (d), (e), (f), (g), (h), (i) or (j), above, as well as polypeptides having an amino acid sequence with at least 90% similarity, and more preferably at least 95% similarity, to those above.

Further embodiments of the invention are directed to isolated nucleic acid molecules comprising a polynucleotide sequence at least 70% or at least 80% or 85% identical, more preferably at least 90%, 92% or 94% identical, and still more preferably at least 95%, 96%, 97%, 98% or 99% identical to a polynucleotide having a nucleotide sequence selected from the group consisting of: (a) a nucleotide sequence encoding the TNF-gamma-beta polypeptide having the complete amino acid sequence in SEQ ID NO:20 (i.e., positions 1 to 251 of SEQ ID NO:20); (b) a nucleotide sequence encoding the TNF-gamma-beta polypeptide having the complete amino acid sequence in SEQ ID NO:20 excepting the N-terminal methionine (i.e., positions 2 to 251 of SEQ ID NO:20); (c) a nucleotide sequence encoding the mature TNF-gamma-beta polypeptide having the amino acid sequence in SEQ ID NO:20 shown as positions 62 to 251 of SEQ ID NO:20; (d) a nucleotide sequence encoding the mature TNF-gamma-beta polypeptide having the amino acid sequence in SEQ ID NO:20 shown as positions 60 to 251 of SEQ ID NO:20; (e) a nucleotide sequence encoding a mature TNF-gamma-beta polypeptide having the amino acid sequence in SEQ ID NO:20 shown as positions 72 to 251 of SEQ ID NO:20; (f) a nucleotide sequence encoding the intracellular domain of the TNF-gamma-beta polypeptide having the amino acid sequence in SEQ ID NO:20 shown as positions 1 to 35 of SEQ ID NO:20; (g) a nucleotide sequence encoding the intracellular domain of the TNF-gamma-beta polypeptide having the amino acid sequence in SEQ ID NO:20 shown as positions 1 to 35 of SEQ ID NO:20; (h) a nucleotide sequence encoding the extracellular domain of the TNF-gamma-beta polypeptide having the amino acid sequence in SEQ ID NO:20 shown as positions 62 to 251 of SEQ ID NO:20; (i) a nucleotide sequence encoding the extracellular domain of the TNF-gamma-beta polypeptide having the amino acid sequence in SEQ ID NO:20 shown as positions 60 to 251 of SEQ ID NO:20; (j) a nucleotide sequence encoding the extracellular domain of the TNF-gamma-beta polypeptide having the amino acid sequence in SEQ ID NO:20 shown as positions 62 to 251 of SEQ ID NO:20; (k) a nucleotide sequence encoding the TNF-gamma-beta polypeptide having the complete amino acid sequence encoded by the cDNA clone HEMCZ56 contained in ATCC™ Deposit No. 203055; (1) a nucleotide sequence encoding the TNF-gamma-beta polypeptide having the complete amino acid sequence excepting the N-terminal methionine encoded by the cDNA clone HEMCZ56 contained in ATCC™ Deposit No. 203055; (m) a nucleotide sequence encoding the mature TNF-gamma-beta polypeptide having the amino acid sequence encoded by the cDNA clone HEMCZ56 contained in ATCC™ Deposit No. 203055; (n) a nucleotide sequence encoding the intracellular domain of the TNF-gamma-beta polypeptide having the amino acid sequence encoded by the cDNA clone HEMCZ56 contained in ATCC™ Deposit No. 203055; (o) a nucleotide sequence encoding the extracellular domain of the TNF-gamma-beta polypeptide having the amino acid sequence encoded by the cDNA clone HEMCZ56 contained in ATCC™ Deposit No. 203055; and (p) a nucleotide sequence complementary to any of the nucleotide sequences in (a), (b), (c), (d), (e), (f), (g), (h), (i), (j), (k), (1), (m), (n), (o) or (p), above. The polypeptides of the present invention also include polypeptides having an amino acid sequence at least 80% or 85% identical, more preferably at least 90%, 92% or 94% identical, and still more preferably 95%, 96%, 97%, 98% or 99% identical to those described in (a), (b), (c), (d), (e), (f), (g), (h), (i), (j), (k), (1), (m), (n) or (o), above, as well as polypeptides having an amino acid sequence with at least 90% similarity, and more preferably at least 95% similarity, to those above.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the TNF-gamma polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be the entire nucleotide sequence shown in FIGS. 1A-1C (SEQ ID NO:1) and FIGS. 20A and B (SEQ ID NO:19), or any fragment as described herein.

As a practical matter, whether any particular nucleic acid molecule is at least 70%, 80%, 85%, 90%, 92%, 94%, 95%, 96%, 97%, 98% or 99% identical to, for instance, the nucleotide sequence shown in FIGS. 1A-1C (SEQ ID NO:1), FIGS. 20A and B (SEQ ID NO:19), or to the nucleotide sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711).

Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

In further embodiments, the present invention is directed to polynucleotides having at least a 70% identity, preferably at least 80%, 85% or 90% and more preferably at least a 92%, 94%, 95%, 96%, 97%, 98% or 99% identity to a polynucleotide which encodes the polypeptide of SEQ ID NO:2 as well as fragments thereof, which fragments have at least 30 bases and preferably at least 50 bases and to polypeptides encoded by such polynucleotides.

In further embodiments, the present invention is directed to polynucleotides having at least a 70% identity, preferably at least 90% and more preferably at least a 95% identity to a polynucleotide which encodes the polypeptide of SEQ ID NO:20 as well as fragments thereof, which fragments have at least 30 bases and preferably at least 50 bases and to polypeptides encoded by such polynucleotides.

The present application is directed to nucleic acid molecules at least 70%, 80%, 85%, 90%, 92%, 94%, 95%, 96%, 97%, 98% or 99% identical to the polynucleotide sequence shown in FIGS. 1A-1C (SEQ ID NO:1), FIGS. 20A and B (SEQ ID NO:19), or to the nucleic acid sequence of the deposited cDNA clones, or fragments thereof, irrespective of whether they encode a polypeptide having TNF-gamma functional activity. This is because even where a particular nucleic acid molecule does not encode a polypeptide having TNF-gamma functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TNF-gamma functional activity include, inter alia, (1) isolating the TNF-gamma gene or allelic variants thereof in a cDNA library; (2) in situ hybridization (e.g., "FISH") to metaphase chromosomal spreads to provide precise chromosomal location of the TNF-gamma gene, as described in Verma et al., *Human Chromosomes: A Manual of Basic Techniques*, Pergamon Press, N.Y. (1988); and (3) Northern Blot analysis for detecting TNF-gamma mRNA expression in specific tissues.

Preferred, however, are nucleic acid molecules having sequences at least 70%, 80%, 85%, 90%, 92%, 94%, 95%, 96%, 97%, 98% or 99% identical to the nucleic acid sequence shown in FIGS. 1A-1C (SEQ ID NO:1), FIGS. 20A and B (SEQ ID NO:19), or to the nucleic acid sequence of the deposited cDNA clones, or fragments thereof, which do, in fact, encode a polypeptide having TNF-gamma functional activity. By "a polypeptide having TNF-gamma functional activity" is intended polypeptides exhibiting activity similar, but not necessarily identical, to an activity of the TNF-gamma polypeptide of the invention (either the full-length protein or, preferably, the mature protein), as measured in a particular immunoassay and/or biological assay. For example, TNF-gamma activity can be measured using an apoptosis assay as described in Example 7, by determining the relative ability of TNF-gamma to inhibit the FGF-2-induced formation of capillary-like tubular structure formation in cultures of ABAE cells as described in detail in Example 9 or in a chorioallantoic membrane (CAM) angiogenesis assay as described in Example 10, by its effect(s) on the activation of cellular NF-kappaB and c-Jun kinase (JNK) as described in Example 12, and in several additional ways described in the remaining Examples and in the art.

Of course, due to the degeneracy of the genetic code, one of ordinary skill in the art will immediately recognize that a large number of the nucleic acid molecules having a sequence at least 70%, 80%, 85%, 90%, 92%, 94%, 95%, 96%, 97%, 98%, or 99% identical to the nucleic acid sequence of the deposited cDNA or the nucleic acid sequence shown in FIGS. 1A-1C (SEQ ID NO:1), FIGS. 20A and 20B (SEQ ID NO:19), or fragments thereof, will encode a polypeptide "having TNF-gamma activity." In fact, since degenerate variants of these nucleotide sequences all encode the same polypeptide, in many instances, this will be clear to the skilled artisan even without performing the above described assay. It will be further recognized in the art that, for such nucleic acid molecules that are not degenerate variants, a reasonable number will also encode a polypeptide having TNF-gamma activity. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in J.U. Bowie et al., "Deciphering the Message in Protein Sequences: Tolerance to Amino Acid Substitutions," Science 247:1306-1310 (1990), wherein the authors indicate that proteins are surprisingly tolerant of amino acid substitutions.

Additional embodiments of the invention are directed to isolated nucleic acid molecules comprising a polynucleotide which encodes the amino acid sequence of a TNF-gamma polypeptide (e.g., a TNF-gamma polypeptide fragment described herein) having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, 10-20 conservative amino acid substitutions, 5-10 conservative amino acid substitutions, 1-5 conservative amino acid substitutions, 3-5 conservative amino acid substitutions, or 1-3 conservative amino acid substitutions. Of course, in order of ever-increasing preference, it is highly preferable for a polynucleotide which encodes the amino acid sequence of a TNF-gamma polypeptide to have an amino acid sequence which contains not more than 10, 9, 8, 7, 6, 5, 4, 3, 2 or 1 conservative amino acid substitutions.

Additional embodiments of the invention are directed to exclusions of publicly available polynucleotide sequences. Many polynucleotide sequences, such as EST sequences, are publicly available and accessible through sequence databases. Some of these sequences are related to SEQ ID NO:1 and/or SEQ ID NO:19 and may have been publicly available prior to conception of the present invention. Preferably, such related polynucleotides are specifically excluded from the scope of the present invention. To list every related sequence would be cumbersome. Thus, preferably excluded from the present invention are one or more polynucleotides comprising a nucleotide sequence described by the general formula of $a^1$-$b^1$ where $a^1$ is any integer between 1 to 2410 of SEQ ID NO:1, $b^1$ is an integer of 15 to 2425, where both $a^1$ and $b^1$ correspond to the positions of nucleotide residues shown in SEQ ID NO:1, and where $b^1$ is greater than or equal to $a^1+14$. Similarly, preferably excluded from the present invention are one or more polynucleotides comprising a nucleotide sequence described by the general formula of $a^2$-$b^2$, where $a^2$ is any integer between 1 to 1101 of SEQ ID NO:19, $b^2$ is an integer of 15 to 1116, where both $a^2$ and $b^2$ correspond to the positions of nucleotide residues shown in SEQ ID NO:19, and where $b^2$ is greater than or equal to $a^2+14$.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of TNF-gamma coding sequence, but do not comprise all or a portion of any TNF-gamma intron. In another embodiment, the nucleic acid comprising TNF-gamma coding sequence does not contain coding sequences of a genomic flanking gene (i.e., 5' or 3' to the TNF-gamma gene in the genome).

In specific embodiments, the polynucleotides of the invention are less than 100,000 kb, 50,000 kb, 10,000 kb, 1,000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of TNF-gamma-alpha or TNF-gamma-beta coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide sequences set forth in SEQ ID NO:1 or SEQ ID NO:19, respectively. In further embodiments, polynucleotides of the invention comprise at least 15, at least 30, at least 50, at least 100, or at least 250, at least 500, or at least 1000 contiguous nucleotides of TNF-gamma-alpha or TNF-gamma-beta coding sequence, but do not comprise all or a portion of any TNF-gamma intron. In another embodiment, the nucleic acid comprising TNF-gamma-alpha or TNF-gamma-beta coding sequence does not contain coding sequences of a genomic flanking gene (i.e., 5' or 3' to the TNF-gamma gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

Polynucleotide Assays

The invention also encompasses the use of TNF-gamma polynucleotides to detect complementary polynucleotides, such as, for example, as a diagnostic reagent for detecting diseases or susceptibility to diseases related to the presence of mutated TNF-gamma-alpha or TNF-gamma-beta. Such diseases are related to an under-expression of TNF-gamma-alpha or TNF-gamma-beta, such as, for example, abnormal cellular proliferation such as tumors and cancers.

Individuals carrying mutations in the human TNF-gamma gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163-166 (1986)) prior to analysis. RNA or cDNA may also be used for the same purpose. As an example, PCR primers complementary to the nucleic acid encoding TNF-gamma-alpha or TNF-gamma-beta can be used to identify and analyze TNF-gamma mutations. For example, deletions and insertions can be detected by a change in size of the amplified product in comparison to the normal genotype. Point mutations can be identified by hybridizing amplified DNA to radiolabeled TNF-gamma RNA or alternatively, radiolabeled TNF-gamma antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with, any description of sequences herein. A license may be required to make, use or sell the deposited materials, and no such license is hereby granted.

Vectors and Host Cells

The present invention also relates to vectors which include the isolated polynucleotides of the present invention, host cells which are genetically engineered with the recombinant vectors, or which are otherwise engineered to produce the polypeptides of the invention, and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the TNF-gamma genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operably associated with an appropriate expression control sequence(s) (promoter) to direct mRNA synthesis. As representative examples of such promoters, there may be mentioned: LTR or SV40 promoter, the *E. coli* lac or trp, the phage lambda P promoter and other promoters known to control expression of genes in prokaryotic or eukaryotic cells or their viruses. The expression vector also contains a ribosome-binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase, glutamine synthase, or neomycin resistance for eukaryotic cell culture, or such as tetracycline or ampicillin resistance in *E. coli*.

Vectors which use glutamine synthase (GS) or DHFR as the selectable markers can be amplified in the presence of the drugs methionine sulphoximine or methotrexate, respectively. The availability of drugs which inhibit the function of the enzymes encoded by these selectable markers allows for selection of cell lines in which the vector sequences have been amplified after integration into the host cell's DNA. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors that may be used according to the present invention are commercially available from suppliers including, for example, Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are herein incorporated by reference.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and Sf9; animal cells such as CHO, NSO, COS or Bowes melanoma, adenoviruses, plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably associated with the sequence. Large numbers of suitable vectors and promoters are known to those of skill in the art, and are commercially available. The following vectors are provided by way of example. Bacterial: pHE4-5 (ATCC™ Accession No. 209311; and variations thereof), pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lad, lacZ, T3, T7, gpt, lambda P, P, and trp. Eukaryotic promoters include CMV immediate early, HSV thymidine kinase, early and late SV40, LTRs from retroviruses, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular. Biology, (1986)).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TNF-gamma coding sequence), and/or to include genetic material (e.g., heterologous polynucleotide sequences) that is operably associated with TNF-gamma polynucleotides of the invention, and which activates, alters, and/or amplifies endogenous TNF-gamma polynucleotides. For example, techniques known in the art may be used to operably associate heterologous control regions (e.g., promoter and/or enhancer) and endogenous TNF-gamma polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice.

As a representative, but nonlimiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman (*Cell* 23:175 (1981)), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The TNF-gamma polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The invention encompasses TNF-gamma-alpha and TNF-gamma-beta polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

The present invention further encompasses encompasses TNF-gamma-alpha and/or TNF-gamma-beta polypeptides or fragments thereof conjugated to a diagnostic agent (e.g. a detectable agent) and/or therapeutic agent. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the polypeptide (or fragment thereof) or indirectly, through an intermediate (such as, for example, a linker known in the art) using techniques known in the art. See, for example, U.S. Pat. No. 4,741,900 for metal ions which can be conjugated to polypeptides for use as diagnostics and/or therapeutics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113}In$, $^{115}In$), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$. A preferred radioisotope label is $^{111}I$. Another preferred radioactive label is $^{90}Y$. Another preferred radioactive label is $^{131}I$.

Further, a TNF-gamma-alpha and/or TNF-gamma-beta polypeptide or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$ or other radioisotopes such as, for example, $^{103}Pd$, $^{133}Xe$, $^{131}I$, $^{68}Ge$, $^{57}Co$, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators useful for conjugating radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N",N"'-tetraacetic acid (DOTA). In other specific embodiments, the DOTA is attached to the polypeptide of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chloramubcil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention may also be used to target and destroy specific cell types, such as T cells, particularly cancerous T cells. Thus, the present invention further encompasses methods and compositions for killing cells of hematopoietic origin, comprising, or alternatively consisting of, contacting TNF-gamma alpha and/or TNF-gamma-beta polypeptide or fragment or variant thereof (e.g., TNF-gamma alpha and/or TNF-gamma-beta polypeptide or fragment or variant thereof conjugated to a radioisotope, cytotoxin or cytotoxic pro-drug) with cells of hematopoietic origin. In preferred embodiments, the cells of hematopoietic origin are T cells. In other non-exclusive preferred embodiments, the cells of hematopoietic origin are cancerous T cells.

The present invention further encompasses methods and compositions for killing cells of hematopoietic origin, comprising, or alternatively consisting of, administering to an animal, preferably a human, in which such killing of hematopoietic cells is desired, a TNF-gamma alpha and/or TNF-gamma-beta polypeptide or fragment or variant thereof (e.g., TNF-gamma alpha and/or TNF-gamma-beta polypeptide or fragment or variant thereof conjugated to a radioisotope, cytotoxin or cytotoxic pro-drug) in an amount effective to kill cells of hematopoietic origin. In preferred embodiments, the cells of hematopoietic origin are T cells. In preferred embodiments, the cells of hematopoietic origin are cancerous T cells.

Techniques known in the art may be applied to label polypeptides and antibodies (as well as fragments and variants of polypeptides and antibodies) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

In addition, polypeptides of the invention can be chemically synthesized using techniques known in the art. For example, a peptide corresponding to a fragment of the TNF-gamma-alpha or TNF-gamma-beta polypeptides of the invention can be synthesized by use of a peptide synthesizer. Furthermore, if desired, nonclassical amino acids or chemical amino acid analogs can be introduced as a substitution or addition into the sequence. Non-classical amino acids include but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

At least fifteen TNF-gamma-alpha expression constructs have been generated by the inventors herein to facilitate the production of TNF-gamma polypeptides of several sizes and in several systems. Of these, four have been constructed which encode a full-length TNF-gamma polypeptide. The full-length constructs are: (i) pQE9TNFg-27/147, (ii) pQE70TNFg, (iii) pC1TNFg, and pcDNA3TNFg. In the case of the first expression construct listed (pQE9TNFg-27/147), the construct was used to produce a full-length TNF-gamma-alpha polypeptide with an N-terminal six histidine amino acid tag according to the method of Example 1. A full-length TNF-gamma-alpha polypeptide lacking the histidine tag was produced in bacteria by using the pQE70TNFg construct essentially as was done in Example 1. In addition, a full-length TNF-gamma-alpha polypeptide lacking a histidine tag was produced in mammalian cells by using either the pC1TNFg or pcDNA3TNFg constructs according to the method of Example 3. Further, the mature TNF-gamma-alpha polypeptide was produced and secreted from mammalian cells under direction of the interleukin (IL)-6 signal peptide from a construct designated pcDNA3/IL6TNFg-1/149 (see Example 11).

The remaining TNF-gamma-alpha expression constructs were used to express various TNF-gamma muteins from bacterial, baculoviral, and mammalian systems. Four N-terminal deletion mutations have been generated using the pQE60 bacterial expression vector. These N-terminal deletion mutation constructs are: (i) pQE60TNFg-3/147 (representing a possible mature TNF-gamma polypeptide; the polypeptide expressed by this construct is identical to amino acid residues 107-251 of the TNF-gamma-beta of SEQ ID NO:20), (ii) pQE6OTNFg12/147 (representing amino acid residues 12-147 of SEQ ID NO:2 and residues 116-251 of SEQ ID NO:20), (iii) pQE6OTNFg22/147 (representing amino acid residues 22-147 of SEQ ID NO:2 and residues 126-251 of SEQ ID NO:20), and (iv) pQE60TNFg28/147 (representing amino acid residues 28-147 of SEQ ID NO:2 and residues 132-251 of SEQ ID NO:20). Each of these expression constructs can be used to produce a TNF-gamma polypeptide in a bacterial system which exhibits an N-terminal deletion of 24, 38, 48, and 54 amino acids, respectively, with regard to the full-length TNF-gamma-alpha polypeptide or an N-terminal deletion of 106, 115, 125, and 131 amino acids, respectively, with regard to the full-length TNF-gamma-beta polypeptide.

Further N-terminal deletion mutation bacterial expression constructs have been generated. A construct designated pHE4 VEGI T30-L174 has been generated using the bacterial expression vector pHE4 to express amino acids threonine-30 to leucine-174 of the TNF-gamma-alpha sequence shown in FIGS. 1A and 1B (residues threonine-3 to leucine-147 of SEQ ID NO:2) which correspond exactly to amino acid residues threonine-107 to leucine-251 of the TNF-gamma-beta sequence shown in FIGS. 20A and 20B (residues threonine-107 to leucine-251 of SEQ ID NO:20). Additional bacterial expression constructs generated include pQE9.VEGI.his.T28-L174, pHE4.VEGI.T28-L174, pHE4.VEGI.T51-L174, and pHE4.VEGI.T58-L174. These constructs are based on either the pQE9 or pHE4 bacterial expression vectors. The construct designations indicate the expression vector, the gene name, and the amino acid residues expressed by the construct (e.g. pQE9.VEGI.T28-L174 indicates that the pQE9 bacterial expression vector is used to express amino acids threonine (T)-28 through leucine (L)-174 of the TNF-gamma-alpha polypeptide (VEGI is a laboratory designation for TNF-gamma-alpha)).

A TNF-gamma expression construct has been generated which can be used to produce a secreted mature TNF-gamma polypeptide from a mammalian system. The construct has been designated pCl/IL6TNFg-3/147. It encodes the signal peptide from the human IL-6 gene fused to the mature TNF-gamma sequence. A similar construct has been generated which contains the CK-beta8 signal peptide (amino acids −21 to −1 of the CK-beta8 sequence disclosed in published PCT application PCT/US95/09058; filed Jun. 23, 95) fused to the amino terminus of amino acids 12-149 of TNF-gamma-alpha (SEQ ID NO:2; that is, amino acids 116-251 of TNF-gamma-beta (SEQ ID NO:20)) in the context of the pC4 mammalian expression vector. This construct has been designated pC4/CK-beta8TNFg12/147. A variant of this construct has been generated which can be used to express amino acids 12-147 of TNF-gamma fused to the human IgG Fc region at the TNF-gamma carboxy terminus. This fusion protein is also secreted under the direction of the CK-beta8 signal peptide and has been designated pC4/CK-beta8TNFg1/147/Fc. The sequence of the human Fc portion of the fusion molecule is shown in SEQ ID NO:18. Other sequences could be used which are known to those of skill in the art.

Amino acids −3 to 147 of TNF-gamma-alpha (SEQ ID NO:2; which correspond to amino acid residues 102 to 251 of TNF-gamma-beta (SEQ ID NO:20)) can be expressed and secreted from a baculovirus system by using a construct designated pA2GPTNFg-3/147. This expression construct encodes the mature TNF-gamma coding sequence fused at its amino terminus to the baculoviral GP signal peptide.

Two retroviral TNF-gamma expression constructs have also been generated. The first of these has been designated pG1SamEN/TNFg-3/149. This expression construct can be used to produce full-length TNF-gamma protein from a mammalian system. A related construct, pG1SamEN/CK-beta8TNFg12/149, has been generated which can be used to produce and secrete mature TNF-gamma protein from a mammalian system under the direction of the CK-beta8 signal peptide.

Further polypeptides of the present invention include polypeptides which have at least 80%, 85% or 90% similarity, more preferably at least 92%, 94% or 95% similarity, and still more preferably at least 96%, 97%, 98% or 99% similarity to those described above. The polypeptides of the invention also comprise those which are at least 80% or 85% identical, more preferably at least 90%, 92%, 94% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

In preferred embodiments, polynucleotides of the invention include nucleotides 1-543 (or 4-543 if the vector supplies an amino-terminal ATG) of SEQ ID NO:25 inserted in-frame into any of the expression constructs described herein (such, for example, pHE4, pHE4b, pHE4-5, pA2, pA2GP, pC4, pC4/CK-beta8, pG1SamEN, pG1SamEN/CK-beta8, etc.). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma-beta polypeptides described above, and the polypeptides encoded thereby. The present invention also encompasses the above polynucleotide sequences fused to a heterologous polynucleotide sequence (such as, for example, a polynucleotide sequence encoding the Fc region of a human immunoglobulin or FLAG (see, for example, Example 16)), and the polypeptides encoded thereby.

In additional preferred embodiments, polynucleotides of the invention include nucleotides 214-753 of SEQ ID NO:20 inserted in-frame into any of the expression constructs described herein (such, for example, pHE4, pHE4b, pHE4-5, pA2, pA2GP, pC4, pC4/CK-beta8, pG1SamEN, pG1SamEN/CK-beta8, etc.). In these embodiments, the vector or the TNF-gamma-beta polynucleotide of the invention may contribute an amino-terminal ATG codon. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma-beta polypeptides described above, and the polypeptides encoded thereby. The present invention also encompasses the above polynucleotide sequences fused to a heterologous polynucleotide sequence (such as, for example, a polynucleotide sequence encoding the Fc region of a human immunoglobulin or FLAG (see, for example, Example 16)), and the polypeptides encoded thereby.

Polypeptides and Fragments

The present invention further relates to an isolated TNF-gamma-alpha polypeptide which has the deduced amino acid sequence of FIGS. 1A and 1B (SEQ ID NO:2) or which has the amino acid sequence encoded by the deposited cDNA HUVEO91, as well as fragments, analogs and derivatives of such polypeptide.

The present invention also relates to a TNF-gamma-beta polypeptide which has the deduced amino acid sequence of FIGS. 20A and 20B (SEQ ID NO:20) or which has the amino acid sequence encoded by the deposited cDNA HEMCZ56, as well as fragments, analogs and derivatives of such polypeptide.

The polypeptides and polynucleotides of the present invention are preferably provided in an isolated form, and preferably are purified to a point within the range of near complete (e.g., >90% pure) to complete (e.g., >99% pure) homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Also intended as an "isolated polypeptide" are polypeptides that have been purified partially or substantially from a recombinant host cell. For example, a recombinantly produced version of a TNF-gamma polypeptide can be substantially purified by the one-step method described by Smith and Johnson (*Gene* 67:31-40 (1988)). Such polynucleotides could be part of a vector and/or such polynucleotides or polypeptides could be part of a composition, and still be isolated in that such vector or composition is not part of its natural environment. Isolated polypeptides and polynucleotides according to the present invention also include such molecules produced naturally or synthetically. Polypeptides and polynucleotides of the invention also can be purified from natural or recombinant sources using anti-TNF-gamma antibodies of the invention in methods which are well known in the art of protein purification.

The terms "fragment," "derivative" and "analog" when referring to the polypeptides of FIGS. 1A and 1B or FIGS. 20A and 20B, and those polypeptides encoded by the deposited cDNAs, means a polypeptide which retains a TNF-gamma functional activity, i.e., displays one or more functional activities associated with a full-length and/or mature TNF-gamma polypeptide disclosed in FIGS. 1A and B (SEQ ID NO:2), FIGS. 20A and B (SEQ ID NO:20), disclosed elsewhere herein, and/or encoded by one or both of the deposited clones (HUVEO91 and HEMCZ56). As one example, such fragments, derivatives, or analogs, which have the desired immunogenicity or antigenicity can be used, for example, in immunoassays, for immunization, for inhibition of TNF-gamma activity, etc. Thus, a specific embodiment of the invention relates to a TNF-gamma fragment that can be bound by an antibody that specifically binds the TNF-gamma polypeptide sequence disclosed in FIGS. 1A and B (SEQ ID NO:2), FIGS. 20A and B (SEQ ID NO:20)), and/or which is encoded by one or both of the deposited clones (HUVEO91 and HEMCZ56).

As another example, TNF-gamma fragments, derivatives or analogs which have TNF-gamma biological activity (e.g., a mature TNF-gamma-alpha polypeptide or the extracellular domain of a TNF-gamma-beta polypeptide) are provided. TNF-gamma fragments, derivatives, and analogs that retain, or alternatively lack a desired TNF-gamma property of interest (e.g., inhibition of cell proliferation, tumor inhibition, inhibition of angiogenesis, anti-arthritis by the inhibition of angiogenesis and/or endothelial cell proliferation associated with invading pannus in bone and cartilage, an inducer of NF-kappaB and c-Jun kinase (JNK), an inducer of cell adhesion, and as an inducer apoptosis (See Examples, particularly Examples 12-15)) can be used as inducers or inhibitors, respectively, of such properties and its physiological correlates.

The polypeptides of the invention may exist as a membrane bound receptor having a transmembrane region and an intra- and extracellular region or they may exist in soluble form wherein the transmembrane domain is lacking. One example of such a form of TNF-gamma is the TNF-gamma-beta polypeptide sequence shown in FIGS. 20A and B (SEQ ID NO:20) which contains a transmembrane, intracellular and extracellular domain, as described herein.

It will be recognized in the art that some amino acid sequences of the TNF-gamma polypeptide can be varied without significant effect of the structure or function of the protein. If such differences in sequence are contemplated, it should be remembered that there will be critical areas on the protein which determine activity. Thus, the invention further includes variations of the TNF-gamma polypeptide which show substantial TNF-gamma polypeptide activity or which include regions of TNF-gamma protein such as the polypeptide fragments disclosed herein. Such variants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie et al., *Science* 247:1306-1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the polypeptide of SEQ ID NO:2, or of SEQ ID NO:20, or the fragment, derivative or analog of the polypeptide of SEQ ID NO:2, or of SEQ ID NO:20, or the polypeptides encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature form of the TNF-gamma polypeptide is fused with another compound, such as a compound to increase the half-life of the polypeptide (for example, polyethylene glycol), or (iv) one in which the additional amino acids are fused to the above form of the polypeptide, such as an IgG Fc peptide, human serum albumin or a fragment or variant thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), a leader or secretory sequence, or a sequence which is employed for purification of the above form of the polypeptide or a proprotein sequence. Such fragments, derivatives and analogs are deemed to be within the scope of those skilled in the art from the teachings herein.

Thus, the TNF-gamma of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

Embodiments of the invention are directed to polypeptides which comprise the amino acid sequence of a TNF-gamma polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the TNF-gamma polynucleotide sequence described herein. Of course, in order of ever-increasing preference, it is highly preferable for a peptide or polypeptide to have an amino acid sequence which comprises the amino acid sequence of a TNF-gamma polypeptide, which contains at least one, but not more than 10, 9, 8, 7, 6, 5, 4, 3, 2 or 1 conservative amino acid substitutions.

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In further specific embodiments, the number of substitutions, additions or deletions in the amino acid sequence of FIGS. 1A and B (SEQ ID NO:2), FIGS. 20 A and B (SEQ ID NO:20), a polypeptide sequence encoded by the deposited clones, and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 150-50, 100-50, 50-20, 30-20, 20-15, 20-10, 15-10, 10-1, 5-10, 1-5, 1-3 or 1-2.

To improve or alter the characteristics of TNF-gamma polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nud Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses TNF-gamma derivatives and analogs that have one or more amino acid residues deleted, added, or substituted to generate TNF-gamma polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TNF-gamma polypeptides of the invention, and/or an amino acid deletion at the second position of any one or more such recognition sequences will prevent glycosylation of the TNF-gamma polypeptide at the modified tripeptide sequence (see, e.g., Miyajimo et al., EMBO J 5(6):1193-1197).

Additionally, the techniques of gene-shuffling, motif-shuffling, exon-shuffling, and/or codon-shuffling (collectively referred to as "DNA shuffling") may be employed to modulate the activities of TNF-gamma-alpha and/or TNF-gamma-beta thereby effectively generating agonists and antagonists of TNF-gamma-alpha and/or TNF-gamma-beta. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S. *Trends Biotechnol.* 16(2):76-82 (1998); Hansson, L. O., et al., *J. Mol. Biol.* 287:265-76 (1999); and Lorenzo, M. M. and Blasco, R. *Biotechniques* 24(2):308-13 (1998) (each of these patents and publications are hereby incorporated by reference). In one embodiment, alteration of TNF-gamma-alpha and/or TNF-gamma-beta polynucleotides and corresponding polypeptides may be achieved by DNA shuffling. DNA shuffling involves the assembly of two or more DNA segments into a desired TNF-gamma-alpha and/or TNF-gamma-beta molecule by homologous, or site-specific, recombination. In another embodiment, TNF-gamma-alpha and/or TNF-gamma-beta polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TNF-gamma-alpha and/or TNF-gamma-beta may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, AIM-I (International Publication No. WO 97/33899), AIM-II (International Publication No. WO 97/34911), APRIL (J. Exp. Med. 188(6):1185-1190), endokine-alpha (International Publication No. WO 98/07880), Neutrokine-alpha (International Publication No. WO 98/18921), OPG, OX40, and nerve growth factor (NGF), and soluble forms of Fas, CD30, CD27, CD40 and 4-IBB, DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892, TR10 (International Publication No. WO 98/54202), 312C2 (International Publication No. WO 98/06842), TR11, TR11SV1, TR11SV2, TR12, and TNF-R1, TRAMP/DR3/APO-3/WSULARD, TRAIL-R1/DR4/APO-2, TRAIL-R2/DR5, DcR1/TRAIL-R3/TRID/LIT, DcR2/TRAIL-R4, CAD, TRAIL, TRAMP, v-FLIP.

In further preferred embodiments, the heterologous molecules are any member of the TNF family.

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g.,. agonistic or antagonistic antibodies), and/or anti-CD40 antibodies (e.g., agonistic or antagonistic antibodies).

Amino acids in the TNF-gamma protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331-340 (1967); Robbins, et al., *Diabetes* 36:838-845 (1987); Cleland, et al., *Crit. Rev. Therapeutic Drug Carrier Systems* 10:307-377 (1993)).

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells et al., Philos. Trans. R. Soc. London SerA 317:415 (1986)).

Since TNF-gamma is a member of the TNF-related protein family, to modulate rather than completely eliminate biological activities of TNF-gamma preferably additions, substitutions, or deletions are made in sequences encoding amino acids in the conserved TNF-like domain, i.e., in positions 17-147 of SEQ ID NO:2 or positions 121-251 of SEQ ID NO:20, more preferably in residues within this region which are not conserved in all members of the TNF-related protein family (see FIGS. 2A-2C). Also forming part of the present invention are isolated polynucleotides comprising nucleic acid sequences which encode the above TNF-gamma variants.

Several amino acids of the TNF-gamma polypeptide are highly conserved across the known members of the TNF-related protein family. By making a specific mutation in TNF-gamma in such residues as tryptophan-15 (as numbered in SEQ ID NO:2), leucine-35, glycine-41, tyrosine-43, tyrosine-46, glutamine-48, leucine-90, leucine-116, glycine-119, aspartic acid-120, phenylalanine-141, phenylalanine-142, and leucine-147, it is likely that a noticeable effect on biological activity will be observed. These identical amino acid residues are, of course, present in the corresponding positions of TNF-gamma-beta shown in SEQ ID NO:20.

The present invention also encompasses fragments of the above-described TNF-gamma polypeptides. Polypeptide fragments of the present invention include polypeptides comprising an amino acid sequence contained in SEQ ID NO:2, encoded by the cDNA contained in the deposited clone (HUVEO91), or encoded by nucleic acids which hybridize (e.g. under stringent hybridization conditions) to the nucleotide sequence contained in the deposited clones, that shown in FIGS. 1A-1C (SEQ ID NO:1) and/or FIGS. 20A and 20B (SEQ ID NO:19), or the complementary strand thereto.

Polypeptide fragments may be "free-standing" or comprised within a larger polypeptide of which the fragment forms a part or region, most preferably as a single continuous region. Representative examples of polypeptide fragments of the invention, included, for example, fragments that comprise or alternatively, consist of, from about amino acid residues, 1 to 20, 21 to 40, 41 to 60, 61 to 83, 84 to 100, 101 to 120, 121 to 140, 141 to 160, 160 to 167, 161 to 174, 161 to 180, 181 to 200, 201 to 220, 221 to 240, 241 to 251 of SEQ ID NO:2 and/or SEQ ID NO:20. Moreover, polypeptide fragments can be at least about 20, 30, 40, 50, 60, 70, 80, 90, 100, 110, 120, 130, 140 or 150 amino acids in length. In this context "about" includes the particularly recited ranges, larger or smaller by several (i.e. 5, 4, 3, 2 or 1) amino acids, at either extreme or at both extremes.

In other embodiments, the fragments or polypeptides of the invention (i.e., those described herein) are not larger than 250, 225, 200, 185, 175, 170, 165, 160, 155, 150, 145, 140, 135, 130, 125, 120, 115, 110, 105, 100, 90, 80, 75, 60, 50, 40, 30 or 25 amino acids residues in length.

Further preferred embodiments encompass polypeptide fragments comprising, or alternatively consisting of, the mature domain of TNF-gamma-alpha (amino acid residues 1-147 of SEQ ID NO:2), the intracellular domain of TNF-gamma-beta (amino acid residues 1-35 of SEQ ID NO:20), the transmembrane domain of TNF-gamma-beta (amino acid residues 36-61 of SEQ ID NO:20), the transmembrane domain of TNF-gamma-beta (amino acid residues 36-59 of SEQ ID NO:20), the extracellular domain of TNF-gamma-beta (amino acid residues 62-251 of SEQ ID NO:20), and/or the extracellular domain of TNF-gamma-beta (amino acid residues 60-251 of SEQ ID NO:20).

In specific embodiments, polypeptide fragments of the invention comprise, or alternatively, consist of, amino acid residues leucine-35 to valine-49, tryptophan-104 to leucine-116, glycine-119 to serine-127, lysine-139 to leucine-147 of SEQ ID NO:2). These domains are regions of high identity identified by comparison of the TNF family member polypeptides shown in FIGS. 2A, 2B, and 2C.

Among the especially preferred fragments of the invention are fragments characterized by structural or functional attributes of TNF-gamma. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of TNF-gamma. Certain preferred regions are those disclosed in FIG. 17 and include, but are not limited to, regions of the aforementioned types identified by analysis of the amino acid sequence depicted in FIGS. 1A and B, such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Additionally, analogs of the invention include a proprotein which can be activated by cleavage of the proprotein portion to produce an active mature polypeptide.

In another embodiment, the invention provides a TNF-gamma polypeptide (e.g., fragment) comprising, or alternatively, consisting of, an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope". The number of immunogenic epitopes of a protein generally is less than the number of antigenic epitopes (see, for instance, Geysen, et al., *Proc. Natl. Acad. Sci. USA* 81:3998-4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660-666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl termini. Antigenic epitope-bearing peptides and polypeptides of the invention are therefore useful to raise antibodies, including monoclonal antibodies that bind specifically to a polypeptide of the invention (see, for instance, Wilson, et al., *Cell* 37:767-778 (1984)).

Figure 17:
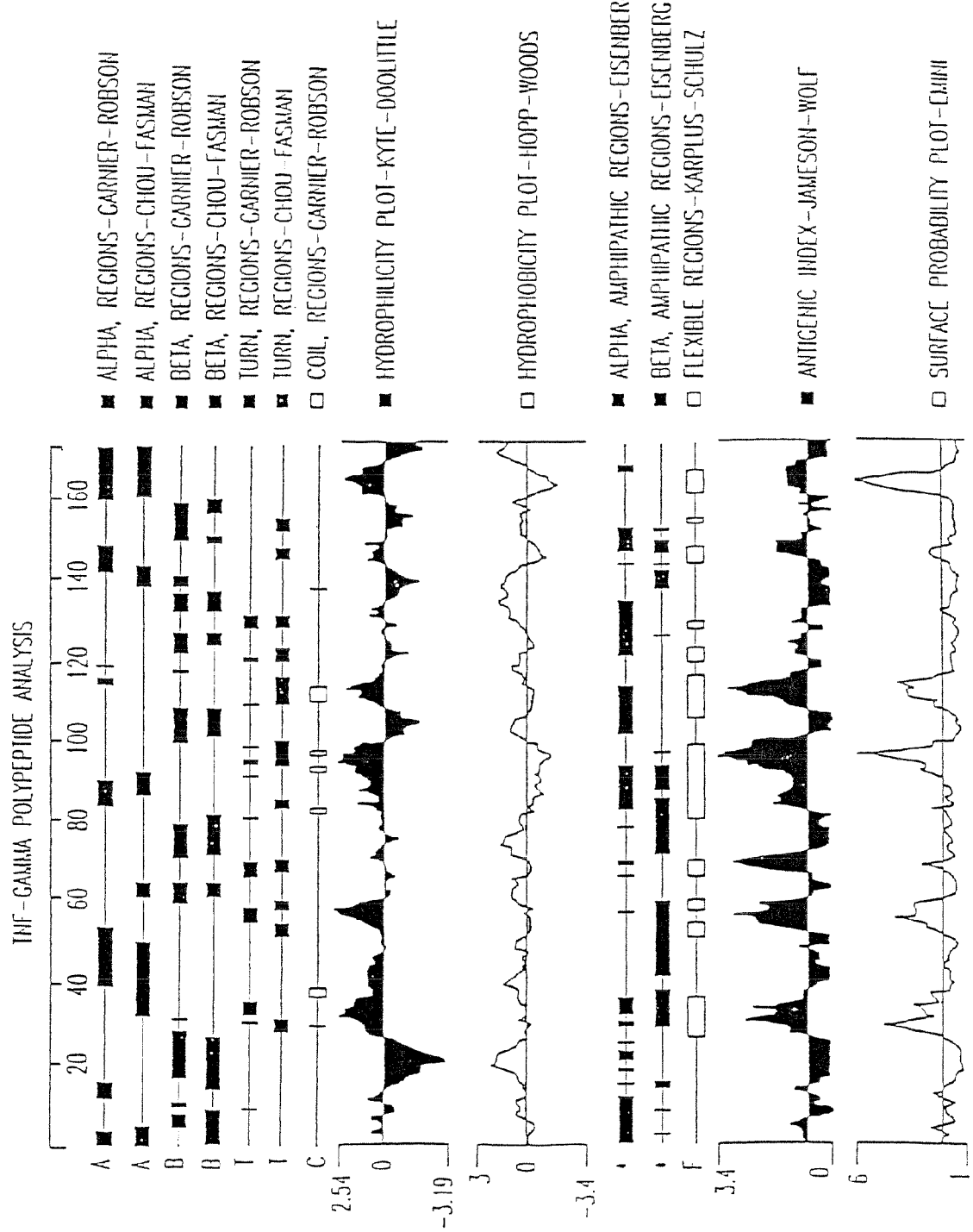
FIG. 17 shows an analysis of the TNF-gamma-alpha amino acid sequence (SEQ ID NO:2). Alpha, beta, turn and coil regions; hydrophilicity and hydrophobicity; amphipathic regions; flexible regions; antigenic index and surface probability are shown, as predicted using the default parameters of the recited computer programs. In the "Antigenic Index or Jameson-Wolf" graph, the positive peaks indicate locations of the highly antigenic regions of the TNF-gamma protein, i.e., regions from which epitope-bearing peptides of the invention can be obtained.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate TNF-gamma-specific antibodies include: a polypeptide comprising amino acid residues from about Thr-24 to about Asn-32 in SEQ ID NO:2; a polypeptide comprising amino acid residues from about Ile-37 to about Ile-45 in SEQ ID NO:2; a polypeptide comprising amino acid residues from about Met-54 to about Arg-62 in SEQ ID NO:2; a polypeptide comprising amino acid residues from about Gln-63 to about Asp-71 in SEQ ID NO:2; a polypeptide comprising amino acid residues from about Glu-57 to about Gly-65 in SEQ ID NO:2; a polypeptide comprising amino acid residues from about Val-80 to about Thr-88 in SEQ ID NO:2; a polypeptide comprising amino acid residues from about Leu-116 to about Val-124 in SEQ ID NO:2; and a polypeptide comprising amino acid residues from about Asp-133 to about Phe-141 in SEQ ID NO:2. These polypeptide fragments have been determined to bear antigenic epitopes of the TNF-gamma protein by the analysis of the Jameson-Wolf antigenic index, as shown in FIG. 17, above.

One of ordinary skill in the art may easily determine antigenic regions for TNF-gamma-beta by using data prepared through a DNA*STAR analysis of the TNF-gamma-beta polypeptide sequence (SEQ ID NO:20) using the default parameters and selecting regions with a high antigenic index as described above.

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998-4002. However, antibodies can be made to any antigenic epitope, regardless of whether it is an immunogenic epitope, by using methods such as phage display. See e.g., Petersen G. et al. (1995) Mol. Gen. Genet. 249:425-431. Therefore, included in the present invention are both immunogenic epitopes and antigenic epitopes.

A list of exemplified amino acid sequences comprising immunogenic epitopes is described above. It is pointed out that the list of immunogenic epitopes only lists amino acid residues comprising epitopes predicted to have the highest degree of antigenicity using the algorithm of Jameson and Wolf, (1988) Comp. Appl. Biosci. 4:181-186 (said references incorporated by reference in their entireties). The Jameson-Wolf antigenic analysis was performed using the computer program PROTEAN, using default parameters (Version 3.11 for the Power Macintosh, DNASTAR, Inc., 1228 South Park Street Madison, Wis.). Portions of polypeptides not listed in the above list of immunogenic epitopes are not considered non-immunogenic. The immunogenic epitopes listed above is an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5, 194,392; 4,433,092; and 5,480,971 (said references incorporated by reference in their entireties).

It is particularly pointed out that the amino acid sequences listed above comprise immunogenic epitopes. The list of immunogenic epitopes lists only the critical residues of immunogenic epitopes determined by the Jameson-Wolf analysis. Thus, additional flanking residues on either the N-terminal, C-terminal, or both N- and C-terminal ends may be added to the sequences listed above to generate an epitope-bearing polypeptide of the present invention. Therefore, the immunogenic epitopes listed above may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full-length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full-length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full-length polypeptide of the present invention. Specifically, each and every integer between 7 and the number of amino acid residues of the full-length polypeptide are included in the present invention. Further, immuno- and antigenic epitope-bearing fragments may be specified in the same way for TNF-gamma-beta by using the techniques described herein.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10-20 mgs of 248 individual and distinct 13 residue peptides representing single amino acid variants of a segment of the HAI polypeptide, all of which were prepared and characterized (by ELISA-type binding studies) in less than four weeks (Houghten, R. A. Proc. Natl. Acad. Sci. USA 82:5131-5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously (Houghten et al. (1985) Proc. Natl. Acad. Sci. 82:5131-5135 at 5134.

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347-2354. If in vivo immunization is used, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 ggs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof) may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84-86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958-3964. Nucleic acids encoding the above epitopes can also be recombined with a gene of interest as an epitope tag to aid in detection and purification of the expressed polypeptide.

The epitope-bearing peptides and polypeptides of the produced by any conventional means (see, for example, Houghten, R. A., et al., *Proc. Natl. Acad. Sci. USA* 82:5131-5135 (1985); and U.S. Pat. No. 4,631,211 to Houghten, et al. (1986)).

Epitope-bearing peptides and polypeptides of the invention invention have uses which include, but are not limited to, inducing antibodies according to methods well known in the art (see, for instance, Sutcliffe, et aL, supra; Wilson, et aL, supra; Chow, M., et al., *Proc. Natl. Acad. Sci. USA* 82:910-914; and Bittle, F. J., et aL, *J Gen. Virol.* 66:2347-2354 (1985)). Immunogenic epitope-bearing peptides of the invention, i.e., those parts of a protein that elicit an antibody response when the whole protein is the immunogen, are identified according to methods known in the art (see, for instance, Geysen, et al, supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest (e.g. DR3). Similarly, U.S. Pat. No. 5,480,971, issued to Houghten and colleagues, on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, TNF-gamma-alpha and/or TNF-gamma-beta polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84-86 (1988)). Fusion proteins that have a disulfide-linked dimeric structure due to the IgG part can also be more efficient in binding and neutralizing other molecules than the monomeric TNF-gamma protein or protein fragment alone (Fountoulakis, et al., *J. Biochem.* 270:3958-3964 (1995)). As an example, one such TNF-gamma-Fc fusion has been produced herein as described above.

Fragments (i.e., portions) of the TNF-gamma polypeptides of the present on have uses which include, but are not limited to, intermediates for producing full-length polypeptides.

For many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984-2988 (1993)) reported modified KGF proteins that had heparin binding activity even if 3, 8, or 27 N-terminal amino acid residues were missing. Further, several investigators have reported TNF-alpha muteins in which two, four or seven N-terminal amino acids had been removed which showed a 2- to 3-fold increase in functional activity when compared to the naturally-occurring TNF-alpha polypeptide (Creasey, A. A., et al., *Cancer Res.* 47:145-149 (1987); Sidhu, R. S. and Bollon, A. P. *Anticancer Res.* 9:1569-1576 (1989); Kamijo, R., et al., *Biochem. Biophys. Res. Comm.* 160:820-827 (1989)). Further, even if deletion of one or more amino acids from the N-terminus or C-terminus of a protein results in modification or loss of one or more biological functions of the protein, other TNF-gamma functional activities may still be retained In the present case, since the proteins of the invention are members of the TNF polypeptide family, deletions of N-terminal amino acids up to the leucine residue at position 35 of SEQ ID NO:2 (which corresponds exactly to the leucine residue at position 134 of SEQ ID NO:20) may retain some biological activity such as regulation of growth and differentiation of many types of hematopoietic and endothelial cells. Polypeptides having further N-terminal deletions including the leucine-36 residue in SEQ ID NO:2 (corresponding to leucine-135 in SEQ ID NO:20) would not be expected to retain such biological activities because it is known that this residue in TNF-related polypeptides is in the beginning of the conserved domain required for biological activities.

However, even if deletion of one or more amino acids from the N-terminus of a full-length TNF-gamma polypeptide results in modification or loss of one or more biological functions of the polypeptide, other biological activities may still be retained. Thus, the ability of the shortened polypeptide to induce and/or bind to antibodies which recognize the full-length or mature form of the polypeptide generally will be retained when less than the majority of the residues of the full-length or mature polypeptide are removed from the N-terminus. Whether a particular polypeptide lacking N-terminal residues of a complete polypeptide retains such immunologic activities can readily be determined by routine methods described herein and otherwise known in the art.

Accordingly, the present invention further provides polypeptides having one or more residues deleted from the amino terminus of the amino acid sequence of the TNF-gamma-alpha shown in SEQ ID NO:2, up to the leucine residue at position number 35, and polynucleotides encoding such polypeptides. In particular, the present invention provides polypeptides comprising the amino acid sequence of residues $n^1$-149 of SEQ ID NO:2, where $n^1$ is an integer in the range of −27 to 35, and 35 is the position of the first residue from the N-terminus of the complete TNF-gamma polypeptide (shown in SEQ ID NO:2) believed to be required for regulation of growth and differentiation of many types of hematopoietic and endothelial cells.

In specific embodiments, the invention provides polynucleotides encoding polypeptides comprising, or alternatively, consisting of, a member selected from the group consisting of the amino acid sequence of residues: −27 to 147, −26 to 147, −25 to 147, −24 to 147, −23 to 147, −22 to 147, −21 to 147, −20 to 147, −19 to 147, −18 to 147, −17 to 147, −16 to 147, −15 to 147, −14 to 147, −13 to 147, −12 to 147, −11 to 147, −10 to 147, −9 to 147, −8 to 147, −7 to 147, −6 to 147, −5 to 147, −4 to 147, −3 to 147, −2 to 147, −1 to 147, 1 to 147, 2 to 147, 3 to 147, 4 to 147, 5 to 147, 6 to 147, 7 to 147, 8 to 147, 9 to 147, 10 to 147, 11 to 147, 12 to 147, 13 to 147, 14 to 147, 15 to 147, 16 to 147, 17 to 147, 18 to 147, 19 to 147, 20 to 147, 21 to 147, 22 to 147, 23 to 147, 24 to 147, 27 to 147, 26 to 147, 27 to 147, 28 to 147, 29 to 147, 30 to 147, 31 to 147, 32 to 147, 33 to 147, 34 to 147, and 35 to 147 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNFgamma polypeptides described above, and the polypeptides encoded thereby. The present invention also encompasses the above polynucleotide sequences fused to a heterologous polynucleotide sequence, and the polypeptides encoded thereby.

Accordingly, the present invention further provides polypeptides having one or more residues deleted from the amino terminus of the amino acid sequence of the TNF-gamma-beta shown in SEQ ID NO:20, up to the leucine residue at position number 134, and polynucleotides encoding such polypeptides. In particular, the present invention provides polypeptides comprising the amino acid sequence of residues $n^2$-251 of SEQ ID NO:20, where $n^2$ is an integer in the range of 1 to 134, and 135 is the position of the first residue from the N-terminus of the complete TNF-gamma-beta polypeptide (shown in SEQ ID NO:20) believed to be required for regulation of growth and differentiation of many types of hematopoietic and endothelial cells activity of the TNF-gamma-beta polypeptide.

In specific embodiments, the invention provides polynucleotides encoding polypeptides comprising, or alternatively, consisting of, a member selected from the group consisting of the amino acid sequence of residues: 1 to 251, 2 to 251, 3 to 251, 4 to 251, 5 to 251, 6 to 251, 7 to 251, 8 to 251, 9 to 251, 10 to 251, 11 to 251, 12 to 251, 13 to 251, 14 to 251, 15 to 251, 16 to 251, 17 to 251, 18 to 251, 19 to 251, 20 to 251, 21 to 251, 22 to 251, 23 to 251, 24 to 251, 25 to 251, 26 to 251, 27 to 251, 28 to 251, 29 to 251, 30 to 251, 31 to 251, 32 to 251, 33 to 251, 34 to 251, 35 to 251, 36 to 251, 37 to 251, 38 to 251, 39 to 251, 40 to 251, 41 to 251, 41 to 251, 42 to 251, 43 to 251, 44 to 251, 45 to 251, 46 to 251, 47 to 251, 48 to 251, 49 to 251, 50 to 251, 51 to 251, 52 to 251, 53 to 251, 54 to 251, 55 to 251, 56 to 251, 57 to 251, 58 to 251, 59 to 251, 60 to 251, 61 to 251, 62 to 251, 63 to 251, 64 to 251, 65 to 251, 66 to 251, 67 to 251, 68 to 251, 69 to 251, 70 to 251, 71 to 251, 72 to 251, 73 to 251, 74 to 251, 75 to 251, 76 to 251, 77 to 251, 78 to 251, 79 to 251, 80 to 251, 81 to 251, 82 to 251, 83 to 251, 84 to 251, 85 to 251, 86 to 251, 87 to 251, 88 to 251, 89 to 251, 90 to 251, 91 to 251, 92 to 251, 93 to 251, 94 to 251, 95 to 251, 96 to 251, 97 to 251, 98 to 251, 99 to 251, 100 to 251, 101 to 251, 102 to 251, 103 to 251, 104 to 251, 105 to 251, 106 to 251, 107 to 251, 108 to 251, 109 to 251, 110 to 251, 111 to 251, 112 to 251, 113 to 251, 114 to 251, 115 to 251, 116 to 251, 117 to 251, 118 to 251, 119 to 251, 120 to 251, 121 to 251, 122 to 251, 123 to 251, 124 to 251, 125 to 251, 126 to 251, 127 to 251, 128 to 251, 129 to 251, 130 to 251, 131 to 251, 133 to 251, 134 to 251, and 134 to 251 of SEQ ID NO:20. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma polypeptides described above, and the polypeptides encoded thereby. The present invention also encompasses the above polynucleotide sequences fused to a heterologous polynucleotide sequence, and the polypeptides encoded thereby.

As mentioned above, even if deletion of one or more amino acids from the N-terminus of a polypeptide results in modification of loss of one or more biological functions of the polypeptide, other biological activities may still be retained. Thus, the ability of the shortened TNF-gamma-alpha mutein to induce and/or bind to antibodies which recognize the full-length or mature form of the polypeptide generally will be retained when less than the majority of the residues of the full-length or mature polypeptide are removed from the N-terminus. Whether a particular polypeptide lacking N-terminal residues of a complete protein retains such immunologic activities can readily be determined by routine methods described herein and otherwise known in the art. It is not unlikely that a TNF-gamma-alpha mutein with a large number of deleted N-terminal amino acid residues may retain some biological or immunogenic activities. In fact, peptides composed of as few as six TNF-gamma-alpha amino acid residues may often evoke an immune response.

Accordingly, the present invention further provides polypeptides having one or more residues deleted from the amino terminus of the predicted mature amino acid sequence of the TNF-gamma-alpha shown in FIGS. 1A and 1B (SEQ ID NO:2), up to the phenylalanine residue at position number 169 of the sequence shown in FIGS. 1A and 1B (which corresponds to position number 142 of SEQ ID NO:2) and polynucleotides encoding such polypeptides. In particular, the present invention provides polypeptides comprising the amino acid sequence of residues $n^3$-174 of the sequence shown in FIGS. 1A and 1B ($n^3$-147 of SEQ ID NO:2), where $n^3$ is an integer in the range of 1 to 169, and 170 is the position of the first residue from the N-terminus of the complete TNF-gamma-alpha polypeptide believed to be required for at least immunogenic activity of the TNF-gamma-alpha polypeptide.

More in particular, the invention provides polynucleotides encoding polypeptides comprising, or alternatively consisting of, a member selected from the group consisting of the amino acid sequence of residues of R-2 to L-174; R-3 to L-174; F-4 to L-174; L-5 to L-174; S-6 to L-174; K-7 to L-174; V-8 to L-174; Y-9 to L-174; S-10 to L-174; F-11 to L-174; P-12 to L-174; M-13 to L-174; R-14 to L-174; K-15 to L-174; L-16 to L-174; 1-17 to L-174; L-18 to L-174; F-19 to L-174; L-20 to L-174; V-21 to L-174; F-22 to L-174; P-23 to L-174; V-24 to L-174; V-25 to L-174; R-26 to L-174; Q-27 to L-174; T-28 to L-174; P-29 to L-174; T-30 to L-174; Q-31 to L-174; H-32 to L-174; F-33 to L-174; K-34 to L-174; N-35 to L-174; Q-36 to L-174; F-37 to L-174; P-38 to L-174; A-39 to L-174; L-40 to L-174; H-41 to L-174; W-42 to L-174; E-43 to L-174; H-44 to L-174; E-45 to L-174; L-46 to L-174; G-47 to L-174; L-48 to L-174; A-49 to L-174; F-50 to L-174; T-51 to L-174; K-52 to L-174; N-53 to L-174; R-54 to L-174; M-55 to L-174; N-56 to L-174; Y-57 to L-174; T-58 to L-174; N-59 to L-174; K-60 to L-174; F-61 to L-174; L-62 to L-174; L-63 to L-174; 1-64 to L-174; P-65 to L-174; E-66 to L-174; S-67 to L-174; G-68 to L-174; D-69 to L-174; Y-70 to L-174; F-71 to L-174; 1-72 to L-174; Y-73 to L-174; S-74 to L-174; Q-75 to L-174; V-76 to L-174; T-77 to L-174; F-78 to L-174; R-79 to L-174; G-80 to L-174; M-81 to L-174; T-82 to L-174; S-83 to L-174; E-84 to L-174; C-85 to L-174; S-86 to L-174; E-87 to L-174; 1-88 to L-174; R-89 to L-174; Q-90 to L-174; A-91 to L-174; G-92 to L-174; R-93 to L-174; P-94 to L-174; N-95 to L-174; K-96 to L-174; P-97 to L-174; D-98 to L-174; S-99 to L-174; I-100 to L-174; T-101 to L-174; V-102 to L-174; V-103 to L-174; 1-104 to L-174; T-105 to L-174; K-106 to L-174; V-107 to L-174; T-108 to L-174; D-109 to L-174; S-110 to L-174; Y-111 to L-174; P-112 to L-174; E-113 to L-174; P-114 to L-174; T-115 to L-174; Q-116 to L-174; L-117 to L-174; L-118 to L-174; M-119 to L-174; G-120 to L-174; T-121 to L-174; K-122 to L-174; S-123 to L-174; V-124 to L-174; C-125 to L-174; E-126 to L-174; V-127 to L-174; G-128 to L-174; S-129 to L-174; N-130 to L-174; W-131 to L-174; F-132 to L-174; Q-133 to L-174; P-134 to L-174; 1-135 to L-174; Y-136 to L-174; L-137 to L-174; G-138 to L-174; A-139 to L-174; M-140 to L-174; F-141 to L-174; S-142 to L-174; L-143 to L-174; Q-144 to L-174; E-145 to L-174; G-146 to L-174; D-147 to L-174; K-148 to L-174; L-149 to L-174; M-150 to L-174; V-151 to L-174; N-152 to L-174; V-153 to L-174; S-154 to L-174; D-155 to L-174; 1-156 to L-174; S-157 to L-174; L-158 to L-174; V-159 to L-174; D-160 to L-174; Y-161 to L-174; T-162 to L-174; K-163 to L-174; E-164 to L-174; D-165 to L-174; K-166 to L-174; T-167 to L-174; F-168 to L-174; and F-169 to L-174 of the TNF-gamma-alpha sequence shown in Figures IA and 1B (the TNF-gamma-alpha amino acid sequence shown in FIGS. 1A and 1B is identical to that in SEQ ID NO:2, however, the numbering scheme differs between the two; the numbering of the above amino acid residues in this case reflects that of FIGS. 1A and 1B). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma polypeptides described above, and the polypeptides encoded thereby. The present invention also encompasses the above polynucleotide sequences fused to a heterologous polynucleotide sequence, and the polypeptides encoded thereby.

Accordingly, the present invention further provides polypeptides having one or more residues deleted from the amino terminus of the predicted mature amino acid sequence of the TNF-gamma-beta shown in SEQ ID NO:20, up to the phenylalanine residue at position number 246 and polynucleotides encoding such polypeptides. In particular, the present invention provides polypeptides comprising the amino acid sequence of residues $n^4$-251 of SEQ ID NO:20, where $n^4$ is an integer in the range of 2 to 246, and 247 is the position of the first residue from the N-terminus of the complete TNF-gamma-beta polypeptide believed to be required for at least immunogenic activity of the TNF-gamma-beta protein.

More in particular, the invention provides polynucleotides encoding polypeptides comprising, or alternatively consisting of, a member selected from the group consisting of the amino acid sequence of residues of A-2 to L-251; E-3 to L-251; D-4 to L-251; L-5 to L-251; G-6 to L-251; L-7 to L-251; S-8 to L-251; F-9 to L-251; G-10 to L-251; E-11 to L-251; T-12 to L-251; A-13 to L-251; S-14 to L-251; V-15 to L-251; E-16 to L-251; M-17 to L-251; L-18 to L-251; P-19 to L-251; E-20 to L-251; H-21 to L-251; G-22 to L-251; S-23 to L-251; C-24 to L-251; R-25 to L-251; P-26 to L-251; K-27 to L-251; A-28 to L-251; R-29 to L-251; S-30 to L-251; S-31 to L-251; S-32 to L-251; A-33 to L-251; R-34 to L-251; W-35 to L-251; A-36 to L-251; L-37 to L-251; T-38 to L-251; C-39 to L-251; C-40 to L-251; L-41 to L-251; V-42 to L-251; L-43 to L-251; L-44 to L-251; P-45 to L-251; F-46 to L-251; L-47 to L-251; A-48 to L-251; G-49 to L-251; L-50 to L-251; T-51 to L-251; T-52 to L-251; Y-53 to L-251; L-54 to L-251; L-55 to L-251; V-56 to L-251; S-57 to L-251; Q-58 to L-251; L-59 to L-251; R-60 to L-251; A-61 to L-251; Q-62 to L-251; G-63 to L-251; E-64 to L-251; A-65 to L-251; C-66 to L-251; V-67 to L-251; Q-68 to L-251; F-69 to L-251; Q-70 to L-251; A-71 to L-251; L-72 to L-251; K-73 to L-251; G-74 to L-251; Q-75 to L-251; E-76 to L-251; F-77 to L-251; A-78 to L-251; P-79 to L-251; S-80 to L-251; H-81 to L-251; Q-82 to L-251; Q-83 to L-251; V-84 to L-251; Y-85 to L-251; A-86 to L-251; P-87 to L-251; L-88 to L-251; R-89 to L-251; A-90 to L-251; D-91 to L-251; G-92 to L-251; D-93 to L-251; K-94 to L-251; P-95 to L-251; R-96 to L-251; A-97 to L-251; H-98 to L-251; L-99 to L-251; T-100 to L-251; V-101 to L-251; V-102 to L-251; R-103 to L-251; Q-104 to L-251; T-105 to L-251; P-106 to L-251; T-107 to L-251; Q-108 to L-251; H-109 to L-251; F-110 to L-251; K-111 to L-251; N-112 to L-251; Q-113 to L-251; F-114 to L-251; P-115 to L-251; A-116 to L-251; L-117 to L-251; H-118 to L-251; W-119 to L-251; E-120 to L-251; H-121 to L-251; E-122 to L-251; L-123 to L-251; G-124 to L-251; L-125 to L-251; A-126 to L-251; F-127 to L-251; T-128 to L-251; K-129 to L-251; N-130 to L-251; R-131 to L-251; M-132 to L-251; N-133 to L-251; Y-134 to L-251; T-135 to L-251; N-136 to L-251; K-137 to L-251; F-138 to L-251; L-139 to L-251; L-140 to L-251; 1-141 to L-251; P-142 to L-251; E-143 to L-251; S-144 to L-251; G-145 to L-251; D-146 to L-251; Y-147 to L-251; F-148 to L-251; 1-149 to L-251; Y-150 to L-251; S-151 to L-251; Q-152 to L-251; V-153 to L-251; T-154 to L-251; F-155 to L-251; R-156 to L-251; G-157 to L-251; M-158 to L-251; T-159 to L-251; S-160 to L-251; E-161 to L-251; C-162 to L-251; S-163 to L-251; E-164 to L-251; I-165 to L-251; R-166 to L-251; Q-167 to L-251; A-168 to L-251; G-169 to L-251; R-170 to L-251; P-171 to L-251; N-172 to L-251; K-173 to L-251; P-174 to L-251; D-175 to L-251; S-176 to L-251; 1-177 to L-251; T-178 to L-251; V-179 to L-251; V-180 to L-251; 1-181 to L-251; T-182 to L-251; K-183 to L-251; V-184 to L-251; T-185 to L-251; D-186 to L-251; S-187 to L-251; Y-188 to L-251; P-189 to L-251; E-190 to L-251; P-191 to L-251; T-192 to L-251; Q-193 to L-251; L-194 to L-251; L-195 to L-251; M-196 to L-251; G-197 to L-251; T-198 to L-251; K-199 to L-251; S-200 to L-251; V-201 to L-251; C-202 to L-251; E-203 to L-251; V-204 to L-251; G-205 to L-251; S-206 to L-251; N-207 to L-251; W-208 to L-251; F-209 to L-251; Q-210 to L-251; P-211 to L-251; I-212 to L-251; Y-213 to L-251; L-214 to L-251; G-215 to L-251; A-216 to L-251; M-217 to L-251; F-218 to L-251; S-219 to L-251; L-220 to L-251; Q-221 to L-251; E-222 to L-251; G-223 to L-251; D-224 to L-251; K-225 to L-251; L-226 to L-251; M-227 to L-251; V-228 to L-251; N-229 to L-251; V-230 to L-251; S-231 to L-251; D-232 to L-251; I-233 to L-251; S-234 to L-251; L-235 to L-251; V-236 to L-251; D-237 to L-251; Y-238 to L-251; T-239 to L-251; K-240 to L-251; E-241 to L-251; D-242 to L-251; K-243 to L-251; T-244 to L-251; F-245 to L-251; and F-246 to L-251 of the TNF-gamma-beta sequence shown in SEQ ID NO:20. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma polypeptides described above, and the polypeptides encoded thereby. The present invention also encompasses the above polynucleotide sequences fused to a heterologous polynucleotide sequence, and the polypeptides encoded thereby.

Similarly, many examples of biologically functional C-terminal deletion muteins are known. For instance, Interferon gamma shows up to ten times higher activities by deleting 8 to 10 amino acid residues from the carboxy terminus of the protein (Dobeli, et al., *J. Biotechnology* 7:199-216 (1988)). Further, several investigators have reported biologically inactive TNF-alpha muteins in which as few as two amino acids had been removed from the C-terminus (Carlino, J. A., et al., *J. Biol. Chem.* 262:958-961 (1987); Creasey, A. A., et al., *Cancer Res.* 47:145-149 (1987); Sidhu, R. S. and Bollon, A. P. Anticancer Res. 9:1569-1576 (1989); Gase, K., et al., *Immunology* 71:368-371 (1990)).

In the present case, since the proteins of the invention are members of the TNF polypeptide family, deletions of C-terminal amino acids up to the leucine at position 146 of SEQ ID NO:2 (which corresponds to the leucine at position 250 of SEQ ID NO:20) may retain some biological activity such as regulation of growth and differentiation of many types of hematopoietic and endothelial cells. Polypeptides having further C-terminal deletions including the leucine residue at position 146 of SEQ ID NO:2 (or the leucine residue at position 250 of SEQ ID NO:20) would not be expected to retain such biological activities because it is known that this residue in TNF-related polypeptides is in the beginning of the conserved domain required for biological activities.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

In additional embodiments, the present invention further provides polypeptides having one or more residues removed from the carboxy terminus of the amino acid sequence of the TNF-gamma-alpha shown in SEQ ID NO:2, up to the leucine residue at position 146 of SEQ ID NO:2, and polynucleotides encoding such polypeptides. In particular, the present invention provides polypeptides having the amino acid sequence of residues $-27-m^1$ of the amino acid sequence in SEQ ID NO:2, where $m^1$ is any integer in the range of 146 to 147, and residue 146 is the position of the first residue from the C-terminus of the complete TNF-gamma-alpha polypeptide (shown in SEQ ID NO:2) believed to be required for regulation of growth and differentiation of many types of hematopoietic and endothelial cells by the TNF-gamma-alpha polypeptide.

More in particular, the invention provides polynucleotides encoding polypeptides having the amino acid sequence of residues $-27-146$ and $-27-147$ of SEQ ID NO:2. Polynucleotides encoding these polypeptides also are provided.

The present invention also provides polypeptides having one or more residues removed from the carboxy terminus of the amino acid sequence of the TNF-gamma-beta shown in SEQ ID NO:20, up to the leucine residue at position 250 of SEQ ID NO:20, and polynucleotides encoding such polypeptides. In particular, the present invention provides polypeptides having the amino acid sequence of residues $1-m^2$ of the amino acid sequence in SEQ ID NO:20, where $m^2$ is any integer in the range of 250 to 251, and residue 249 is the position of the first residue from the C-terminus of the complete TNF-gamma-beta polypeptide (shown in SEQ ID NO:20) believed to be required for regulation of growth and differentiation of many types of hematopoietic and endothelial cells.

More in particular, the invention provides polynucleotides encoding polypeptides having the amino acid sequence of residues 1-250 and 1-251 of SEQ ID NO:20. Polynucleotides encoding these polypeptides also are provided.

The invention also provides polypeptide fragments comprising, or alternatively consisting of, one or more amino acids deleted from both the amino and the carboxyl termini of TNF-gamma-alpha, which may be described generally as having residues $n^1-m^1$ of SEQ ID NO:2, where n and m are integers as described above. The invention further provides polypeptides having one or more amino acids deleted from both the amino and the carboxyl termini of TNF-gamma-beta, which may be described generally as having residues $n^2-m^2$ of SEQ ID NO:20, where $n^2$ and $m^2$ are integers as described above.

As mentioned above, even if deletion of one or more amino acids from the C-terminus of a polypeptide results in modification of loss of one or more biological functions of the polypeptide, other biological activities may still be retained. Thus, the ability of the shortened TNF-gamma-alpha mutein to induce and/or bind to antibodies which recognize the full-length or mature of the polypeptide generally will be retained when less than the majority of the residues of the complete or mature polypeptide are removed from the C-terminus. Whether a particular polypeptide lacking C-terminal residues of a full-length polypeptide retains such immunologic activities can readily be determined by routine methods described herein and otherwise known in the art. It is not unlikely that a TNF-gamma-alpha mutein with a large number of deleted C-terminal amino acid residues may retain some biological or immunogenic activities. In fact, peptides composed of as few as six TNF-gamma-alpha amino acid residues may often evoke an immune response.

Accordingly, the present invention further provides polypeptides having one or more residues deleted from the carboxy terminus of the amino acid sequence of the TNF-gamma-alpha shown in FIGS. 1A and 1B (or in SEQ ID NO:2), up to the serine residue at position number 6 in FIGS. 1A and 1B (or –22 in SEQ ID NO:2), and polynucleotides encoding such polypeptides. In particular, the present invention provides polypeptides comprising the amino acid sequence of residues $1-m^3$ of SEQ ID NO:2, where $m^3$ is an integer in the range of 6 to 174, and 6 is the position of the first residue from the C-terminus of the complete TNF-gamma-alpha polypeptide believed to be required for at least immunogenic activity of TNF-gamma-alpha.

More in particular, the invention provides polynucleotides encoding polypeptides comprising, or alternatively consisting of, a member selected from the group consisting of the amino acid sequence of residues M-1 to L-173; M-1 to F-172; M-1 to A-171; M-1 to G-170; M-1 to F-169; M-1 to F-168; M-1 to T-167; M-1 to K-166; M-1 to D-165; M-1 to E-164; M-1 to K-163; M-1 to T-162; M-1 to Y-161; M-1 to D-160; M-1 to V-159; M-1 to L-158; M-1 to S-157; M-1 to I-156; M-1 to D-155; M-1 to S-154; M-1 to V-153; M-1 to N-152; M-1 to V-151; M-1 to M-150; M-1 to L-149; M-1 to K-148; M-1 to D-147; M-1 to G-146; M-1 to E-145; M-1 to Q-144; M-1 to L-143; M-1 to S-142; M-1 to F-141; M-1 to M-140; M-1 to A-139; M-1 to G-138; M-1 to L-137; M-1 to Y-136; M-1 to I-135; M-1 to P-134; M-1 to Q-133; M-1 to F-132; M-1 to W-131; M-1 to N-130; M-1 to S-129; M-1 to G-128; M-1 to V-127; M-1 to E-126; M-1 to C-125; M-1 to V-124; M-1 to S-123; M-1 to K-122; M-1 to T-121; M-1 to G-120; M-1 to M-119; M-1 to L-118; M-1 to L-117; M-1 to Q-116; M-1 to T-115; M-1 to P-114; M-1 to E-113; M-1 to P-112; M-1 to Y-111; M-1 to S-110; M-1 to D-109; M-1 to T-108; M-1 to V-107; M-1 to K-106; M-1 to T-105; M-1 to I-104; M-1 to V-103; M-1 to V-102; M-1 to T-101; M-1 to I-100; M-1 to S-99; M-1 to D-98; M-1 to P-97; M-1 to K-96; M-1 to N-95; M-1 to P-94; M-1 to R-93; M-1 to G-92; M-1 to A-91; M-1 to Q-90; M-1 to R-89; M-1 to I-88; M-1 to E-87; M-1 to S-86; M-1 to C-85; M-1 to E-84; M-1 to S-83; M-1 to T-82; M-1 to M-81; M-1 to G-80; M-1 to R-79; M-1 to F-78; M-1 to T-77; M-1 to V-76; M-1 to Q-75; M-1 to S-74; M-1 to Y-73; M-1 to I-72; M-1 to F-71; M-1 to Y-70; M-1 to D-69; M-1 to G-68; M-1 to S-67; M-1 to E-66; M-1 to P-65; M-1 to I-64; M-1 to L-63; M-1 to L-62; M-1 to F-61; M-1 to K-60; M-1 to N-59; M-1 to T-58; M-1 to Y-57; M-1 to N-56; M-1 to M-55; M-1 to R-54; M-1 to N-53; M-1 to K-52; M-1 to T-51; M-1 to F-50; M-1 to A-49; M-1 to L-48; M-1 to G-47; M-1 to L-46; M-1 to E-45; M-1 to H-44; M-1 to E-43; M-1 to W-42; M-1 to H-41; M-1 to L-40; M-1 to A-39; M-1 to P-38; M-1 to F-37; M-1 to Q-36; M-1 to N-35; M-1 to K-34; M-1 to F-33; M-1 to H-32; M-1 to Q-31; M-1 to T-30; M-1 to P-29; M-1 to T-28; M-1 to Q-27; M-1 to R-26; M-1 to V-25; M-1 to V-24; M-1 to P-23; M-1 to F-22; M-1 to V-21; M-1 to L-20; M-1 to F-19; M-1 to L-18; M-1 to I-17; M-1 to L-16; M-1 to K-15; M-1 to R-14; M-1 to M-13; M-1 to P-12; M-1 to F-11; M-1 to S-10; M-1 to Y-9; M-1 to V-8; M-1 to K-7; and M-1 to S-6 of the sequence of the TNF-gamma-alpha sequence shown in FIGS. 1A and 1B (the TNF-gamma-alpha amino acid sequence shown in FIGS. 1A and 1B is identical to that in SEQ ID NO:2, however, the numbering scheme differs between the two; the numbering of the above amino acid residues in this case reflects that of FIGS. 1A and 1B). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TNF-gamma-alpha polypeptide, which may be described generally as having residues $n^3$-$m^3$ of SEQ ID NO:2, where $n^3$ and $m^3$ are integers as described above. Polynucleotides encoding the polypeptides are also encompassed by the invention.

The present invention further provides polypeptides having one or more residues deleted from the carboxy terminus of the amino acid sequence of the TNF-gamma-beta shown in SEQ ID NO:20, up to the glycine residue at position number 6, and polynucleotides encoding such polypeptides. In particular, the present invention provides polypeptides comprising the amino acid sequence of residues 1-$m^4$ of SEQ ID NO:20, where $m^4$ is an integer in the range of 6 to 250, and 6 is the position of the first residue from the C-terminus of the complete TNF-gamma-beta polypeptide believed to be required for at least immunogenic activity of the TNF-gamma-beta protein.

More in particular, the invention provides polynucleotides encoding polypeptides comprising, or alternatively consisting of, a member selected from the group consisting of the amino acid sequence of residues M-1 to L-250; M-1 to F-249; M-1 to A-248; M-1 to G-247; M-1 to F-246; M-1 to F-245; M-1 to T-244; M-1 to K-243; M-1 to D-242; M-1 to E-241; M-1 to K-240; M-1 to T-239; M-1 to Y-238; M-1 to D-237; M-1 to V-236; M-1 to L-235; M-1 to S-234; M-1 to I-233; M-1 to D-232; M-1 to S-231; M-1 to V-230; M-1 to N-229; M-1 to V-228; M-1 to M-227; M-1 to L-226; M-1 to K-225; M-1 to D-224; M-1 to G-223; M-1 to E-222; M-1 to Q-221; M-1 to L-220; M-1 to S-219; M-1 to F-218; M-1 to M-217; M-1 to A-216; M-1 to G-215; M-1 to L-214; M-1 to Y-213; M-1 to I-212; M-1 to P-211; M-1 to Q-210; M-1 to F-209; M-1 to W-208; M-1 to N-207; M-1 to S-206; M-1 to G-205; M-1 to V-204; M-1 to E-203; M-1 to C-202; M-1 to V-201; M-1 to S-200; M-1 to K-199; M-1 to T-198; M-1 to G-197; M-1 to M-196; M-1 to L-195; M-1 to L-194; M-1 to Q-193; M-1 to T-192; M-1 to P-191; M-1 to E-190; M-1 to P-189; M-1 to Y-188; M-1 to S-187; M-1 to D-186; M-1 to T-185; M-1 to V-184; M-1 to K-183; M-1 to T-182; M-1 to I-181; M-1 to V-180; M-1 to V-179; M-1 to T-178; M-1 to I-177; M-1 to S-176; M-1 to D-175; M-1 to P-174; M-1 to K-173; M-1 to N-172; M-1 to P-171; M-1 to R-170; M-1 to G-169; M-1 to A-168; M-1 to Q-167; M-1 to R-166; M-1 to I-165; M-1 to E-164; M-1 to S-163; M-1 to C-162; M-1 to E-161; M-1 to S-160; M-1 to T-159; M-1 to M-158; M-1 to G-157; M-1 to R-156; M-1 to F-155; M-1 to T-154; M-1 to V-153; M-1 to Q-152; M-1 to S-151; M-1 to Y-150; M-1 to 1-149; M-1 to F-148; M-1 to Y-147; M-1 to D-146; M-1 to G-145; M-1 to S-144; M-1 to E-143; M-1 to P-142; M-1 to 1-141; M-1 to L-140; M-1 to L-139; M-1 to F-138; M-1 to K-137; M-1 to N-136; M-1 to T-135; M-1 to Y-134; M-1 to N-133; M-1 to M-132; M-1 to R-131; M-1 to N-130; M-1 to K-129; M-1 to T-128; M-1 to F-127; M-1 to A-126; M-1 to L-125; M-1 to G-124; M-1 to L-123; M-1 to E-122; M-1 to H-121; M-1 to E-120; M-1 to W-119; M-1 to H-118; M-1 to L-117; M-1 to A-116; M-1 to P-115; M-1 to F-114; M-1 to Q-113; M-1 to N-112; M-1 to K-111; M-1 to F-110; M-1 to H-109; M-1 to Q-108; M-1 to T-107; M-1 to P-106; M-1 to T-105; M-1 to Q-104; M-1 to R-103; M-1 to V-102; M-1 to V-101; M-1 to T-100; M-1 to L-99; M-1 to H-98; M-1 to A-97; M-1 to R-96; M-1 to P-95; M-1 to K-94; M-1 to D-93; M-1 to G-92; M-1 to D-91; M-1 to A-90; M-1 to R-89; M-1 to L-88; M-1 to P-87; M-1 to A-86; M-1 to Y-85; M-1 to V-84; M-1 to Q-83; M-1 to Q-82; M-1 to H-81; M-1 to S-80; M-1 to P-79; M-1 to A-78; M-1 to F-77; M-1 to E-76; M-1 to Q-75; M-1 to G-74; M-1 to K-73; M-1 to L-72; M-1 to A-71; M-1 to Q-70; M-1 to F-69; M-1 to Q-68; M-1 to V-67; M-1 to C-66; M-1 to A-65; M-1 to E-64; M-1 to G-63; M-1 to Q-62; M-1 to A-61; M-1 to R-60; M-1 to L-59; M-1 to Q-58; M-1 to S-57; M-1 to V-56; M-1 to L-55; M-1 to L-54; M-1 to Y-53; M-1 to T-52; M-1 to T-51; M-1 to L-50; M-1 to G-49; M-1 to A-48; M-1 to L-47; M-1 to F-46; M-1 to P-45; M-1 to L-44; M-1 to L-43; M-1 to V-42; M-1 to L-41; M-1 to C-40; M-1 to C-39; M-1 to T-38; M-1 to L-37; M-1 to A-36; M-1 to W-35; M-1 to R-34; M-1 to A-33; M-1 to S-32; M-1 to S-31; M-1 to S-30; M-1 to R-29; M-1 to A-28; M-1 to K-27; M-1 to P-26; M-1 to R-25; M-1 to C-24; M-1 to S-23; M-1 to G-22; M-1 to H-21; M-1 to E-20; M-1 to P-19; M-1 to L-18; M-1 to M-17; M-1 to E-16; M-1 to V-15; M-1 to S-14; M-1 to A-13; M-1 to T-12; M-1 to E-11; M-1 to G-10; M-1 to F-9; M-1 to S-8; M-1 to L-7; and M-1 to G-6 of the sequence of the TNF-gamma-beta sequence shown in SEQ ID NO:20. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the TNF-gamma polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TNF-gamma-beta polypeptide, which may be described generally as having residues $n^4$-$m^4$ of SEQ ID NO:20, where $n^4$ and $m^4$ are integers as described above. Polynucleotides encoding these polypeptides are also encompassed by the invention.

Further embodiments of the invention are directed to polypeptide fragments comprising, or alternatively, consisting of, amino acids described by the general formula $m^x$ to $n^x$, where m and n correspond to any one of the amino acid residues specified above for these symbols, respectively, and x represents any integer. Polynucleotides encoding these polypeptides are also encompassed by the invention.

In additional embodiments, the present invention provides polynucleotides encoding polypeptides comprising the amino acid sequence of residues 72-$m^4$ of FIG. 1 (i.e., SEQ ID NO:2), where $m^4$ is an integer from 78 to 250, corresponding to the position of the amino acid residue in SEQ ID NO:20. For example, the invention provides polynucleotides encoding polypeptides comprising, or alternatively consisting of, a member selected from the group consisting of the amino acid sequence of residues L-72 to L-250; L-72 to F-249; L-72 to A-248; L-72 to G-247; L-72 to F-246; L-72 to F-245; L-72 to T-244; L-72 to K-243; L-72 to D-242; L-72 to E-241; L-72 to K-240; L-72 to T-239; L-72 to Y-238; L-72 to D-237; L-72 to V-236; L-72 to L-235; L-72 to S-234; L-72 to I-233; L-72 to D-232; L-72 to S-231; L-72 to V-230; L-72 to N-229; L-72 to V-228; L-72 to M-227; L-72 to L-226; L-72 to K-225; L-72 to D-224; L-72 to G-223; L-72 to E-222; L-72 to Q-221; L-72 to L-220; L-72 to S-219; L-72 to F-218; L-72 to M-217; L-72 to A-216; L-72 to G-215; L-72 to L-214; L-72 to Y-213; L-72 to I-212; L-72 to P-211; L-72 to Q-210; L-72 to F-209; L-72 to W-208; L-72 to N-207; L-72 to S-206; L-72 to G-205; L-72 to V-204; L-72 to E-203; L-72 to C-202; L-72 to V-201; L-72 to S-200; L-72 to K-199; L-72 to T-198; L-72 to G-197; L-72 to M-196; L-72 to L-195; L-72 to L-194; L-72 to Q-193; L-72 to T-192; L-72 to P-191; L-72 to E-190; L-72 to P-189; L-72 to Y-188; L-72 to S-187; L-72 to D-186; L-72 to T-185; L-72 to V-184; L-72 to K-183; L-72 to T-182; L-72 to I-181; L-72 to V-180; L-72 to V-179; L-72 to T-178; L-72 to I-177; L-72 to S-176; L-72 to D-175; L-72 to P-174; L-72 to K-173; L-72 to N-172; L-72 to P-171; L-72 to R-170; L-72 to G-169; L-72 to A-168; L-72 to Q-167; L-72 to R-166; L-72 to I-165; L-72 to E-164; L-72 to S-163; L-72 to. C-162; L-72 to E-161; L-72 to S-160; L-72 to T-159; L-72 to M-158; L-72 to G-157; L-72 to R-156; L-72 to F-155; L-72 to T-154; L-72 to V-153; L-72 to Q-152; L-72 to S-151; L-72 to Y-150; L-72 to I-149; L-72 to F-148; L-72 to Y-147; L-72 to D-146; L-72 to G-145; L-72 to S-144; L-72 to E-143; L-72 to P-142; L-72 to I-141; L-72 to L-140; L-72 to L-139; L-72 to F-138; L-72 to K-137; L-72 to N-136; L-72 to T-135; L-72 to Y-134; L-72 to N-133; L-72 to M-132; L-72 to R-131; L-72 to N-130; L-72 to K-129; L-72 to T-128; L-72 to F-127; L-72 to A-126; L-72 to L-125; L-72 to G-124; L-72 to L-123; L-72 to E-122; L-72 to H-121; L-72 to E-120; L-72 to W-119; L-72 to H-118; L-72 to L-117; L-72 to A-116; L-72 to P-115; L-72 to F-114; L-72 to Q-113; L-72 to N-112; L-72 to K-111; L-72 to F-110; L-72 to H-109; L-72 to Q-108; L-72 to T-107; L-72 to P-106; L-72 to T-105; L-72 to Q-104; L-72 to R-103; L-72 to V-102; L-72 to V-101; L-72 to T-100; L-72 to L-99; L-72 to H-98; L-72 to A-97; L-72 to R-96; L-72 to P-95; L-72 to K-94; L-72 to D-93; L-72 to G-92; L-72 to P-91; L-72 to A-90; L-72 to R-89; L-72 to L-88; L-72 to P-87; L-72 to A-86; L-72 to Y-85; L-72 to V-84; L-72 to Q-83; L-72 to Q-82; L-72 to H-81; L-72 to S-80; L-72 to P-79; L-72 to A-78; of the sequence of the TNF-gamma-beta sequence shown in SEQ ID NO:20. The present application is also directed to nucleic acid molecules comprising, or alternatively, consisting of, a polynucleotide sequence at least 85%, 90%, 92%, 94%, 95%, 96%, 97%, 98% or 99% identical to the polynucleotide sequence described above. The present invention also encompasses these polynucleotide sequences fused to a heterologous polynucleotide sequence. Polypeptides encoded by these nucleic acids and/or polynucleotide sequences are also encompassed by the invention.

Specific embodiments of the invention are directed to nucleotide sequences encoding a polypeptide consisting of a portion of the complete TNF-gamma-alpha amino acid sequence encoded by the cDNA clone contained in ATCC™ Deposit No. 75927, where this portion excludes from 1 to about 62 amino acids from the amino terminus of the complete amino acid sequence encoded by the cDNA clone contained in ATCC™ Deposit No. 75927, or about 1 amino acid from the carboxy terminus, or any combination of the above amino terminal and carboxy terminal deletions, of the complete amino acid sequence encoded by the cDNA clone contained in ATCC™ Deposit No. 75927. Polynucleotides encoding all of the above deletion mutant polypeptide forms also are provided.

In another embodiment, the invention is directed to a nucleotide sequence encoding a polypeptide consisting of a portion of the complete TNF-gamma-beta amino acid sequence encoded by the cDNA clone contained in ATCC™ Deposit No. 203055, where this portion excludes from 1 to about 134 amino acids from the amino terminus of the complete amino acid sequence encoded by the cDNA clone contained in ATCC™ Deposit No. 203055, or excludes a number of amino acids from the amino terminus of the complete amino acid sequence encoded by the cDNA clone contained in ATCC™ Deposit No. 203055 (where the number is selected from any integer from 1 to 134), or about 1 amino acid from the carboxy terminus, or any combination of the above amino terminal and carboxy terminal deletions, of the complete amino acid sequence encoded by the cDNA clone contained in ATCC™ Deposit No. 203055. Polynucleotides encoding all of the above polypeptides are also encompassed by the invention.

The invention further provides an isolated TNF-gamma polypeptide comprising an amino acid sequence selected from the group consisting of: (a) the amino acid sequence of the full-length TNF-gamma-alpha polypeptide having the complete amino acid sequence shown in SEQ ID NO:2 (i.e., positions -27 to 147 of SEQ ID NO:2); (b) the amino acid sequence of the full-length TNF-gamma-alpha polypeptide having the complete amino acid sequence shown in SEQ ID NO:2 excepting the N-terminal methionine (i.e., positions -26 to 147 of SEQ ID NO:2); (c) the amino acid sequence of the predicted mature TNF-gamma-alpha polypeptide having the amino acid sequence at positions 1-147 in SEQ ID NO:2 (d) the complete amino acid sequence encoded by the cDNA clone HUVEO91 contained in the ATCC™ Deposit No. 75927; (e) the complete amino acid sequence excepting the N-terminal methionine encoded by the cDNA clone contained in the ATCC™ Deposit No. 75927; and (f) the complete amino acid sequence of the predicted mature TNF-gamma polypeptide encoded by the cDNA clone HUVEO91 contained in the ATCC™ Deposit No. 75927. The polypeptides of the present invention also include polypeptides having an amino acid sequence at least 70% identical, at least 80% or 85% identical, more preferably at least 90%, 92% or 94% identical, and still more preferably 95%, 96%, 97%, 98% or 99% identical to those described in (a), (b), (c), (d), (e) or (f), above, or fragments thereof, as described herein.

The invention further provides an isolated TNF-gamma polypeptide comprising an amino acid sequence selected from the group consisting of (a) the amino acid sequence of the full-length TNF-gamma-beta polypeptide having the complete amino acid sequence shown in SEQ ID NO:20 (i.e., positions 1 to 251 of SEQ ID NO:20); (b) the amino acid sequence of the full-length TNF-gamma-beta polypeptide having the complete amino acid sequence shown in SEQ ID NO:20 excepting the N-terminal methionine (i.e., positions 2 to 251 of SEQ ID NO:20); (c) the amino acid sequence of the predicted mature TNF-gamma-beta polypeptide having the amino acid sequence at positions 62-251 in SEQ ID NO:20; (d) the complete amino acid sequence encoded by the cDNA clone HEMCZ56 contained in the ATCC™ Deposit No. 203055; (e) the complete amino acid sequence excepting the N-terminal methionine encoded by the cDNA clone HEMCZ56 contained in the ATCC™ Deposit No. 203055; and (f) the complete amino acid sequence of the predicted mature TNF-gamma polypeptide encoded by the cDNA clone HEMCZ56 contained in the ATCC™ Deposit No. 203055. The polypeptides of the present invention also include polypeptides having an amino acid sequence at least 70% identical, at least 80% or 85% identical, more preferably at least 90%, 92% or 94% identical, and still more preferably 95%, 96%, 97%, 98% or 99% identical to those described in (a), (b), (c), (d), (e) or (f), above, or fragments thereof, as described herein. In specific embodiments, these polypeptides are at least 10 amino acids, at least 15 amino acids, at least 20 amino acids, at least 25 amino acids, at least 30 amino acids and more preferably at least 50 amino acids.

By a polypeptide having an amino acid sequence at least, for example, 95% "identical" to a reference amino acid sequence of a TNF-gamma polypeptide is intended that the amino acid sequence of the polypeptide is identical to the reference sequence except that the polypeptide sequence may include up to five amino acid alterations per each 100 amino acids of the reference amino acid of the TNF-gamma polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and B (SEQ ID NO:2), the amino acid sequence encoded by deposited cDNA clone HUVEO91, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty-1, Joining Penalty=20, Randomization Group Length=0, Cutoff Score=l, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

The polypeptides of the present invention also include the polypeptide of SEQ ID NO:20 (in particular the extracellular domain of the polypeptide) as well as polypeptides which have at least 70% similarity (preferably at least 70% identity) to the polypeptide of SEQ ID NO:20 and more preferably at least 90% similarity (more preferably at least 90% identity) to the polypeptide of SEQ ID NO:20 and still more preferably at least 95% similarity (still more preferably at least 95% identity) to the polypeptide of SEQ ID NO:20 and also include portions of such polypeptides with such portion of the polypeptide generally containing at least 30 amino acids and more preferably at least 50 amino acids.

Further polypeptides of the present invention include polypeptides have at least 70% similarity, at least 90% similarity, more preferably at least 95% similarity, and still more preferably at least 96%, 97%, 98% or 99% similarity to those polypeptides described herein. The polypeptides of the invention also comprise those which are at least 70% identical, at least 80% identical, more preferably at least 90% or 95% identical, still more preferably at least 96%, 97%, 98% or 99% identical to the polypeptides disclosed herein. In specific embodiments, such polypeptides comprise at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC™ deposit No. 75927 or encoded by a polynucleotide that hybridizes to the complement of the sequence of SEQ ID NO:1 or contained in ATCC™ deposit No. 75927 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The present invention also encompasses polypeptides comprising, or alternatively consisting of, an epitope of the polypeptide having an amino acid sequence of SEQ ID NO:20, or an epitope of the polypeptide sequence encoded by a polynucleotide sequence contained in ATCC™ deposit No. 203055 or encoded by a polynucleotide that hybridizes to the complement of the sequence of SEQ ID NO:19 or contained in ATCC™ deposit No. 203055 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:19), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance; by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See generally, U.S. Pat. Nos. 5,605,793; 5,811, 238; 5,830,721; 5,834,252; and 5,837,458, and Patten et al., Curr. Opinion Biotechnol. 8:724-33(1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. In another embodiment, alteration of polynucleotides corresponding to SEQ ID NO:19 and the polypeptides encoded by these polynucleotides may be achieved by DNA shuffling. In one embodiment, alteration of polynucleotides corresponding to SEQ ID NO:25 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

The TNF-gamma-alpha and TNF-gamma-beta polypeptides (proteins) of the invention may be in monomers or multimers (i.e., dimers, trimers, tetramers and higher multimers). In specific embodiments, the polypeptides of the invention are monomers, dimers, trimers or tetramers. In additional embodiments, the multimers of the invention are at least dimers, at least trimers, or at least tetramers.

In a preferred embodiment, a TNF-gamma-beta polypeptide of the invention is a trimer.

In a highly preferred embodiment, a TNF-gamma-beta polypeptide comprising, or alternatively consisting of, amino acid residues 72-251 of SEQ ID NO:20 and/or amino acid residues 1-181 of SEQ ID NO:26 is a trimer. The subunits of the highly preferred trimer may or may not include an amino-terminal methionine residue. In this embodiment, the trimer consists of, or alternatively comprises, a homomultimer. Also in this embodiment, the trimer may consist of, or alternatively comprise, a heteromultimer.

Multimers encompassed by the invention may be homomers or heteromers. As used herein, the term homomer, refers to a multimer containing only TNF-gamma-alpha and/or TNF-gamma-beta polypeptides of the invention (including TNF-gamma-alpha and/or TNF-gamma-beta fragments, variants, and fusion proteins, as described herein). These homomers may contain TNF-gamma-alpha and/or TNF-gamma-beta polypeptides having identical or different amino acid sequences. In a specific embodiment, a homomer of the invention is a multimer containing only TNF-gamma-alpha and/or TNF-gamma-beta polypeptides having an identical amino acid sequence. In another specific embodiment, a homomer of the invention is a multimer containing TNF-gamma-alpha and/or TNF-gamma-beta polypeptides having different amino acid sequences. In specific embodiments, the multimer of the invention is a homodimer (e.g., containing TNF-gamma-alpha polypeptides having identical or different amino acid sequences) or a homotrimer (e.g., containing TNF-gamma-alpha polypeptides having identical or different amino acid sequences). In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the TNF-gamma-alpha and/or TNF-gamma-beta polypeptides of the invention. In a specific embodiment, the multimer of the invention is a heterodimer, a heterotrimer, or a heterotetramer. In additional embodiments, the homomeric multimer of the invention is at least a heterodimer, at least a heterotrimer, or at least a heterotetramer.

Multimers of the invention may be the result of hydrophobic, hydrophilic, ionic and/or covalent associations. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent interactions with and/or between the TNF-gamma-alpha and/or TNF-gamma-beta polypeptides of the invention. Such covalent interactions may involve one or more amino acid residues corresponding to those recited in SEQ ID NO:2 or SEQ ID NO:20 or SEQ ID NO:26, or corresponding to one or more amino acid residues encoded by the clone HUVEO91, or corresponding to one or more amino acid residues encoded by the clone HEMCZ56). Alternatively, such covalent interactions may involve one or more amino acid residues contained in the heterologous polypeptide sequence in a TNF-gamma-alpha and/or TNF-gamma-beta fusion protein, such as for example, heterologous sequence contained in a TNF-gamma-alpha-Fc fusion protein (as described herein), and heterologous sequence contained in a fusion with heterologous polypeptide sequence from another TNF family ligand/receptor member, such as, for example, osteoprotegerin, that is capable of forming covalently associated multimers.

The invention also encompasses fusion proteins in which the full-length TNF-gamma polypeptide or fragment, variant, derivative, or analog thereof is fused to an unrelated protein. Fusion proteins of the invention may be constructed as direct fusion of TNF-gamma polypeptide (or fragment, variant, derivative, or analog) and a heterologous sequence, or may be constructed with a spacer or adapter region having one or more amino acids inserted between the two portions of the protein. Optionally, the spacer region may encode a protease cleavage site. The precise site of the fusion is not critical and may be routinely varied by one skilled in the art in order to maximize binding characteristics and/or biological activity of the homologous and/or heterologous sequence(s). The fusion proteins of the invention can be routinely designed on the basis of the TNF-gamma nucleotide and polypeptide sequences disclosed herein. For example, as one of skill in the art will appreciate, TNF-gamma-alpha and/or TNF-gamma-beta polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394, 827; Traunecker, et aL, *Nature* 331:84-86 (1988)). Fusion proteins that have a disulfide-linked dimeric structure due to the IgG part can also be more efficient in binding and neutralizing other molecules than the monomeric TNF-gamma protein or protein fragment alone (Fountoulakis, et al., *J. Biochem.* 270:3958-3964 (1995)). As an example, one such TNF-gamma-Fc fusion has been produced herein as described above. In other embodiments, the full length TNF-gamma polypeptide or fragment, variant, derivative, or analog thereof is fused to one or more other heterologous polypeptide sequences that are capable of forming multimeric formations, such as, for example, the dimerization domain of osteoprotegrin (see, e.g.,. EP 0 721 983, U.S. Pat. No. 5,478,925, and International Publication No. WO 98/49305, each of which is herein incorporated by reference in its entirety). Additional examples of TNF-gamma fusion proteins that are encompassed by the invention include, but are not limited to, fusion of the TNF-gamma polypeptide sequence to any amino acid sequence that allows the fusion protein to be displayed on the cell surface; or fusions to an enzyme, fluorescent protein, or luminescent protein which provides a marker function.

Modifications of chimeric OPG polypeptides are encompassed by the invention and include post-translational modifications (e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are chemically modified derivatives of OPG which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

The polypeptides of the present invention have uses which include, but are not limited to, molecular weight marker on SDS-PAGE gels or on molecular sieve gel filtration columns using methods well known to those of skill in the art.

Functional Activities

The functional activity of TNF-gamma polypeptides, and fragments, variants derivatives, and analogs thereof, can be assayed by various methods.

For example, in one embodiment where one is assaying for the ability to bind or compete with full-length TNF-gamma polypeptide for binding to anti-TNF-gamma antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TNF-ligand is identified, binding can be assayed, e.g., by means well known in the art. In another embodiment, physiological correlates of TNF-gamma binding to its substrates (signal transduction) can be assayed.

In addition, assays described herein (see Examples 5, 6, and 9-15, and otherwise known in the art may routinely be applied to measure the ability of TNF-gamma polypeptides and fragments, variants derivatives and analogs thereof to elicit TNF-gamma related biological activity (e.g., to inhibit, or alternatively promote, cell proliferation, tumor formation, angiogenesis, NF-kB activation and cell adhesion in vitro or in vivo).

Other methods will be known to the skilled artisan and are within the scope of the invention.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Additional polypeptides of the invention relate to antibodies and T-cell antigen receptors (TCR) which immunospecifically bind a polypeptide, polypeptide fragment, or variant of SEQ ID NO:20, and/or an epitope, of the present invention (as determined by immunoassays well known in the art for assaying specific antibody-antigen binding). Additional polypeptides of the invention relate to antibodies and T-cell antigen receptors (TCR) which immunospecifically bind a polypeptide, polypeptide fragment, or variant of SEQ ID NO:26, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a preferred embodiment, the immunoglobulin is an IgG1 isotype. In a preferred embodiment, the immunoglobulin is an IgG2 isotype. In another preferred embodiment, the immunoglobulin is an IgG4 isotype. Immunoglobulins may have both a heavy and light chain.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention specifically bind TNF-gamma-alpha and/or TNF-gamma-beta or fragments or variants thereof with a dissociation constant or $K_D$ less than or equal to $5\times10^{-6}$ M, $10^{-6}$M, $5\times10^{-7}$ M, $10^7$M, $5\times10^{-8}$ M, or $10^{-8}$M. Even more preferably, antibodies of the invention bind specifically bind TNF-gamma-alpha and/or TNF-gamma-beta or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $10^{-14}$M, $5\times10^{-15}$ M, or $10^{-15}$ M. The invention encompasses antibodies that bind TNF-gamma-alpha and/or TNF-gamma-beta with a dissociation constant or $K_D$ that is within any one of the ranges that are between each of the individual recited values.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivation by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 20 and Example 34). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well-known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV.

In general, the sample containing human B cells is innoculated with EBV, and cultured for 3-4 weeks. A typical source of EBV is the culture supernatant of the B95-8 cell line (ATCC™ #VR-1492). Physical signs of EBV transformation can generally be seen towards the end of the 3-4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g., SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, 6,075,181; and 6,114,598 which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:20. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:26.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072

(1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. 5,474,981; Gillies et al., PNAS 89:1428-1432 (1992); Fell et al., J. Immunol. 146:2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. The polypeptides corresponding to a polypeptide, polypeptide fragment, or a variant of SEQ ID NO:20 may be fused or conjugated to the above antibody portions to increase the in vivo half life of the polypeptides or for use in immunoassays using methods known in the art. Further, the polypeptides corresponding to SEQ ID NO:20 may be fused or conjugated to the above antibody portions to facilitate purification.

One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium alladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators useful for conjugating radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, B-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. 5,985, 660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, and anti-retroviral agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention specifically bind TNF-gamma-alpha and/or TNF-gamma-beta or fragments or variants theref with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind specifically bind TNF-gamma-alpha and/or TNF-gamma-beta or fragments or variants thereof with a dissociation constant or $K_D$ less than or equal to $5\times10^{-9}$ M, $10^{-9}$ M, $5\times10^{-10}$ M, $10^{-10}$ M, 5x–11 M, $10^{-11}$ M, $5\times10^{-12}$ M, $^{10-12}$ M, $5\times10^{-13}$ M, $10^{-13}$ M, $5\times10^{-14}$ M, $10^{-14}$M, $5\times10^{-14.5}$M, or $10^{-15}$ M. The invention encompasses antibodies that bind TNF-gamma-alpha and/or TNF-gamma-beta with a dissociation constant or $K_D$ that is within any one of the ranges that are between each of the individual recited values.

In particular embodiments, the present invention provides a method of diagnosing, treating, preventing or ameliorating inflammatory diseases or disorders comprising, administering to an animal, preferably a human, in which such treatment, prevention or amelioration is desired an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to treat, prevent or ameliorate the inflammatory disease or disorder. In additional specific embodiments, the inflammatory disease or disorder is inflammatory bowel disease. In additional specific embodiments, the inflammatory disease or disorder is encephalitis. In additional specific embodiments, the inflammatory disease or disorder is atherosclerosis. In specific embodiments, the inflammatory disease or disorder is psoriasis. The present invention further provides compositions comprising the anti-TNF-gamma-alpha and/or anti-TNF-gamma-beta antibodies and a carrier for use in the above-described method of diagnosing, treating, preventing or ameliorating inflammatory diseases and disorders.

In specific embodiments, the present invention provides a method of diagnosing, treating, preventing or ameliorating inflammation comprising administering to an animal, preferably a human, in which such treatment, prevention or amelioration is desired an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to treat, prevent or ameliorate the inflammation. The present invention further provides compositions comprising the anti-TNF-gamma-alpha and/or anti-TNF-gamma-beta antibodies and a carrier for use in the above-described method of diagnosing, treating, preventing or ameliorating inflammation.

In specific embodiments, the present invention provides a method of diagnosing, treating, preventing or ameliorating graft versus host disease (GVHD) comprising administering to an animal, preferably a human, in which such treatment, prevention or amelioration is desired an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to treat, prevent or ameliorate the GVHD. The present invention further provides compositions comprising the anti-TNF-gamma-alpha and/or anti-TNF-gamma-beta antibodies and a carrier for use in the above-described method of diagnosing, treating, preventing or ameliorating GVHD.

In other embodiments, the present invention provides a method of diagnosing, treating, preventing or ameliorating autoimmune diseases and disorders comprising administering to an animal, preferably a human, in which such treatment, prevention or amelioration is desired an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to treat, prevent or ameliorate the autoimmune disease or disorder. In specific embodiments, the autoimmune disease or disorder is systemic lupus erythematosus. In specific embodiments, the autoimmune disease or disorder is arthritis, particularly rheumatoid arthritis. In specific embodiments, the autoimmune disease or disorder is multiple sclerosis. In specific embodiments, the autoimmune disease or disorder is Crohn's disease. In specific embodiments, the autoimmune disease or disorder is autoimmune encephalitis. The present invention further provides compositions comprising the anti-TNF-gamma-alpha and/or anti-TNF-gamma-beta antibodies and a carrier for use in the above-described method of diagnosing, treating, preventing or ameliorating autoimmune diseases and disorders.

In specific embodiments, the present invention provides a method of diagnosing, treating, preventing or ameliorating allergy or asthma comprising administering to an animal, preferably a human, in which such treatment, prevention or amelioration is desired an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to treat, prevent or ameliorate the allergy or asthma. The present invention further provides compositions comprising the anti-TNF-gamma-alpha and/or anti-TNF-gamma-beta antibodies and a carrier for use in the above-described method of diagnosing, treating, preventing or ameliorating allergy or asthma.

The present invention further encompasses methods and compositions for reducing Tcell activation, comprising contacting an effective amount of anti-TNF-gamma-alpha and/or anti-TNF-gamma-beta antibody (or other TNF-gamma-alpha and/or TNF-gamma-beta antagonist such as a DR3- or TR6-Fc fusion protein see Example 35) with cells of hematopoietic origin, wherein the effective amount of the anti-TNF-gamma-alpha and/or anti-TNF-gamma-beta antibody reduces T cell activation. In preferred embodiments, the cells of hematopoietic origin are T cells. In other preferred embodiments, the effective amount of the anti-TNF-gamma-alpha and/or anti-TNF-gamma-beta antibody reduces TNF-gamma-alpha and/or TNF-gamma beta induced T cell activation.

The present invention further encompasses methods and compositions for reducing Tcell activation comprising, or alternatively consisting of, administering to an animal, preferably a human, in which such reduction is desired, an antibody that specifically binds TNF-gamma-alpha and/or TNF-gamma-beta (or a TNF-gamma-alpha and/or TNF-gamma-beta antagonist such as a DR3- or TR6-Fc fusion protein, see Example 35) or fragment or variant thereof in an amount effective to reduce T cell activation. The present invention further provides compositions comprising the anti-TNF-gamma-alpha and/or anti-TNF-gamma-beta antibodies and a carrier for use in the above-described method of reducing T cell activation.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Transgenics

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection ((each of the following references is hereby incorporated by reference) Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines ((the following reference is hereby incorporated by reference) Van der Putten et al., Proc. Natl. Acad. Sci., USA 82:6148-6152 (1985)), blastocysts or embryos; gene targeting in embryonic stem cells ((each of the following references is hereby incorporated by reference) Thompson et al., Cell 56:313-321 (1989)); electroporation of cells or embryos (Lo, 1983, Mol Cell. Biol. 3:1803-1814 (1983)); introduction of the polynucleotides of the invention using a gene gun ((the following reference is hereby incorporated by reference) see, e.g., Ulmer et al., Science 259:1745 (1993); introducing nucleic acid constructs into embryonic pluripotent stem cells and transferring the stem cells back into the blastocyst; and sperm-mediated gene transfer ((the following reference is hereby incorporated by reference) Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence ((each of the following references is hereby incorporated by reference) Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. ((the following reference is hereby incorporated by reference) Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. ((the following reference is hereby incorporated by reference) Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TNF-gamma-alpha and/or TNF-gamma-beta polypeptides, studying conditions and/or disorders associated with aberrant TNF-gamma-alpha and/or TNF-gamma-beta expression, and in screening for compounds effective in ameliorating such conditions and/or disorders.

Endogenous gene expression can also be reduced by inactivating or "knocking out" the gene and/or its promoter using targeted homologous recombination. ((each of the following references is hereby incorporated by reference) E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene ((each of the following references is hereby incorporated by reference) e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. ((each of the following references is hereby incorporated by reference) See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well-known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In a specific embodiment, a transgenic expression construct was generated using the pAC vector to express amino acid residues T-28 through L-174 of SEQ ID NO:2. In another specific embodiment, a transgenic expression construct was generated using the pTR vector to express amino acid residues T-28 through L-174 of SEQ ID NO:2.

Diagnostics

The present inventors have discovered that TNF-gamma is expressed in human umbilical vein endothelial cells, induced endothelial cells, macrophages, and substantia nigra tissue. For a number of immune and circulatory systems-related disorders, substantially altered (increased or decreased) levels of TNF-gamma-alpha and/or TNF-gamma-beta gene expression can be detected in immune and circulatory systems tissue or other cells or bodily fluids (e.g., sera, plasma, urine, synovial fluid or spinal fluid) taken from an individual having such a disorder, relative to a "standard" TNF-gamma-alpha and/or TNF-gamma-beta gene expression level, that is, the TNF-gamma-alpha and/or TNF-gamma-beta expression level in immune and circulatory systems tissues or bodily fluids from an individual not having the immune and circulatory systems disorder. Thus, the invention provides a diagnostic method useful during diagnosis of a immune and circulatory systems disorder, which involves measuring the expression level of the gene encoding the TNF-gamma-alpha and/or TNF-gamma-beta protein in immune and circulatory systems tissue or other cells or body fluid from an individual and comparing the measured gene expression level with a standard TNF-gamma-alpha and/or TNF-gamma-beta gene expression level, whereby an increase or decrease in the gene expression level compared to the standard is indicative of an immune and circulatory systems disorder.

In particular, it is believed that certain tissues in mammals with cancer of the immune and circulatory systems express significantly reduced levels of the TNF-gamma-alpha and/or TNF-gamma-beta protein and mRNA encoding the TNF-gamma-alpha and/or TNF-gamma-beta protein when compared to a corresponding "standard" level. Further, it is believed that enhanced levels of the TNF-gamma-alpha and/or TNF-gamma-beta protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a immune and circulatory systems disorder, including cancers of these systems, which involves measuring the expression level of the gene encoding the TNF-gamma-alpha and/or TNF-gamma-beta protein in immune and circulatory systems tissue or other cells or body fluid from an individual and comparing the measured gene expression level with a standard TNF-gamma-alpha and/or TNF-gamma-beta gene expression level, whereby an increase or decrease in the gene expression level compared to the standard is indicative of an immune and circulatory systems disorder.

Where a diagnosis of a disorder in the immune and circulatory systems, including diagnosis of a tumor, has already been made according to conventional methods, the present invention is useful as a prognostic indicator, whereby patients exhibiting depressed TNF-gamma-alpha and/or TNF-gamma-beta gene expression will experience a worse clinical outcome relative to patients expressing the gene at a level nearer the standard level.

By "assaying the expression level of the gene encoding the TNF-gamma-alpha and/or TNF-gamma-beta protein" is intended qualitatively or quantitatively measuring or estimating the level of the TNF-gamma-alpha and/or TNF-gamma-beta protein or the level of the mRNA encoding the TNF-gamma-alpha and/or TNF-gamma-beta protein in a first biological sample either directly (e.g., by determining or estimating absolute protein level or mRNA level) or relatively (e.g., by comparing to the TNF-gamma-alpha and/or TNF-gamma-beta protein level or mRNA level in a second biological sample). Preferably, the TNF-gamma-alpha and/or TNF-gamma-beta protein level or mRNA level in the first biological sample is measured or estimated and compared to a standard TNF-gamma-alpha and/or TNF-gamma-beta protein level or mRNA level, the standard being taken from a second biological sample obtained from an individual not having the disorder or being determined by averaging levels from a population of individuals not having a disorder of the immune and circulatory systems. As will be appreciated in the art, once a standard TNF-gamma-alpha and/or TNF-gamma-beta protein level or mRNA level is known, it can be used repeatedly as a standard for comparison.

By "biological sample" is intended any biological sample obtained from an individual, body fluid, cell line, tissue culture, or other source which contains TNF-gamma-alpha and/ or TNF-gamma-beta protein or mRNA. As indicated, biological samples include body fluids (such as sera, plasma, urine, synovial fluid and spinal fluid) which contain free TNF-gamma-alpha and/or TNF-gamma-beta protein, immune and circulatory systems tissue, and other tissue sources found to express complete or mature TNF-gamma-alpha and/or TNF-gamma-beta or a TNF-gamma-alpha and/or TNF-gamma-beta receptor. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described by Chomczynski and Sacchi (*Anal. Biochem.* 162: 156-159 (1987)). Levels of mRNA encoding the TNF-gamma-alpha and/or TNF-gamma-beta protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying TNF-gamma-alpha and/or TNF-gamma-beta protein levels in a biological sample can occur using antibody-based techniques. For example, TNF-gamma-alpha and/or TNF-gamma-beta protein expression in tissues can be studied with classical immunohistological methods (Jalkanen, M., et al., *J. Cell. Biol.* 101:976-985 (1985); Jalkanen, M., et al., *J. Cell. Biol.* 105:3087-3096 (1987)). Other antibody-based methods useful for detecting TNF-gamma-alpha and/or TNF-gamma-beta protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying TNF-gamma-alpha and/or TNF-gamma-beta protein levels in a biological sample obtained from an individual, TNF-gamma-alpha and/or TNF-gamma-beta protein can also be detected in vivo by imaging. Antibody labels or markers for in vivo imaging of TNF-gamma-alpha and/or TNF-gamma-beta protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TNF-gamma-alpha and/or TNF-gamma-beta protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TNF-gamma-alpha and/or TNF-gamma-beta protein. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Therapeutics

As noted above, TNF-gamma-alpha and/or TNF-gamma-beta polynucleotides and polypeptides are useful for diagnosis of conditions involving abnormally high or low expression of TNF-gamma-alpha and/or TNF-gamma-beta activities. Given the cells and tissues where TNF-gamma-alpha and/or TNF-gamma-beta is expressed as well as the activities modulated by TNF-gamma-alpha and/or TNF-gamma-beta, it is readily apparent that a substantially altered (increased or decreased) level of expression of TNF-gamma-alpha and/or TNF-gamma-beta in an individual compared to the standard or "normal" level produces pathological conditions related to the bodily system(s) in which TNF-gamma-alpha and/or TNF-gamma-beta is expressed and/or is active.

It will also be appreciated by one of ordinary skill that, since the TNF-gamma-alpha and/or TNF-gamma-beta proteins of the invention are members of the TNF family the mature secreted form of the protein may be released in soluble form from the cells which express TNF-gamma by proteolytic cleavage. Therefore, when TNF-gamma-alpha and/or TNF-gamma-beta mature form or soluble extracellular domain is added from an exogenous source to cells, tissues or the body of an individual, the protein will exert its physiological activities on its target cells of that individual. Also, cells expressing this type II transmembrane protein may be added to cells, tissues or the body of an individual and these added cells will bind to cells expressing receptor for TNF-gamma-alpha and/or TNF-gamma-beta, whereby the cells expressing TNF-gamma-alpha and/or TNF-gamma-beta can cause actions (e.g. regulation of endothelial cell growth and regulation) on the receptor-bearing target cells.

Therefore, it will be appreciated that conditions caused by a decrease in the standard or normal level of TNF-gamma-alpha and/or TNF-gamma-beta activities in an individual, particularly disorders of the immune and circulatory systems, can be treated, prevented, diagnosed, and/or detected by administration of TNF-gamma-alpha and/or TNF-gamma-beta polypeptide (in the form of the mature protein). Thus, the invention also provides a method of treatment, prevention, diagnosis, and/or detection of an individual in need of an increased level of TNF-gamma-alpha and/or TNF-gamma-beta activity comprising administering to such an individual a pharmaceutical composition comprising an amount of an isolated TNF-gamma-alpha and/or TNF-gamma-beta polypeptide of the invention, particularly a mature form of the TNF-gamma-alpha and/or TNF-gamma-beta protein of the invention, effective to increase the TNF-gamma-alpha and/or TNF-gamma-beta activity level in such an individual.

Polynucleotides and/or polypeptides of the invention and/or agonists and/or antagonists thereof are useful in the treatment, prevention, diagnosis, and/or detection of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), dementia, graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides, polypeptides, antibodies, and/or agonists or antagonists of the present invention may be useful in treating, preventing, diagnosing and/or prognosing diseases, disorders, and/or conditions of/associated with the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune system associated diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

In another embodiment, a polypeptide of the invention, or polynucleotides, antibodies, agonists, or antagonists corresponding to that polypeptide, may be used to treat diseases and disorders of the immune system and/or to inhibit or enhance an immune response generated by cells associated with the tissue(s) in which the polypeptide of the invention is expressed.

Polynucleotides, polypeptides, antibodies, and/or agonists or antagonists of the present invention may be useful in treating, preventing, diagnosing, and/or prognosing immunodeficiencies, including both congenital and acquired immunodeficiencies. Examples of B cell immunodeficiencies in which immunoglobulin levels B cell function and/or B cell numbers are decreased include: X-linked agammaglobulinemia (Bruton's disease), X-linked infantile agammaglobulinemia, X-linked immunodeficiency with hyper IgM, non X-linked immunodeficiency with hyper IgM, X-linked lymphoproliferative syndrome (XLP), agammaglobulinemia including congenital and acquired agammaglobulinemia, adult onset agammaglobulinemia, late-onset agammaglobulinemia, dysgammaglobulinemia, hypogammaglobulinemia, unspecified hypogammaglobulinemia, recessive agammaglobulinemia (Swiss type), Selective IgM deficiency, selective IgA deficiency, selective IgG subclass deficiencies, IgG subclass deficiency (with or without IgA deficiency), Ig deficiency with increased IgM, IgG and IgA deficiency with increased IgM, antibody deficiency with normal or elevated Igs, Ig heavy chain deletions, kappa chain deficiency, B cell lymphoproliferative disorder (BLPD), common variable immunodeficiency (CVID), common variable immunodeficiency (CVI) (acquired), and transient hypogammaglobulinemia of infancy.

In specific embodiments, ataxia-telangiectasia or conditions associated with ataxia-telangiectasia are treated, prevented, diagnosed, and/or prognosing using the polypeptides or polynucleotides of the invention, and/or agonists or antagonists thereof.

Examples of congenital immunodeficiencies in which T cell and/or B cell function and/or number is decreased include, but are not limited to: DiGeorge anomaly, severe combined immunodeficiencies (SCID) (including, but not limited to, X-linked SCID, autosomal recessive SCID, adenosine deaminase deficiency, purine nucleoside phosphorylase (PNP) deficiency, Class II MHC deficiency (Bare lymphocyte syndrome), Wiskott-Aldrich syndrome, and ataxia telangiectasia), thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In specific embodiments, DiGeorge anomaly or conditions associated with DiGeorge anomaly are treated, prevented, diagnosed, and/or prognosed using polypeptides or polynucleotides of the invention, or antagonists or agonists thereof.

Other immunodeficiencies that may be treated, prevented, diagnosed, and/or prognosed using polypeptides or polynucleotides of the invention, and/or agonists or antagonists thereof, include, but are not limited to, chronic granulomatous disease, Chediak-Higashi syndrome, myeloperoxidase deficiency, leukocyte glucose-6-phosphate dehydrogenase deficiency, X-linked lymphoproliferative syndrome (XLP), leukocyte adhesion deficiency, complement component deficiencies (including C1, C2, C3, C4, C5, C6, C7, C8 and/or C9 deficiencies), reticular dysgenesis, thymic alymphoplasia-aplasia, immunodeficiency with thymoma, severe congenital leukopenia, dysplasia with immunodeficiency, neonatal neutropenia, short limbed dwarfism, and Nezelof syndrome-combined immunodeficiency with Igs.

In a preferred embodiment, the immunodeficiencies and/or conditions associated with the immunodeficiencies recited above are treated, prevented, diagnosed and/or prognosed using polynucleotides, polypeptides, antibodies, and/or agonists or antagonists of the present invention.

In a preferred embodiment polynucleotides, polypeptides, antibodies, and/or agonists or antagonists of the present invention could be used as an agent to boost immunoresponsiveness among immunodeficient individuals. In specific embodiments, polynucleotides, polypeptides, antibodies, and/or agonists or antagonists of the present invention could be used as an agent to boost immunoresponsiveness among B cell and/or T cell immunodeficient individuals.

The polynucleotides, polypeptides, antibodies, and/or agonists or antagonists of the present invention may be useful in treating, preventing, diagnosing and/or prognosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, diagnosed and/or prognosed by polynucleotides, polypeptides, antibodies, and/or agonists or antagonists of the present invention include, but are not limited to, one or more of the following: systemic lupus erythematosus, rheumatoid arthritis, ankylosing spondylitis, multiple sclerosis, autoimmune thyroiditis, Hashimoto's thyroiditis, autoimmune hemolytic anemia, hemolytic anemia, thrombocytopenia, autoimmune thrombocytopenia purpura, autoimmune neonatal thrombocytopenia, idiopathic thrombocytopenia purpura, purpura (e.g., Henloch-Scoenlein purpura), autoimmunocytopenia, Goodpasture's syndrome, Pemphigus vulgaris, myasthenia gravis, Grave's disease (hyperthyroidism), and insulin-resistant diabetes mellitus.

Additional disorders that are likely to have an autoimmune component that may be treated, prevented, and/or diagnosed with the compositions of the invention include, but are not limited to, type II collagen-induced arthritis, antiphospholipid syndrome, dermatitis, allergic encephalomyelitis, myocarditis, relapsing polychondritis, rheumatic heart disease, neuritis, uveitis ophthalmia, polyendocrinopathies, Reiter's Disease, Stiff-Man Syndrome, autoimmune pulmonary inflammation, autism, Guillain-Barre Syndrome, insulin dependent diabetes mellitus, and autoimmune inflammatory eye disorders.

Additional disorders that are likely to have an autoimmune component that may be treated, prevented, diagnosed and/or prognosed with the compositions of the invention include, but are not limited to, scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity), infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional disorders that may have an autoimmune component that may be treated, prevented, diagnosed and/or prognosed with the compositions of the invention include, but are not limited to, chronic active hepatitis (often characterized, e.g., by smooth muscle antibodies), primary biliary cirrhosis (often characterized, e.g., by mitochondria antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulomatous, degenerative, and atrophic disorders.

In a preferred embodiment, the autoimmune diseases and disorders and/or conditions associated with the diseases and disorders recited above are treated, prevented, diagnosed and/or prognosed using for example, antagonists or agonists, polypeptides or polynucleotides, or antibodies of the present invention. In a specific preferred embodiment, rheumatoid arthritis is treated, prevented, and/or diagnosed using polynucleotides, polypeptides, antibodies, and/or agonists or antagonists of the present invention.

In another specific preferred embodiment, systemic lupus erythematosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention.

In another specific preferred embodiment IgA nephropathy is treated, prevented, and/or diagnosed using polynucleotides, polypeptides, antibodies, and/or agonists or antagonists of the present invention.

In a preferred embodiment, the autoimmune diseases and disorders and/or conditions associated with the diseases and disorders recited above are treated, prevented, diagnosed and/or prognosed using polynucleotides, polypeptides, antibodies, and/or agonists or antagonists of the present invention In preferred embodiments, polypeptides, antibodies, polynucleotides and/or agonists or antagonists of the present invention are used as an immunosuppressive agent(s).

Polynucleotides, polypeptides, antibodies, and/or agonists or antagonists of the present invention may be useful in treating, preventing, prognosing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells, including but not limited to, leukopenia, neutropenia, anemia, and thrombocytopenia. Alternatively, polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

Allergic reactions and conditions, such as asthma (particularly allergic asthma) or other respiratory problems, may also be treated, prevented, diagnosed and/or prognosed using polypeptides, antibodies, or polynucleotides of the invention, and/or agonists or antagonists thereof. Moreover, these molecules can be used to treat, prevent, prognose, and/or diagnose anaphylaxis, hypersensitivity to an antigenic molecule, or blood group incompatibility.

Additionally, polypeptides or polynucleotides of the invention, and/or agonists or antagonists thereof, may be used to treat, prevent, diagnose and/or prognose IgE-mediated allergic reactions. Such allergic reactions include, but are not limited to, asthma, rhinitis, and eczema. In specific embodiments, polynucleotides, polypeptides, antibodies, and/or agonists or antagonists of the present invention may be used to modulate IgE concentrations in vitro or in vivo.

Moreover, polynucleotides, polypeptides, antibodies, and/or agonists or antagonists of the present invention have uses in the diagnosis, prognosis, prevention, and/or treatment of inflammatory conditions. For example, since polypeptides, antibodies, or polynucleotides of the invention, and/or agonists or antagonists of the invention may inhibit the activation, proliferation and/or differentiation of cells involved in an inflammatory response, these molecules can be used to prevent and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can effect virtually any tissue of the body. Accordingly, polynucleotides, polypeptides, and antibodies of the invention, as well as agonists or antagonists thereof, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In specific embodiments, polypeptides, antibodies, or polynucleotides of the invention, and/or agonists or antagonists thereof, are useful to diagnose, prognose, prevent, and/or treat organ transplant rejections and graft-versus-host disease. Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing experimental allergic and hyperacute xenograft rejection.

In other embodiments, polypeptides, antibodies, or polynucleotides of the invention, and/or agonists or antagonists thereof, are useful to diagnose, prognose, prevent, and/or treat immune complex diseases, including, but not limited to, serum sickness, post streptococcal glomerulonephritis, polyarteritis nodosa, and immune complex-induced vasculitis.

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

In another embodiment, polypeptides, antibodies, polynucleotides and/or agonists or antagonists of the present invention are used as a vaccine adjuvant that enhances immune responsiveness to an antigen. In a specific embodiment, polypeptides, antibodies, polynucleotides and/or agonists or antagonists of the present invention are used as an adjuvant to enhance tumor-specific immune responses.

In another specific embodiment, polypeptides, antibodies, polynucleotides and/or agonists or antagonists of the present invention are used as an adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of HIV/AIDS, respiratory syncytial virus, Dengue, rotavirus, Japanese B encephalitis, influenza A and B, parainfluenza, measles, cytomegalovirus, rabies, Junin, Chikungunya, Rift Valley Fever, herpes simplex, and yellow fever.

In another specific embodiment, polypeptides, antibodies, polynucleotides and/or agonists or antagonists of the present invention are used as an adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B.

In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Neisseria meningitidis, Streptococcus pneumoniae*, Group B streptococcus, *Shigella* spp., Enterotoxigenic *Escherichia coli*, Enterohemorrhagic *E. coli*, and *Borrelia burgdorferi*.

In another specific embodiment, polypeptides, antibodies, polynucleotides and/or agonists or antagonists of the present invention are used as an adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria) or *Leishmania*.

In another specific embodiment, polypeptides, antibodies, polynucleotides and/or agonists or antagonists of the present invention may also be employed to treat infectious diseases including silicosis, sarcoidosis, and idiopathic pulmonary fibrosis; for example, by preventing the recruitment and activation of mononuclear phagocytes.

In another specific embodiment, polypeptides, antibodies, polynucleotides and/or agonists or antagonists of the present invention are used as an antigen for the generation of antibodies to inhibit or enhance immune mediated responses mediated by polypeptides of the invention.

In one embodiment, polypeptides, antibodies, polynucleotides and/or agonists or antagonists of the present invention are administered to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production and immunoglobulin class switching (e.g., IgG, IgA, IgM, and IgE), and/or to increase an immune response.

In another specific embodiment, polypeptides, antibodies, polynucleotides and/or agonists or antagonists of the present invention are used as a stimulator of B cell responsiveness to pathogens.

In another specific embodiment, polypeptides, antibodies, polynucleotides and/or agonists or antagonists of the present invention are used as an activator of T cells.

In another specific embodiment, polypeptides, antibodies, polynucleotides and/or agonists or antagonists of the present invention are used as an inhibitor of T cell function.

In another specific embodiment, polypeptides, antibodies, polynucleotides and/or agonists or antagonists of the present invention are used as an agent that elevates the immune status of an individual prior to their receipt of immunosuppressive therapies.

In another specific embodiment, polypeptides, antibodies, polynucleotides and/or agonists or antagonists of the present invention are used as an agent to induce higher affinity antibodies.

In another specific embodiment, polypeptides, antibodies, polynucleotides and/or agonists or antagonists of the present invention are used as an agent to increase serum immunoglobulin concentrations.

In another specific embodiment, polypeptides, antibodies, polynucleotides and/or agonists or antagonists of the present invention are used as an agent to accelerate recovery of immunocompromised individuals.

In another specific embodiment, polypeptides, antibodies, polynucleotides and/or agonists or antagonists of the present invention are used as an agent to boost immunoresponsiveness among aged populations and/or neonates.

In another specific embodiment, polypeptides, antibodies, polynucleotides and/or agonists or antagonists of the present invention are used as an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

In another specific embodiment, polypeptides, antibodies, polynucleotides and/or agonists or antagonists of the present invention are used as an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

In another specific embodiment, polypeptides, antibodies, polynucleotides and/or agonists or antagonists of the present invention are used as an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In another specific embodiment, polypeptides, antibodies, polynucleotides and/or agonists or antagonists of the present invention are used as a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonism of antigen presentation may be useful as an anti-tumor treatment or to modulate the immune system.

In another specific embodiment, polypeptides, antibodies, polynucleotides and/or agonists or antagonists of the present invention are used as an agent to direct an individual's immune system towards development of a humoral response (i.e. TH2) as opposed to a TH1 cellular response.

In another specific embodiment, polypeptides, antibodies, polynucleotides and/or agonists or antagonists of the present invention are used as a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

In another specific embodiment, polypeptides, antibodies, polynucleotides and/or agonists or antagonists of the present invention are used as a stimulator of B cell production in pathologies such as AIDS, chronic lymphocyte disorder and/or Common Variable Immunodeficiency.

In another specific embodiment, polypeptides, antibodies, polynucleotides and/or agonists or antagonists of the present invention are used as a therapy for generation and/or regeneration of lymphoid tissues following surgery, trauma or genetic defect. In another specific embodiment, polypeptides, antibodies, polynucleotides and/or agonists or antagonists of the present invention are used in the pretreatment of bone marrow samples prior to transplant.

In another specific embodiment, polypeptides, antibodies, polynucleotides and/or agonists or antagonists of the present invention are used as a gene-based therapy for genetically inherited disorders resulting in immuno-incompetence/immunodeficiency such as observed among SCID patients.

In another specific embodiment, polypeptides, antibodies, polynucleotides and/or agonists or antagonists of the present invention are used as a means of activating monocytes/macrophages to defend against parasitic diseases that effect monocytes such as *Leishmania*.

In another specific embodiment, polypeptides, antibodies, polynucleotides and/or agonists or antagonists of the present invention are used as a means of regulating secreted cytokines that are elicited by polypeptides of the invention.

In another embodiment, polypeptides, antibodies, polynucleotides and/or agonists or antagonists of the present invention are used in one or more of the applications described herein, as they may apply to veterinary medicine.

In another specific embodiment, polypeptides, antibodies, polynucleotides and/or agonists or antagonists of the present invention are used as a means of blocking various aspects of immune responses to foreign agents or self. Examples of diseases or conditions in which blocking of certain aspects of immune responses may be desired include autoimmune disorders such as lupus, and arthritis, as well as immunoresponsiveness to skin allergies, inflammation, bowel disease, injury and diseases/disorders associated with pathogens.

In another specific embodiment, polypeptides, antibodies, polynucleotides and/or agonists or antagonists of the present invention are used as a therapy for preventing the B cell proliferation and Ig secretion associated with autoimmune diseases such as idiopathic thrombocytopenic purpura, systemic lupus erythematosus and multiple sclerosis.

In another specific embodiment, polypeptides, antibodies, polynucleotides and/or agonists or antagonists of the present invention are used as a inhibitor of B and/or T cell migration in endothelial cells. This activity disrupts tissue architecture or cognate responses and is useful, for example in disrupting immune responses, and blocking sepsis.

In another specific embodiment, polypeptides, antibodies, polynucleotides and/or agonists or antagonists of the present invention are used as a therapy for chronic hypergammaglobulinemia evident in such diseases as monoclonal gammopathy of undetermined significance (MGUS), Waldenstrom's disease, related idiopathic monoclonal gammopathies, and plasmacytomas.

In another specific embodiment, polypeptides, antibodies, polynucleotides and/or agonists or antagonists of the present invention may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes.

The polypeptides, antibodies, polynucleotides and/or agonists or antagonists of the present invention may also be employed to treat idiopathic hyper-eosinophilic syndrome by, for example, preventing eosinophil production and migration.

In another specific embodiment, polypeptides, antibodies, polynucleotides and/or agonists or antagonists of the present invention are used to enhance or inhibit complement mediated cell lysis.

In another specific embodiment, polypeptides, antibodies, polynucleotides and/or agonists or antagonists of the present invention are used to enhance or inhibit antibody dependent cellular cytotoxicity.

In another specific embodiment, polypeptides, antibodies, polynucleotides and/or agonists or antagonists of the present invention may also be employed for treating atherosclerosis, for example, by preventing monocyte infiltration in the artery wall.

In another specific embodiment, polypeptides, antibodies, polynucleotides and/or agonists or antagonists of the present invention may be employed to treat adult respiratory distress syndrome (ARDS).

In another specific embodiment, polypeptides, antibodies, polynucleotides and/or agonists or antagonists of the present invention may be useful for stimulating wound and tissue repair, stimulating angiogenesis, and/or stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to diagnose, prognose, treat, and/or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, bloodborne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii. Other diseases and disorders that may be prevented, diagnosed, prognosed, and/or treated with polynucleotides or polypeptides, and/or agonists of the present invention include, but are not limited to, HIV infection, HTLV-BLV infection, lymphopenia, phagocyte bactericidal dysfunction anemia, thrombocytopenia, and hemoglobinuria.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to diagnose, prognose, prevent, and/or treat cancers or neoplasms including immune cell or immune tissue-related cancers or neoplasms. Examples of cancers or neoplasms that may be prevented, diagnosed, or treated by polynucleotides, polypeptides, antibodies, and/or agonists or antagonists of the present invention include, but are not limited to, acute myelogenous leukemia, chronic myelogenous leukemia, Hodgkin's disease, non-Hodgkin's lymphoma, acute lymphocytic anemia (ALL) Chronic lymphocyte leukemia, plasmacytomas, multiple myeloma, Burkitt's lymphoma, and/or EBV-transformed diseases.

In another specific embodiment, polypeptides, antibodies, polynucleotides and/or agonists or antagonists of the present invention are used as a therapy for decreasing cellular proliferation of Large B-cell Lymphomas.

In another specific embodiment, polypeptides, antibodies, polynucleotides and/or agonists or antagonists of the present invention are used as a means of decreasing the involvement of B cells and Ig associated with Chronic Myelogenous Leukemia.

In specific embodiments, the compositions of the invention are used as an agent to boost immunoresponsiveness among B cell immunodeficient individuals, such as, for example, an individual who has undergone a partial or complete splenectomy.

Antagonists of the invention include, for example, binding and/or inhibitory antibodies, antisense nucleic acids, ribozymes or soluble forms of the polypeptides of the present invention (e.g., Fc fusion protein). Agonists of the invention include, for example, binding or stimulatory antibodies, and soluble forms of the polypeptides (e.g., Fc fusion proteins), polypeptides, antibodies, polynucleotides and/or agonists or antagonists of the present invention may be employed in a composition with a pharmaceutically acceptable carrier, e.g., as described herein.

In another embodiment, polypeptides, antibodies, polynucleotides and/or agonists or antagonists of the present invention are administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741). Administration of polypeptides, antibodies, polynucleotides and/or agonists or antagonists of the present invention to such animals is useful for the generation of monoclonal antibodies against the polypeptides, antibodies, polynucleotides and/or agonists or antagonists of the present invention.

Polynucleotides and/or polypeptides of the invention and/or agonists and/or antagonists thereof are useful in promoting angiogenesis and/or wound healing (e.g., wounds, burns, and bone fractures).

Polynucleotides and/or polypeptides of the invention and/or agonists and/or antagonists thereof are also useful as an adjuvant to enhance immune responsiveness. In specific embodiments, the polynucleotides and or polypeptides of the invention and/or agonists and/or antagonists thereof are used as an adjuvant to enhance immune responsiveness to specific antigens. In particular, polynucleotides and or polypeptides of the invention and/or agonists and/or antagonists thereof are used as an adjuvant to enhance anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, transplantation and burns, or may be used to boost immune response and/or recovery in the elderly and/or immunocompromised individuals. Alternatively, polynucleotides and/or polypeptides of the invention and/or agonists and/or antagonists thereof are useful as immunosuppressive agents, for example in the treatment, prevention, diagnosis, and/or detection of autoimmune disorders. In specific embodiments, polynucleotides and/or polypeptides of the invention are used to treat, prevent, diagnose, and/or detect chronic inflammatory, allergic or autoimmune conditions, such as those described herein or are otherwise known in the art.

Since TNF-gamma-alpha and TNF-gamma-beta belong to the TNF superfamily, they also modulate angiogenesis. In addition, since TNF-gamma-alpha and/or TNF-gamma-beta inhibit immune cell functions, it will have a wide range of anti-inflammatory activities. TNF-gamma-alpha and/or TNF-gamma-beta may be employed as an anti-neovascularizing agent to treat, prevent, diagnose, and/or detect solid tumors by stimulating the invasion and activation of host defense cells, e.g., cytotoxic T-cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. TNF-gamma-alpha and/or TNF-gamma-beta may also be employed to inhibit T-cell proliferation by the inhibition of IL-2 biosynthesis for the treatment, prevention, diagnosis, and/or detection of T-cell mediated auto-immune diseases and lymphocytic leukemias. TNF-gamma-alpha and/or TNF-gamma-beta may also be employed to stimulate wound healing, both via the recruitment of debris clearing- and connective tissue promoting- inflammatory cells. In this same manner, TNF-gamma-alpha and/or TNF-gamma-beta may also be employed to treat, prevent, diagnose, and/or detect other fibrotic disorders, including liver cirrhosis, osteoarthritis and pulmonary fibrosis. TNF-gamma-alpha and/or TNF-gamma-beta also increases the presence of eosinophils which have the distinctive function of killing the larvae of parasites that invade tissues, as in schistosomiasis, trichinosis and ascariasis. TNF-gamma-alpha and/or TNF-gamma-beta may also be employed to regulate hematopoiesis, by regulating the activation and differentiation of various hematopoietic progenitor cells, for example, to release mature leukocytes from the bone marrow following chemotherapy, i.e., in stem cell mobilization. TNF-gamma-alpha and/or TNF-gamma-beta may also be employed to treat, prevent, diagnose, and/or detect sepsis.

It is well-known in the art that, in addition to a specific cellular function, cellular receptor molecules may also often be exploited by a virus as a means of initiating entry into a potential host cell. For example, it was recently discovered by Wu and colleagues (J. Exp. Med. 185:1681-1691 (1997)) that the cellular chemokine receptor CCR5 functions not only as a cellular chemokine receptor, but also as a receptor for macrophage-tropic human immunodeficiency virus (HIV)-1. In addition, RANTES, MIP-1alpha, and MIP-1beta, which are agonists for the cellular chemokine receptor CCR5, inhibit entry of various strains of HIV-1 into susceptible cell lines (Cocchi, F., et al., Science 270:1811-1815 (1995)). Thus, the invention also provides a method of treating, preventing, diagnosing, and/or detecting an individual exposed to, or infected with, a virus through the prophylactic or therapeutic administration of TNF-gamma-alpha and/or TNF-gamma-beta, or an agonist or antagonist thereof, to block or disrupt the interaction of a viral particle with the TNF-gamma-alpha and/or TNF-gamma-beta receptor and, as a result, block the initiation or continuation of viral infectivity.

The TNF-gamma-alpha and/or TNF-gamma-beta of the present invention binds to the TNF-gamma-alpha and/or TNF-gamma-beta receptor and, as such, is likely to block immuno- and endothelial cell-tropic viral infections. Expression patterns of the cDNA clone encoding the present invention suggests that this molecule is expressed primarily in endothelial cells and select hematopoietic tissues. When considered together, these observations suggest that agonists and antagonists, including a receptor, of TNF-gamma-alpha and/or TNF-gamma-beta may be useful as a method of blocking or otherwise regulating the infectivity of immunotropic viral infections. A non-limiting list of viruses which infect humans and can infect cells of the hematopoietic system includes such retroviruses as HIV-1, HIV-2, human T-cell lymphotropic virus (HTLV)-I, and HTLV-II, as well as other DNA and RNA viruses such as herpes simplex virus (HSV)-1, HSV-2, HSV-6, cytomegalovirus (CMV), Epstein-Barr virus (EBV), herpes samirii, adenoviruses, rhinoviruses, influenza viruses, reoviruses, and the like.

The ability of TNF-gamma-alpha and/or TNF-gamma-beta of the present invention, or agonists or antagonists thereof, to prophylactically or therapeutically block viral infection may be easily tested by the skilled artisan. For example, Simmons and coworkers (Science 276:276-279 (1997)) and Arenzana-Seisdedos and colleagues (Nature 383: 400 (1996)) each outline a method of observing suppression of HIV-1 infection by an antagonist of the CCR5 chemokine receptor and of the CC chemokine RANTES, respectively, in cultured peripheral blood mononuclear cells. Cells are cultured and infected with a virus, HIV-1 in both cases noted above. An agonist or antagonist of the CC chemokine or its receptor is then immediately added to the culture medium. Evidence of the ability of the agonist or antagonist of the chemokine or cellular receptor is determined by evaluating the relative success of viral infection at 3, 6, and 9 days postinfection.

Administration of a pharmaceutical composition comprising an amount of an isolated TNF-gamma-alpha and/or TNF-gamma-beta, or an agonist or antagonist thereof, of the invention to an individual either infected with a virus or at risk for infection with a virus is performed as described below.

Since TNF-gamma has been shown to induce activation of cellular NF-kB and c-jun N-terminal kinase (JNK), it is also useful in therapeutically regulating such cellular and immune systemic disorders as tumors and tumor metastases, infections by bacteria, viruses, and other parasites, immunodeficiencies, inflammatory diseases, lymphadenopathy, autoimmune diseases, graft versus host disease, autoimmunity, arthritis, leukemias, lymphomas, immunosuppression, inflammatory bowel disease, myelosuppression, and related sequelae.

The present invention is also useful for treatment, prevention, diagnosis, and/or detection of various immune and circulatory system-related disorders in mammals, preferably humans. Such disorders include tumors (a nonlimiting list of human tumors includes breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like) and tumor metastasis, infections by bacteria, viruses, and other parasites, immunodeficiencies, inflammatory diseases, lymphadenopathy, autoimmune diseases, graft versus host disease, and any disregulation of immune and circulatory systems cell function including, but not limited to, autoimmunity, arthritis, leukemias, lymphomas, immunosuppression, immunity, humoral immunity, inflammatory bowel disease, myelo suppression, and the like.

TNF-gamma-alpha and/or TNF-gamma-beta polypeptides or polynucleotides encoding TNF-gamma-alpha and/or TNF-gamma-beta of the invention (including TNF-gamma-alpha and/or TNF-gamma-beta agonists or antagonists) may be used to treat, prevent, diagnose, and/or detect cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

The naturally occurring balance between endogenous stimulators and inhibitors of angiogenesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., Biotech. 9:630-634 (1991); Folkman et al., N. Engl. J. Med., 333:1757-1763 (1995); Auerbach et al., J. Microvasc. Res. 29:401-411 (1985); Folkman, Advances in Cancer Research, eds. Klein and Weinhouse, Academic Press, New York, pp. 175-203 (1985); Patz, Am. J. Opthalmol. 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442-447 (1987).

The present invention provides for treatment, prevention, diagnosis, and/or detection of diseases or disorders associated with neovascularization by administration of the TNF-gamma-alpha and/or TNF-gamma-beta polynucleotides and/or polypeptides of the invention (including TNF-gamma-alpha and/or TNF-gamma-beta agonists and/or antagonists). Malignant and metastatic conditions which can be treated, prevented, diagnosed, and/or detected with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)):

Additionally, ocular disorders associated with neovascularization which can be treated, prevented, diagnosed, and/or detected with the TNF-gamma-alpha and/or TNF-gamma-beta polynucleotides and polypeptides of the present invention (including TNF-gamma-alpha and/or TNF-gamma-beta agonists and TNF-gamma-alpha and/or TNF-gamma-beta antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704-710 (1978) and Gartner et al., Surv. Ophthal. 22:291-312 (1978).

Additionally, disorders which can be treated, prevented, diagnosed, and/or detected with the TNF-gamma-alpha and/or TNF-gamma-beta polynucleotides and polypeptides of the present invention (including TNF-gamma-alpha and/or TNF-gamma-beta agonists and TNF-gamma-alpha and/or TNF-gamma-beta antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

In a similar fashion, TNF-gamma-alpha and/or TNF-gamma-beta may be used to treat, prevent, diagnose, and/or detect rheumatoid arthritis (RA) by inhibiting the increase in angiogensis or the increase in endothelial cell proliferation required to sustain an invading pannus in bone and cartilage as is often observed in RA. Endothelial cell proliferation is increased in the synovia of RA patients as compared to patients with osteoarthritis (OA) or unaffected individuals. Neovascularization is needed to sustain the increased mass of the invading pannus into bone and cartilage. Inhibition of angiogenesis is associated with a significant decrease in the severity of both early and chronic arthritis in animal models.

Figure 7A:
FIG. 7A consists of photographs of WEHI 164 cells which are untreated (FIG. 7Aa) and after exposure to TNF-alpha (FIG. 7Ab), TNF-gamma (FIG. 7Ac), and TNF-beta (FIG. 7Ad). Cells which have an elongated non-round morphology have been lysed. The various TNF molecules were added at a concentration of approximately 0.5 µg/ml. Photographs were taken 72 hours after addition of the various TNF molecules.
Figure 7A:
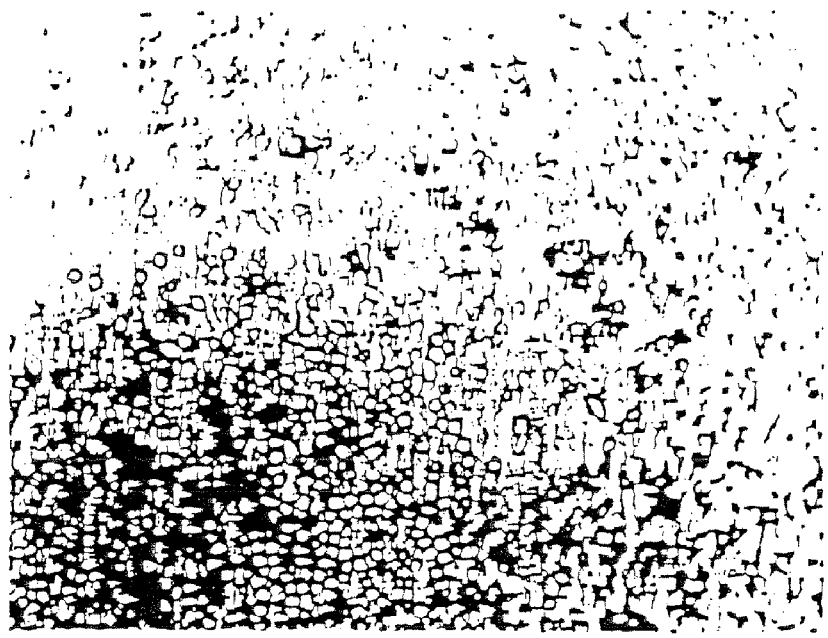
Figure 7A:
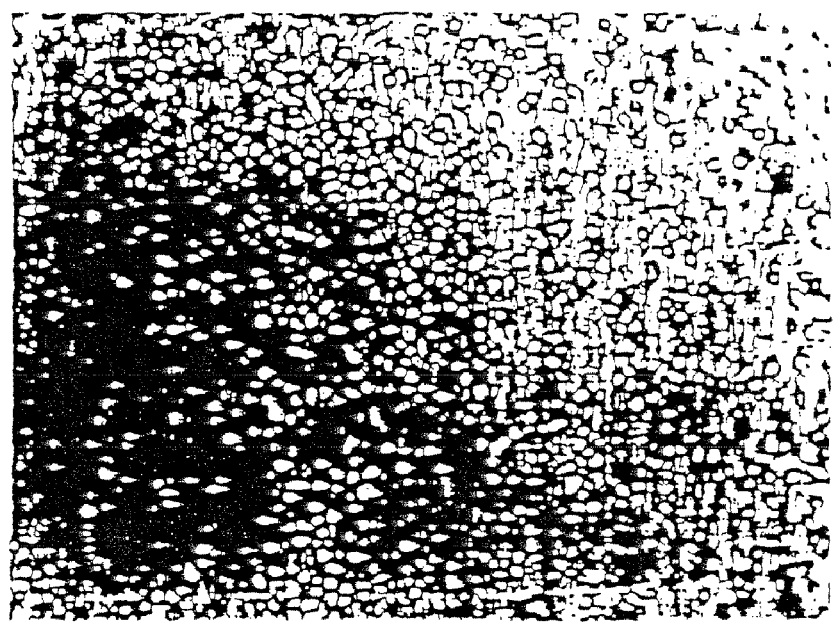
Figure 7B:
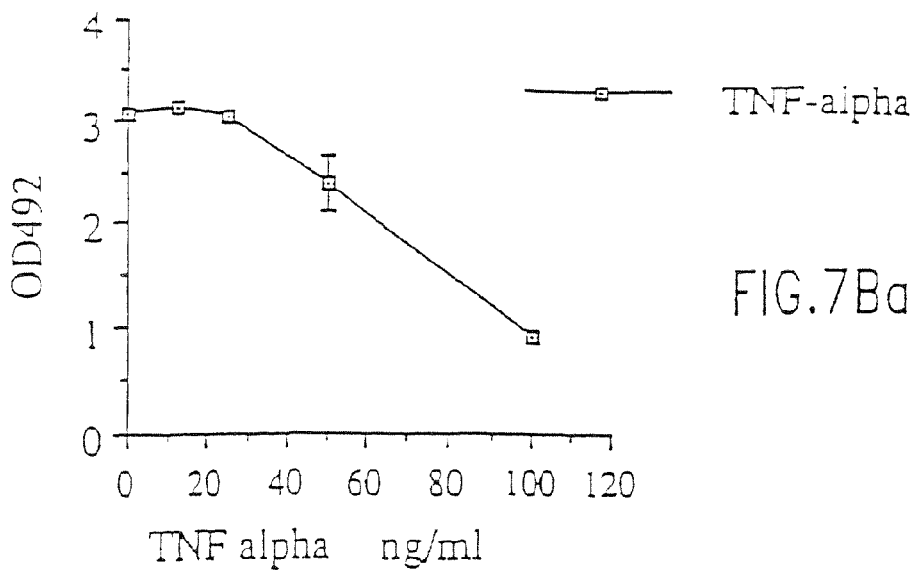
FIG. 7B illustrates the ability of TNF-gamma (FIG. 7Bc) in comparison to TNF-alpha (FIG. 7Ba) and TNF-beta (FIG. 7Bb) to inhibit WEHI 164 cell growth.
Figure 7B:
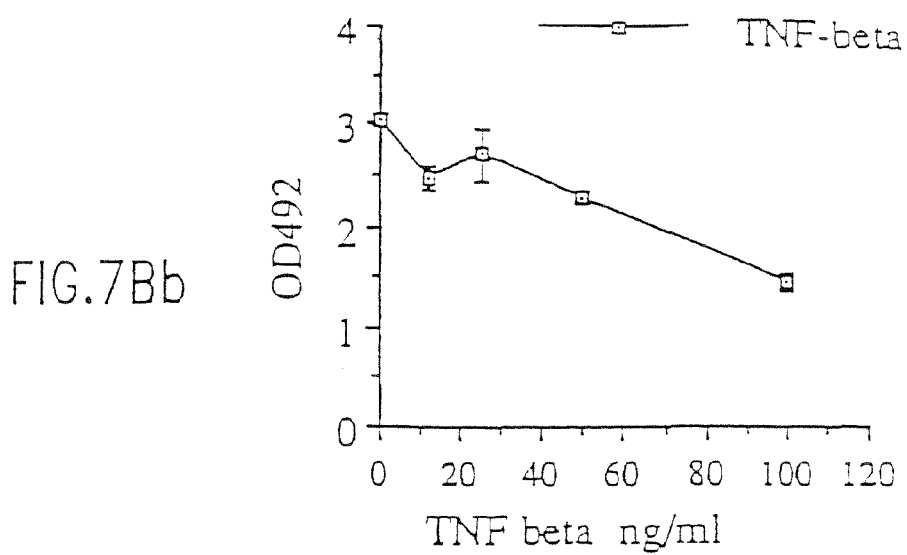
Figure 7B:
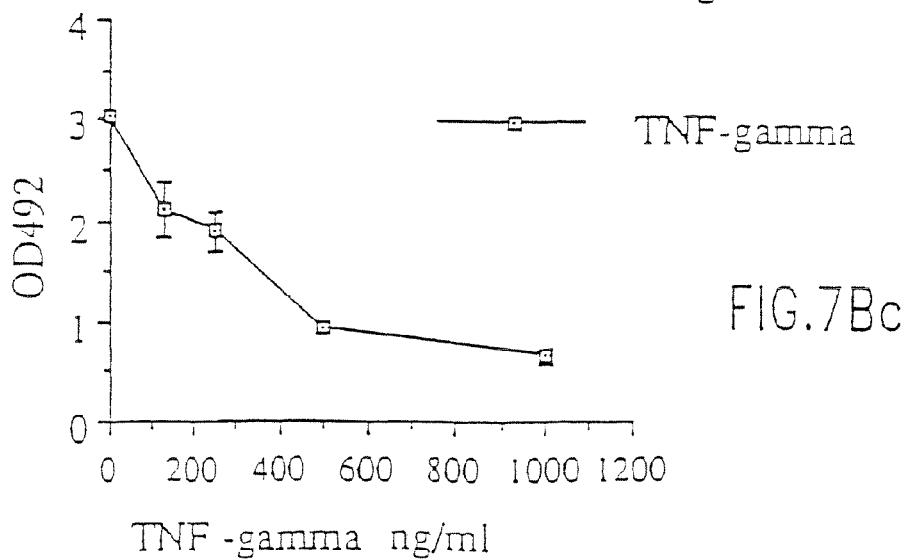
Figure 8B:
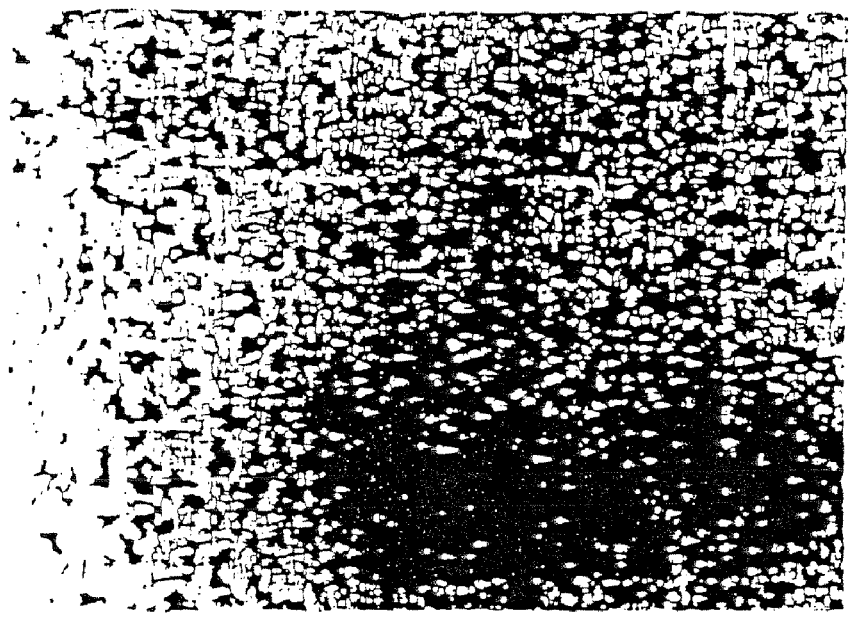
FIG. 8 illustrates the ability of recombinant TNF-alpha (FIG. 8B), TNF-beta (FIG. 8D), and TNF-gamma (FIG. 8C) to induce morphological change in L929 cells with respect to untreated L929 cells (FIG. 8A). The morphology change is indicated by dark round cells. Cells were treated with the various recombinant TNF molecules (produced in E. coli) at approximately 0.5 µg/ml. The photographs were taken 72 hours after the addition of the various TNF molecules. The morphology change indicates that the cells have been killed.
Figure 8A:
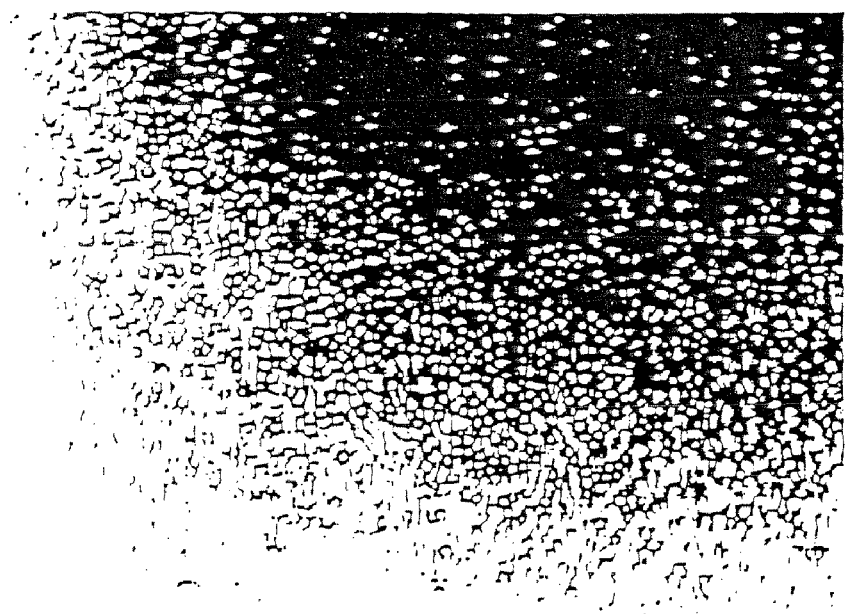
Figure 8D:
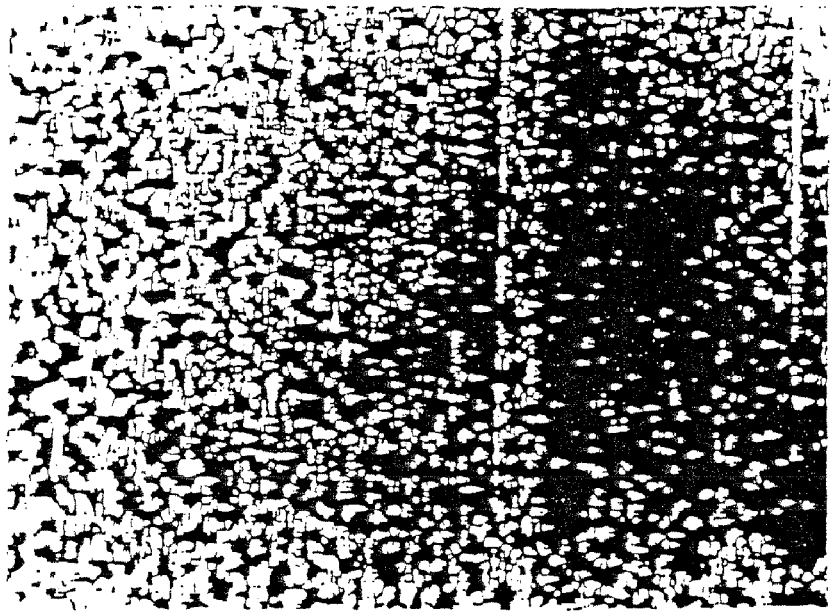
Figure 8C:
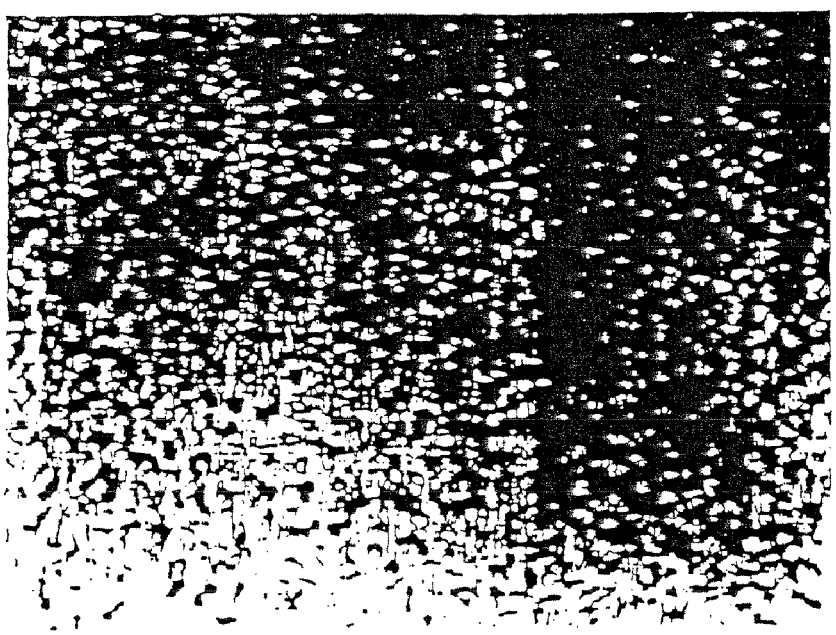
Figure 12:
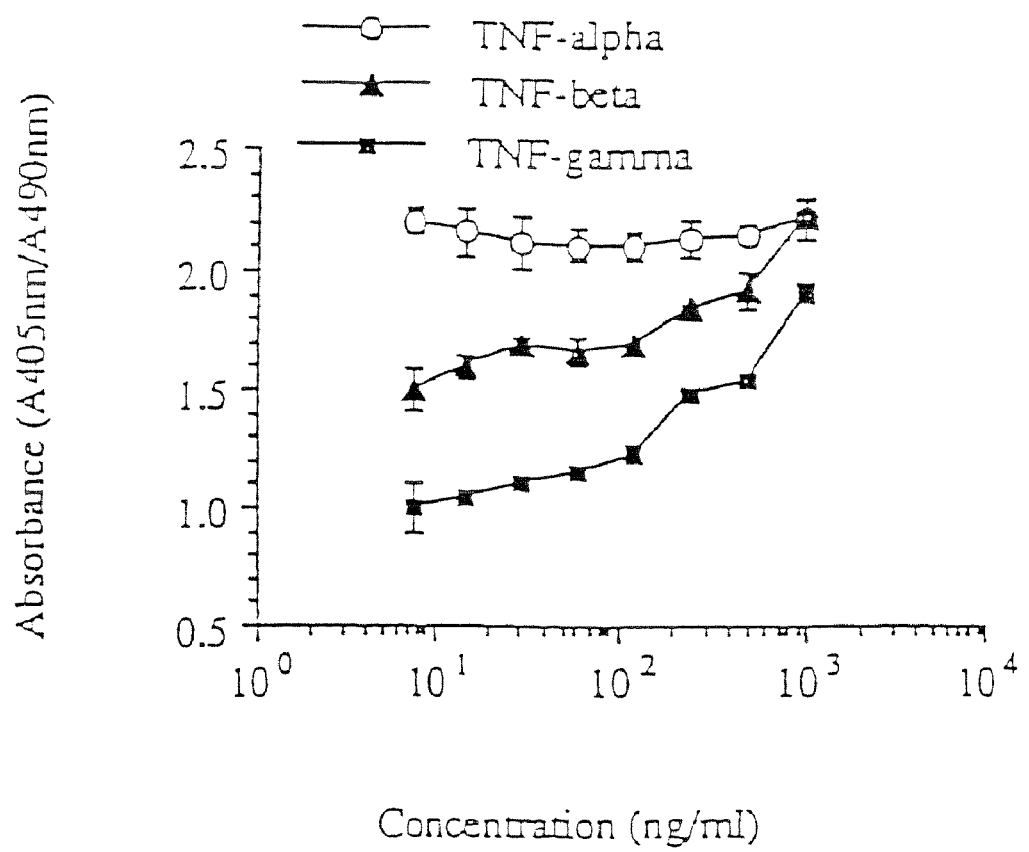
FIG. 12 illustrates the ability of recombinant TNF-gamma (represented by squares), TNF-alpha (represented by circles), and TNF-beta (represented by triangles) to induce WEHI 164 cell death. Cell death is inversely proportional to the ratio of absorbance at 405 nm to that at 490 nm).

The TNF-gamma-alpha and/or TNF-gamma-beta polypeptide of the present invention may be employed to inhibit tumor cell growth or neoplasia. The TNF-gamma-alpha and/or TNF-gamma-beta polypeptide may be responsible for tumor destruction through apoptosis which is characterized by membrane blebbing (zeiosis), condensation of cytoplasma and the activation of an endogenous endonuclease (FIG. 12). As shown in Table 1, TNF-gamma has strong cytotoxic activity for the cell lines tested which have abnormal cellular proliferation and regulation, for example the fibrosarcoma and carcinoma cell line. This is also illustrated in FIGS. 7A, 7B, and 8 where it is shown that TNF-gamma has the ability to inhibit L929 and WEHI 164 cell growth through cytotoxic activity. WEHI 164 cells are mouse fibrosarcoma cells. A preferable method of administering the TNF-gamma is by injection directly into the tumor.

Diseases or conditions that may be treated, prevented, diagnosed, and/or detected with the polynucleotides or polypeptides of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

The cell adhesion activity of TNF-gamma may be employed for wound healing. As shown in Table 1 and FIG. 9, TNF-gamma has a strong endothelial cell proliferation effect which is an indication that TNF-gamma plays a role in wound healing. TNF-gamma's cell adhesive effects may also play a role in wound healing.

TNF-gamma may also be employed to treat, prevent, diagnose, and/or detect diseases which require growth promotion activity, for example, restenosis. As stated above, TNF-gamma is shown to have strong proliferation effects on endothelial cell growth. Accordingly, TNF-gamma may also be employed to regulate hematopoiesis and endothelial cell development.

The TNF-gamma polypeptide, through its ability to stimulate the activation of T-cells, is an important mediator of the immune response. Accordingly, this polypeptide may be used to stimulate an immune response against a variety of parasitic, bacterial and viral infections. TNF-gamma may lyse virus-infected cells and, therefore, be employed to arrest HIV infected cells.

The TNF-gamma polypeptide may also be employed to treat, prevent, diagnose, and/or detect autoimmune diseases such as Type I diabetes by enhancing the T-cell proliferative response.

Figure 10:
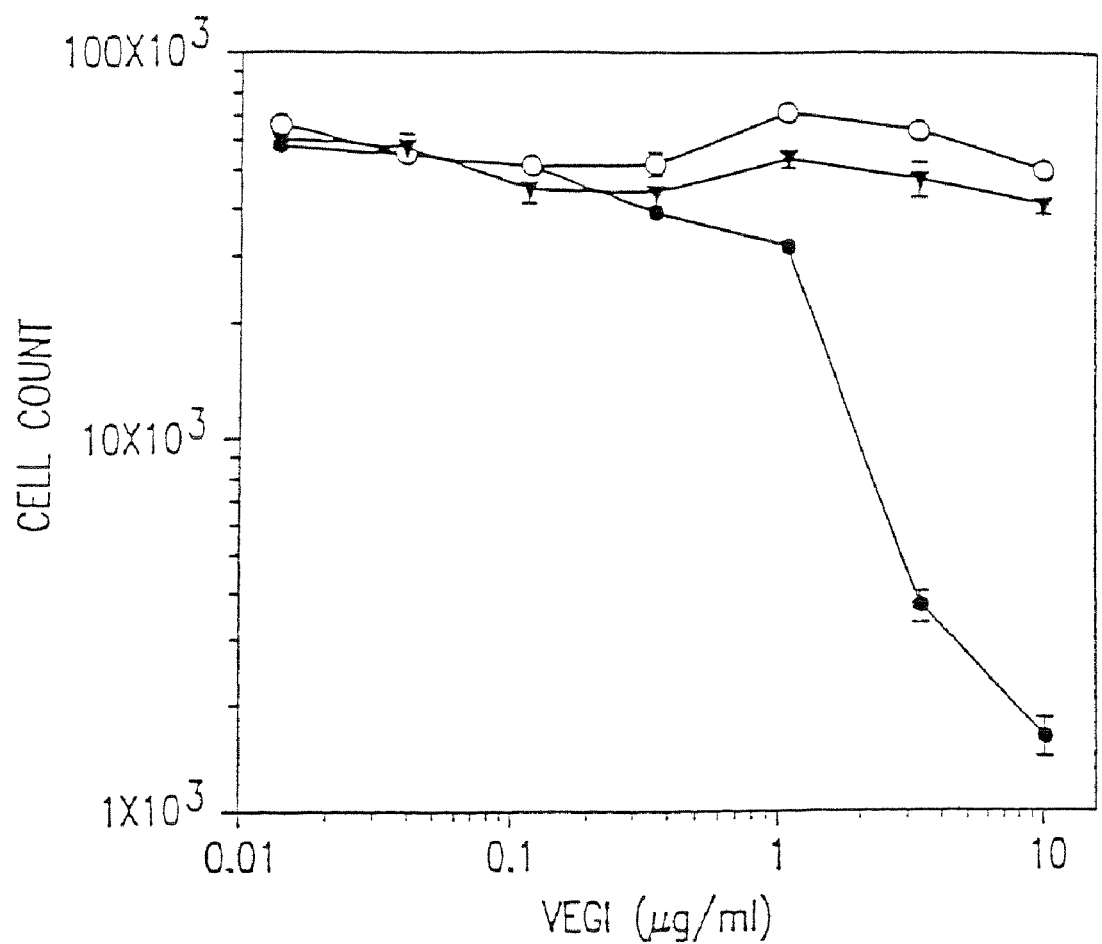
FIG. 10 shows the effect of TNF-gamma on the proliferation of endothelial cell and breast cancer cells. The number of cells are plotted against TNF-gamma concentration as indicated (TNF-gamma is designated "VEGI" in this figure). Inhibition of the growth of adult bovine aortic endothelial (ABAE) cells (dark circles), but not that of MDA-MB-231 (dark triangles) or MDA-MB-435 (open circles) cells, is shown. The cells were seeded at $2 \times 10^3$ cells/well in triplicate in 24-well plates. The ABAE cell culture media contained IMEM (Life Technologies, Inc., Rockville, Md.) supplemented with 10% FCS and (1 ng/ml) FGF-2. The cultures were maintained at 37° C., 5% $CO_2$, for 6 days. The cells were then trypsinized, and the number of cells determined by using a Coulter counter. One-fifth of the total number of recovered ABAE cells is shown in order to normalize the comparison with the MDA-MB-231 and MDA-MB-435 cells.

TNF-gamma may be used to inhibit the proliferation of endothelial cells, for example, aortic endothelial cells. As illustrated in FIG. 10, at concentrations of up to 10 µg/ml, TNF-gamma can nearly completely inhibit the growth of endothelial cells while having no apparent effect on the growth of human breast cancer cells. As a result, TNF-gamma can be used to treat, prevent, diagnose, and/or detect diseases and disorders in which inhibition of endothelial cell growth is advantageous Inhibiting the growth of endothelial cells is desirable in the treatment of many types of cancers which depend on the generation of new blood vessels to support growth of the tumor. TNF-gamma can be used to inhibit the growth of such tumors by inhibiting the growth of endothelial cells which are a major cellular component of the blood vessel. Evidence of the ability of TNF-gamma to be effectively used in this fashion is presented in FIGS. 16A and 16B. These experiments are discussed in greater detail below.

In particular, TNF-gamma can be used to regulate endothelial cell growth when endothelial cells have already begun proliferating. Such a situation may arise when angiogenesis is occurring as a tumor-supporting mechanism as described above. Endogenous TNF-gamma expression is reduced in proliferating cultures of endothelial cells, whereas the expression of endogenous TNF-gamma is enhanced in quiescent endothelial cell cultures (FIG. 4). As a result, it is preferable to use TNF-gamma of the present invention to reduce the rate of cell growth in cultures of proliferating endothelial cells, for example, during the increase in size of a tumor in a cancerous state.

Figure 14:
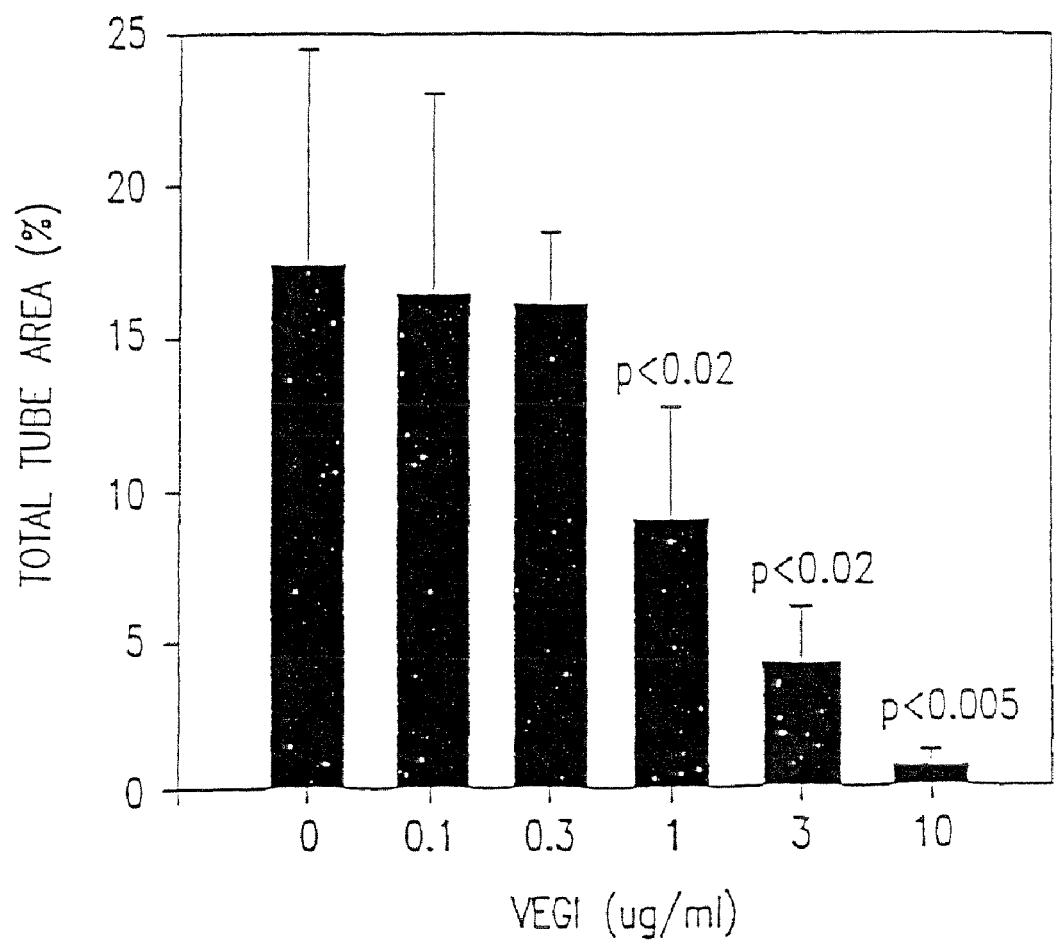
FIG. 14 demonstrates the effect of TNF-gamma on the ability of ABAE cells to form capillary-like tubes on collagen gels. The ability of recombinant TNF-gamma (residues 12-147 as shown in SEQ ID NO:2 and designated "VEGI" in this figure) to inhibit the formation of capillary-like tubes by ABAE cells is shown. The p-values (t-test) given above the columns are obtained by comparing the extent of the capillary-like tube formation by ABAE cells in the presence of various concentrations of TNF-gamma, as indicated, to that when TNF-gamma is absent from the culture media.
Figure 15:
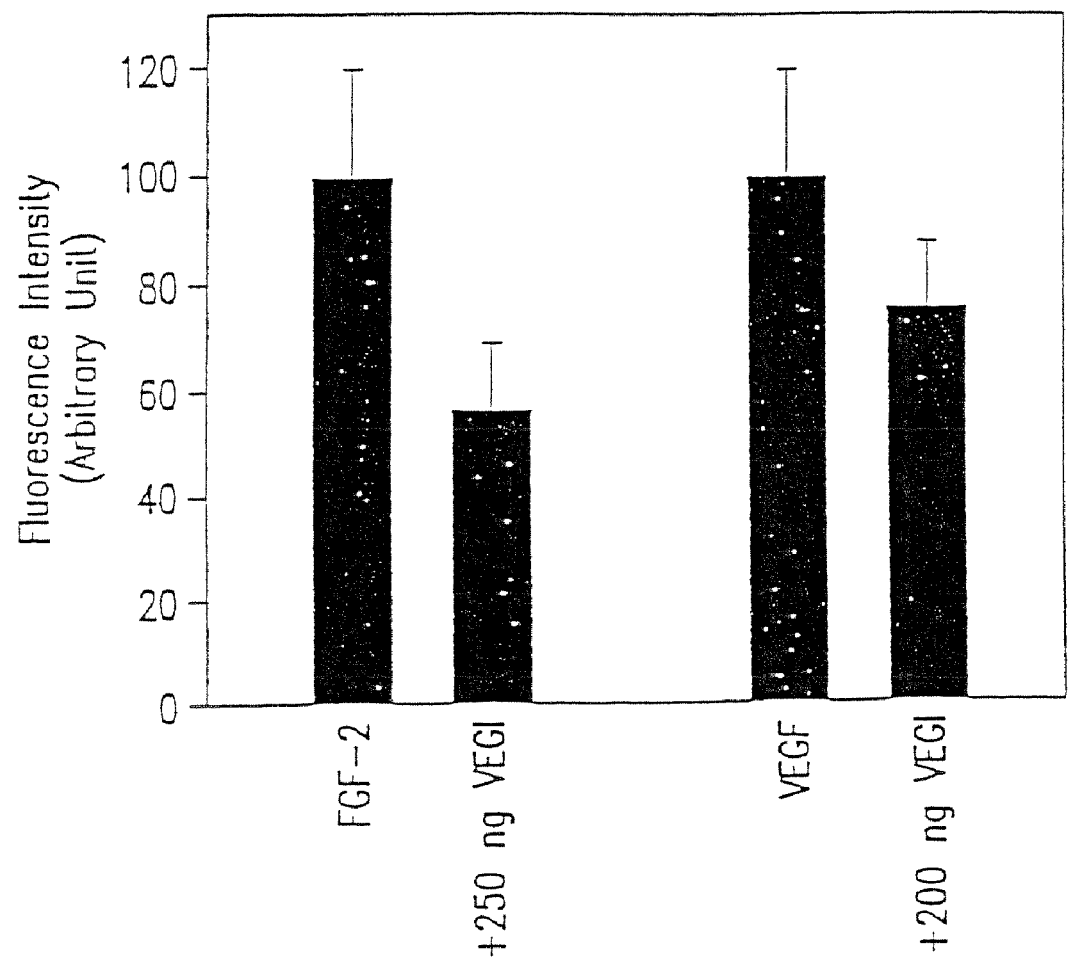
FIG. 15 shows the inhibition of angiogenesis in collagen gels placed on chicken embryonic chorioallantoic membrane (CAM) by TNF-gamma. The growth of new capillary vessels into collagen gel pellets placed on the CAM was induced by either FGF-2 (100 ng) or VEGF (250 ng). The extent of angiogenesis in the gels was determined by evaluation of the fluorescence intensity of FITC-dextran injected into the CAM circulation. Inhibition of the capillary vessel growth by the recombinant TNF-gamma (designated "VEGI" in this figure), as indicated by a lower value than 100, is shown. The experiment was carried out in triplicate.

TNF-gamma of the present invention has been used to reduce the formation of capillary-like tubular structures formed by endothelial cells in vitro. As illustrated in FIG. 14, TNF-gamma of the present invention can be used to inhibit the formation of endothelial cells organized into capillary-like tubular structures in response to angiogenic factors such as FGF-2. Furthermore, isolated TNF-gamma of the present invention can also be used to inhibit the growth and organization of endothelial cells into capillary vessels in a modified chicken embryo chorioallantoic membrane (CAM), as shown in FIG. 15. As a result, TNF-gamma of the present invention can be used to inhibit the formation of capillaries or capillary-like structures from endothelial cells in vitro.

TNF-gamma of the present invention can be used as an anti-cancer agent. As illustrated in FIG. 16, TNF-gamma was used to inhibit the growth of human breast cancer cells in a xenograft tumor model. Despite the high tumorigenicity of these cells, treatment with TNF-gamma of the present invention resulted in a marked inhibition of the growth of the xenograft tumors. TNF-gamma, or a mutein thereof, of the present invention, can be used to treat, prevent, diagnose, and/or detect a number of cancers including, but not limited to, breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like.

The polynucleotides and polypeptides of the present invention may be employed as research reagents and materials for discovery of treatment, prevention, diagnosis, and/or detection of human disease.

TABLE 2

Summary of TNF-gamma activity

| Cell lines | Source and type | Cytotoxicity | Proliferation | Differentiation | Adhesion |
|---|---|---|---|---|---|
| L929 | mouse fibroblast | + | − | − | − |

TABLE 2-continued

Summary of TNF-gamma activity

| Cell lines | Source and type | Cytotoxicity | Proliferation | Differentiation | Adhesion |
|---|---|---|---|---|---|
| WEHI 164 | mouse fibrosarcoma | +++ | − | − | − |
| NRK-54E | rat kidney epithelial-like | + | − | − | − |
| THP-1 | human monocytic leukemia | + | − | ++ | ++ |
| HL-60 | human promyelocytic leukemia | − | − | − | ++ |
| Raji | human Burkitt's lymphoma | − | − | − | − |
| Jurkat | human T-cell lymphoma | ++ | − | − | − |
| Primary | HUVEC | − | ++ | − | ? |
| Primary | human aterial endothelial | +* | ++ | − | ? |
| A-431 | human epidermoid carcinoma | ++ | − | − | − |
| 293 | human embryonal kidney | − | ++ | − | − |

Legend:
*At high dose only. The numbers of "+" indicate the relative level of activities. "−" indicates no detected activity at the concentration range tested.

This invention provides a method for identification of the receptor for TNF-gamma. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to TNF-gamma, and a cDNA library created from this RNA is divided into pools and used to transfect COS cells or other cells that are not responsive to TNF-gamma. Transfected cells which are grown on glass slides are exposed to labeled TNF-gamma. TNF-gamma can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled TNF-gamma can be photoaffinity-linked with cell membrane or extract preparations that express the receptor molecule. Cross-linked material is resolved by PAGE and exposed to X-ray film. The labeled complex containing the TNF-gamma-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

TNF-gamma does not bind significantly to two soluble TNF receptors, sTNF-RI (p55) and sTNF-RII (p75). Accordingly, TNF-gamma may have activities inclusive of and additional to known TNF proteins (see FIG. 13).

Formulations and Administration

The TNF-gamma polypeptide composition will be formulated and dosed in a fashion consistent with good medical practice, taking into account the clinical condition of the individual patient (especially the side effects of treatment with TNF-gamma polypeptide alone), the site of delivery of the TNF-gamma polypeptide composition, the method of administration, the scheduling of administration, and other factors known to practitioners. The "effective amount" of TNF-gamma polypeptide for purposes herein is thus determined by such considerations.

The antagonists may be employed in a composition with a pharmaceutically acceptable carrier, e.g., as hereinafter described.

The TNF-gamma polypeptides and agonists and antagonists of the present invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 micrograms/kg body weight and in most cases they will be administered in an amount not in excess of about 8 mg/Kg body weight per day. In most cases, the dosage is from about 10 micrograms/kg to about 1 mg/kg body weight daily, taking into account the routes of administration, symptoms, etc.

The compositions of the invention may be administered alone or in combination with other therapeutic agents. Therapeutic agents that may be administered in combination with the compositions of the invention, include but not limited to, other members of the TNF family, chemotherapeutic agents, antibiotics, growth factors, steroidal and non-steroidal anti-inflammatories, conventional immunotherapeutic agents, cytokines, chemokines, growth factors, radiotherapy and/or or radiation therapy. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. In certain embodiments, compositions of the invention are administered in combination with one or more other therapeutic agents (including, for example, a one or more chemotherapeutic agents and/or radiotherapy and/or radiation therapy), wherein either or both the compositions of the invention and/or one or more of the therapeutic agents are administered at standard, reduced or increased dosages.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, AIM-I (International Publication No. WO 97/33899), AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfmavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

Additionally, immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), butixocort propionate (WarnerLambert).

In a preferred embodiment, the compositions of the invention are administered in combination with carboplatin and paclitaxel or with cisplatin and etoposide.

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the compositions of the invention are administered alone or in combination with an anti-inflammatory agent. Anti-inflammatory agents that may be administered with the compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In one embodiment, the compositions of the invention are administered in combination with one or more chemokines. In specific embodiments, the compositions of the invention are administered in combination with an alpha (CxC) chemokine selected from the group consisting of alpha interferon inducible protein-10 (IP-10), interleukin-8 (IL-8), platelet factor-4 (PF4), neutrophil activating protein (NAP-2), GRO-alpha, GRO-alpha, GRO-alpha, neutrophil-activating peptide (ENA-78), granulocyte chemoattractant protein-2 (GCP-2), and stromal cell-derived factor-1 (SDF-1, or pre-B cell stimulatory factor (PBSF)); and/or an alpha (CC) chemokine selected from the group consisting of: RANTES (regulated on activation, normal T expressed and secreted), macrophage inflammatory protein-1 alpha (MIP-1 alpha), macrophage inflammatory protein-1 alpha (MIP-1 alpha), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 alpha (MIP-1 alpha), macrophage inflammatory protein-3alpha (MIP-3 alpha), macrophage inflammatory protein-3 alpha (MIP-3 alpha), macrophage inflammatory protein-4 (MIP-4/DC-CK-1/PARC), eotaxin, Exodus, and 1-309; and/or the alpha (C) chemokine, lymphotactin.

In an additional embodiment, the compositions of the invention (e.g., antagonists) are administered in combination with angiogenic proteins or compounds. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above-mentioned references are incorporated herein by reference herein.

In additional embodiments, the compositions of the invention are administered in combination with anti-angiogenic proteins or compounds and/or antagonists thereof.

In additional embodiments, the compositions of the invention are administered, either alone or in combination with one or more additional agents or compounds (as described herein), in a dose-cycling fashion. For example, a composition of the invention may be administered in repeatedly increasing and decreasing doses either alone, in unison with one or more additional agents or compounds, or in a complementary dose-cycling fashion with one or more additional agents or compounds (such that the dose of the composition of the invention is relatively high in concert with a relatively low dose of one or more additional agents or compounds and vice versa). In a preferred embodiment, dose-cycling with one or more compositions of the invention administered, either alone or in combination with one or more additional agents or compounds, is used to treat tumors. In another preferred embodiment, dose-cycling with one or more compositions of the invention administered, either alone or in combination with one or more additional agents or compounds, is used to inhibit angiogenesis (either in part or in full). In a highly preferred embodiment, dose-cycling with one or more compositions of the invention administered, either alone or in combination with one or more additional agents or compounds, is used to inhibit angiogenesis (either in part or in whole) and to thereby treat a tumor.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Gene Therapy

The TNF-gamma polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well known in the art and are apparent from the teachings herein. For example, cells may be engineered by the use of a retroviral particle containing RNA encoding a polypeptide of the present invention.

Similarly, cells may be engineered in vivo for expression of a polypeptide in vivo by, for example, procedures known in the art. For example, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described by Miller and colleagues (*Biotechniques* 7:980-990 (1989)), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, b-2, b-AM, PA12, T19-14X, VT-19-17-H2, CRE, b-CRIP, GP+E-86, GP+envAm12, and DAN cell lines as described by Miller (*Human Gene Therapy* 1:5-14 (1990)), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Agonists and Antagonists—Assays and Molecules

This invention is also related to a method of screening compounds to identify those which mimic TNF-gamma (agonists) or prevent the effect of TNF-gamma (antagonists). An example of such a method takes advantage of the ability of TNF-gamma to significantly stimulate the proliferation of human endothelial cells in the presence of the comitogen Con A. Endothelial cells are obtained and cultured in 96-well flat-bottomed culture plates (Costar, Cambridge, Mass.) in RPM1 1640 supplemented with 10% heat-inactivated fetal bovine serum (Hyclone Labs, Logan, Utah), 1% L-glutamine, 100 U/ml penicillin, 100 micrograms/ml streptomycin, 0.1% gentamycin (Gibco Life Technologies, Grand Island, N.Y.) in the presence of 2 micrograms/ml of Con-A (Calbiochem, La Jolla, Calif.). Con-A, and the compound to be screened are added to a final volume of 0.2 ml. After 60 h at 37° C., cultures are pulsed with 1 microCi of [$^3$H]thymidine (5 Ci/mmol; 1 Ci=37 BGq; NEN) for 12-18 h and harvested onto glass fiber filters (PhD; Cambridge Technology, Watertown, Mass.). Mean [$^3$H]thymidine incorporation (cpm) of triplicate cultures is determined using a liquid scintillation counter (Beckman Instruments, Irvine, Calif.). Significant [$^3$H]-thymidine incorporation indicates stimulation of endothelial cell proliferation.

Alternatively, the response of a known second messenger system following interaction of TNF-gamma and receptor would be measured and compared in the presence or absence of the compound. Such second messenger systems include but are not limited to, cAMP guanylate cyclase, ion channels or phosphoinositide hydrolysis.

To assay for antagonists, the assay described above is performed, however, in this assay TNF-gamma is added along with the compound to be screened and the ability of the compound to inhibit [$^3$H]thymidine incorporation in the presence of TNF-gamma, indicates that the compound is an antagonist to TNF-gamma. Alternatively, TNF-gamma antagonists may be detected by combining TNF-gamma and a potential antagonist with membrane-bound TNF-gamma receptors or recombinant receptors under appropriate conditions for a competitive inhibition assay. TNF-gamma can be labeled, such as by radioactivity, such that the number of TNF-gamma molecules bound to the receptor can determine the effectiveness of the potential antagonist.

Alternatively, a mammalian cell or membrane preparation expressing the TNF-gamma receptor is incubated with labeled TNF-gamma in the presence of the compound. The ability of the compound to enhance or block this interaction could then be measured.

In another aspect of this embodiment the invention provides a method for identifying a receptor protein or other ligand-binding protein which binds specifically to a TNF-gamma polypeptide (e.g. DR3). For example, a cellular compartment, such as a membrane or a preparation thereof, may be prepared from a cell that expresses a molecule that binds TNF-gamma. The preparation is incubated with labeled TNF-gamma and complexes of TNF-gamma bound to the receptor or other binding protein are isolated and characterized according to routine methods known in the art. Alternatively, the TNF-gamma polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds TNF-gamma, such as a molecule of a signaling or regulatory pathway modulated by TNF-gamma. The preparation is incubated with labeled TNF-gamma in the absence or the presence of a candidate molecule which may be a TNF-gamma agonist or antagonist. The ability of the candidate molecule to bind the binding molecule is reflected in decreased binding of the labeled ligand. Molecules which bind gratuitously, i.e., without inducing the effects of TNF-gamma on binding the TNF-gamma binding molecule, are most likely to be good antagonists. Molecules that bind well and elicit effects that are the same as or closely related to TNF-gamma are agonists.

TNF-gamma-like effects of potential agonists and antagonists may by measured, for instance, by determining activity of a second messenger system following interaction of the candidate molecule with a cell or appropriate cell preparation, and comparing the effect with that of TNF-gamma or molecules that elicit the same effects as TNF-gamma. Second messenger systems that may be useful in this regard include but are not limited to AMP guanylate cyclase, ion channel or phosphoinositide hydrolysis second messenger systems.

Another example of an assay for TNF-gamma antagonists is a competitive assay that combines TNF-gamma and a potential antagonist with membrane-bound TNF-gamma receptor molecules or recombinant TNF-gamma receptor molecules under appropriate conditions for a competitive inhibition assay. TNF-gamma can be labeled, such as by radioactivity, such that the number of TNF-gamma molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing TNF-gamma-induced activities, thereby preventing the action of TNF-gamma by excluding TNF-gamma from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TNF-gamma. The antisense RNA oligonucleotide hybridizes to the mRNA in vivo and blocks translation of the mRNA molecule into TNF-gamma polypeptide. The oligonucleotides described above can also be delivered to cells such that the antisense RNA or DNA may be expressed in vivo to inhibit production of TNF-gamma protein.

Antibodies specific to TNF-gamma may be used as antagonists by binding to TNF-gamma and preventing it from binding to its receptor. Monoclonal antibodies are particularly effective in this regard. Antibodies specific to the TNF-gamma receptor, however, may mediate distinct cellular responses which tend to agonize the effects of TNF-gamma upon interaction with its receptor.

Potential TNF-gamma antagonists also include TNF-gamma mutants which bind to the TNF-gamma receptor and elicit no second messenger response to effectively block the receptor from its natural ligand. Specifically designed oligonucleotides and small molecules may also bind to the TNF-gamma receptor (e.g., DR3) and block it from TNF-gamma. Examples of small molecules include but are not limited to small peptides or peptide-like molecules.

Another potential TNF-gamma antagonist is a soluble form of the TNF-gamma receptor which binds to TNF-gamma and prevents it from interacting with membrane-bound TNF-gamma receptors. In this way, the receptors are not stimulated by TNF-gamma.

Another potential TNF-gamma antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of TNF-gamma. The antisense RNA oligonucleotide hybridizes to the mRNA in vivo and blocks translation of the mRNA molecule into the TNF-gamma polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of TNF-gamma.

TNF-alpha antagonists may also be employed to treat, prevent, diagnose, and/or detect cachexia which is a lipid clearing defect resulting from a systemic deficiency of lipoprotein lipase which is suppressed by TNF-gamma. The TNF-gamma antagonists are also employed to treat, prevent, diagnose, and/or detect cerebral malaria in which TNF-gamma appears to play a pathogenic role. The antagonists may also be employed to treat, prevent, diagnose, and/or detect rheumatoid arthritis by inhibiting TNF-gamma induced production of inflammatory cytokines such as IL-1 in the synovial cells. When treating and/or preventing arthritis TNF-gamma is preferably injected intra-articularly.

The TNF-gamma antagonists may also be employed to prevent graft rejection by preventing the stimulation of the immune system in the presence of a graft by TNF-gamma.

The TNF-gamma antagonists may also be employed to treat, prevent, diagnose, and/or detect osteoporosis since TNF-gamma may induce bone resorption.

Antagonists to TNF-gamma may also be employed as anti-inflammation agents since TNF-gamma mediates an enhanced inflammatory response.

The antagonists may also be used to treat, prevent, diagnose, and/or detect endotoxic shock, also referred to as septic shock. This critical condition results from an exaggerated response to bacterial or other types of infection. This response leads to elevated levels of TNF-gamma which causes shock and tissue injury.

The present invention also relates to a diagnostic assay for detecting altered levels of TNF-gamma protein in various tissues since an over-expression of the proteins compared to normal control tissue samples may detect the presence of a disease or susceptibility to a disease, for example, tumors and cerebral malaria. Assays used to detect levels of TNF-gamma protein in a sample derived from a host are well known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the TNF-gamma antigen, preferably a monoclonal antibody. In addition a reporter antibody is prepared against the monoclonal antibody. To the reporter antibody is attached a detectable reagent such as radioactivity, flourescence or in this example a horseradish peroxidase enzyme. A sample is removed from a host and incubated on a solid support, e.g. a polystyrene dish that binds the proteins in the sample. Any free protein binding sites on the dish are then covered by incubating with a non-specific protein like BSA. Next, the monoclonal antibody is incubated in the dish during which time the monoclonal antibodies attach to any TNF-gamma proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to TNF-gamma. Unattached reporter antibody is then washed out. Peroxidase substrates are then added to the dish and the amount of color developed in a given time period is a measurement of the amount of TNF-gamma protein present in a given volume of patient sample when compared against a standard curve.

A competition assay may be employed wherein antibodies specific to TNF-gamma are attached to a solid support and labeled TNF-gamma and a sample derived from the host are passed over the solid support and the amount of label detected, for example by liquid scintillation chromatography, can be correlated to a quantity of TNF-gamma in the sample.

A "sandwich" assay is similar to an ELISA assay. In a "sandwich" assay TNF-gamma is passed over a solid support and binds to antibody attached to a solid support. A second antibody is then bound to the TNF-gamma. A third antibody which is labeled and specific to the second antibody is then passed over the solid support and binds to the second antibody and an amount can then be quantitated.

All of the applications of TNF-gamma described, whether or not explicitly described herein, also apply to veterinary medicine (in the context of, for example, mice, rats, rabbits, hamsters, guinea pigs, pigs, micro-pigs, goats, sheep, cows and non-human primates, e.g., baboons, monkeys, and chimpanzees).

Gene Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3' untranslated region of the sequence is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Utilizing the techniques described above, the chromosomal location of TNF-gamma was determined with very high confidence to be 9q32. Previous chromosomal mapping studies have linked several developmental defects to loci in this area of chromosome 9. In addition, bladder and esophageal cancers have also been associated with chromosomal abnormalities at this locus. See, e.g., Habuchi, T., et al., *Genomics* 48:277-88 (1998); Habuchi, T., et al., *Hum. Molec. Genet.* 6:913-19 (1997); Nishiyama, H., et al., *Genes Chromosomes Cancer* 26:171-75 (1999); Miura, K., et al., *Cancer Res.* 56:1629-34 (1996); and Nishiwaki, T., et al., *Genes Chromosomes Cancer* 27:169-76 (2000).

EXAMPLES

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures, unless otherwise stated. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456-457 (1973).

Example 1

Bacterial Expression and Purification of TNF-Gamma

Figure 5:
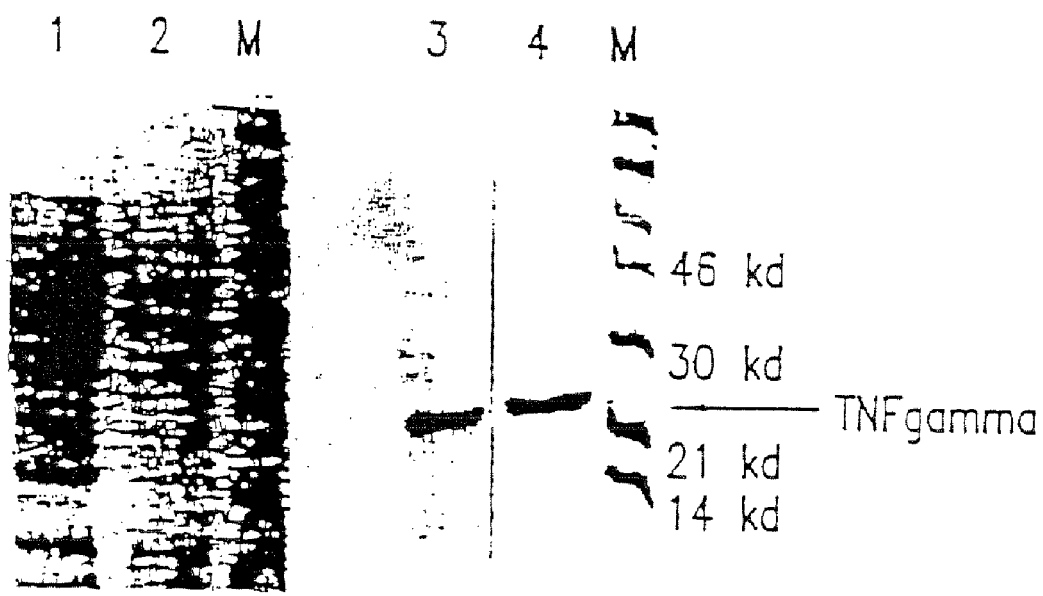
FIG. 5 is a photograph of a polyacrylamide gel electrophoresis analysis of TNF-gamma protein. TNF-gamma was produced by bacterial expression and purified as described in Example 1.

The DNA sequence encoding the full-length TNF-gamma ORF, ATCC™ Deposit No. 75927, was initially amplified using PCR oligonucleotide primers corresponding to the 5' and 3' sequences of the TNF-gamma protein. Additional nucleotides corresponding to TNF-gamma were added to the 5' and 3' sequences respectively. The 5' oligonucleotide primer is shown as SEQ ID NO:13 and has the sequence 5'-GCG CGG ATC CAC CAT GAG ACG CTT TTT AAG CAA AGT C-3' which contains a Bam HI restriction enzyme site followed by the first 24 nucleotides of TNF-gamma coding sequence starting from the initiating methionine codon. The 3' sequence 5'-CGC GTC TAG ACT ATA GTA AGA AGG CTC CAA AGA AGG-3' (SEQ ID NO:14) contains sequences complementary to an Xba I site and 22 nucleotides of TNF-gamma. The restriction enzyme sites correspond to the restriction enzyme sites in the bacterial expression vector pQE-9 (Qiagen). pQE-9 was then digested with Bam HI and Xba I. The amplified sequences were ligated into pQE-9 and were inserted in frame with the sequence encoding for the histidine tag and the RBS. The ligation mixture was then used to transform an *E. coli* strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$_{600}$) of between 0.4 and 0.6. IPTG ("Isopropyl-B-D-thiogalactopyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 M Guanidine HCl (Guanidine HCl concentrations of greater than or equal to 2.5 M were empirically found to result in a higher level of purity of recovered recombinant protein). After clarification, solubilized TNF-gamma was purified from this solution by chromatography on a Nickel-Chelate column under conditions that allow for tight binding by proteins containing the 6-His tag (Hochuli, E. et al., J. Chromatography 411:177-184 (1984)). TNF-gamma was further purified by a second run on the Nickel-chelate column. TNF-gamma (90% pure) was eluted from the column in 6 M guanidine HCl pH 5.0 and for the purpose of renaturation was dialyzed in PBS buffer. The expression product was electrophoresed by SDS-PAGE, and the results may be seen in FIG. 5 where lanes labeled "M" contain molecular weight markers; lane 1 is induced cell lysate; lane 2 is uninduced call lysate; lane 3 is the TNF-gamma protein after two Nickel-chelate column purifications; lane 4 is the TNF-gamma protein after 1 column purification.

One of ordinary skill in the art will recognize that bacterial expression vectors other than pQE-9 may also be used to express TNF-gamma. One such preferred bacterial expression vector is pHE4-5. pHE4-5 may be obtained as pHE4-5/MPIFΔ23 plasmid DNA (this construct contains an unrelated insert which encodes an unrelated ORF). The pHE4-5/MPIFΔ23 plasmid was deposited with the American Type Culture Collection on Sep. 30, 1997 (Accession No. 209311). The ATCC™ is located at 10801 University Boulevard, Manassas, Va. 20110-2209, USA. Using the Nde I and Asp 718 restriction sites flanking the unrelated MPIF ORF insert, one of ordinary skill in the art could easily use current molecular biological techniques to replace the unrelated ORF in the pHE4-5/MPIFΔ23 plasmid with the TNF-gamma ORF, or variations thereof, of the present invention.

In a specific embodiment, a bacterial expression construct was generated using the pHE-4 vector to express amino acid residues T-51 through L-174 of SEQ ID NO:2.

In another specific embodiment, a bacterial expression construct was generated using the pHE-4 vector to express amino acid residues T-58 through L-174 of SEQ ID NO:2.

In a specific embodiment, a bacterial expression construct was generated using the pHE-4 vector to express amino acid residues T-28 through L-174 of SEQ ID NO:2.

In a specific embodiment, a bacterial expression construct was generated using the pHE-4 vector to express amino acid residues T-30 through L-174 of SEQ ID NO:2.

In a specific embodiment, a bacterial expression construct was generated using the pQE-9 vector to express amino acid residues T-28 through L-174 of SEQ ID NO:2 fused to a 5' histidine tag.

In a specific embodiment, a bacterial expression construct was generated using the pHE-4 vector to express amino acid residues L-72 through L-172 of SEQ ID NO:20.

In a specific embodiment, a bacterial expression construct was generated using the pHE-4 vector to express amino acid residues L-72 through L-251 of SEQ ID NO:20 fused to a 5' histidine tag.

In a specific embodiment, a bacterial expression construct was generated using the pHE-4 vector to express amino acid residues L-72 through L-251 of SEQ ID NO:20 fused to a 3' histidine tag.

In a specific embodiment, a bacterial expression construct was generated using the pHE-4 vector to express amino acid residues L-172 through L-251 of SEQ ID NO:20 fused to a 5' lacZ tag.

In a preferred embodiment, a polynucleotide encoding amino acid residues Leu-72 through Leu-251 of a TNF-gamma-beta polypeptide (e.g., as shown in SEQ ID NO:20 or as shown in SEQ ID NO:26) is cloned into a bacterial expression vector (e.g., pHE-4, pHE4-0 or pHE4b-0) and expressed in SG13009, W3110 (ton A-) or M15/REP4 E. coli cells.

Also in a preferred embodiment, TNF-gamma-beta of the invention is produced and isolated from SG13009, W3110 or M15/REP4 E. coli cultures using the following protocol.

Production of TNF-Gamma-Beta Protein
Stage I: (SI)—Shake Flasks

Media contains Phytone, Yeast Extract, L-Methionine, and NaCl is prepared in shake flasks. The gene for aminoglycoside 3' phosphotransferase (kanR) is encoded on the expression plasmid so kanamycin is typically added to the seed medium to provide selective pressure for cells maintaining the plasmid. MCB or WCB vials are thawed and used to inoculate shake flasks. The shake flasks are bottom-baffled and covered with a permeable top to maximize the transfer of gases (oxygen, carbon dioxide, etc.). The shake flasks are incubated in a temperature-controlled shaker/incubator. Growth in the flasks is monitored using a spectrophotometer set in the visible wave-length. One or more 100, 150, 350, and/or 650 liter fermenters may be used for the production of TNF-gamma-beta. All product contact parts are constructed of Type 1 Borosilicate glass, 316 L stainless steel, medical grade Silicone, Teflon or other FDA approved materials. When a sufficient optical density (e.g., $A_{600}$=1–4) is attained in the seed vessel, the culture is used to inoculate either a production fermenter or a seed fermenter (SII). Typically, shake-flasks are used to inoculate small production fermenters (<100L). A seed fermenter (SII) is used to prepare the larger volume of inoculum required by larger production fermenters.

Stage II (S2)—Seed Fermenter

Fermenters are engineered to provide a controlled environment for the growth of bacteria. Many of the fermenter's functions are preprogrammed and automated. They have agitators for mixing and have the capability of controlling many conditions including temperature, pH and dissolved oxygen. All gasses enter and exit through a hydrophobic 0.2 μm filter to maintain sterility. Typically, the SII fermentation uses the same medium as SI including kanamycin. Dissolved oxygen is controlled using aeration, agitation, oxygen supplementation and back-pressure. pH is typically controlled using acid (e.g., phosphoric acid) and base (e.g., ammonium hydroxide) addition. Antifoam (e.g. Sigma Antifoam A) is used to neutralize foam. After inoculation with shake flasks, the SII fermenter is grown until the desired optical density is reached (e.g., $A_{600}$=1–4). The S2 fermenter is used to inoculate the production fermenter.

Stage III (S3):—Production Fermenter.

The production fermenter is batched with production medium (see table 3 below) and heat sterilized. A defined, high cell density fermentation medium is under development. After the fermenter has equilibrated to process temperature, batch nutrients (see table 3 below) are added. Dissolved oxygen is controlled using aeration, agitation, oxygen supplementation and back-pressure. pH is typically controlled using acid (e.g., phosphoric acid) and base (e.g., ammonium hydroxide) addition. S3 is inoculated by the culture from either a shake flasks or a seed fermenter. The cells are grown to a predetermined induction optical density (e.g., $A_{600}$=1–4). pHE4 plasmid is designed to suppress the transcription of recombinant TNF-gamma-beta until desired. IPTG is added to the fermentation to stop the suppression (induce) of transcription of TNF-gamma-beta. At a specified time after induction, the fermentation is concluded. Time limits for S3 are under development. All operations involving open handling of cultures, medium, or product are conducted using aseptic techniques in laminar flow hoods. Liquids are transferred in closed systems by overpressure using compressed air or a peristaltic pump to minimize the risk of introducing contaminants.

TABLE 3

Fermentation Media and Supplements.

| Batch Medium currently contains: | Batch Supplements currently contains: |
|---|---|
| $KH_2PO_4$ | Glucose |
| $Na_2HPO_4$ | Zinc Sulfate 7-hydrate |
| NaCl | Ferric Chloride 6-hydrate |
| $NH_4Cl$ | Manganese Chloride 4-hydrate |
| Casamino Acids | Cupric Sulfate 5-hydrate |
| Tryptone | Cobalt Chloride 6-hydrate |
| Yeast Extract | Boric Acid |
| L-Cysteine | Hydrochloric Acid |
| Tryptophan | Magnesium Sulfate 7-hydrate |
| L-Histidine | Molybdic Acid Sodium Salt Dihydrate |
| Uridine-HCl Monohydrate | $CaCl_2$ |
| | Thiamine-HCL |

In specific embodiments, the concentrations of Batch Supplements are varied. In one embodiment, the concentration of zinc sulfate 7-hydrate is varied. In a specific embodiment, the concentration of zinc sulfate is increased by 0.25-fold, 0.75-fold, 1-fold, 1.25-fold, 1.5-fold, 1.75-fold, 2-fold, 2.5-fold, 3-fold, 4-fold, 5-fold, 7.5-fold, 10-fold, 15-fold, 20-fold, 50-fold, 100-fold, 250-fold, 500-fold, 750-fold, or 1000-fold.

TNF-gamma-beta is produced in the cytosol and maintained inside the cell membrane. Cells are typically collected using centrifugation or filtration. Cell paste is either processed immediately or is stored at or below −20° C. Stability studies of cell paste will be conducted to establish expiration dating.

Recovery of TNF-Gamma-Beta Protein
Step 1 Cell Harvest

The induced cell suspension is harvested between 4 and 8 hours post IPTG induction. The TNF-gamma-beta containing cell paste is obtained with continuous flow centrifugation. Following centrifugation, the cell paste is used immediately or stored at −80° C.

Step 2 Cell Supernatant Production

The cell paste is suspended in 50 mM Tris-HCl buffer pH 8.0 in a 10-fold volume of the cell paste. The cell suspension is homogenized and the supernatant is produced by removal of cell debris with continuous flow centrifugation.

Purification of TNF-Gamma-Beta Protein

Unless stated otherwise, the process is conducted at 4-8° C.

Step 1 Chromatography on QAE 550C Column

The supernatant is loaded onto a QAE 550C column (weak anion exchanger, TosoHaas) which is equilibrated with 50 mM Tris-HCl, pH 8.0 containing 2 mM $CaCl_2$. The column is washed with the same buffer and then theTNF-gamma-beta is eluted with 125 mM NaCl and 2 mM $CaCl_2$ in 50 mM Tris-HCl, pH 8.0. The elution is monitored by ultraviolet (UV) absorbance at 280 nm. Fractions are collected across the eluate peak, analyzed by SDS-PAGE, and appropriate fractions are pooled.

Step 2 Chromatography on Q-Sepharose Fast Flow (Q/FF)

The QAE pool is loaded onto a Q/FF (strong anion exchanger, Pharmacia) column equilibrated with 50 mM Tris-HCl containing 125 mM NaCl and 2 mM $CaCl_2$, pH 8.0. The column then is washed with the same buffer. The TNF-gamma-beta is in the fraction of flow through. The loading and wash are monitored by ultraviolet (UV) absorbance at 280 nm.

Step 3 Chromatography on Toyopearl Butyl 650S Column

The HQ50 pool is mixed with ammonium sulfate to produce a final concentration of 0.8 M and is loaded onto Toyopearl Butyl 650C (Hydrophobic interaction resin, TosoHaas) column equilibrated in 0.8 M ammonium sulfate in 100 mM Tris-HCl pH 7.3. The column is then washed with a linear gradient elution of TNF-gamma-beta with 100 mM Tris-HCl pH 7.3 followed by a 20% ethanol wash. The elution is monitored by ultraviolet (UV) absorbance at 280 nm and conductivity. Fractions are collected across the eluate peak, analyzed by SDS-PAGE. Appropriate fractions are pooled.

Step 4 Concentration on Toyopearl Butyl 650S

The Butyl purified TNF-gamma-beta is mixed with ammonium sulfate to produce a final concentration 0.8 M and is loaded onto a smaller Toyopearl Butyl 650C (Hydrophobic interaction resin, TosoHaas) column equilibrated in 0.8 M ammonium sulfate in 100 mM Tris-HCl pH 7.3. TNF-gamma-beta is eluted by stepwise with 100 mM Tris-HCl, pH 7.3.

Step 5 Chromatography on Superdex 200 Column

The Butyl concentrated TNF-gamma-beta is loaded onto a Superdex 200 (Sizing Exclusive Chromatography, Pharmacia) column equilibrated in 10 mM sodium citrate, 150 mM sodium chloride, pH 6.0. Fractions are collected across the eluate peak and are analyzed by SDS-PAGE. Appropriate fractions (>90% purity) are pooled.

Step 6 Ultrafiltration, Filtration and Fill

The purified TNF-gamma-beta is placed into a 5 KD MW cutoff membrane device to concentrate a target concentration. Then the protein concentration of purified TNF-gamma-beta is determined by absorbance at 280 nm using TNF-gamma-beta extinction coefficient value (1 UV unit for 1 mg/ml). TNF-gamma-beta formulation is adjusted to its final protein concentration with the appropriate buffer and filtered via 0.22 micrometer filter under controlled conditions. The filtrate (bulk substance) is stored in suitable sterilized container at 2-8° C. (short-term storage) or at or below −20° C. (long-term storage).

Example 2

Cloning and Expression of TNF-Gamma Using the Baculovirus Expression System

The DNA sequence encoding the full length TNF-gamma protein, ATCC™ No. 75927, was amplified using PCR oligonucleotide primers corresponding to the 5' and 3' sequences of the gene: The 5' primer has the sequence 5'-GCG CGG ATC CAC CAT GAG ACG CTT TTT AAG CAA AGT C-3' (SEQ ID NO:15) and contains a Bam HI restriction enzyme site (in bold) followed by 24 nucleotides of the TNF-gamma gene (the initiation codon for translation "ATG" is underlined). The 3' primer has the sequence 5'-CGC GTC TAG ACT ATA GTA AGA AGG CTC CAA AGA AGG-3' (SEQ ID NO:16) and contains the cleavage site for the restriction endonuclease Xba I and 22 nucleotides complementary to the 3' non-translated sequence of the TNF-gamma gene. The amplified sequences were isolated from a 1% agarose gel using a commercially available kit ("Geneclean," BIO 101 Inc., La Jolla, Calif.). The fragment was then digested with the endonucleases Bam HI and Xba I and then purified again on a 1% agarose gel. This fragment was designated F2.

The vector pA2 (modification of pVL941 vector, discussed below) was used for the expression of the TNF-gamma protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases Bam HI and Xba I. The polyadenylation site of the simian virus SV40 is used for efficient polyadenylation. For an easy selection of recombinant virus the beta-galactosidase gene from *E. coli* was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could have been used in place of pA2, such as pRG I, pAc373, pVL941 and pAcIM1 (Luckow, V. A. and Summers, M. D., Virology, 170:31-39).

The plasmid was digested with the restriction enzymes Bam HI and Xba I and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA was designated V2.

Fragment F2 and the dephosphorylated plasmid V2 were ligated with T4 DNA ligase. *E. coli* XL1 blue cells were then transformed. The sequence of the cloned fragment was confirmed by DNA sequencing.

5 μg of the plasmid pBac TNF-gamma was cotransfected with 1.0 μg of a commercially available linearized baculovirus ("BaculoGold baculovirus DNA", Pharmingen, San Diego, Calif.) using the lipofection method (Feigner et al. Proc. Natl. Acad. Sci. USA, 84:7413-7417 (1987)).

1 μg of BaculoGold virus DNA and 5 μg of the plasmid pBac TNF-gamma were mixed in a sterile well of a microtiter plate containing 50 μl of serum free Grace's medium (Life Technologies Inc., Gaithersburg, Md.). Afterwards, 10 μl Lipofectin plus 90 μl Grace's medium were added, mixed and incubated for 15 minutes at room temperature. Then the transfection mixture was added dropwise to the Sf9 insect cells (ATCC™ CRL 1711) seeded in a 35 mm tissue culture plate with 1 ml Grace' medium without serum. The plate was rocked back and forth to mix the newly added solution. The plate was then incubated for 5 hours at 27° C. After 5 hours, the transfection solution was removed from the plate and 1 ml of Grace's insect medium supplemented with 10% fetal calf serum was added. The plate was put back into an incubator and cultivation continued at 27° C. for four days.

After four days, the supernatant was collected and a plaque assay performed essentially as described by Summers and Smith (supra). As a modification, an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the virus was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Figure 6:
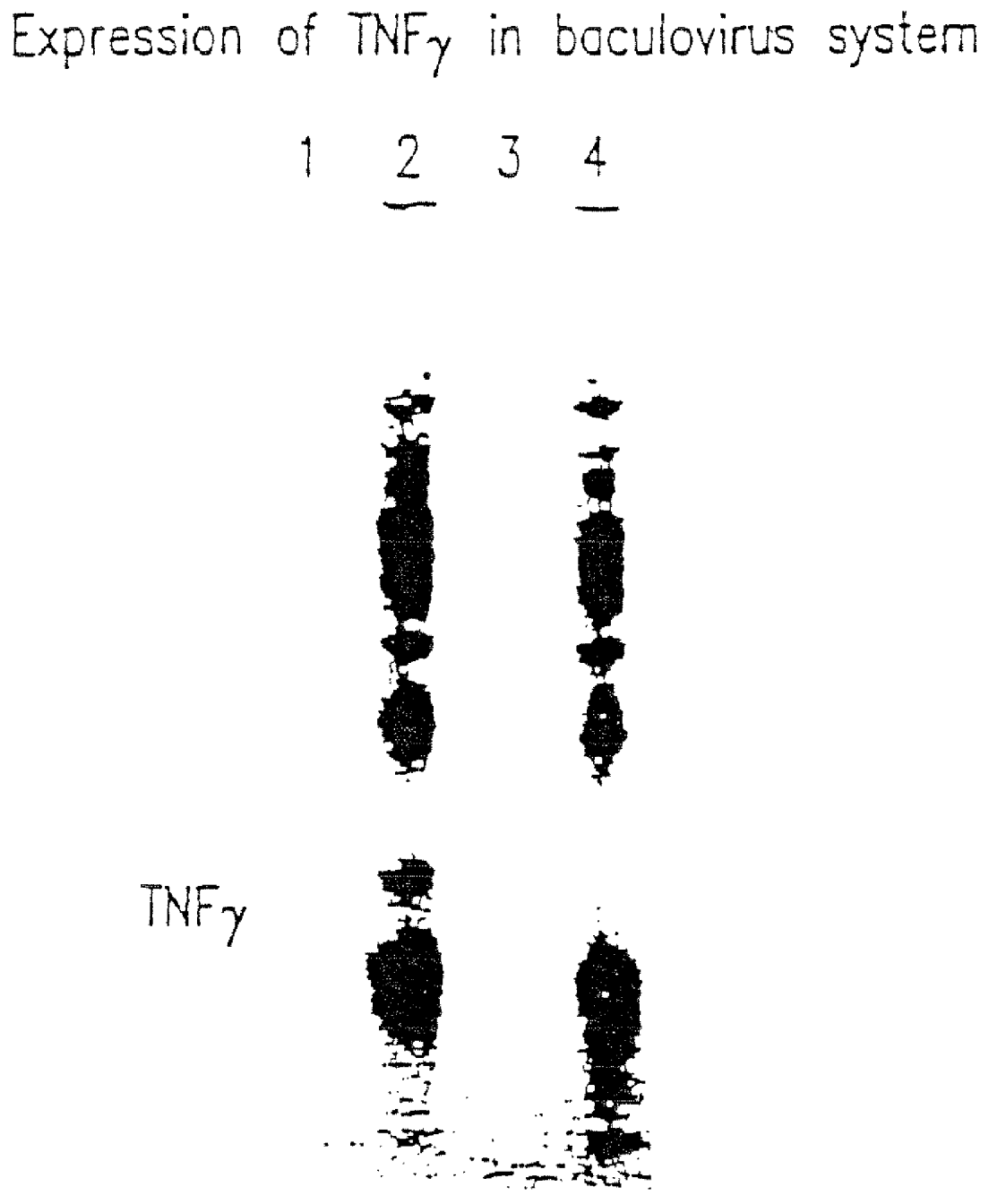

Sf9 cells were grown in Grace's medium supplemented with 10% heat-inactivated FBS. The cells were infected with the recombinant baculovirus V-TNF-gamma at a multiplicity of infection (MOI) of 2. Six hours later the medium was removed and replaced with SF900 II medium minus methionine and cysteine (Life Technologies Inc., Gaithersburg). 42 hours later 5 μCi of [35S]-methionine and 5 μCi [35S]-cysteine (Amersham) were added. The cells were further incubated for 16 hours before they were harvested by centrifugation and the labeled proteins visualized by SDS-PAGE and autoradiography. FIG. 6 illustrates a gel where lanes 1 and 3 are the medium of the TNF-gamma and control cultures and lanes 2 and 4 are the cell lysates of the TNF-gamma and the control cultures.

In a specific embodiment, a baculoviral expression construct was generated using the pA2SPst vector to express amino acid residues V-25 through L-174 of SEQ ID NO:2.

In a specific embodiment, a baculoviral expression construct was generated using the pA2GP vector to express amino acid residues T-28 through L-174 of SEQ ID NO:2 fused to a 5' lacZ tag.

In a specific embodiment, a baculoviral expression construct was generated using the pA2SPst vector to express amino acid residues A-61 through L-251 of SEQ ID NO:20.

In a specific embodiment, a baculoviral expression construct was generated using the pA2GP vector to express amino acid residues L-71 through L-251 of SEQ ID NO:20.

In a specific embodiment, a baculoviral expression construct was generated using the pA2GP vector to express amino acid residues L-71 through L-251 of SEQ ID NO:20 fused to a 5' lacZ tag.

In a specific embodiment, a baculoviral expression construct was generated using the pA2 vector to express amino acid residues M-1 through L-251 of SEQ ID NO:20.

Example 3

Expression of Recombinant TNF-Gamma in COS Cells

The expression of plasmid, TNF-gamma-HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, an SV40 intron, and a polyadenylation site. A DNA fragment encoding the entire TNF-gamma precursor and a hemagglutinin antigen (HA) tag fused in frame to its 3' end was cloned into the polylinker region of the vector. Therefore, the recombinant protein expression is under the direction of the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to our target protein allows easy detection of the recombinant protein with an antibody that recognizes the HA epitope.

The plasmid construction strategy is described as follows: The DNA sequence encoding TNF-gamma, ATCC™ #75927, was constructed by PCR on the original EST cloned using two primers: the 5' primer (SEQ ID NO:15) contains a Bam HI site followed by 24 nucleotides of TNF-gamma coding sequence starting from the initiation codon; the 3' sequence 5'-CGC TCT AGA TCA AGC GTA GTC TGG GAC GTC GTA TGG ATA GTA AGA AGG CTC CAA AG-3' (SEQ ID NO:17) contains complementary sequences to Xba I site, translation stop codon, HA tag and the last 18 nucleotides of the TNF-gamma coding sequence (not including the stop codon). Therefore, the PCR product contained a Bam HI site, TNF-gamma coding sequence followed by HA tag fused in frame, a translation termination stop codon next to the HA tag, and an Xba I site. The PCR amplified DNA fragment and the vector, pcDNAI/Amp, were digested with Bam HI and Xba I restriction enzymes and ligated together. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant TNF-gamma, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the TNF-gamma HA protein was detected by radiolabelling and immunoprecipitation method. (E. Harlow, D. Lane, Antibodies: A Laboratory Manual, Cold Spring Harbor Laboratory Press, (1988)). Cells were labeled for 8 hours with [35S]—S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5; Wilson, I. et al., Id. 37:767 (1984)). Both cell lysate and culture media were precipitated with an HA-specific monoclonal antibody. Precipitated proteins were then analyzed on 15% SDS-PAGE gels.

In a specific embodiment, a mammalian expression construct was generated using the pC4 vector to express amino acid residues M-1 through L-251 of SEQ ID NO:20.

In a specific embodiment, a mammalian expression construct was generated using the pC4SPst vector to express amino acid residues A-61 through L-251 of SEQ ID NO:20.

In a specific embodiment, a mammalian expression construct was generated using the pC4 vector to express amino acid residues L-72 through L-251 of SEQ ID NO:20 fused to the Fc region of human immunoglobulin, as described supra.

In a specific embodiment, a mammalian expression construct was generated using the pC4SP vector to express amino acid residues L-72 through L-251 of SEQ ID NO:20 fused to lacZ at the amino terminus.

In a specific embodiment, a mammalian expression construct was generated using the pC4 vector to express amino acid residues M-1 through L-174 of SEQ ID NO:2.

In a specific embodiment, a mammalian expression construct was generated using the pC4SP vector to express amino acid residues T-28 through L-174 of SEQ ID NO:2.

In a specific embodiment, a mammalian expression construct was generated using the pC4SPst vector to express amino acid residues V-25 through L-174 of SEQ ID NO:2.

In a specific embodiment, a mammalian expression construct was generated using the pC4SP vector to express amino acid residues T-28 through L-174 of SEQ ID NO:2 fused to lacZ at the amino terminus.

Example 4

Expression Pattern of TNF-Gamma in Human Tissue

RNA blot analysis was carried out to examine the levels of expression of TNF-gamma in human tissues. Total cellular RNA samples were isolated with RNAzol™ B system (Biotecx Laboratories, Inc. 6023 South Loop East, Houston, Tex. 77033). About 2 µg (for the RNA blot of FIG. 3A) of total RNA isolated from each human tissue specified was separated on 1% agarose-formaldehyde gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng TNF-gamma cDNA, to produce [32P]-labeled TNF-gamma cDNA. The labeled DNA was purified with a Select-G-50 column (5 Prime-3 Prime, Inc. 5603 Arapahoe Road, Boulder, Colo. 80303). The filter was then hybridized with radioactive labeled full-length TNF-gamma gene at 1,000,000 cpm/ml in 0.5 M NaPO4, pH 7.4 and 7% SDS overnight at 65° C. After being washed twice at room temperature and twice at 60° C. with 0.5×SSC, 0.1% SDS, the X-ray film was then exposed to the blot at −70° C. overnight with an intensifying screen. The message RNA for TNF-gamma is abundant in kidney.

Figure 3B:
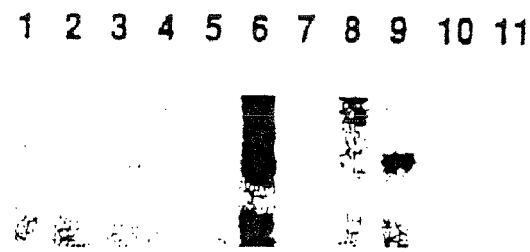
FIG. 3B is an RNA blot analysis showing that TNF-gamma is expressed predominantly in HUVEC cells (human umbilical vein endothelial cells; lane 9). Lane 6 and lane 8 are non-specific smears. RNA from the cell lines indicated were probed with labeled TNF-gamma-alpha cDNA. Lane 1 is CAMA1 (breast cancer); lane 2 AN3CA (uterine cancer); lane 3, SK.UT.1 (uterine cancer); lane 4, MG63 (osteoblastoma); lane 5, HOS (osteoblastoma); lane 6, MCF7 (breast cancer); lane 7, OVCAR-3 (ovarian cancer); lane 8, CAOV-3 (ovarian cancer); lane 9, HUVEC; lane 10, AOSMIC (smooth muscle); lane 11, foreskin fibroblast.

The same reaction was done to obtain the results shown in FIG. 3B, with the exception that 10 µg poly-A RNA isolated from the indicated tissues was used. In this experiment, the messenger RNA encoding TNF-gamma is expressed predominantly in HUVEC cells (FIG. 3B; lane 9), but not in other cell lines examined; for example; lane 1 is CAMA1 (breast cancer); lane 2 is AN3CA (uterine cancer); lane 3 is SK.UT.1 (uterine cancer); lane 4 is MG63 (osteoblastoma); lane 5 is HOS (osteoblastoma); lane 6 is MCF7 (breast cancer); lane 7 is OVCAR-3 (ovarian can lane 8 is CAOV-3 (ovarian cancer); lane 10 is AOSMIC (smooth muscle); and lane 11 is foreskin fibroblast.

Northern blot analyses were also performed to determine the relative expression level of the TNF-gamma RNA with respect to the proliferation state of HUVEC cell cultures. In these experiments, identical amounts of total RNA isolated from HUVEC cells (15 µg) were electrophoretically separated and blotted as described above. RNA was isolated from cultures 1, 2, 3, 4, 6, and 7 days post-seeding. As illustrated in FIG. 4, TNF-gamma RNA (labeled "VEGI") was only seen at low levels in newly seeded cultures (days 1, 2, and 3). However, expression of TNF-gamma RNA was apparent as the HUVEC cells in the cultures began to reach confluence (days 4, 6, and 7). These experiments indicate that TNF-gamma expression increases as cells in a culture or tissue begin to reach the quiescent state of non- or reduced-proliferation.

In other experiments performed essentially as described above, the TNF-gamma-alpha transcript has been detected in many different human tissues, e.g., placenta, lung, kidney, skeletal muscle, pancreas, spleen, prostate, small intestine, and colon. Further experiments have shown that expression of the TNF-gamma-alpha molecule was greatest in a subset of endothelial cells, such as human umbilical vein endothelial cells (HUVECs) and human uterine myometrial microvascular endothelial cells (HMMVECs), but not in human pulmonary artery endothelial cells (HPAEC), human iliac artery endothelial cells (HIAEC), or human coronary artery endothelial cells (HCAEC). The transcript for TNF-gamma-beta has also been detected in placenta, lung, kidney, prostate, small intestine, stomach, liver, kidney, and pancreas, HUVECs, HMMVECs, human aortic endothelial cells (HAECs), and human microvascular endothelial cells (HUMECs).

Example 5

Ability of Recombinant TNF-Gamma to Inhibit WEHI 164, ABAE, and L929 Cell Growth, and to Induce Cell Adhesion in HL-60 Cells The adherent target cells were prepared from confluent cultures by trypsinization in PBS, and non-adherent target cells were harvested from stationary cultures and washed once with medium. Target cells were suspended at 3×10⁵ cells/ml in medium containing 10% FCS. 0.1 ml aliquots were dispensed into 96-well flat-bottomed microtiter plates containing 0.1 ml serially diluted test samples of cells (WEHI 164 and L929). Incubation was continued for 70 hours. TNF-alpha, TNF-beta and bacterially-produced TNF-gamma were added at a 0.5 µg/ml concentration. The cytotoxicity and proliferation activity was quantified using an MTS assay performed by the addition of 20 μl of MTS and phenazine methosulfate (PMS) solution to each well. After a three hour incubation, the OD at 492 nm was measured by an ELISA plate reader. The OD492 is proportional to the number of viable cells in the wells. The percent of cytotoxicity was calculated as follows: % cytotoxicity=(100−$OD_{experimental}$/$OD_{control}$)× 100. The photographs were taken after 72 hours. As shown by FIGS. 7A and 8, TNF-gamma induced a morphology change which appeared as dark round cells (indicating killed cells).

Figure 9A:
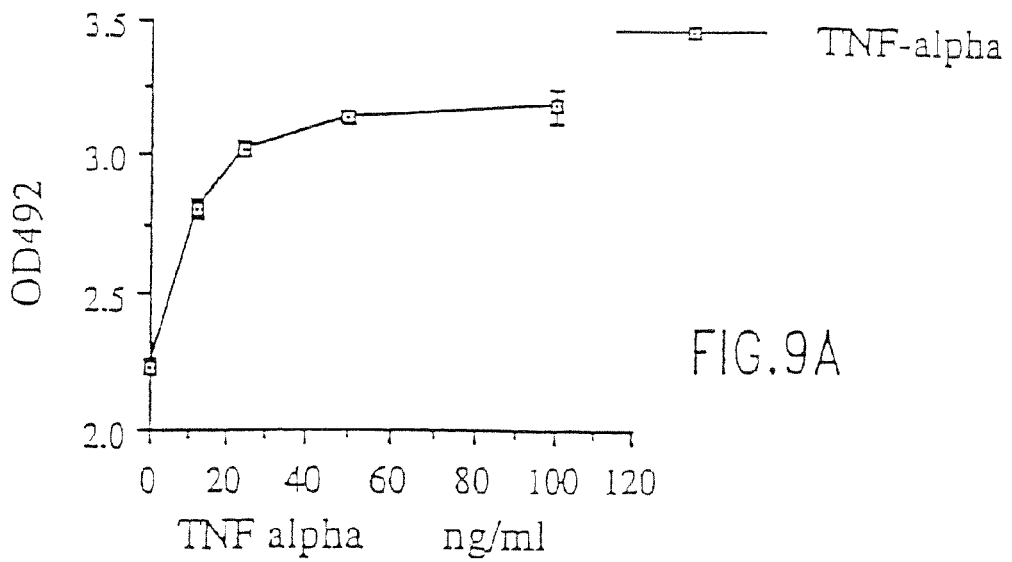
FIG. 9 is a graphical illustration of the effect of TNF-gamma (FIG. 9C), TNF-alpha (FIG. 9A), and TNF-beta (FIG. 9B) on venous endothelial cells. Cell proliferation after venous endothelial cells were treated with commercially available TNF-alpha and TNF-beta and E. coli produced TNF-gamma was quantified using an MTS assay.
Figure 9B:
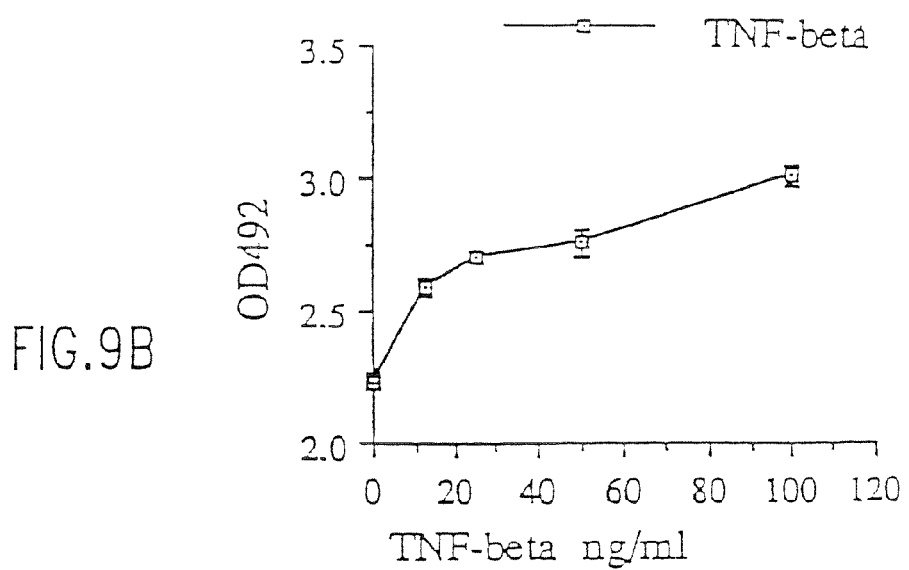
Figure 9C:
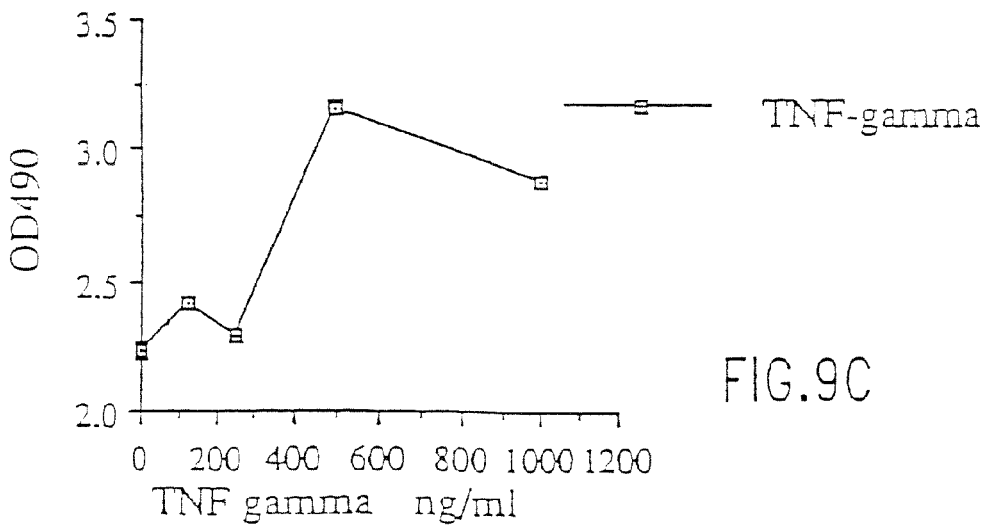

In the graph of FIG. 7B, the assay was performed as described above, however, increasing amounts of TNF-alpha, TNF-beta and TNF-gamma were added to the cultures. The results indicate that TNF-gamma is a dose-dependent inhibitor of the growth of the endothelial cell line WEHI 164, but not of the fibroblast cell line L929 (FIGS. 8 and 9).

A truncated form of the TNF-gamma polypeptide consisting of amino acids 12-147 of the complete TNF-gamma amino acid sequence shown as SEQ ID NO:2 (designated TNF-gamma12-147) was also used to examine the effect of TNF-gamma on endothelial cell growth. Treatment of adult bovine aortic endothelial (ABAE) cells with TNF-gamma12-147 resulted in nearly complete inhibition of the growth of cells in the ABAE culture, but not of cells in the breast cancer cell lines MDA-MB-435 or MDA-MB-231 (FIG. 10; TNF-gamma is designated "VEGI" in this figure). Nearly complete inhibition of the growth of the endothelial cells was achieved at 10 μg/ml TNF-gamma39-174, with a half-maximum inhibitory concentration value (IC50) of approximately 1 μg/ml (approximately 70 nM).

Figure 11B:
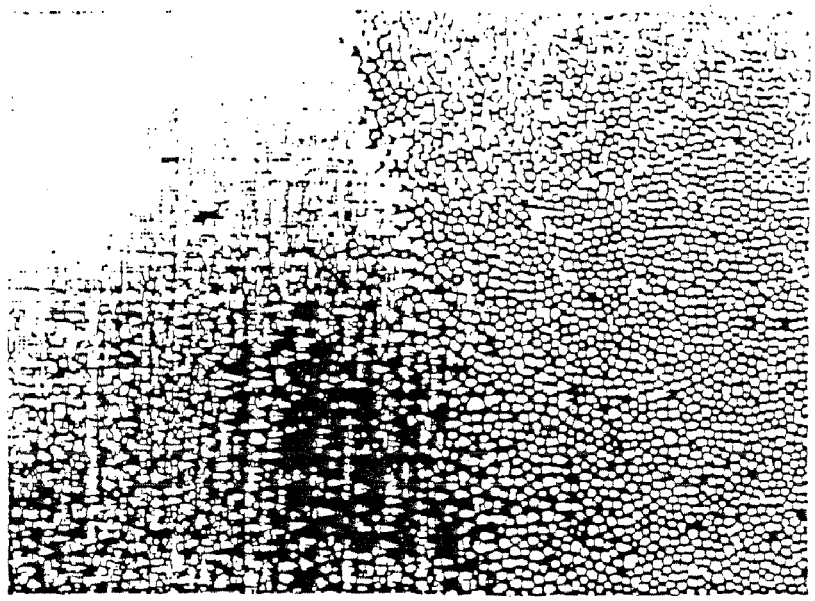
FIG. 11 is a photograph of HL60 cells, with control (FIG. 11A) showing the HL60 cells being spread apart; TNF-alpha (FIG. 11B) and TNF-gamma (FIG. 11C) induce cell adhesion and cell-cell contact as illustrated by the cells adhering together in the lower right.
Figure 11A:
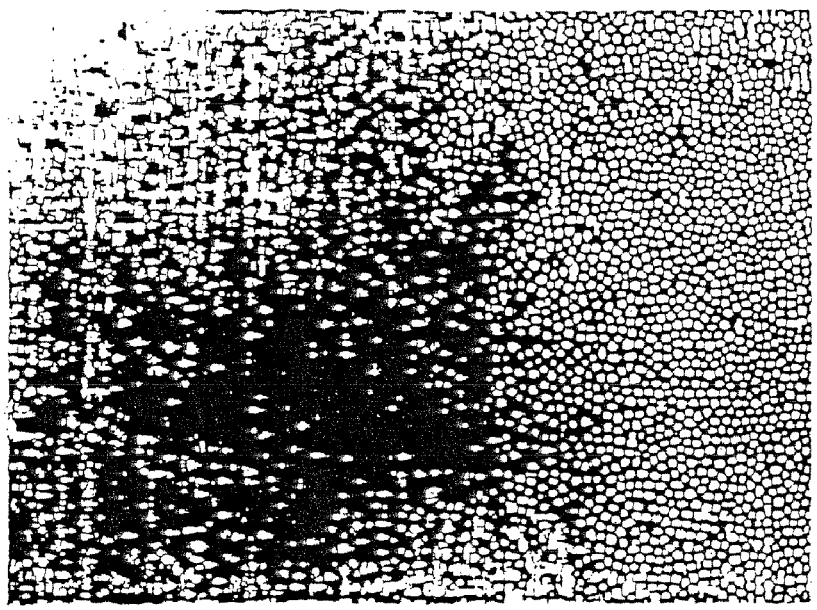
Figure 11C:

To test adhesion ability of TNF-gamma, HL-60 cells were used and cell adhesion and cell-cell contact were measured by observation under the microscope and scored subjectively by two independent investigators. FIG. 11 illustrates the ability of TNF-gamma to induce cell adhesion. Cultures which were not treated with TNF-gamma contained cells which had spread throughout the culture dish. However, cultures which were treated with TNF-gamma, contained cells which were clearly aggregated together.

Example 6

Measurement of Apoptosis Ability of TNF-Gamma

In a first incubation step, anti-histone antibody was fixed adsorptively on the wall of a microtiter plate module. Subsequently, non-specific binding sites on the wall were saturated by treatment with incubation buffer (e.g., blocking solution). During the second incubation step, the nucleosomes contained in the WEHI 164 cell sample treated with the TNF-alpha, TNF-beta or bacterially-produced TNF-gamma were bound via their histone components to the immobilized anti-histone antibody. In the third incubation step, anti-DNA-peroxidase (POD) reacted with the DNA component of the nucleosomes. After removal of all unbound peroxidase conjugate by a washing step, the amount of peroxidase retained in the immunocomplex was determined spectrophotometrically using the substrate ABTS (2,2'-azino-di-[3-ethylbenzthiazoline sulfonate]). Anti-histone antibody reacted with the histones H1, H2A, H2B, H3, and H4 from the sample. Anti-DNA POD antibody bound to single- and double-stranded DNA. Therefore, the ELISA allowed the detection of mono- and oligonucleosomes and may be applied to measure apoptotic cell death. The level of cell death was measured by the amount of cytoplasmic histone-associated DNA fragments which was indicated by the ratio of the absorbances observed at 405 and 490 nm (A405/A490). The results of these experiments are illustrated in FIG. 12 (See Boehringer Mannheim Catalogue, 0990 C 93 2 1541170).

As shown in FIG. 12, WEHI 164 cells were induced to undergo increasingly high levels of apoptosis, resulting in cell death, in the presence of increasing amounts of TNF-gamma. This effect was also observed in the presence of increasing amounts of the control TNF-beta or in the presence of any of the analyzed levels of the control TNF-alpha.

Example 7

Receptor Binding Assay Using TNF-Gamma

Figure 13:
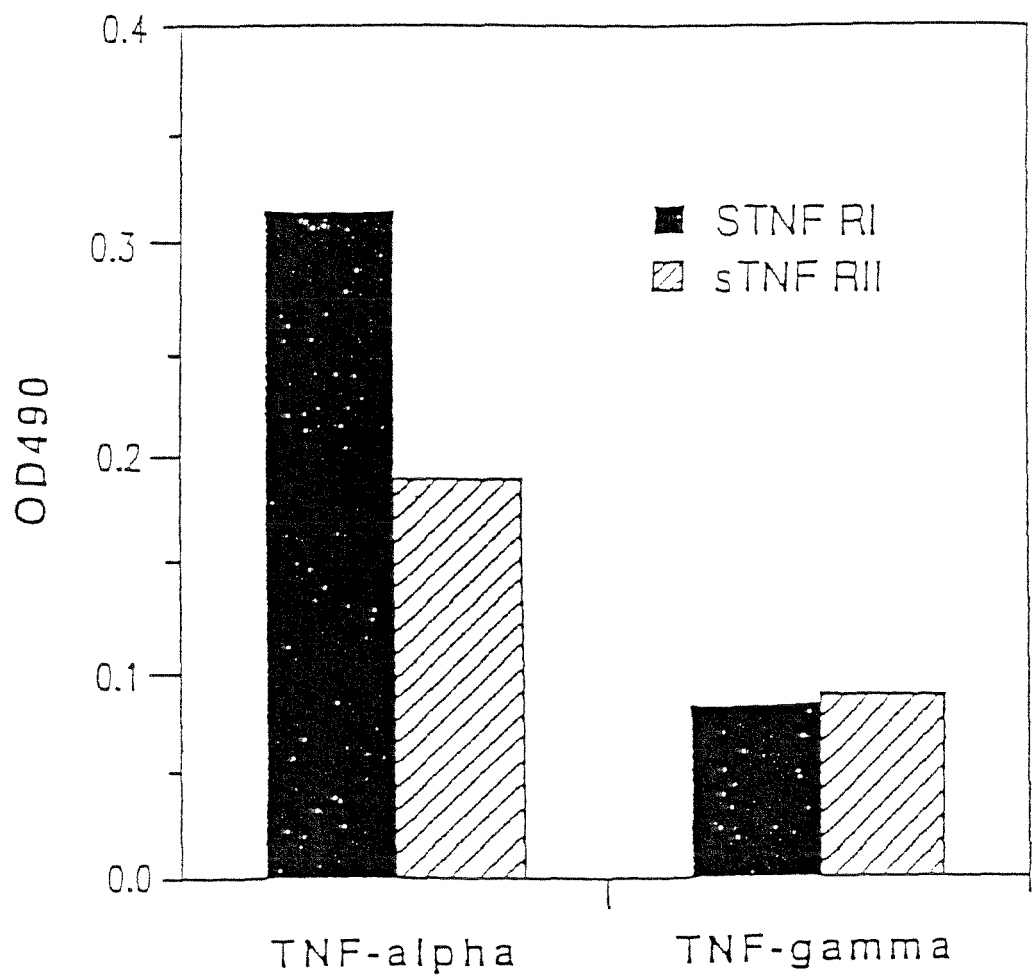
FIG. 13 illustrates that TNF-gamma does not significantly bind to two known soluble TNF receptors, namely sTNF RI (p55; solid bars) and sTNF RH (p75; hatched bars).

TNF-alpha and bacterially-produced TNF-gamma were purified by Ni-NTA affinity chromatography using the 6-His tag fused to the terminus of the recombinant proteins. 1 μg/well of either protein was added to a nickel chelate-coated 96-well plate (Xenopore Corp.) and incubated for 2 hours. After washing three times, 100 ng of human soluble TNF receptors (specifically, sTNF RI or sTNF RII) was added to each well and incubated for 2 hours. The plate was then washed three times and alkaline phosphatase-labeled polyclonal antibodies raised against either sTNF RI or sTNF RII was added in a total volume of 200 μl. An aliquot of substrate solution (200 μl) was then added to each well and the plate was incubated for an additional 2 hours. The OD was then measured using an ELISA reader (at a test wavelength of 450 nm and a correction wavelength of 590 nm). The results shown in FIG. 13 illustrate that TNF-gamma does not bind significantly to sTNF-receptors when compared to the control binding observed with TNF-alpha.

Example 8

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask. At this time, fresh media is added (e.g., Ham's F12 media, supplemented with 10% FBS, penicillin, and streptomycin). The culture is then incubated at 37° C. for approximately one week. At this time, fresh media is added and subsequently changed every 2-3 days. After an additional two weeks in culture, a monolayer of fibroblasts will have emerged. The monolayer is trypsinized and scaled into larger flasks.

pMV-7 (Kirschmeier, P. T. et al, DNA, 7:219-25 (1988)), which is flanked by the long terminal repeats of the Moloney murine sarcoma virus, is digested with Eco RI and Hind III, and, subsequently, treated with calf intestinal phosphatase. The linear vector is fractionated on agarose gel and purified using glass beads.

The cDNA encoding a polypeptide of the present invention is amplified using PCR primers which correspond to the 5' and 3' end sequences respectively. The 5' primer containing an Eco RI site and the 3' primer includes a Hind III site. Equal quantities of the Moloney murine sarcoma virus linear backbone and the amplified Eco RI and Hind III fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and, subsequently, the media is harvested from a 10 cm plate of confluent producer cells. The spent media, containing the infectious viral particles, is filtered through a millipore filter to remove detached producer cells. This media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it may be necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 9

In Vitro Angiogenesis Assay

This assay was used to determine the relative ability of TNF-gamma12-147 to inhibit the FGF-2-induced formation of capillary-like tubular structures in cultures of adult bovine aortic endothelial (ABAE) cells. Three-dimensional collagen gel plates (24-well) were prepared by addition of 0.5 ml chilled solution of 0.7 mg/ml of rat tail type I collagen (Becton Dickinson Labwares, Bedford, Mass.) to each well containing 1× DMEM and adjusting to neutral pH with NaHCO3. After formation of collagen gel (about 1-2 mm thickness), ABAE cells were seeded at $5 \times 10^4$ cells/well. The cultures were maintained in a humidified 5% CO2 incubator at 37° C. in DMEM containing 10% calf serum (HyClone, Logan, Utah) supplemented with L-glutamine (2 mM) until the cultures reached confluence. The medium was then replaced with fresh medium containing 20 ng/ml of FGF-2. The effect of TNF-gamma12-147 as an inhibitor of FGF-2-induced formation of capillary-like tubular structures in ABAE cultures was analyzed by supplementing the culture medium with 0.1, 0.3, 1, 3, or 10 µg/ml of TNF-gamma12-147. All cultures were then maintained at 37° C. for an additional 48 hours and then discontinued by fixation with cold methanol (−20° C.).

The abundance of capillary-like structures formed by ABAE cells was analyzed by using a Kotron IBAS Image Analyzer assisted with a Hamamatsu C2400 video camera and a Zeiss Axioshop microscope. The abundance of the capillary-like structures were measured as percentages of the white areas over the total areas measured. As a control, the EC50 value for the angiogenic factor FGF-2 to stimulate in vitro angiogenesis was about 5 ng/ml. As a further control, a maximum stimulatory effect was observed at 10 ng/ml of FGF-2.

As shown in FIG. 14 (in which TNF-gamma is designated "VEGI"), observable inhibition of FGF-2-induced tube formation in ABAE cultures was observed by the addition of 1, 3, and 10 µg/ml of TNF-gamma12-147 (labeled as VEGI). The IC50 value for the inhibition of FGF-2-induced tube formation was approximately 1 µg/ml, which was similar to that observed for the inhibition of endothelial cell growth (see Example 5).

Example 10

Chicken Embryonic Chorioallantoic Membrane (CAM) Angiogenesis Assay

The CAM assay was carried out essentially as described by Nguyen and colleagues (*Microvasc. Res.* 47:31-40 (1994)) and Iruela-Arispe and Dvorak (*Thromb. Haemost.* 78:672-677 (1997)). The method is based on the growth of new capillary vessels into a collagen gel pellet placed directly on the chorioallantoic membrane (CAM). Angiogenic factors such as endostatin (2 micrograms), FGF-2 (100 ng), VEGF (250 ng), or bFGF (10, 500, and 1000 ng) were embedded in collagen gel pellets and placed in contact with the CAM. Quantification of angiogenesis in the gels was carried out 24 hours after the placement of the gel pellets by using a Nikon fluorescence microscope. The images were transferred to a Power PC 100 AV, using a CCD Sony camera. Fluorescence intensity was evaluated with NH Image 1.61 software. Fluorescence intensity for the positive controls (which contained an angiogenic factor alone) was considered as the maximum angiogenic response, and set, arbitrarily, at 100. Due to the variability of the assay, inhibition greater than 20% was considered significant.

As an experimental determination of the effect of TNF-gamma on the FGF-2- or VEGF-induced angiogenesis, bacterially-produced TNF-gamma (250 ng) was mixed with either FGF-2 (100 ng) or VEGF (250 ng) and embedded in collagen gel pellets. The pellets were then placed in contact with the CAM as described above. As shown in FIG. 15 (in which TNF-gamma is designated "VEGI"), TNF-gamma markedly inhibited new capillary growth into collagen gels.

In another experiment, 50, 100, 250, 500, 1000 or 2000 ng of TNF-gamma-beta were analyzed for a reduction in bFGF-induced stimulation of neovascularization in the CAM assay. By the 72 hour timepoint in this experiment, 1000 and 2000 ng of TNF-gamma-beta reduced bFGF-stimulated angiogenesis to a level indistinguishable from control levels not receiving bFGF.

Example 11

In Vivo Tumorigenicity Assay

An in vivo analysis of the potential effect of TNF-gamma on angiogenesis was performed using a xenograft tumor model. In this experimental approach, one million human breast carcinoma cells (MDA-MB-231 or MDA-MB-435) were injected into the mammary fat pad of female nude mice either alone or mixed with chinese hamster ovary (CHO) cells transfected with TNF-gamma or CHO cells transfected only with the CHO-vector ($5 \times 10^6$ cells per mouse). The TNF-gamma polypeptide expressed in these experiments consisted of the polypeptide shown as SEQ ID NO:2 excluding the N-terminal 22 amino acids. The N-terminal 22 amino acids of this TNF-gamma mutein were replaced by the secretory signal peptide of human interleukin-6 (Hirano, T., et al., *Nature* 324:73-76 (1986)).

Mice which were coinjected with human breast carcinoma cells and either TNF-gamma-expressing CHO cells or vector-transfected CHO cells were then randomized and tumors were measured twice weekly. The tumor size was assessed by measuring perpendicular diameters with a caliper and calculated by multiplying the measurements of diameters in two dimensions. Data are presented in FIGS. 16A and 16B as the mean+/−standard deviation of six mice in each group.

Figure 16A:
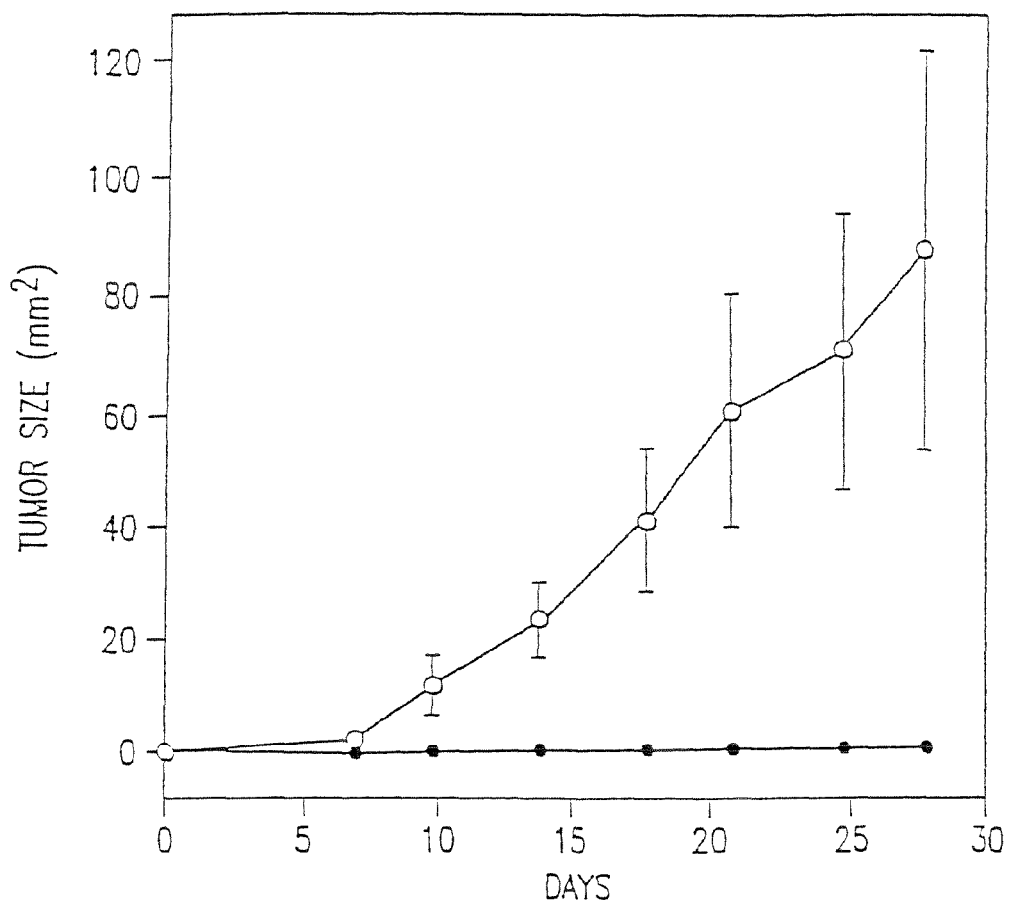
FIG. 16 illustrates the inhibition of growth of human breast cancer xenograft tumors in athymic nude mice by TNF-gamma. Mixtures of TNF-gamma-overexpressing or vector-transfected CHO cells ($5 \times 10^6$ cells per injection) and human breast cancer cells ($1 \times 10^6$ cells per injection) were injected into the mammary fat pads of the nude mice. Tumor sizes (area) were monitored following injection. The sizes of the MDA-MB-231 xenograft tumors ($mm^2$) were plotted as a function of days post-inoculation (FIG. 16A). The sizes of the MDA-MB-435 xenograft tumors ($mm^2$) were plotted as a function of days post-inoculation (FIG. 16B). Open circles represent values of tumors co-inoculated with vector-transfected CHO cells, whereas closed circles represent values of tumors co-inoculated with TNF-gamma-transfected CHO cells.
Figure 16B:
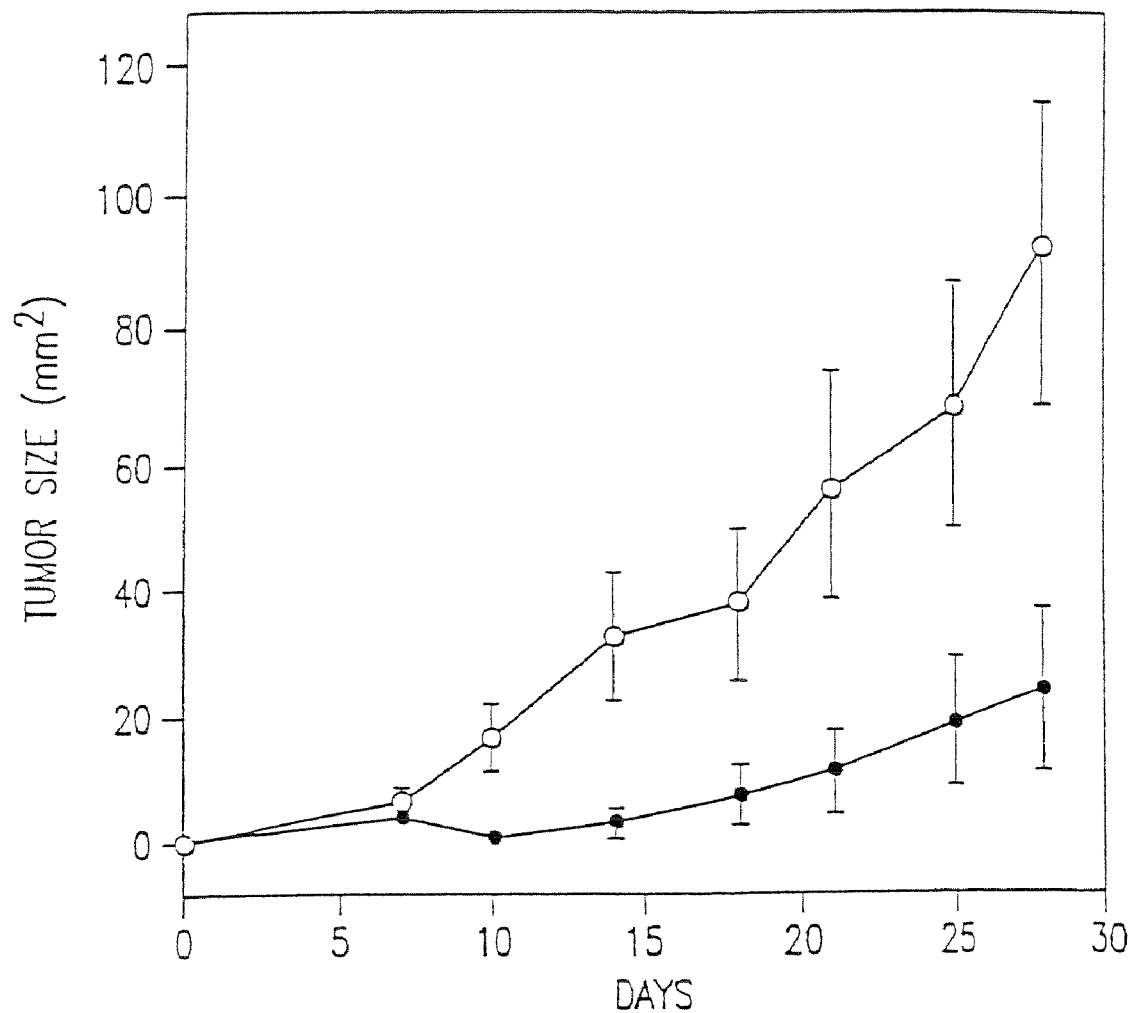

Results presented in FIGS. 16A and 16B (in which TNF-gamma is designated "VEGI") illustrate the sizes of the MDA-MB-231 and MDA-MB-435, respectively, xenograft tumors ($mm^2$) as a function of time (days postinoculation). Tumors were measured beginning on day zero and approximately at 5 day intervals through approximately the twenty-eighth day. In each case, tumors which resulted from breast carcinoma cells coinjected with TNF-gamma-expressing CHO cells (represented by the closed circles in FIGS. 16A and 16B) remained significantly smaller in size than those which resulted from breast carcinoma cells coinjected with vector-only CHO cells (represented by the open circles in FIGS. 16A and 16B).

Example 12

Induction of NF-KappaB and c-Jun Kinase (JNK) by TNF-Gamma

Activation of cellular NF-kappaB is preceded by the phosphorylation, ubiquitination, and ultimate degradation of an endogenous NF-kappaB inhibitor molecule designated IkBa. Degradation of the inhibitor allows the p65 subunit of NF-kappaB to translocate to the nucleus where it can act as a transcriptional regulator. For this reason, a electrophoretic mobility shift analysis (EMSA) is an appropriate method for analyzing activation of cellular NF-kappaB by treatment of cultured cells with TNF-gamma.

In these analyses cells ($2 \times 10^6$ per ml) were treated with different concentrations (0.1-1.0 µg/ml) of bacterially-produced TNF-gamma at 37° C. for 12 hours. Nuclear extracts were then prepared from the cultured cells and EMSA was performed as is well-known in the art and essentially as described (Singh, S. and Aggarwal, B. B. *J. Biol. Chem.* 270:10631-10636 (1995)).

Treating U-937 cells with TNF-gamma for 12 hours resulted in increase in DNA-binding by the p65 subunit of NF-kappaB. Peak activation of DNA-binding by p65 was observed when U-937 cells were treated with 1 µg/ml TNF-gamma for 12 hours. However, treatment of U-937 cells with as little as 0.2 µg/ml TNF-gamma for 12 hours resulted in an observable increase in p65 DNA-binding. TNF-gamma was observed to activate p65 DNA-binding over basal levels from 30 minutes to 18 hours after the initiation of treatment in U-937 cells.

These experiments were elaborated by determining a degradation profile for I-kappaBa in U-937 cells in response to treatment with TNF-gamma. A time course of I-kappaBa degradation was determined by Western blot analysis, a technique that is well-known by one of ordinary skill in the art and has been described by Singh and Aggarwal (*J. Biol. Chem.* 270:24995-25000 (1995)). I-kappaBa was completely degraded when U-937 cells were treated with 0.1-1.0 µg/ml TNF-gamma for 12 hours.

The cellular kinase designated c-Jun kinase (JNK) is an early event in cellular activation. The activation of JNK by TNF-gamma was analyzed as an additional method of determining cellular reaction to treatment with TNF-gamma. The JNK kinase activation assay is well-known by one of skill in the art and has been described by Derijard and colleagues (*Cell* 76:1025-1029 (1994)). After treatment of U-937 cells with 0.1 to 3.0 µg/ml of TNF-gamma for 12 hours, the cells were harvested and assayed for JNK kinase activity. By 6 and 12 hours, JNK activity had increased 2- and 3.6-fold, respectively.

Example 13

Effect of TNF-Gamma in Treating Adjuvant-Induced Arthritis in Rats

An analysis of the use of TNF-gamma to treat rheumatoid arthritis (RA) may be performed through the use of an adjuvant-induced arthritis (AIA) model in rats. AIA is a well-characterized and reproducible animal model of rheumatoid arthritis which is well-known to one of ordinary skill in the art (Pearson, *Ann. Rheum. Dis.* 15:379 (1956); Pearson & Wood, *Arthritis Rheum.* 2:440 (1959)). TNF-gamma is expected to inhibit the increase in angiogensis or the increase in endothelial cell proliferation required to sustain the invading pannus in bone and cartilage observed in this animal model of RA. Lewis and BB rats (available from Charles River Lab, Raleigh, N.C. and the University of Massachusetts Medical Center, Worcester, Mass.) are used as the common and responsive strains for adjuvant-induced arthritis in these experiments.

Initiation of the arthritic condition is induced by the intradermal injection of 0.1 ml adjuvant (5 mg/ml) into the base of the tail. Groups of 5 to 6 rats receive either 0.1 to 1.0 mg/kg TNF-gamma or vehicle intra-articularly 20 days after the injection of adjuvant. At this timepoint, acute inflammation reaches a maximal level and chronic pannus formation will have just begun. The effect of TNF-gamma on pannus formation is analyzed radiologically once each week after day 15 following adjuvant challenge essentially as described by Taurog and colleagues (*J. Exp. Med.* 162:962 (1985)). Briefly, rats are anesthetized with ether or chloral hydrate and positioned so that both hind limbs are X-rayed together. The X-ray film is examined blindly using a scoring system of 0-3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect TNF-gamma has elicited on these joints.

Finally, TNF-gamma- and vehicle-treated animals undergo a clinical evaluation twice per week to assess hind paw volume using a plethysmometer system and body weight.

Example 14

DR3 Ligand (TNF-gamma) is a Novel Anti-Tumor Cytokine Existing in Two Different Forms and Differentially Expressed in Different Tissues and Cells Background:

TNF (tumor necrosis factor) superfamily members play very important roles in cell activation, proliferation, differentiation, apoptosis, cytotoxicity and immune regulation. Members of TNF ligand and receptor superfamily are often overexpressed in various human cancer cells and/or activated lymphocytes, their extracellular accessibility makes them excellent potential targets for specific antitumor therapy and immunomodulating therapy. Over the past few years the list of molecules belonging to the TNF receptor and ligand superfamily has grown rapidly. The TNF ligand family of cytokines consist of over 13 type II transmembrane proteins (except TNF-beta), the TNF receptor superfamily consist of over 18 type I transmembrane proteins except OPG, also known as OCIF or TR1, which is a secreted protein, and TRID/DcR1/TRIAL-R3, which is a GPI-linked cell surface molecule.

Several TNF receptor superfamily members as well as some of the intracellular signal transducers involved in apoptosis contain a stretch of amino acids, approximately 60 to 80 amino acid long, referred to as the "death domain". These death domain-containing receptors, such as TNFR1, Fas/Apo-1/CD95, DR3 (also known as Wsl, Apo3, TRAMP or LARD), DR4, DR5 or TRAIL-R2, upon activation by their ligands, recruit various proteins that mediate cell death through the death domain. These proteins in turn recruit other proteins via their death domains or death effector domains to transduce the death signal. TNFR1 is expressed in most tissues and cell types and is involved in transducing three major types of signals: activation of the transcription factor NF-kappaB, c-jun N-terminal protein kinase and apoptosis. Whereas Fas is expressed in lymphocytes, liver, heart, lung, kidney, and ovary. In contrast, DR3 is predominantly expressed in spleen, thymus, and peripheral blood lymphocytes. The ligand for DR3 has not yet been identified. DR3 interacts with TRADD, associates with RIP ordinarily only weakly, but associates strongly when TRADD is overexpressed. In the presence of TRADD, it also associates strongly with FADD. These results suggest that the mechanism of DR3-induced apoptosis is similar to that induced by Fas and TNFR1. Like TNFR1, DR3 also activates NF-kappaB.

We have identified several novel TNF receptor and ligand superfamily members using several search strategies. One novel TNF-like ligand, TNF-gamma, was predominantly expressed in endothelial cells. Although TNF-gamma shares some of the activities TNF, it does not bind to TNFR1 and TNFR2, indicating that TNF-gamma binds to a distinct receptor. Here we show that TNF-gamma binds to DR3 in several receptor-ligand binding assays. Interestingly, TNF-gamma exists in two different forms which are differentially expresses in different cells and tissues.

Results and Discussion:

We have identified several novel TNF receptor and ligand superfamily members from HGS database which contains over 1.5 million ESTs from over 620 cDNA libraries. One novel TNF-like ligand predominantly expressed in an endothelial cell library exhibited 20-30% sequence homology to other members of the TNF family. The protein was named TNF-gamma-alpha (or VEGIa for Vascular Endothelial derived tumor Growth Inhibitor alpha). Subsequent database analysis and library screening identified a novel splicing variant of TNF-gamma-alpha, designated TNF-gamma-beta (or VEGIbeta). This isoform was found predominantly in cDNA libraries of TNFalpha- and IL-1-induced endothelial cells, monocyte and activated T-cells. The cDNA for TNF-gamma-alpha encodes 174 amino acid residues and TNF-gamma-beta encodes 251 amino acids. Both proteins have characteristics of type II transmembrane proteins. They only differ at the N-terminus which corresponds to the intracellular and transmembrane domains (FIGS. 18A-D and 19).

Recombinant TNF-gamma induces apoptosis in several cell lines such as bovine pulmonary artery endothelial cells and adult bovine aortic endothelial cells. [Bovine pulmonary artery endothelial cells were incubated with various concentrations of TNF-gamma for 48 hours. The apoptosis was assessed by nuclear staining with Hoechst 33342 fluorescence dye (10 mg/ml).] TNF-gamma also induces nuclear factor-kappaB (NF-kappaB) and c-Jun N-terminal kinase (JNK) activation, inhibits angiogenesis in vitro. [U937 cells were transfected using lipofectamine (following manufacturer's instruction) with 0.2 mg of reporter plasmid (NF-kappaB-SEAP). The transfected U937 cells were collected and added to the 96-well plate (200 ml/well) with various concentrated of TNF-gamma. After Incubation at 37° C. for 72 hr, the NF-kappaB activity was measured with luminometer at absorbance of 450 nm.]

To identify the novel receptor and ligand pairs, several receptor-ligand binding assays were established. Recombinant soluble TNF-gamma containing the entire ectodomain binds to DR3-Fc fusion protein immobilized on BIACORE™ chip, purified DR3-Fc also binds to BIACORE™ chip immobilized with TNF-gamma. [Purified DR3-Fc or TNF-gamma was analyzed on a BIACORE™ instrument flowcell derivatized with TNF-gamma or DR3-Fc. The shown data represents the net bound (off-rate) region of the plot after binding of TNF-gamma to immobilized DR3-Fc receptor, or binding of DR3-Fc to immobilized TNF-gamma, which is measured in relative mass units (RU) versus time. The binding conditions were performed at high receptor chip densities under diffusion-limited conditions.] Using immunoprecipitation techniques, recombinant TNF-gamma was co-immunoprecipitated by DR3-Fc, but not LTbR-Fc immunoadhesins. [The Fc-extracellular domains of DR3 or Fc alone and the corresponding ligands were prepared and binding assays were performed as described elsewhere. The respective Fc-fusions were precipitated with protein G-Sepharose and co-precipitated soluble ligands were detected by immunoblotting with anti-TNF-gamma antibody. Blotting and detection was performed as described in BM Chemiluminescence Western Blotting kit protocol.]

To further demonstrate the interaction between DR3 and TNF-gamma, we screened several cell lines for cell surface expression of TNF-gamma using polyclonal antibody to recombinant soluble TNF-gamma. Consistent with the Northern blot analysis, peripheral blood mononuclear cells (PBMC) and human umbilical vein endothelial cells (HUVEC) express TNF-gamma on the cell surface by immunostaining with antibody to TNF-gamma. [Cells were collected by trypsinization or aspiration, and centrifuged at 1500-2000 rpm for 5 min. The cell pellets were resuspended and washed in 5 ml ice-cold PBS twice. The cells were incubated for 30 min at 40° C. with antibody (10 mg/ml) to TNF-gamma to detected expression of TNF-gamma on cell surface, with DR3-Fc or LTbR-Fc (10 mg/ml) for receptor and ligand binding in the binding buffer (HBSS containing 10% BSA, 20 mM HEPES, pH 7.2, 0.02% $NaN_3$). Purified human IgG (25 mg/ml) was used as control. Cells were then washed and stained with phycoerythrin (PE) conjugated to goat anti-rabbit or anti-human IgG at 20 mg/ml. Fluorescence was analyzed by a FACscan flow cytometer (Becton Dickinson, Mountain View, Calif.).] Two tumor cell lines (MC-38/TNF-gamma and MDA-231/TNF-gamma) transfected with TNF-gamma also express TNF-gamma on the cell surface. FACS analysis showed that here is a shift in the most population following exposure MC-38/TNF-gamma cells to DR3-Fc, indicating cell-surface binding between TNF-gamma and DR3. Similarly, a shift in the MDA-231 cells transfected with TNF-gamma was observed. In addition, DR3-Fc protein also binds to HUVEC cells and PBMC. It is noteworthy that DR3 expression and TNF-gamma binding to PBMC declined after prolonged stimulation with PHA. As predicated, DR3-Fc inhibits the TNF-gamma induced NF-kB activated in a dose-dependent manner. [U937 cells were transfected using lipofectamine (following manufacturer's instructions) with 0.2 mg of reporter plasmid (NF-kB-SEAP). The transfected U937 cells were collected and added to the 96-well plate (200 ml/well) with various concentration of DR3-Fc receptor and 100 ng/ml of TNF-gamma. After incubation at 37° C. for 72 hr, the NF-kB activity was measured with luminometer at absorbance of 450 nm.]

TNF-gamma maps to the chromosomal location within band 9q32. This chromosomal location is close to CD30L (9q33), but is different from the genes for TNFalpha, LTalpha and LTbeta which are tightly linked within the MHC complex on chromosome 6. Interestingly, the TNF-gamma receptor, DR3, was assigned to the long arm of chromosome 1, region p36.2, is localized to a region where CD30, TNFR2 and OX40 have been mapped.

Consistent with the role of TNF-gamma and DR3 in apoptosis and immune regulation as well as interaction of DR3 with TNF-gamma, local production of TNF-gamma caused complete tumor suppression in vivo in a syngeneic MC-38 murine colon cancer models. In the same animal model, local production of soluble DR3, which may block TNF-gamma function, promotes tumor growth. [The full-length TNF-gamma and extracellular domain of DR3 was cloned into pcDNA3 expression vector and transfected to MCA 38 cells, respectively. After selection and cloning, three clones from each constructs were picked for tumorigenicity study. MCA 38 cells (1×10⁶ cells/mouse) expressing TNF-gamma or DR3 extracellular domain were injected into C57BL6/6 mice. The tumor size was assessed by measuring perpendicular diameters with a caliper and calculated by multiplying the measurements of diameters in two dimensions. Data are represented as the mean+/−SD of 6 mice in each group.] It is clear that most immune cells and cancer cells can express more than one TNF receptor (even more than one death receptor) and ligand superfamily member. The existence of multiple receptors for one ligand or multiple ligands for one receptor, and multiple splicing variant forms of receptor or ligand suggests an unexpected complexity in the regulation of apoptosis and immune function. These receptors and ligands appear to be functionally redundant, but their expression patterns are different, suggesting a distinct tissue or cell specific involvement in a particular function. Moreover, the expression of these ligands and receptors may differ at the level of individual cell types within tissues and the expression level on the same cell type may also differ.

It is estimated that 10% of genes can be alternatively spliced, but in many cases the function of proteins produced remains obscure. To examine the potential functional significance of the two splicing variants of TNF-gamma, PCR analysis was performed in over 100 cDNA libraries. These results are shown in the following table:

Differential expression pattern of DR3, TNF-gamma-alpha, and TNF-gamma-beta

| Library | DR3 | TNF-γα | TNF-γβ |
|---|---|---|---|
| Normal Tissue | | | |
| Liver | + | | + |
| Lymph node | + | | + |
| Tonsil | + | | |
| Bone marrow | + | | |
| Spleen | + | | |
| Heart | + | | |
| Thymus | + | | + |
| Pericardium | + | | |
| Brain | + | | |
| Lung | | | + |
| Skeletal muscle | | | |
| Placenta | | | + |
| Prostate | | | + |
| Pituitary | | | |
| Testis | + | | + |
| Colon | | | |
| Pancreas | + | | |
| Kidney | | | + |
| Kidney cortex | | + | |
| Pulmonary | | | |
| Adipose | + | + | |
| Ovary | + | | + |
| Cerebellum | | | |
| Hippocampus | | | |
| Hyperthalamus | | | |
| Olfactory epithelium | | + | + |
| Striatum depression | | + | |
| Pineal gland | | | |
| Fetal tissue | | | |
| 8 week embryo | + | | + |
| 9 week embryo | + | | |
| Fetal brain | + | + | + |
| Fetal kidney | + | | + |
| Fetal heart | + | + | + |
| Fetal thymus | + | | |
| Fetal lung | + | | + |
| Fetal liver | + | | |
| Fetal spleen | + | | |
| Abnormal tissue and cell | | | |
| Hepatocellular tumor | + | | |
| Hodgkin's lymphoma | + | | |
| Rhabdomyosarcoma | | | + |
| Nasal polyps | | | |
| Spleen, metastatic melanoma | | | |
| Spleen, chronic lymphocytic leukemia | | | |
| Healing wound (skin) | + | | + |
| B-cell lymphoma | | | |
| Hemangiopericytoma | | | |
| Pancreas tumor | + | | |
| Burned skin | + | | |
| Prostate cancer, stage C | | | |
| U937 cell | + | | |
| Ovarian tumor | | | + |
| Colon cancer, metasticized to liver | + | | + |
| Colon Cancer | | | |
| Crohn's disease | | | |
| Rejected kidney | + | | + |
| T-cell lymphoma | | | + |
| Ovary tumor | | | |
| Endometrial tumor | | | |
| Skin tumor | | | |
| Pancreatic carcinoma | | + | |
| Jurkat cells | | | + |
| Hela cell line | + | | + |
| LNCAP + 0.3 nM androgen | | | + |
| LNCAP + 30 nM androgen | + | | + |
| Normal cell | | | |
| HUVEC. | + | + | + |
| Dermal endothelial, | | | + |
| Resting T cell | | | |
| Activated T cell (12 hr) | | | |
| Activated T cell (16 hr) | + | | |
| Activated T cell (24 hr) | + | | + |
| T cell helper I | | | |
| T cell helper II | + | | |
| CD34+ | | | + |
| Primary dendritic cells, | + | | |
| Eosinophils | | | |
| Monocytes | + | | + |
| Osteoblasts | | | |

-continued

Differential expression pattern of DR3, TNF-gamma-alpha, and TNF-gamma-beta

| Library | DR3 | TNF-γα | TNF-γβ |
|---|---|---|---|
| Keratinocyte | | + | + |
| Stromal endometrial cells | | | |
| Stromal cell TF274 | | | |

As shown in the table, DR3 and two forms of TNF-gamma are differentially expressed in different tissues and cells. In the libraries tested, DR3 was found to be expressed in most tissues, in activated T-cells, monocytes, dendritic cells, TH2 cells, and several other cell lines (such as U937, HeLa) and tumor tissues (such as hepatocellular tumor and Hodgkin's lymphoma). DR3 expression was increased in LNCAP prostate carcinoma cell line treated with 30 nM of synthetic androgen. TNF-gamma-alpha is only expressed in a few tissues or cells such as fetal brain, fetal heart, adipose, kidney cortex, olfactory epithelium, pancreatic carcinoma and HUVEC. In contrast, TNF-gamma-beta has a much broader expression pattern. At the cellular level, only endothelial cell, activated T-cells, monocytes, keratinocytes, HeLa and Jurkat cells express TNF-gamma-beta. Only HUVEC, fetal brain, and fetal heart cDNA libraries express both forms of TNF-gamma and DR3. TNF-gamma-alpha, TNF-gamma-beta, and DR3 are not expressed in resting T-cells or early stage of activated T-cells (12 hr). DR3 becomes detectable at 16 hr, and both DR3 and TNF-gamma-beta become detectable in T-cells at 24 hr after PHA stimulation. The time-dependent induction of DR3 and then TNF-gamma-beta in activated T-cells suggest that DR3 and TNF-gamma may play an important role in activation induced apoptosis.

Northern blot and cDNA database analysis indicated that DR3 expression is found predominantly in tissues with high content of lymphocytes, TNF-gamma is predominantly expressed in endothelial cells, monocytes and activated T-cells. Thus, DR3 and TNF-gamma may be involved in the activation-induced apoptosis and the negative selection of lymphocytes. The expression pattern of DR3, TNF-gamma-alpha, and TNF-gamma-beta by different cells and tissues. Expression of different splicing variant forms of DR3 or TNF-gamma is likely to set the balance between susceptibility and protection from DR3-mediated apoptosis. It is clear that the pathway leading to apoptosis is highly regulated process and involving a series of proteins.

Another ligand for DR3, named as Apo3L has been described recently, which was also published as Tweak. Unlike TNF-gamma, Apo-3L/Tweak expressed in a wide variety of tissues. The interrelationship and functional importance between these two DR3 ligands remain to be investigated.

Conclusion:

One pair of novel receptor and ligand of TNF superfamily, DR3 and TNF-gamma, has been identified. Unlike other ligands of TNF family, TNF-gamma exists in two different forms and is differentially expressed in different cells and tissues. It has been suggested that one of the mechanisms for regulating DR3 function is through alternative splicing of DR3. Alternative pre-mRNA splicing generates at least 11 isoforms of DR3, providing a range of functional outcomes that may help shape the immune response. Our data suggested that DR3 function can also be regulated through alternative splicing and differentially expression of its ligand, TNF-gamma. These findings have great impact on how we view the regulation of apoptosis and TNF receptor superfamily function. Identification of two differentially expressed DR3 ligand variants raised the possibility to selectively modulate apoptosis, immune response and immune surveillance of tumor. Further characterization of physiological and pathological function of two differentially expressed TNF-gamma may provide new insights into the biological activities and physiological function as well as therapeutic application of TNF receptor and ligand superfamily Understanding the role and mechanisms of action of these genes should allow us to develop ways to regulate apoptosis and cell proliferation in a variety of physiological and pathological conditions.

Materials and Methods:

Apoptosis Assay:

Bovine pulmonary artery endothelia cells (BPAEC) were incubated with various concentrations of TNF-gamma for 48 hours. Apoptosis was assessed morphologically and by nuclear staining with Hoechst 33342 fluorescence dye (10 mg/ml) in triplicate. Live and apoptotic cells were scored in four random fields, about 1,000 cells were counted. The DNA fragmentation was analyzed as described previously.

BIACORE™ Receptor-Ligand Binding Assay

Generation of recombinant receptor DR3-Fc fusion protein and recombinant TNF-gamma were described in previous papers. Purified TNF-gamma or DR3-Fc was immobilized on BIACORE™ respectively. Purified DR3-Fc or TNF-gamma was analyzed on a BIACORE™ instrument flowcell derivatized with TNF-gamma or DR3-Fc. The net bound (off-rate) region of the plot after binding of TNF-gamma to immobilized DR3-Fc receptor, or binding of DR3-Fc to immobilized TNF-gamma, was measured in relative mass units (RU) versus time. The binding conditions were performed at high receptor chip densities under diffusion-limited conditions.

Co-Immunoprecipitation and Western Blot Analysis

Polyclonal antisera against TNF-gamma were prepared in rabbits as described previously (Ni, J., et al., *J. Biol. Chem.* 272:10853-10858, (1997)). The Fc-extracellular domains of DR3 or Fc alone and the corresponding ligands were prepared and binding assays were performed as described elsewhere. The respective Fc-fusions were precipitated with protein G-Sepharose and co-precipitated soluble ligands were detected by immunoblotting with anti-TNF-gamma antibody. The samples were loaded into a gel [NOVEX Pre-Cast Gels] (4-20% Tris-Glycine Gel). Blotting and detection was performed as described in BM Chemiluminescence Western Blotting kit protocol.

FACS Analysis

Cells were collected by trypsinization or aspiration, and centrifuged at 1500-2000 rpm for 5 min. The cell pellets were resuspended and washed in 5 ml ice-cold PBS twice. The cells were incubated for 30 min at 40° C. with antibody (10 mg/ml) to TNF-gamma to detected expression of TNF-gamma on cell surface, with DR3-Fc or LTbR-Fc (10 mg/ml) for receptor and ligand binding in the binding buffer (HBSS containing 10% BSA, 20 mM HEPES, pH 7.2, 0.02% NaN3). Purified human IgG (25 mg/ml) was used as a control. Cells were then washed and stained with phycoerythrin (PE) conjugated to goat anti-rabbit or anti-human IgG at 20 mg/ml. Fluorescence was analyzed by a FACscan flow cytometer (Becton Dickinson, Mountain View, Calif.).

NF-KappaB-SEAP (Secreted alkaline phosphatase) Reporter Assay

U937 cells were transfected using lipofectamine (following manufacturer's instructions) with 0.2 mg of reporter plasmid (NF-kappaB-SEAP). The transfected U937 cells were collected and added to the 96-well plate (200 ml/well) with various concentration of active TNF-gamma or inactivated (boiled) TNF-gamma or in combination with various concentration DR3-Fc receptor and 100 ng/ml of TNF-gamma. After Incubation at 37° C. for 72 hr, the NF-kappaB activity was measured with luminometer at absorbance of 450 nm.

Tissue and Cell Distribution Analysis Using PCR on a Large Collection of cDNA Libraries and cDNA Database:

To study the tissue distribution of DR3, TNF-gamma-alpha and TNF-gamma-beta, two gene specific primers were synthesized for each gene. Over 100 cDNA libraries are tested and the libraries gave a positive predicted size signal are indicated as +.

In Vivo Tumorigenicity Assay:

The full length TNF-gamma and extracellular domain of DR3 was cloned into pcDNA3 expression vector (Invitrogen, Carlsbad, Calif.) and transfected to MCA 38 cells, respectively. Subsequent to transfection, G418 selection, and cloning, three clones from each constructs were picked for tumorigenicity study. The expression of TNF-gamma and DR3 in MCA 38 cells were confirmed by Northern analysis. MCA 38 cells ($1 \times 10^6$ cells/mouse) expressing TNF-gamma or DR3 extracellular domain were injected into C57BL6/6 mice. Mice then were randomized and tumors were measured twice weekly. The tumor size was assessed by measuring perpendicular diameters with a caliper and calculated by multiplying the measurements of diameters in two dimensions. Data are represented as the mean+/−SD of 6 mice in each group.

Example 15

TNF-Gamma-Alpha, a Novel Member of TNF Cytokine Family, Causes Endothelial Cell Apoptosis Background:

TNF-gamma-alpha is a novel protein with a molecular weight of 22 kD that was recently identified by searching the Human Genome Sciences (HGS) cDNA database (Tan, K. B., et al, *Gene* 204:35-46 (1997)). TNF-gamma-alpha is a type II membrane protein and exhibits about 30% sequence homology to human tumor necrosis factor alpha (TNFalpha). This newly identified member of the TNF family has been demonstrated to be abundantly expressed in endothelial cells as well as in kidney, lung and prostate. TNF-gamma-alpha expression in HL-60 and THP1 cells was induced by PMA treatment. Radiation hybrid mapping localized TNF-gamma gene on chromosome 9q32, near CD30L. Because of its overexpression in endothelial cells, TNF-gamma-alpha has been suggested to possibly play a role in vascular functions (Tan, K. B., et al, *Gene* 204:35-46). The present study was undertaken to explore whether TNF-gamma-alpha induces endothelial cell apoptosis, a phenomenon suggested to be one cause of endothelial cell damage contributing to various inflammatory disorders and cardiovascular dysfunction (Bryant, D., et al, *Circulation* 97:1375-1381 (1998)). To examine this possibility, we used bovine pulmonary artery endothelial cells (BPAEC) to which TNFalpha-induced apoptosis has been demonstrated (Polunovsky, V. A., et al., *Exp. Cell Res.* 214: 584-594 (1994)). Apoptosis was detected on the basis of morphological (including ultrastructural) and biochemical characteristics (DNA fragmentation). In addition, we studied the effects of TNF-gamma-alpha on the activity of stress kinases, stress-activated protein kinase (SAPK/JNK) and p38 mitogen-activated protein kinase (p38 MAPK), and the caspases. Both signaling pathways are believed to be implicated in programmed cell death (Xia, Z., et al., *Science* 270: 1326-1331 (1995)). The expression of Fas and Bcl-2 in TNF-gamma-alpha-stimulated BPAEC was also determined in view of the death-promoting effect of Fas and the anti-apoptotic effect of Bcl-2 (Nagata, S. and Golstein, P. *Science* 267:1449-1456 (1995)).

Materials and Methods:

Materials

TNF-gamma-alpha protein (22 kD) was provided by HGS. Ac-YVAD-AMC and Ac-DEVD-AMC were purchased from American Peptide (Sunnyvale, Calif., USA). ZVAD-fmk and Ac-YVAD-CHO were obtained from Enzyme Systems (Dublin, Calif., USA) and Peptides International (Louisville, Ky., USA), respectively. Ac-DQMD-AMC, Ac-LEED-AMC, Ac-VETD-AMC and anti-p38 MAPK mAb were provided by SmithKline Beecham (SB) Pharmaceuticals (King of Prussia, Pa., USA). Ac-IETD-AMC and mouse-anti-human JNK mAb were purchased from Biomol Research Laboratories (Plymouth Meeting, Pa., USA) and PharMingen (San Diego, Calif., USA), respectively. Mouse soluble TNF receptor 1(sT-NFR1) and TNF receptor 2 (sTNFR2) was obtained from R&D Systems (Minneapolis, Minn., USA).

Cell Cultures

BPAEC were obtained from the American Type Culture Collection (Rockville, Md., USA). The cells were grown in DMEM supplemented with 10% heat-inactivated FCS in a humidified environment of 5% $CO_2$/85% air at 37° C. as previously described (Yue, T. L., et al., *Mol. Pharmacol.* 51:951-962 (1997)). Cells at a subconfluent density were used. Before experiments, the medium was changed to DMEM contained 2% FCS. BPAEC from passages 17-20were used in all studies.

Morphological Assessment and Quantification of Apoptosis

To quantify cells undergoing apoptosis, cell monolayers were fixed and stained with Hoechst 33324 (Molecular probe, Eugene, Oreg., USA) as described previously (Yue, T. L., et al., *Mol. Pharmacol.* 51:951-962 (1997)). The morphological features of apoptosis (cell shrinkage, chromatin condensation, blebbing, and fragmentation) were monitored by fluorescence microscopy. Transmission electron microscopy study was done as reported previously (Yue, T. L., et al., *Mol. Pharmacol.* 51:951-962 (1997)).

DNA Fragmentation Analysis

DNA ladder: Cells treated with vehicle or TNF-gamma-alpha were lysed in lysis buffer containing 100 mM NaCl, 10 mM Tris-HCl, pH 8.0, 2.5 mM EEDTA, 0.5% SDS, and 100 micrograms/ml protein kinase K. The lysates were incubated at 55° C. for 16 h. After incubation, the lysates were gently extracted three times with pheno/chloroform/isoamyl alcohol, precipitated in ethanol, treated with DNAse-free RNAse, re-extracted, and precipitated again as described previously. DNA electrophoresis was carried out in 1.8% agarose gels containing ethidium bromide, and DNA fragmentations were visualized under ultraviolet light.

In situ end-labeling (TUNEL): BPAEC were cultured in two-chamber slides (Nunc) and treated with TNF-gamma-alpha for 8 to 24 h. In situ detection of apoptotic cells was performed by using terminal deoxyribonucleotide transferase-mediated dUTP nick end labeling with an ApopTag in situ apoptosis detection kit (Oncor) following the manufacturer's recommendation.

Stress-Activated Protein Kinase (SAJPK/JNK) Assay

SAPK activity was measured using GST-c-Jun$_{(1-81)}$ as bound to glutathione-Sepharose 4B as described previously (Yuc, T. L., et al., *Mol. Pharmacol.* 51:951-962 (1997)). Briefly, the cells were treated with vehicle or TNF-gamma-alpha, washed, and lysed in lysis buffer. The nuclear-free supernatant was normalized for protein content and immunoprecipitated with anti-SAPK antibody-conjugated Sepharose beads. The mixture was rotated 4° C. for 3 h. The phosphorylation buffer containing GST-c-Jun$_{(1-80)}$, 10 µC[g-$^{32}$ P]-ATP, 125 µM ATP and 100 mM MgCl, was added to the SAPK-bound beads in assay buffer. The reaction was terminated after 20 min at 30° C. by addition of protein loading buffer and heated at 90° C. for 3 min. Phosphorylated proteins were resolved in 10% SDA-polyacrylamide gel electrophoresis followed by autoradiography. The intensity of the bands was quantified by PhosphorImager (Yuc, T. L., et al., *J. Mol. Cell. Cardiol.* 30:495-507 (1998)).

p38 MAPK Assay

The cell lysates prepared as above were immuno-precipitated with anti-p38 MAKP antibody bound to protein A agarose for 4 h at 4° C. The beads were washed with lysis buffer and then with kinase buffer as described previously (Kumar, S. M., et al., *J. Biol. Chem.* 271:30864-30869 (1996)). The immune-complex kinase assay was initiated by the addition of 25 ml of kinase buffer containing 2 µg of GST-ATF2 and 50 micromolar [gamma-$^{32}$P] ATP(20 Ci/mmol). The phosphorylated products were resolved by SDA-PAGE and visualized by Phosphorimager.

In Vitro Transfection of Dominant-Interfering Mutant of c-JUN in BP AEC

The cells were plated in two-chamber slides. The cells were cotransfected with 0.5 µg/ml of Pegfp-c-1 (Clontech; Li, Y. and Horwitz, M. S. *Biotechnology* 23:1026-1028) as a fluorescent marker of transfected cells together with 1 µg/ml of either the empty cloning vector pCDNA 1 (control) or the dominant-interfering c-Jun mutant pcDNA1-FlagΔ169 (Xia, Z., et al., *Science* 270:1326-1331 (1995)) using Calphos Maximizer Transfection Kit (Clontech) according to the manufacturer's recommendation. Following transfection, the cells were allowed to recover in complete medium for 24 h. The cells were treated with TNF-gamma-alpha and the number of apoptotic cells was assessed by nuclear staining after fixation as described in Methods.

Caspase Activity Assay

The cells were treated with vehicle of TNF-gamma-alpha. Caspase activity assays were performed as reported previously (Yuc, T. L., et al., supra). Briefly, cells were harvested and suspended in buffer containing 25 mM HEPES, pH 7.5, 10% sucrose, 0.1% CHAPS, 2 mM DDT, 5 mM PMSF, and 1 µM pepstatin A. The suspension was forced through a 25 gauge needle 10 times to break cells. The homogenate was centrifuged at 100,000×g for 1 h, and the cleared lysates were used for enzyme assays. Cell extracts (5-20 µg protein) were diluted into the assay buffer (Table 2) and preincubated for 10 min at 30° C. prior to the addition of the substrates. Levels of released 7-amino-4-methylcocmarin (AMC) were measured with a Cytofluor-4000 fluorescent plate reader (Perseptive Biosystems) at an excitation and emission wavelengths of 360 nm and 460 nm, respectively.

Immunohistochemical Analysis for Fas, Bcl-2 and Caspase-3 Expression

The cells were cultured in two-chamber slides. After treatment with vehicle or TNF-gamma-alpha, the cells were fixed with 4% paraformaldehyde for 30 min at 4° C. and then changed to cold PBS. The cells were treated with 0.2% Triton X-100 for 40 min at 4° C., washed with cold PBS and then non-specific immunoglobulin binding sites were blocked with normal goat serum (Vector Laboratories) for 1 h at room temperature. The cell samples were incubated with the primary antibody mouse anti-human Fas (Upstate Biotechnology), mouse anti-human Bcl-2 (DAKO) or rabbit anti-human CPP32 p17 peptide polyclonal antisera (SmithKline Beecham), for 1 h at room temperature. As a negative control, the cell samples were incubated with nonimmune IgG (for Bcl-2 and CPP32) or IgM (for Fas) instead of the primary antibody. After incubation with the primary antibody, cells were washed with PBS and then incubated for 30 min with a secondary antibody conjugated to fluorescein isothiocyanate. Cells were washed, treated with Veetashield mounting medium (Vector Laboratories) and viewed by fluorescence microscopy (Olympus IX70).

Statistical Analysis

All values are represented as mean±S.E.M. of n independent experiments. Statistical evaluation was performed by using one-way analysis of variance. Differences with a value of p<0.05 were considered significant.

Results:

TNF-Gamma-Alpha Induces Apoptosis in BPAEC

When BPAEC were exposed to TNF-gamma-alpha the cells shrunk and retracted from their neighboring cells, and the cytoplasma became condensed. Cells stained with Hoechst 33324 and assessed by fluorescence microscopy demonstrated condensed chromatin of fragmented nuclei and blebbing of the plasma membrane. The study with transmission electron microscopy showed that TNF-gamma-alpha-treated BPAEC contained many cells undergoing morphologic alterations characteristic of apoptosis including condensation of chromatin and appearance of apoptotic bodies. The characteristic degradation of DNA into oligonucleosomal-length fragmentation was observed when the cells were exposed to TNF-gamma-alpha (30-300 ng/ml) for 24 h. The DNA fragments in situ was further visualized by using TUNEL method. A considerable fraction of endothelial cells treated with TNF-gamma-alpha showed positive staining; no positively stained cells were found in the vehicle-treated cultures.

TNF-gamma-alpha-induced endothelial cell apoptosis was a time- and concentration-dependent process with an $EC_{30}$ value of 72 ng/ml. A significant increase in the number of cells with apoptotic morphological changes was apparent 6-8 h after exposure of the cells to TNF-gamma-alpha. Under similar conditions, TNF-alpha at 10 ng/ml induced apoptosis in PEAPC by 16.7±3.2% (n=4).

Effects of sTNFR1 and sTNFR2 on TNF-Gamma-Alpha-Induced Apoptosis in BPAEC

Activation of SAPK/JNK and p-38 MAPK

With regard to the effects of TNF-gamma-alpha on SAPK/JNK activity in BPAEC, exposure of endothelial cells to TNF-gamma-alpha induced a rapid activation of SAPK/JNK. A significant increase in SAPK/JNK activity was detected 20 min after stimulation, peaked at 40 min. and then returned to the basal levels after 60 min. TNF-gamma-alpha-induced activation of SAPK/JNK in endothelial cells is a concentration-dependent process. Some basal activities of SAPK/JNK activity was increased by 5.6±1.4 folds (p<0.05 n=4) and 9.1±1.8 folds (p<0.01 n=6) over the basal level in the presence of 50 and 300 ng/ml of TNF-gamma-alpha, respectively. TNF-gamma-alpha activated p38 MAPK in BPAEC with a similar time course as SAPK/JNK but to a lesser extent. The peak of p38 MAKP activity was increased by 3.1±0.5 and 3.8±0.4 folds over the basal level in the presence of 100 and 300 ng/ml of TNF-gamma-alpha, respectively.

Effects on TNF-Gamma-Alpha-Induced Apoptosis by Expression of Dominant-Interfering Mutant of c-JUN in BPAEC or by the p38 MAPK Inhibitor, SB203580

To investigate the role of SAPK/JNK in TNF-gamma-alpha-induced apoptosis in BPAEC, we transfected BPAEC with a dominant-interfering mutant of c-JUN, pCDNA1-FlagΔ169, in which a deletion in the NH2-terminal transactivation domain that includes the binding site for JNK (Xia, Z., et al., supra). Expression of dominant-interfering c-JUN construct in BPAEC reduced TNF-gamma-alpha-induced apoptosis by 62.8% (p<0.05). TNF-gamma-alpha-induced apoptosis in BPAEC was also attenuated by a specific p38 MAPK inhibitor, SB203580, in a concentration dependent manner. In the presence of 3 and 10 µM of SB203580, TNF-gamma-alpha-induced BPAEC apoptosis was reduced by 33% (p<0.05) and 51% (p<0.01), respectively. No further inhibition was observed when the concentration of SB203580 was increased.

Activation of Caspases in BPAEC by TNF-Gamma-Alpha

TNF-gamma-alpha-induced BPAEC apoptosis was attenuated by ZVAD-fmk, an irreversible cell-permeable inhibitor of caspase (Jocobson, N. L., et al., *Cell Biol.* 133:1041-1051 (1996)), added to the culture medium 1 h prior to TNF-gamma-alpha treatment. Under the same conditions, the addition of Ac-YYAD-CHO, a relatively specific inhibitor of caspase-1 (Thorberry, N. A., et al., *Nature (Lond)* 356:768-774 (1992)), up to 100 µM showed no effect in enhancing BPAEC rescue. To further determine which of the caspase family members are activated in the TNF-gamma-alpha-induced apoptotic process in the endothelial cells, we examined cell extracts for proteolytic activity. The relative rates of AMC formation were measured with a series of defined peptide sequence variants that are relatively specific for caspase 1, 3, 4, 7, or 8 under the optimal conditions as described previously (Yuc, T. L., et al., supra). Similar results were observed from three repeated experiments. Cell extracts from TNF-gamma-alpha-treated BPAEC were highly active on Ac-DEVD-AMC and to a lesser extent on Ac-DQMD-AMC, but not active on the remaining three substrates which are more specific for caspase 1, 4, and 8. The proteolytic activity appeared at 6 h after the cells were treated with TNF-gamma-alpha, peaked at 24 h, and gradually returned to basal levels within 48 h. The relative velocities of four substrate hydrolysis rates by the TNF-gamma-alpha-treated cell extracts and recombinant caspase-3 were compared. The relative velocities of the two enzyme sources of four substrates were very similar.

To further confirm that caspase-3 is activated by TNF-gamma-alpha in BPAEC, immunocytochemical detection of its enzymatically active form, the 17-kD subunit, was performed. The antibody was raised against a peptide from the C-terminal portion of the p17 subunit. The neoepitope antibody only binds caspase-3 if there has been specific cleavage between the "p-10" and "p-20" subunits. Using this neoepitope antibody, only processed caspase-3 is detected, but not the porenzyme (Yuc, T. L., et al., supra). The 17 kD subunit of caspase-3 was detected in TNF-gamma-alpha-treated but not vehicle-treated BPAEC, and was localized with fragmented nuclei within the cells.

Discussion:

The studies presented in this paper demonstrate that TNF-gamma-alpha, a novel TNF-like cytokine and a type II transmembrane protein, induces intensive apoptosis in cultured endothelial cells as reflected by morphological and biochemical criteria. Under our experimental conditions, spontaneous BPAEC death was approximately 2-4% which is in accord with a previous observation (Polunovsky, V. A., et al., supra). The effect of TNF-gamma-alpha was concentration-dependent with an $EC_{80}$ value of 72 ng/ml (3.5 nM) and a significant number of apoptotic cells was detected 6-8 h after treatment. Moreover, the expression of pro-apoptotic gene, Fas, was demonstrated in TNF-gamma-alpha-treated BPAEC, which is consistent with that observed in apoptotic endothelial cells reported previously (Yuc, T. L., et al., supra).

The receptor(s) mediating TNF-gamma-alpha activity has not been identified as yet. To examine whether TNF-gamma-alpha acts via distinct receptor(s), we tested the effects of sTNFR1 and sTNFR2 on TNF-gamma-alpha-induced apoptosis in BPAEC. These two TNFRs have been shown previously to block the cell surface TNFR1 and TNFR2 mediated TNF bioactivities on responsive cell lines (data from R&D Systems). Neither sTNFR1 nor sTNFR2 inhibited the effect of TNF-gamma-alpha on BPAEC. In contrast, TNFa-induced apoptosis in BPAEC was significantly reduced by sTNFL The results suggest clearly that TNF-gamma-alpha-induced cell death is independent of sTNFR1 or TNFR2.

Recent research efforts on TNF family members have demonstrated that TNFa and Fas activate stress protein kinases, SAPK/JNK and p38 MAPK, in a variety of cell types (Sluss, H. K., et al., *Cell Biol.* 14:8376-8384 (1994)), however, the effects of other members of this family on SAPK and p38 MAPK are not well studies. Moreover, controversies regarding the role of SAPK/JNK and p38 MAPK in TNFa or Fas-mediated cell death have been reported. For example, TNFa-induced apoptosis is dependent on JNK activity in U937 cells (Verjeij, M., et al., *Nature (Lond)* 380:75-79 (1995); Zanke, B. W., et al., *Curr. Biol.* 6:606-613 (1996)) but not in fibroblasts (Reinhard, C., et al., *EMBO J.* 16:1080-1092 (1997)) indicating that the consequences of JNK activation vary considerably among cell types. Fas-mediated JNK activation occurs with a different kinetics from that of TNFa, suggesting that TNFa and Fas most likely activate JNK through a different mechanism (Wilson, D. J., et al., *Eur. J. Immunol.* 26:989-994(1996)). Moreover, Juo, et al., reported recently that blockade of p38 MAPK by a specific p38 MAPK inhibitor did not affect Fas-mediated apoptosis in Jurkat cells (Juo, P., et al., *Mol. Cell Biol.* 17:24-35 (1997)). Therefore, we were interested in finding whether TNF-gamma-alpha activates JNK and p38 MAPK, and what is the role of this activation in TNF-gamma-alpha-mediated apoptosis in BPAEC. The present investigation clearly demonstrates that both JNK and p38 MAPK were rapidly activated by TNF-gamma-alpha in a similar fashion as observed in TNFa-activated U937. Moreover, expression of dominant-interfering mutant of c-JUN in BPAEC reduced TNF-gamma-alpha-induced cell death indicating that TNF-gamma-alpha-induced apoptosis in BPAEC was dependent on JNK activity. To address the potential involvement of p38 MAPK in TNF-gamma-alpha-mediated apoptosis in BPAEC, a specific p38 MAPK inhibitor SB203580 was tested. This inhibitor has been shown to specifically inhibit p38 MAPK activity in vitro with no effect on a variety of kinases tested, including JNK and ERK-1 (Cuenda, A., et al., *FEBS Lett.* 364:229-233 (1995)). TNF-gamma-alpha-induced apoptosis in BPAEC was also reduced by SB203580 in a concentration-dependent manner, indicating that p38 MAPK signaling pathway is involved in TNF-gamma-alpha-mediated BPAEC apoptosis. This effect is different from that observed in Fas-mediated apoptosis in Jurkat cells in which SB203580 had no protective effect (Juo, P., et al., supra). Moreover, TNF-gamma-alpha-induced p38 MAPK activation occurs with must faster kinetics in BPAEC than that observed in Jurkat cells in which the peak of p38 MAPK activation was at 2-4 h after stimulation by Fas, indicating TNF-gamma-alpha and Fas most likely activate p38 MAPK through a different mechanism with a different outcome. Our data further suggests that different members of TNF family may have different signaling pathways to mediate cell death or have different effects in different cell types.

Recent work has supported a central role for the caspase family members, as effectors of apoptosis (Kumar, S. M., et al., supra). However, the role of caspases in endothelial cell apoptosis has not been sufficiently explored. Two characteristic features of the caspase family have been elucidated; they cleave their target proteins after specific aspartic acids, resulting in two subunits that together form the active site of the enzyme (Nicholson, D. W., et al., *Nature (Lond)* 376:37-43 (1995); Kumar, S. M., et al., supra). Among the caspase family, caspase-3 (CPP32) has been considered as a central component of the proteolytic cascade during apoptosis and plays a key role in this family (Wang, X., *EMBO J.* 15:1012-1020 (1996); Woo, M., et al., *Gene Development* 12:806-819 (1998)). TNF-gamma-alpha-induced BPAEC apoptosis was inhibited by ZVAD-fmk, indicating a potential role for the caspase family in this effector pathway for apoptosis. To determine which of the caspase family members are involved, we examined the substrate specificity of proteolytic activity in the extracts from TNF-gamma-alpha-activated BPAEC by measuring the relative rate of AMC formation from 6 different substrates which are relatively specific for caspases 1, 3, 4, 7 and 8 (Talanian, R. V., et al., *J. Biol. Chem.* 272:9677-9682 (1997)). Treatment of BPAEC with TNF-gamma-alpha resulted in a significant increase in proteolytic activity towards DEVD-AMC mainly and DQMD-AMC to some extent, both of which show the relative specificity for caspase-3 (Kumar, S. M., et al., supra). There was no induction in proteolytic activity in TNF-gamma-alpha-activated cell extracts when Ac-YVAD-AMC, LEED-AMC or VETD-AMC were used as the substrate, indicating that caspases 1, 4 and 8 might not be involved. Moreover, comparison of the substrate specificity of the extracts from TNF-gamma-alpha-treated BPAEC with recombinant caspase-3 showed a similar pattern, further suggesting that caspase-3 may be the predominant member in the caspase family activated by TNF-gamma-alpha. Furthermore, immunocytochemical studies detected the active form of caspase-3 in TNF-gamma-alpha treated BPAEC. It was reported that multiple caspase homologues were found in both the cytoplasm and nucleus in etoposide-induced apoptosis in HL-60 cells (Martins, I. M., et al., *J. Biol. Chem.* 272:7421-7430 (1997)). Interestingly, in TNF-gamma-alpha-induced apoptotic BPAEC the immunoreactive 17 kD subunit of caspase-3 was only localized with fragmented nuclei, further indicating a role of caspase-3 in TNF-gamma-alpha-induced apoptosis. Whether this active caspase-3 was transported into the nucleus or the inactive caspase-3 is already in the nucleus awaiting activation promoted by TNF-gamma-alpha requires further investigation. Taken together, these results suggest that caspase-3 was activated by TNF-gamma-alpha-induced cell apoptosis. However, our results cannot exclude other members of this family, especially those closely related to caspase-3, such as caspase-7, in mediating TNF-gamma-alpha-induced apoptosis. Moreover, ZVAD-fmk was less effective at the later time (30 h) compared to the earlier time (14 h) for inhibiting TNF-gamma-alpha-included apoptosis in BPAEC, suggesting a caspase-independent of negative-feedback mechanism may exist at the later phase of TNF-gamma-alpha-induced BPAEC apoptosis.

In summary, the present studies have demonstrated that TNF-gamma-alpha, a novel member of TNF cytokine family, causes endothelial cell apoptosis. TNF-gamma-alpha appears to act through a receptor which is distinct from TNF receptors 1 or 2. The effect of TNF-gamma-alpha is via activation of the stress protein kinases, SAPK/JNK and p38 MAPK., and the caspases, mainly caspase-3 like protease. Apoptotic programmed cell death has been suggested to be a cause of endothelial cell damage contributing to various inflammatory disorders and cardiovascular injury (Karsan, A. *Trends Cardiovasc. Med.* 8:19-24 (1998)). Moreover, endothelial cell apoptosis may be an important mechanism involved in a balance between antiangiogenic and proangiogenic processes, and loss of this balance will lead to a variety of diseases such as solid tumor metastasis and retinopathy (Folkman, J. and Shing, J. *J. Biol. Chem.* 267:10931-10934 (1992); Brooks, P. C., et al., *Cell* 79:1157-1164 (1994)).

Example 16

Protein Fusions of TNF-Gamma Alpha or TNF-Gamma-Beta

TNF-gamma alpha or TNF-gamma-beta polypeptides of the invention are optionally fused to other proteins. These fusion proteins can be used for a variety of applications. For example, fusion of TNF-gamma alpha or TNF-gamma-beta polypeptides to His-tag, HA-tag, protein A, IgG domains, FLAG, and maltose binding protein facilitates purification. (See EP A 394,827; Traunecker, et al., *Nature* 331:84-86 (1988).) Similarly, fusion to IgG-1, IgG-3, and albumin increases the halflife time in vivo. Nuclear localization signals fused to TNF-gamma alpha or TNF-gamma-beta polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein.

In one embodiment, TNF-gamma-alpha or TNF-gamma-beta polynucleotides of the invention are fused to a polynucleotide encoding a "FLAG" polypeptide. Thus, a TNF-gamma-alpha-FLAG or a TNF-gamma-beta-FLAG fusion protein is encompassed by the present invention. The FLAG antigenic polypeptide may be fused to a TNF-gamma-alpha or TNF-gamma-beta polypeptide of the invention at either or both the amino or the carboxy terminus. In preferred embodiments, a TNF-gamma-alpha-FLAG or a TNF-gamma-beta-FLAG fusion protein is expressed from a pFLAG-CMV-5a or a pFLAG-CMV-1 expression vector (available from Sigma, St. Louis, Mo., USA). See, Andersson, S., et al., *J. Biol. Chem.* 264:8222-29 (1989); Thomsen, D. R., et al., *Proc. Natl. Acad. Sci. USA,* 81:659-63 (1984); and Kozak, M., *Nature* 308:241 (1984) (each of which is hereby incorporated by reference). In further preferred embodiments, a TNF-gamma-alpha-FLAG or a TNF-gamma-beta-FLAG fusion protein is detectable by anti-FLAG monoclonal antibodies (also available from Sigma).

In a specific embodiment, a TNF-gamma-beta-FLAG fusion protein expression construct was generated using the pFLAG-CMV-1 vector to express amino acid residues L-72 through L-251 of SEQ ID NO:20 fused to FLAG at the amino terminus.

In another specific embodiment, a TNF-gamma-beta-lacZ-FLAG fusion protein expression construct was generated using the pFLAG-CMV-1 vector to express amino acid residues L-72 through L-251 of SEQ ID NO:20 fused to FLAG and lacZ at the amino terminus.

All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and TNF-gamma alpha or TNF-gamma-beta polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

(SEQ ID NO: 18)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 17

Assays to Detect Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays that allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure:

In Vitro assay—Purified TNF-gamma alpha or TNF-gamma-beta protein, or truncated forms thereof, is assessed for its ability to induce activation, proliferation, differentiation or inhibition and/or death in B-cell populations and their precursors. The activity of TNF-gamma alpha or TNF-gamma-beta protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220). Various dilutions of each sample are placed into individual wells of a 96-well plate to which are added $10^5$ B-cells suspended in culture medium (RPMI 1640 containing 10% FBS, 5× $10^{-5}$M_ME, 100 U/ml penicillin, 10 micro g/micro 1 streptomycin, and $10^{-5}$ dilution of SAC) in a total volume of 150 micro 1. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

In vivo assay—BALB/c mice are injected (i.p.) twice per day with buffer only, or with 2 mg/Kg of TNF-gamma alpha or TNF-gamma-beta protein, or truncated forms thereof. Mice receive this treatment for 4 consecutive days, at which time they are sacrificed and various tissues and serum collected for analyses. Comparison of H&E sections from normal and TNF-gamma alpha or TNF-gamma-beta protein-treated spleens identify the results of the activity of TNF-gamma alpha or TNF-gamma-beta protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from TNF-gamma alpha or TNF-gamma-beta protein-treated mice is used to indicate whether TNF-gamma alpha or TNF-gamma-beta protein specifically increases the proportion of ThB+, CD45R (B220) dull B cells over that which is observed in control mice.

Likewise, a predicted consequence of increased mature B-cell representation in vivo is a relative increase in serum Ig titers. Accordingly, serum IgM and IgA levels are compared between buffer and TNF-gamma alpha or TNF-gamma-beta protein-treated mice.

The studies described in this example tested activity in TNF-gamma alpha or TNF-gamma-beta protein. However, one skilled in the art could easily modify the exemplified studies to test the activity of TNF-gamma alpha or TNFgamma-beta polynucleotides (e.g., gene therapy), agonists, and/or antagonists of TNF-gamma alpha or TNF-gamma-beta.

Example 18

T Cell Proliferation Assay

A CD3-induced proliferation assay is performed on PBMCs and is measured by the uptake of $^3$H-thymidine. The assay is performed as follows. Ninety-six well plates are coated with 100 microliters/well of mAb to CD3 (HIT3a, Pharmingen) or isotype-matched control mAb (B33.1) overnight at 4° C. (1 micrograms/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of TNF-gamma alpha or TNF-gamma-beta protein (total volume 200 microliters). Relevant protein buffer and medium alone are controls. After 48 hours at 37° C., plates are spun for 2 min. at 1000 rpm and 100 microliters of supernatant is removed and stored at −20° C. for measurement of IL-2 (or other cytokines) if an effect on proliferation is observed. Wells are supplemented with 100 microliters of medium containing 0.5 microcuries of $^3$H-thymidine and cultured at 37° C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TNF-gamma alpha or TNF-gamma-beta proteins.

The studies described in this example tested activity in TNF-gamma alpha or TNF-gamma-beta protein. However, one skilled in the art could easily modify the exemplified studies to test the activity of TNF-gamma alpha or TNF-gamma-beta polynucleotides (e.g., gene therapy), agonists, and/or antagonists of TNF-gamma alpha or TNF-gamma-beta.

Example 19

Effect of TNF-Gamma Alpha or TNF-Gamma-Beta on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-alpha, causes a rapid change in surface phenotype (increased expression of MHC class I and II, costimulatory and adhesion molecules, downregulation of FCgammaRII, upregulation of CD83). These changes correlate with increased antigen-presenting capacity and with functional maturation of the dendritic cells.

FACS analysis of surface antigens is performed as follows. Cells are treated 1-3 days with increasing concentrations of TNF-gamma alpha or TNF-gamma-beta or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines.

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of TNF-gamma alpha or TNF-gamma-beta for 24 hours. LPS (100 ng/ml) is added to the cell culture as positive control. Supernatants from the cell cultures are then collected and analyzed for IL-12content using commercial ELISA kit (e.g., R & D Systems (Minneapolis, Minn.)). The standard protocols provided with the kits are used.

Effect on the Expression of MHC Class II, Costimulatory and Adhesion Molecules.

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1-5 days with increasing concentrations of TNF-gamma alpha or TNF-gamma-beta or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival.

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. TNF-gamma alpha or TNF-gamma-beta, agonists, or antagonists of TNF-gamma alpha or TNF-gamma-beta can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 micrograms/ml, and then incubated at room temperature for 5 minutes before FACScan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of TNF-gamma alpha or TNF-gamma-beta and under the same conditions, but in the absence of TNF-gamma alpha or TNF-gamma-beta. For IL-12 production, the cells are primed overnight with IFN-gamma (100 U/ml) in presence of TNF-gamma alpha or TNF-gamma-beta. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

3. Oxidative burst. Purified monocytes are plated in 96-well plates at $2-1 \times 10^5$ cell/well. Increasing concentrations of TNF-gamma alpha or TNF-gamma-beta are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in TNF-gamma alpha or TNF-gamma-beta protein. However, one skilled in the art could easily modify the exemplified studies to test the activity of TNF-gamma alpha or TNF-gamma-beta polynucleotides (e.g., gene therapy), agonists, and/or antagonists of TNF-gamma alpha or TNF-gamma-beta.

Example 20

Production of an Antibody

Hybridoma Technology

Isolation of Antibody Fragments Directed Against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phages are prepared as described in PCT publication WO 92/01047.

M13 delta gene III is prepared as follows: M13 delta gene III helper phage does not encode gene III protein, hence the phage(mid)s displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phages from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 21

Method of Determining Alterations in the TNF-Gamma Alpha or TNF-Gamma-Beta Gene RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TNF-gamma alpha or TNF-gamma-beta are also determined and genomic PCR products analyzed to confirm the results. PCR products harboring suspected mutations in TNF-gamma alpha or TNF-gamma-beta are then cloned and sequenced to validate the results of the direct sequencing.

PCR products of TNF-gamma alpha or TNF-gamma-beta are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in TNF-gamma alpha or TNF-gamma-beta not present in unaffected individuals.

Genomic rearrangements are also observed as a method of determining alterations in the TNF-gamma alpha or TNF-gamma-beta gene. Genomic clones isolated using techniques known in the art are nick-translated with digoxigenindeoxy-uridine 5'-triphosphate (Boehringer Manheim), and FISH performed as described in Johnson, Cg. et al., *Methods Cell Biol*. 35:73-99 (1991). Hybridization with the labeled probe is carried out using a vast excess of human cot-1 DNA for specific hybridization to the TNF-gamma alpha or TNF-gamma-beta genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.*, 8:75 (1991).) Image collection, analysis and chromosomal fractional length measurements are performed using the ISee Graphical Program System. (Inovision Corporation, Durham, N.C.) Chromosome alterations of the genomic region of TNF-gamma alpha or TNF-gamma-beta (hybridized by the probe) are identified as insertions, deletions, and translocations. These TNF-gamma alpha or TNF-gamma-beta alterations are used as a diagnostic marker for an associated disease.

Example 22

Method of Detecting Abnormal Levels of TNF-Gamma Alpha or TNF-Gamma-Beta in a Biological Sample TNF-gamma alpha or TNF-gamma-beta polypeptides can be detected in a biological sample, and if an increased or decreased level of TNF-gamma alpha or TNF-gamma-beta is detected, this polypeptide is a marker for a particular phenotype. Methods of detection are numerous, and thus, it is understood that one skilled in the art can modify the following assay to fit their particular needs.

For example, antibody-sandwich ELISAs are used to detect TNF-gamma alpha or TNF-gamma-beta in a sample, preferably a biological sample. Wells of a microtiter plate are coated with specific antibodies to TNF-gamma alpha or TNF-gamma-beta, at a final concentration of 0.2 to 10 ug/ml. The antibodies are either monoclonal or polyclonal and are produced using technique known in the art. The wells are blocked so that non-specific binding of TNF-gamma alpha or TNF-gamma-beta to the well is reduced.

The coated wells are then incubated for >2 hours at RT with a sample containing TNF-gamma alpha or TNF-gamma-beta. Preferably, serial dilutions of the sample should be used to validate results. The plates are then washed three times with deionized or distilled water to remove unbounded TNF-gamma alpha or TNF-gamma-beta.

Next, 50 microliters of specific antibody-alkaline phosphatase conjugate, at a concentration of 25-400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TNF-gamma alpha or TNF-gamma-beta polypeptide concentration in a sample is then interpolated using the standard curve based on the measured flourescence of that sample.

Example 23

Method of Treating Decreased Levels of TNF-Gamma Alpha or TNF-Gamma-Beta

The present invention relates to a method for treating an individual in need of a decreased level of TNF-gamma alpha or TNF-gamma-beta biological activity in the body comprising, administering to such an individual a composition comprising a therapeutically effective amount of TNF-gamma alpha or TNF-gamma-beta antagonist. Preferred antagonists for use in the present invention are TNF-gamma alpha or TNF-gamma-beta-specific antibodies.

Moreover, it will be appreciated that conditions caused by a decrease in the standard or normal expression level of TNF-gamma alpha or TNF-gamma-beta in an individual can be treated by administering TNF-gamma alpha or TNF-gamma-beta, preferably in a soluble and/or secreted form. Thus, the invention also provides a method of treatment of an individual in need of an increased level of TNF-gamma alpha or TNF-gamma-beta polypeptide comprising administering to such an individual a pharmaceutical composition comprising an amount of TNF-gamma alpha or TNF-gamma-beta to increase the biological activity level of TNF-gamma alpha or TNF-gamma-beta in such an individual.

For example, a patient with decreased levels of TNF-gamma alpha or TNF-gamma-beta polypeptide receives a daily dose 0.1-100 mg/kg of the polypeptide for six consecutive days. Preferably, the polypeptide is in a soluble and/or secreted form.

Example 24

Method of Treating Increased Levels of TNF-Gamma Alpha or TNF-Gamma-Beta

The present invention also relates to a method for treating an individual in need of an increased level of TNF-gamma alpha or TNF-gamma-beta biological activity in the body comprising administering to such an individual a composition comprising a therapeutically effective amount of TNF-gamma alpha or TNF-gamma-beta or an agonist thereof.

Antisense technology is used to inhibit production of TNF-gamma alpha or TNF-gamma-beta. This technology is one example of a method of decreasing levels of TNF-gamma alpha or TNF-gamma-beta polypeptide, preferably a soluble and/or secreted form, due to a variety of etiologies, such as cancer.

For example, a patient diagnosed with abnormally increased levels of TNF-gamma alpha or TNF-gamma-beta is administered intravenously antisense polynucleotides at 0.5, 1.0, 1.5, 2.0 and 3.0 mg/kg day for 21 days. This treatment is repeated after a 7-day rest period if the is determined to be well tolerated.

Example 25

Method of Treatment Using Gene Therapy—Ex Vivo

One method of gene therapy transplants fibroblasts, which are capable of expressing soluble and/or mature TNF-gamma alpha or TNF-gamma-beta polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask; approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TNF-gamma alpha or TNF-gamma-beta can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TNF-gamma alpha or TNF-gamma-beta.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TNF-gamma alpha or TNF-gamma-beta gene is then added to the media and the packaging cells transduced with the vector. The packaging cells now produce infectious viral particles containing the TNF-gamma alpha or TNF-gamma-beta gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TNF-gamma alpha or TNF-gamma-beta protein is produced.

The engineered fibroblasts are then transplanted onto the host, either alone or after having been grown to confluence on cytodex 3 microcarrier beads.

Example 26

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TNF-gamma alpha or TNF-gamma-beta sequences into an animal to increase or decrease the expression of the TNF-gamma alpha or TNF-gamma-beta polypeptide. The TNF-gamma alpha or TNF-gamma-beta polynucleotide may be operatively linked to a promoter or any other genetic elements necessary for the expression of the TNF-gamma alpha or TNF-gamma-beta polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470-479 (1997); Chao J. et al., *Pharmacol. Res.* 35:517-522 (1997); Wolff J. A. *Neuromuscul. Disord.* 7:314-318 (1997); Schwartz B. et al., *Gene Ther.* 3:405-411 (1996); Tsurumi Y. et al., *Circulation* 94:3281-3290 (1996) (incorporated herein by reference).

The TNF-gamma alpha or TNF-gamma-beta polynucleotide constructs may be delivered by any method that delivers injectable materials to the cells of an animal, such as, injection into the interstitial space of tissues (heart, muscle, skin, lung, liver, intestine and the like). The TNF-gamma alpha or TNF-gamma-beta polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TNF-gamma alpha or TNF-gamma-beta polynucleotides may also be delivered in liposome formulations (such as those taught in Feigner P. L. et al. *Ann. NY Acad. Sci.* 772:126-139 (1995), and Abdallah B. et al. *Biol. Cell* 85:1-7 (1995)) which can be prepared by methods well known to those skilled in the art.

The TNF-gamma alpha or TNF-gamma-beta polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TNF-gamma alpha or TNF-gamma-beta polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TNF-gamma alpha or TNF-gamma-beta polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TNF-gamma alpha or TNF-gamma-beta polynucleotide constructs can be delivered to arteries during angioplasty by the catheter used in the procedure.

The dose response effects of injected TNF-gamma alpha or TNF-gamma-beta polynucleotide in muscle in vivo are determined as follows. Suitable TNF-gamma alpha or TNF-gamma-beta template DNA for production of mRNA coding for TNF-gamma alpha or TNF-gamma-beta polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TNF-gamma alpha or TNF-gamma-beta template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 micrometer cross-section of the individual quadriceps muscles is histochemically stained for TNF-gamma alpha or TNF-gamma-beta protein expression. A time course for TNF-gamma alpha or TNF-gamma-beta protein expression may be done in a similar fashion except that quadriceps from different mice are harvested at different times. Persistence of TNF-gamma alpha or TNF-gamma-beta DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TNF-gamma alpha or TNF-gamma-beta naked DNA.

Example 27

Gene Therapy Using Endogenous TNF-Gamma Gene

Another method of gene therapy according to the present invention involves operably associating the endogenous TNF-gamma sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TNF-gamma, flanking the promoter. The targeting sequence will be sufficiently near the 5' end of TNF-gamma so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TNF-gamma sequence. This results in the expression of TNF-gamma in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the TNF-gamma locus, plasmid pUC18 (MBI Fermentas, Amherst, N.Y.) is digested with HindIII. The CMV promoter is amplified by PCR with an XbaI site on the 5' end and a BamHI site on the 3'end. Two TNF-gamma non-coding sequences are amplified via PCR: one TNF-gamma non-coding sequence (TNF-gamma fragment 1) is amplified with a HindIII site at the 5' end and an Xba site at the 3'end; the other TNF-gamma non-coding sequence (TNF-gamma fragment 2) is amplified with a BamHI site at the 5'end and a HindIII site at the 3'end. The CMV promoter and TNF-gamma fragments are digested with the appropriate enzymes (CMV promoter—XbaI and BamHI; TNF-gamma fragment 1—XbaI; TNF-gamma fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5. \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28

Analysis of Endothelial Cell Apoptosis by TNF-Gamma-Beta

Although this example is directed primarily towards TNF-gamma-beta, one of ordinary skill in the art would immediately recognize that the example may be performed essentially as described for any TNF-gamma protein of the invention (i.e., TNF-gamma-alpha and/or TNF-gamma-beta).
Caspase Assay.

An analysis of caspase activity was performed to gain insight into possible mechanisms by which the anti-angiogenic activity of TNF-gamma proteins suppress endothelial cell growth. Caspases are a family of proteolytic enzymes that are activated under many apoptotic conditions. Caspases are a family of cysteine proteases that are activated during the process of programmed cell death. In the response to pro-apoptotic stimuli procaspases are proteolytically converted to active enzymes. The amount of caspase enzymatic activity after treatment with TNF-gamma-beta was measured by determining the amount of cleavage of a chromophore-(pNA) linked caspase specific peptide substrate.

Using substrates specific for different caspases, it was determined that TNF-gamma-beta activates Caspase 3. The substrate DEVD, which is activated by Caspase 3 and somewhat by other caspases, gave the greatest fold induction by TNF-gamma-beta and was selected for activity assays. BAEC cells were treated with 0.0, 2.5, 5.0, 7.5, or 10.0 micrograms/ml TNF-gamma-beta for 20 hours. Cell extracts were isolated and samples of equal protein concentration were incubated with DEVD=pNA peptide substrate for 2 hours. Cleavage of the caspase substrate was detected by spectrophotometric analysis of duplicate cultures. Caspase 3 activity was induced in a concentration dependent manner after treatment of BAEC with TNF-gamma-beta.

An annexin/caspase activation analysis was performed to determine the effect of two batches of TNF-gamma-beta proteins (designated "E1" and "E3") on endothelial cell apoptosis. The experiments were performed essentially as follows. Briefly, bovine aortic endothelial cells ("BAEC") were cultured in Clonetics growth medium (catalog number CC-3121) EBM supplemented with catalog number CC-4143 EGM-MV (supplement). During periods of growth arrest, the cells were cultured in Growth Arrest Media (Human Endothelial SFM Basal Growth Medium, Gibco catalog number 11111-044).

On day one, cells were plated in T75 culture flasks in culture medium and incubated at 37° C. On day two, the culture medium was aspirated and replaced with 10 ml of growth arrest medium ("GA medium"). The cultures were then incubated at 37° C. overnight. On day three, the first activity was to prepare treatments using two flasks of cells per treatment. Aliquots of TNF-gamma-beta and control protein (TNF-alpha) were diluted in GA medium. Prior to adding proteins, 5 ml of media were removed so that the final volume in the flask is 5 ml. Cells were either left untreated or treated with TNF-alpha (100 ng/ml, positive control), TNF-gamma-beta batch E1 (5 micrograms/ml) or TNF-gamma-beta batch E3 (5 micrograms/ml). The cultures were then incubated in GA medium supplemented with either TNF-alpha or TNF-gamma-beta proteins for 20 hrs.

On day four, cells were isolated for Annexin and cell extracts were analyzed for caspase essentially according to the following procedure. First, medium was transferred to labeled 15 ml conical vials. Flasks were washed two at a time with 3 ml/flask of PBS. All media and washes were then pooled. 2 ml trypsin/EDTA was then added per flask and the mixture was incubated for 1-2 minutes at 37° C. When all cells became detached, the contents of each flask was transferred to its appropriate tube. Tubes were then centrifuged in the Sorvall 6000B centrifuge for 7-10 minutes at setting #4.2. The supernatants were then carefully aspirated and the cell pellets were resuspended in 1 ml per treatment of 1×PBS with 0.01% BSA and the cells were counted. Approximately 500,000 cells were held in reserve for Annexin V analysis (see below).

For the caspase assay, the ApoTarget Caspase Colorimetric Protease Assay Sampler Kit (available from BioSource International, Inc., Catalog #KHZ1001) was used essentially according to the manufacturer's instructions. Briefly, the remaining cells were spun down, the supernatant was removed, and the cell pellet was resuspended in 50 ml per $3\times10^6$ cells of chilled lysis buffer. The cells were then incubated on ice for 10 minutes then vortexed for 5 seconds. The tubes were then centrifuged for 1 minute in a microcentrifuge (10,000×g). The supernatant (i.e., the cytosol extract) was then transferred to a fresh tube and kept on ice. The protein concentrations were then determined by the BCA method (Pierce).

The assay was set up in a 96 well microtitre U-bottom plate using 50 micrograms of protein per sample in 50 microliters of lysis buffer. DTT was added to the 2× Reaction Buffer immediately before use (10 mM final concentration) and 50 microliters of 2× reaction buffer with DTT was added to each reaction. Next, 5 ml of the 4 mM caspase substrates (200 mM final concentration) were added to each reaction and the tubes were incubated at 37° C. for 1-2 hours, taking care to keep the samples in the dark during incubation. The samples were then read at 405 nm in a microplate reader. The no substrate values were subtracted and the results plotted. The assay allows fold-increase in the activities of caspases 2, 3, 6, 8, or 9 by direct comparison to the level of the uninduced control.

This assay used two methods to examine the apoptotic actions of TNF-gamma-beta E1 and E3 proteins. Annexin analysis showed an increase in a dead/dying population of cells locating at the midpoint of UL and LL in the TNF-alpha (positive control) and TNF-gamma-beta E1 samples. This population was not seen in untreated or TNF-gamma-beta E3 treated samples. Caspase analysis showed that TNF-alpha and TNF-gamma-beta E1 (but not TNF-gamma-beta E3) induced a >10 fold increase in caspase 2 and 3 activity, and a >5 fold increase in caspase 6 activity. There was a smaller increase in caspase 8 activity. Thus, both assays showed TNF-gamma-beta E1 but not TNF-gamma-beta E3 induced apoptosis in BAECs.

Further experiments have shown that TNF-gamma-beta E1 stimulated caspase 2 activity in a dose-dependent manner in BAECs. Also, TNF-gamma-beta E1 protein induced caspase 3 in BAEC, but caspase 3 activity was not appreciably affected by TNF-gamma-beta E1 in either human microvascular endothelial cells (hMVEC) or in normal human dermal fibroblasts (NHDF). In addition, TNF-gamma-beta E3 protein stimulated caspase 3 activity in human aortic endothelial cells (hAEC).

A detailed caspase activation assay protocol is as follows.
Cell Culture
BAEC Culture Media: EGM-MV Bullet Kit (Clonetics Cat #CC-3125): (10% fetal bovine serum, 1 microgram/ml hydrocortisone, 10 ng/ml hEGF, 3 ng/ml bFGF, and 10 micrograms/ml heparin, 12 ug/ml bovine brain extract, 2× amphotericin B).

BAEC GA Media: Human Endothelial Serum Free Media, Gibco (Cat #11111-044), plus 5 ml of 100× penicillin/streptomycin, +0.1% FBS Day One: Plate BAEC in 100 mm tissue culture dishes in culture media. Incubate ON at 37° C.

Day Two: Aspirate culture media and replace with 10 ml growth arrest (GA) media. Incubate at 37° C. overnight.

Day Three: Prepare treatments. Dilute proteins in GA media. Prior to adding proteins, remove appropriate volume of media so that the final volume per 100 mm dish is 2 ml.

Isolation of Cell Extracts
When incubation time is complete:
Transfer media to labeled 15 ml conical vials. Wash flasks with 1.5 ml/dish of PBS, pooling all media/wash/trypsinized cells according to treatment. Add 2 ml per dish Trypsin/EDTA. Incubate 2-5 minutes at 37° C. Check the cells under the microscope for progress in detaching. Rap the cells off the plate and, if necessary, scrape cells off the plate/flask with a cell lifter (Costar #3008). Transfer contents to their appropriate tubes and centrifuge in the Sorvall 6000B for 7-10 minutes at 2000 RPM.

Carefully aspirate the supernatants. Resuspend the pellets in 1 ml PBS with 0.01% BSA. Transfer 10 microliters to a snap-cap Eppendorf for cell counting. Determine cell count via Trypan Blue exclusion. Spin down remaining cells, carefully remove supernatant with a pipette (Do not aspirate), and resuspend pellet in 100 microliters of chilled lysis buffer per $3\times10^6$ cells. Incubate cells on ice for 10 minutes then vortex for 5 seconds. Centrifuge for 1 minute in a microcentrifuge (10,000×g). Transfer supernatant (cytosol extract) to a fresh tube and freeze at −20° C.

Caspase Activity Measurement
Determine protein concentration by BCA method (Pierce, BCA Protein Assay Kit, #23225). Dilute each supernatant 1:8 in water prior to adding to assay plate. Add all samples and standards in duplicate. After determining the protein concentration of each sample, dilute each cytosol extract to a concentration of 50 micrograms protein per 50 microliters Cell Lysis Buffer (#BY01, Biosource International 1.0 mg/ml). Set up assay on a 96 well microtiter U-bottom plate. Use duplicate samples of 50 micrograms protein for caspase assay. Include samples to be tested without added substrate as a negative control. Add 50 microliters of sample per well. Add 50 microliters of 2× Reaction Buffer (#BR01, Biosource International) containing 10 mM DTT to each sample. Add 5 microliters of the 4 mM substrate (Caspase-3 substrate, #77-900, Biosource International, 200 micromolar final concentration) and incubate at 37° C. for 1.5 hours. Read sample in at 405 nm microplate reader. Subtract the no substrate values from the data samples. Fold-increase in caspase activity can be determined by direct comparison to the level of the uninduced control.

ATF2 Kinase Assay.
The p38/JNK kinases are members of the MAP Kinase signal transduction family. Activation of p38 and JNK occurs prior to apoptosis in a number of cell types. To quantitate p38/JNK kinase activity, the phosphorylation of a peptide substrate (ATF2) is measured. Both p38 and JNK, but not other MAP kinases such as ERKs, phosphorylate the ATF2 substrate. An enzyme-linked antibody specific for the phosphorylated ATF2 substrate is allowed to bind after reaction of the substrate with extracts from cells treated with controls or TNF-gamma-beta, and the amount of bound antibody is detected spectrophotometrically.

Confluent BAEC cells were serum-starved in EBM (1 ml per well) for 1 hour. Cells were then treated with TNF-gamma-beta at 10 micrograms/ml for 0, 10, 20, 40, 60, 80, 100, 120, 140, 160, or 180 minutes. TNFalpha was added to a control well for 20 minutes. After the treatment, the cells were isolated and assayed for JNK/p38 activity. Cultures were analyzed in duplicate.

Using the ATF2 assay, TNF-gamma-beta (at 10 micrograms/ml) induced the activation of p38/JNK in a time-dependent manner. Peak activation (>4-fold over background) occurred 100 minutes after addition of TNF-gamma-beta to BAEC, and the activities persisted for at least the next hour. TNFalpha control strongly activated p38 and JNK with faster kinetics (>1100% of negative control at the 20 minute time point).

The dose-dependancy of TNF-gamma-beta treatment was analyzed by treatment of the cells with 0, 0.004, 0.08, 0.16, 0.31, 0.63, 1.25, 2.5, 5, 10, and 20 micrograms per ml for 80 minutes. Cell lysates were then isolated and assayed for JNK/p38 activity. Cultures were again analyzed in duplicate. TNF-gamma-beta stimulated JNK/p38 kinase activity in BAEC cells in a dose dependent manner. Maximum response (280% of untreated control) was observed at a TNF-gamma-beta concentration of 20 micrograms/ml.

A detailed ATF2 kinase assay protocol is as follows.
Cell Culture

BAEC were serum-starved in EBM (Clonetics, 1 ml per well) for 1 hour. Cells were then treated with TNF-gamma-beta or TNFa control for indicated times at 37° C. After treatment, cells were rinsed once with ice-cold PBS. Cell lists were prepared by adding 0.1 ml (per well of a 6-well plate) of lysine buffer (20 mm Tris-Cl [pH7.5], 250 mM NaCl, 0.5% NP-40, 10% Glycerol, 3 mM EDTA, 3 mM EGTA, 0.5 mM sodium orthovanadate, 1 mM NaF, 1 mM DTT, 1× Boehringer-Mannheim Complete protease inhibitor) to the cells, and incubating for 2 minutes. Cell debris and nuclei were removed by centrifugation. Total protein concentration of the lysates was determined by BCA assay (sigma)
Measurement of ATF2 Phosphorylation Coat microlite 2 plate (Dynex) with of a 10 micrograms/ml solution of GST-ATF2 (residues 19-96) fusion protein (Boston Biologicals), 50 microliters/well. Seal and incubate overnight at room temperature (RT). Wash plate once with wash buffer (PBST) (0.05% Tween 20, PBS). Block unoccupied sites with 150 microliters/well of blocking buffer (1.0% Nonfat Dry Milk, prepared in PBS+0.05% Tween 20 [PBST]). Seal and incubate for 60 minutes at RT. Wash plate three times with PBST. Combine 20 microliters/well of kinase buffer (50 mM Hepes [pH 7.5], 10 mM $MgCl_2$, 2.5 mM NaF, 0.1 mM sodium orthovanadate, 0.02% BSA [fatty acid-free], 0.5 mM DTT, 0.5 mM ATP) and 30 microliters/well of cell lysate to each well. Seal and incubate for 1.5 hours at RT. Wash plate three times with PBST. Add 50 microliters/well of phospho-specific ATF2 antibody (NEB detecting ATF-2 phosphorylated on Thr71) that had been diluted 1:1000. Seal and incubate for 60 minutes at RT. Wash plate three times with PBST. Add 50 microliters/well of AMDEX goat anti-rabbit IgG-alkaline phosphatase (Amersham Pharmacia) that had been diluted 1:8000. Seal and incubate for 60 minutes at RT. Add 50 microliters/well of BM chemiluminescent ELISA AP substrate (Roche) to each well. Incubate for 12 minutes at RT and read on a luminometer at a measurement time of 0.1 seconds/well.

For a reference of the assay, see, Forrer, P., Tamaskovic R., and Jaussi, R. (1998). Enzyme-Linked Immunosorbent Assay for Measurement of JNK, ERK, and p38 Kinase Activities; Biol. Chem. 379(8-9): 1101-1110.

Example 29

Effect of TNF-Gamma on Anti-Angiogenesis in the Cornea

One of ordinary skill in the art would immediately recognize that the following example may be performed essentially as described for any TNF-gamma protein of the invention (i.e., TNF-gamma-alpha and/or TNF-gamma-beta). The corneal angiogenic assay has been recognized commonly as an in vivo assay to evaluate both angiogenic and anti-angiogenic activity of compounds.

Basic FGF ("bFGF") has been tested in this corneal angiogenic assay in various research laboratories for a variety of purposes. It has been shown that bFGF can induce significant angiogenesis in corneas (e.g., in rabbits, rats and mice). Based on the previous studies, bFGF was used in our study of TNF-gamma as an angiogenic factor to induce the growth of blood vessels in rat corneas.

The procedure is relatively common and well known in the art and was performed essentially as follows:
Microsurgical Implantation in the Cornea:

An incision, 1-1.5 mm in length, is made in the center of the cornea with a microsurgery scalpel blade.

Starting at the incision, a micropocket is created between the collagenous layers of the corneal stroma with a Castroviego cyclodialysis spatula. This pocket extends to a point 1-2 mm from the capillary bed at the corneal-scleral limbus.

bFGF, which is incorporated 1:1 into non-inflammatory Hydron polymer (available from Interferon Sciences, New Brunswick, N.J.), is implanted into the pocket.

The implanted eyes receive several drops of neosporin ophthalmic antibiotic post-surgery.
Corneal Blood Perfusion and Harvesting:

Five or seven days after corneal implantation, corneal blood perfusion with colloidal carbon is performed. Corneas are then harvested, fixed, flattened, mounted and photographed for morphology.
Quantification of Angiogenesis:

An image analysis system (IPLab) is used to quantify the corneal angiogenesis. The corneal surface area, which is covered by the new blood vessels, is quantified and used in our current study. After corneal implantation surgery, TNF-gamma, angiostatin or PBS in a volume of 25 microliters was injected into the conjunctival region adjacent to the implantation site. Based on molarities of TNF-gamma and angiostatin, 10 micrograms of TNF-gamma or 5 micrograms of angiostatin were given respectively four times, once a day, during the first four days post-surgery. TNF-gamma and angiostatin were prepared in PBS.

The experimental grouping was follows:

|  | Corneal Implants | |
|---|---|---|
| Treatment: | PBS | bFGF (300 ng) |
| PBS | 6 eyes | 6 eyes |
| Angiostatin | 6 eyes | 6 eyes |
| TNF-gamma | 6 eyes | 6 eyes |
| Total no. eyes: | 18 | 18 |

Seven days after surgery, corneas were harvested and processed for analysis. Angiogenesis was found in the corneas implanted with bFGF, but not in the corneas implanted with pellets containing PBS. After multiple conjunctival injections with PBS, angiostatin or TNF-gamma, there was no obvious vessel growth that was induced by any of those injections in the PBS-implanted corneas. However, conjunctival injections with angiostatin and TNF-gamma significantly slowed down the angiogenic process when compared to the conjuctival injections with PBS in the bFGF-implanted corneas. Thus, TNF-gamma inhibited the growth of blood vessels in corneal angiogenesis assay.

The following protocol may be used to analyze the effects of TNF-gamma on bFGF-induced neovascularization in a rat corneal pocket assay in place or in combination with the protocol set forth above.

bFGF was used to induce neovascularization of the cornea from preexisting pericorneal limbal vessels in two different versions of the assay. First, corneas were surgically implanted with hydrogel plugs containing bFGF. TNF-gamma-beta (0.3, 3.0 or 30 µg) or control proteins (angiostatin, 0.15 and 1.5 µg or myeloid progenitor inhibitory factor, 5.5 µg) were injected subconjunctivally every day for four days in the conjunctival region 1 mm beyond the pericorneal vasculature in the vicinity of where the hydrogel plug was implanted within the cornea. In a separate study using an alternate version of this assay, both bFGF and treatment protein were co-administered on a nitrocellulose filter disk implanted within the rat corneal stroma. Prior to implantation, filter disks were treated with phosphate-buffered saline alone, 1.5 µg/µl BSA, 1.5 TNF-gamma-beta, or 0.05 bFGF plus either 1.5 µg/µl BSA, 0.15-1.5 µg/µl TNF-gamma-beta, or 3 µg/µl angiostatin. In both assays, the surface area of the angiogenic response was quantitated from digital images of treated corneas five days following implantation.

In these experiments, treatment with 30 µg TNF-gamma-beta reduced the FGF-induced neovascularization. The maximal decrease in rat corneal neovascularization induced by bFGF is similar for TNF-gamma-beta and angiostatin. In addition, TNF-gamma-beta administered without a stimulus does not induce corneal neovascularization. Inhibition of bFGF-induced neovascularization by TNF-gamma-beta is dose-dependent. In both systems, negative control proteins had no significant effect on bFGF-induced corneal neovascularization. Thus, the antiangiogenic activity exhibited by TNF-gamma-beta in the rat corneal model is not due to non-specific protein effects.

These studies indicate that TNF-gamma-beta inhibits bFGF-induced angiogenesis in a dose-dependent fashion. The maximal degree of inhibition of angiogenesis produced by TNF-gamma-beta is similar to that of angiostatin or endostatin.

Example 30

Anti-Angiogenic Activity of TNF-Gamma in Tumors

Although this example is directed primarily towards TNF-gamma-beta, one of ordinary skill in the art would immediately recognize that the example may be performed essentially as described for any TNF-gamma protein of the invention (i.e., TNF-gamma-alpha and/or TNF-gamma-beta).

The in vivo tumor growth in dorsal skin chamber has been a valuable model to directly evaluate angiogenesis and blood flow during tumor growth. This model provides a direct and continuous means of non-invasively quantifying the angiogenesis within growing tumors through transparent windows implanted into the skin.

Initially, the possible inhibitory effect of TNF-gamma-beta (batch E5) on angiogenesis in the LS174T colon adenocarcinoma was analyzed essentially as follows.

Mouse Preparation

The surgical procedures were performed in Swiss nude mice. These mice were bred and maintained in a defined-flora environment (gnotobiotic; no aerobic flora). For the surgical procedures, animals (20-30 g) were anesthetized with s.c. injection of a cocktail of 90 mg Ketamine and 9 mg Xylazine per kg body weight. All surgical procedures were performed under aseptic conditions in a horizontal laminar flow hood, with all equipment being steam, gas, or chemically sterilized. During surgery, the body temperature of the animals was kept constant by means of a heated work surface. All mice were housed individually in microisolator cages and all manipulations were done in laminar flow hoods. Buprenorphine (0.1 mg/kg q 12 h) was used as an analgesic for 3 days post implantation.

Dorsal Skin Chamber Implantation

Before implanting chambers, the dorsal skin was prepared with betadine and positioned such that the chamber sandwiched a double layer of skin that extended above the dorsal surface. One layer of skin was removed in a circular area ~15 mm in diameter. The second layer (consisting of epidermis, fascia, and striated muscle) was positioned on the frame of the chamber and covered with a sterile, glass coverslip. The titanium and glass chambers were held in place with suture (stainless steel, 4-0) which was threaded through the extended skin and holes along the top of the chamber. Mice were allowed to recover 72 hours prior to tumor implantation. The coverslip was carefully removed, followed by the addition of 3 microliters of tumor cell suspension. The colon adenocarcinoma, LS174T, was grown in culture to confluence, then trypsinized and washed twice prior to implantation. A new, sterile coverslip was placed on the viewing surface following implantation. Observations of tumor growth and angiogenesis were made for 14 days following the implantation of tumors using intravital microscopy with CCD and SIT cameras. Images were recorded by S-VHS videocassette recorder and direct digital image acquisition.

Experimental Design

Implanted tumors were allowed to grow in the dorsal chambers for 3 days prior to initiation of treatment. Three treatment groups were used (n=5 mice/group) at 50, 25 and 10 mg/kg, BID, i.p. in PBS. The control (0 dose group) received 50 mg/kg BSA in PBS (n=4). Injections were made each day for 12 days. Observations of vascular density and tumor growth were made on days 3, 7, 10 and 14 following tumor implantation. Vascular density was determined by counting individual vessels in adjacent fields across the entire tumor surface and group means were determined for each time point. Tumors were collected for measurement on day 15 following implantation.

Suppression of tumor angiogenesis was observed as a result of TNF-gamma-beta administration in a dose responsive manner. Statistically significant (P<0.05, non-paired t-test) inhibition of new vessel formation could be demonstrated at the 50 mg/kg dose level on days 10 and 14. Estimated tumor volumes, based on diameter and thickness determinations, showed decreasing tumor mass with increasing dose of TNF-gamma-beta. Significant reduction in tumor mass (P<0.05, non-paired t-test) could be seen at both the 25 and 50 mg/kg dose levels. Detailed observation of the tumors in situ on day 10 showed the formation of micro-hemorrhages at the tumor margin, in contrast to the well formed tumor vessels in the mice treated with the BSA control. The implanted tumor cells in the 25 and 50 mg/kg treatment groups had the appearance of thin, poorly vascularized discs, while the tumors in the 10 mg/kg and BSA control (0 mg/kg dose group) developed a thickness of up to 3.75 mm.

Thus, these findings indicate that TNF-gamma-beta is a potent inhibitor of angiogenesis in the LS174T tumor.

In addition to the experimental protocol described above, observations of the establishment of tumor growth and angiogenesis were made for 17 days following the implantation of tumors using intravital microscopy with CCD cameras. Direct digital images were recorded on a S-VHS videocassette recorder. Implanted tumors were allowed to grow in the dorsal chambers for 3 days prior to initiation of treatment. Three treatment groups (n=5 mice/group) received 50, 25 and 10 mg/kg TNF-gamma-beta, BID, via the IP route. The control (0 dose group) received 50 mg/kg BSA in PBS (n=4). Injections were made each day for 12 days. Observations of vascular density and tumor growth were made on days 3, 7, 10 and 14 following tumor implantation. Vascular density was determined by counting individual vessels in adjacent fields across the entire tumor surface and group means were determined for each time point. Tumors were collected for measurement following the last day of treatment. Vascular densities in TNF-gamma-beta-treated mice were significantly reduced at the 50 mg/kg dose (IP) on days 7, 10, and 14.

Following termination of the study, the tumor volumes were calculated from direct measurement. The data indicate that TNF-gamma-beta significantly suppressed tumor growth at the 50 and 25 mg/kg doses, but not the 10 mg/kg dose (IP). Observation of the tumors at day 14 indicated disruption of neovascular formation at the periphery of the implanted tumors at the 50 mg/kg dose. In contrast, tumors treated with vehicle and BSA showed a typical and well developed vascular structure for the LS174T tumor. These findings suggest that TNF-gamma-beta may be able to directly interfere with the remodeling of existing tumor vasculature.

Experiments have also been performed to analyze the effect of TNF-gamma-beta on angiogenesis in an established human adenocarcinoma xenograft. The LS174T colon adenocarcinoma was used to determine if TNF-gamma-beta could reduce the vascular density in an established tumor. Mice were implanted with the dorsal chambers and tumors as described previously. However, the tumors were permitted to grow for 10 days prior to initiation of treatment. Mice were then administered TNF-gamma-beta in three treatment groups (n=5 mice/group) at 50, and 25 mg/kg TNF-gamma-beta, BID, IP in PBS. The control (0 dose group) received 50 mg/kg BSA in PBS. Injections were made each day for 7 days. Vascular density was determined by counting individual vessels in adjacent fields across the entire tumor surface and group means were determined for each time point.

Comparison of vessel densities before treatment and following 7 days of TNF-gamma-beta administration showed a significant reduction in the vascular density of the tumor xenografts at the 50 mg/kg dose and a similar but non-significant trend at the 25 mg/kg dose. Vessel density did not significantly decrease in the BSA control tumors. These findings indicate that the existing vasculature in established tumors can be affected by TNF-gamma-beta treatment at the same doses that prevent early vessel development in microscopic tumors.

The effects of TNF-gamma-beta on murine (syngeneic) primary tumor growth were also analyzed. The effect of TNF-gamma-beta on the growth of a murine tumor was performed with the Lewis lung carcinoma (a murine lung adenocarcinoma) in C57BL/6 mice. The syngeneic Lewis lung carcinoma tumor model has been utilized by several laboratories in the assessment of the antitumor properties of a variety of antiangiogenic and other antitumor agents (Kobayashi et al., 1994; O'Reilly et al., 1994). To assess the activity of TNF-gamma-beta on Lewis lung carcinoma primary tumor growth, TNF-gamma-beta (10-50 mg/kg) was administered twice daily for 14 days by tail vein injection beginning three days following subcutaneous inoculation of $1 \times 10^6$ Lewis lung carcinoma cells in the dorsum of male C57BL/6 mice (n=6/group). Primary tumor volumes were calculated three times per week. Tumor growth was followed out to post-inoculation day 20.

Twice daily administration of TNF-gamma-beta significantly inhibited Lewis lung carcinoma primary tumor growth throughout the 14 day dosing period. Tumor growth also appears to resume following withdrawal of the drug, indicating the reversibility of TNF-gamma-beta-mediated inhibition. The maximal degree of reduction in tumor volume induced by TNF-gamma-beta was approximately 80% relative to the vehicle control. Since all doses produced a maximal response, the $ED_{50}$ for TNF-gamma-beta inhibition of Lewis lung carcinoma tumor growth in this model is less than 10 mg/kg bid.

In a subsequent study, the antitumor activity of twice daily dosing and once per day dosing regimen in the Lewis lung carcinoma model was examined. 72 hours following tumor inoculation, treatment with TNF-gamma-beta began, with animals receiving 0, 1, 3, or 10 mg/kg iv at 250 µl per injection twice per day, or an injection of 0, 3, 10, or 30 mg/kg once per day. The injections continued for 14 days, for a total of 14 or 28 injections in each animal. When treated twice per day, TNF-gamma-beta treated animals displayed a significant reduction in primary tumor volume when compared with vehicle-treated controls. However, single daily dosing of TNF-gamma-beta was not sufficient to inhibit tumor growth at any of the concentrations tested. The tumor volumes of the animals treated twice per day with TNF-gamma-beta did not differ significantly from one another. There was no significant difference apparent in the appearance and general health of animals that were treated twice per day with TNF-gamma-beta in any of the dosing conditions. Likewise, there was also no difference seen between the vehicle-treated mice in the once or twice-per-day dosing regimen. These studies indicate that a dose as low as 1 mg/kg, IV bid, is sufficient to produce inhibition of tumor growth. However, single daily administration IV is not effective in limiting tumor growth.

Example 31

Endothelial Cell Proliferation Assay (ALAMAR BLUE™)

ALAMAR BLUE™ is an oxidation-reduction indicator that both fluoresces and changes color in response to chemical reduction of growth medium resulting from cell growth. The innate metabolic activity of cells can be measured using ALAMAR BLUE™ dye. ALAMAR BLUE™ functions as an electron acceptor that can be reduced by metabolic intermediates (NADPH, FADH, FMNH and cytochromes). Reduction of ALAMAR BLUE™ is accompanied by a measurable shift in fluorescence. ALAMAR BLUE™ does not alter the viability of cells. ALAMAR BLUE™ methodology has been shown to have equal sensitivity as other cell proliferation assays such as $^3$H-thymidine incorporation or MTT reduction. Fluorescence measurements are made by excitation at 530-560 nm and measuring emission at 590 nm. As cells grow in culture, innate metabolic activity results in a chemical reduction of the immediate surrounding environment. Reduction related to growth causes the indicator to change from oxidized (non-fluorescent blue) form to reduced (fluorescent red) form and the total signal is proportional to the total number of cells as well as their metabolic activity.

Endothelial proliferation is an integral process in tumor angiogenesis. A relevant and customary assay is evaluation of the effects of anti-angiogenic agents on the suppression of endothelial cell proliferation. TNF-gamma-beta was directly assessed for its growth inhibitory activity on bovine aortic endothelial cells (BAEC) by ALAMAR BLUE™ growth assays. Growth of BAEC was induced by treatment of the cultures with 0.5% serum and 1 ng/ml bFGF plus or minus TNF-gamma-beta. Growth was assessed after four days by ALAMAR BLUE™ fluorescence. Assays included parallel analysis of TNFalpha inhibition of BAEC growth as a positive control.

TNF-gamma-beta was shown to suppress the proliferation of BAEC in a concentration-dependent manner, as determined by ALAMAR BLUE™ bioassay. Multiple, independently run assays of triplicate cultures gave equivalent dose curves. The $EC_{50}$ for these assays was calculated to be 5.0+/−0.6 micrograms/ml. Human aortic endothelial cells were also shown to be sensitive to the anti-proliferative activity of TNF-gamma-beta.

To test the specificity of TNF-gamma-beta actions, Aortic smooth muscle cells (AoSMC) and normal human dermal fibroblasts (NHDF) were incubated with TNF-gamma-beta in low serum media, or with 5 ng/ml bFGF or 20 ng/ml PDGF-BB. TNF-gamma-beta at doses equal to those used with BAEC (i.e., 1.25, 5, 10, and 20 micrograms/ml) did not affect the growth of AoSMC or NHDF after 96 hours.

A detailed ALAMAR BLUE™ proliferation assay protocol is as follows.

Bovine aortic endothelial cells (BAEC) were plated into 96 well plates in Clonetics EGM-MV 24 h prior to assay. A standard ALAMAR BLUE™ proliferation assay was prepared in serum-free medium (GIBCO HESFM) with 1 ng/ml of bFGF added as a source of endothelial cell stimulation. Dilutions of TNF-gamma-beta protein batches were diluted as indicated. SFM without bFGF was used as a non-stimulated control and Angiostatin was included as a known inhibitory control.

Materials

Bovine Aortic Endothelial Cells (BAEC), Clonetics Inc.
ALAMAR BLUE™ (Biosource Cat #DAL1100)
EGM-2 MV 10% FBS+Pen/Strep+Glutamine (BAEC Growth medium)
GIBCO HESFM, 0.5% FBS (sample dilution media)

Method

BAECs are seeded in growth media at a density of 2000 cells/well in a 96 well plate and placed at 37° C., 5% $CO_2$ overnight. After the overnight incubation of the cells, the growth media is removed and replaced with GIBCO HESFM with 0.5% FBS. The cells are incubated at 37° C., 5% $CO_2$ overnight. The cells are treated with the appropriate dilutions of TNF-gamma-beta or TNFalpha protein samples (prepared in SFM) in triplicate wells with bFGF at a concentration of 1 ng/ml. Additional plate controls include triplicate wells without bFGF and wells with bFGF and medium alone. Once the cells have been treated with the samples, the plates are placed back in the 37° C. incubator for an additional three days. After three days 10 µl of stock ALAMAR BLUE™ solution is added to each well and the plates are placed back in the 37° C. incubator for four hours. The plates are then read at 530 nm excitation and 590 nm emission using the CytoFluor fluorescence reader. Direct output is recorded in relative fluorescence units.

Analysis

Fluorescence units from triplicate samples are averaged and the mean and SD values are plotted against the $log_{10}$ of TNF-gamma-beta dilution using the Prism software package (GraphPad software, San Diego, Calif.). The $EC_{50}$ is determined using a 4 parameter fit of the data. Only a fit with r2 values >0.98 are used for $EC_{50}$ determinations.

In another embodiment, the above protocol is modified only by a synchronization of the cell cycle of BAECs in the culture to be analyzed. Synchronization is obtained by supplementing the GIBCO HESFM with 0.5% FBS (added after the initial overnight incubation detailed above) with 6 micrograms/ml per well of aphidicolon (Sigma), and then continuing with the protocol described above.

Example 32

Endothelial Cell Migration Assay

Cell migration plays a central role in a wide variety of tissues during remodeling processes including angiogenesis. The effect of TNF-gamma-beta on migration was assessed using in vitro wounding of a confluent monolayer of BAEC coupled with a computer-assisted system to automatically collect and analyze the migration data. This model has the advantage of preserving the special relationship of migrating and non-migrating cells in the monolayer as well as allowing fast and reliable quantitation.

A migration index is calculated for each well and represents the mean±SD of the cumulative migration distances for treated cells in triplicate wells. A uniform section of the BAEC monolayer was removed with a plastic probe and cells were cultured in media plus bFGF (10 ng/ml) alone, or with 0, 1, 5, 10 or 20 micrograms/ml of TNF-gamma-beta. Image analysis and determination of the migration index was performed after 24 hours.

This assay system has established that TNF-gamma-beta inhibits migration of BAEC. TNF-gamma-beta inhibited the migration of the BAEC in the dose-dependant manner. TNF-gamma-beta significantly inhibited BAEC migration at the 10 and 20 micrograms/ml concentration.

A detailed protocol for an endothelial cell migration assay is as follows. The following procedures are used for developing a semi-automated system for detecting the migration of the endothelial cells in response to the novel agents.

Wound a confluent monolayer of the Bovine Aortic Endothelial Cells (BAEC) cultured in the 96 well plate. Treat the cells with sera free endothelial cell culture medium containing the agent(s), in triplicate for each concentration, and incubate the cells at 37° C., 5% $CO_2$ for 24 hours. Fix and stain the cells with 10% formalin and 0.1% crystal violet. Create a digital mask in the NIH Image software by modeling the actual size and shape of the original wound area. Then use a formula for calculating the actual distance of each cell migrated from the either side of the wound edges. Acquire and save the images of the cells around the wound using digital video microscopy and image processing software. Cover the image of one field a time with a digital mask to block the cells distributed in the non-wound area and expose only the migrating cells. Capture and counts the cells in the wound area and then measure the raw distance of each cell alone the X-axis. Use the formula to determine the actual distance migrated from either edge of the wounded area of the monolayer. Total the distances of the all cells for each group as migration index (MI), which represents the net effect of an agent on the in vitro migration of the endothelial cells.

Example 33

TNF-Gamma Binding Assays

Preparation of Radiolabeled TNF-Gamma-Beta

Radio-iodination of TNF-gamma-beta was performed using the Iodobead method. Briefly, one Iodobead (Pierce) per reaction was pre-washed with PBS and added to 1 mCi of $NaI^{125}$ in 80 microliters of PBS pH 6.5. The reaction was allowed to proceed for 5 minutes and then 10 micrograms of TNF-gamma-beta was added and incubated for 5 minutes at room temperature. Iodinated protein was separated from unbound radioactivity using a G-25 Sephadex quick spin column previously equilibrated with PBS containing 0.1% BSA. Protein concentration and specific radioactivity of $I^{125}$-Vasolysin were determined by TCA precipitation of pre-column and post-column samples. The specific activity of $I^{125}$-Vasolysin used in the experiment was 15.2 microcuries per microgram.

Competitive Binding Assay to Determine Specific Binding

BAEC, HAEC and NHDF cells were plated ($2\times10^5$ cells/well) in 24 well plate overnight. The binding assay was performed in 500 microliters of binding buffer (Ham's F containing 0.5% BSA and 0.1% sodium azide) containing 0.3 nM $I^{125}$-TNF-gamma-beta in the absence or presence of 100-fold excess of unlabeled TNF-gamma-beta. Binding to cells was performed in triplicates in a 96 well plate using $1\times10^6$ cells in 100 microliters of binding buffer under similar conditions used for other cell types with 0.3 nM $^{125}$I-TNF-gamma-beta. The binding reaction was carried out at room temperature for 2 hr. Cell bound $I^{125}$-TNF-gamma-beta was separated from unbound material by centrifugation through 200 microliters of 1.5 dibutylphthlate/1.0 bis (2-ethyl-hexyl)phthalate oil mixture in a polyethylene microfuge tubes (Bio-Rad) for 20 sec at 12,000 RPM. The microfuge tubes were then frozen quickly in liquid nitrogen and the bottom tip of the tubes was cut off using a tube cutter. Radioactivity in the bottom containing the cell pellet (bound fraction) and the top (unbound fraction) of the tubes were counted by using a gamma counter.

The cells were then washed three times with PBS containing 0.1% BSA and lysed with 1% NP40 solution and counted using a gamma counter.

To determine affinity (Kd) of TNF-gamma-beta binding to cells, binding assay was performed with 0.3 nM $I^{125}$-TNF-gamma-beta in presence of increasing concentrations of unlabeled TNF-gamma-beta (0.01 to 639 nM). The data was analyzed by Prim software (GraphPad Software, San Diego, Calif.) to determine dissociation constant (Kd) and number of binding sites.

Example 34

Generation and Characterization of Anti-TNF-Gamma-Beta Antibodies

Balb/C mice were immunized with TNF-gamma-beta polypeptide (amino acid residues 72-251 of SEQ ID NO:20 according to the following schedule:

| Day | Dose/mouse | Route | Vehicle |
|---|---|---|---|
| 1 | 50 micrograms | Sub-cutaneous | Complete Freund's Adjuvant |
| 13 | 50 micrograms | Sub-cutaneous | Incomplete Freund's Adjuvant |
| 27 | 50 micrograms | Sub-cutaneous | Incomplete Freund's Adjuvant |
| 38 | 10 micrograms | Intra-peritoneal | PBS |
| 59 | 10 micrograms | Intra-peritoneal | PBS |
| 97 | 10 micrograms | Intra-peritoneal | PBS |

After the final immunization, hybridomas were generated according to standard protocols. Hybridomas were initially screened by ELISA for their ability to bind TNF-gamma-beta (amino acid residues 72-251 of SEQ ID NO:20) by ELISA which identified eighteen positive hybridomas: 03C06, 04H08, 06C03, 06D09, 06F03, 08D06, 12D08, 12F11, 14A03, 15B03, 15E09, 16B05, 16H02, 17A03, 17D07, 18G08, 20B01 and 20C05.

Characterization of Murine Monoclonal Anti-TNF-Gamma-Beta Antibodies:

TNF-gamma-beta treatment induces production of secreted alkaline phosphatase in TF-1/SRE reporter cells. Additionally TNF-gamma-beta treatment results in caspase activation in TF-1 cells. The ability of the murine monoclonal antibodies to neutralize these TNF-gamma-beta mediated activities were investigated.

SEAP Assay

The ability of TNF-gamma-beta to generate a signal that activates genes under the regulation of Signal Response Elements (SREs) was examined using TF-1 cell line transfected with an SRE/Secreted Alkaline Phosphatase (SEAP) reporter plasmid. Briefly, a poly-D-lysine coated 96-well plate is seeded with TF-1/SRE-SEAP cells (in RPMI+0.2% Fetal bovine serum) at 75,000 cells per well. Cells were incubated overnight and the media was aspirated the next morning and replaced with media (RPMI+0.2% fetal bovine serum) containing TNF-gamma-beta. Again cells were incubated overnight. After overnight incubation, conditioned media were collected and SEAP activity was determined using the SEAP Reporter Gene Assay available from Roche Molecular Biochemicals (Indianapolis, Ind.) according to the manufacturer's directions. Briefly, Conditioned media were diluted 1:4 into dilution buffer. Samples were incubated at 65 C for 30 minutes to eliminate contaminating AP activity usually present in culture medium. 25 microliters of the heat-inactivated samples were mixed with equal volume of inactivation buffer (containing a mixture of differential alkaline phosphatase inhibitors). Following a 5-minute incubation at room temperature, 50 uL of alkaline phosphatase substrate (CSPD) was added to each well. Chemiluminescence signal was read 10-15 minutes later using a luminometer. TNF-gamma-beta induces SEAP production in a dose dependent fashion.

Antibodies generated against TNF-gamma-beta were tested for the ability to inhibit the TNF-gamma-beta induced SEAP production in TF-1/SRE_SEAP reporter cells. Briefly, 24 micrograms/mL of each antibody (50× molar excess) was mixed with either 200 ng/mL of TNF-gamma-beta in medium (RPMI+0.2% FBS) or in medium alone (RPMI+0.2% FBS) in a total volume of 150 microliters. These solutions were then incubated for 1 hour at room temperature. Fifty microliters of the media containing TNF-gamma-beta+antibody or antibody alone solution was added to the TF-1 cells which were then incubated overnight. After the overnight incubation, the SEAP assay was performed as described above. Using this assay, monoclonal antibodies 12D08, 14A03, 15E09, and 16H02 were identified as potent TNF-gamma-beta neutralizing antibodies.

Caspase Assay

The ability of TNF-gamma-beta to induce caspase activity in TF-1 cells was analyzed using a Homogeneous Fluorimetric Caspases Assay available from Roche Molecular Biochemicals (Indianapolis, Ind.) according to the manufacturer's directions. Briefly, cells growing in microtiter plates are induced to undergo apoptosis, causing an activation of caspase activities. Equal volume of a caspase substrate (Asp-Glu-Val-Asp-Rhodamine 110, or DEVD-R110) solution is then added and incubated for at least 1 hour. During this incubation, cells are being lysed and free R110 is released from the substrate. The level of free R110 is determined fluorimetrically, using a fluorescence reader with excitation filter 470-500 nm and emission filter 500-560 nm.

A black 96-well plate with a clear bottom is seeded with 75,000 TF-1 cells in RPMI containing 1% fetal bovine serum and micrograms/milliliter cyclohexamide. An equal volume of 2× TNF-gamma-beta is then added to the wells and incubated for 5 hours prior to performing the caspase assay. Following the manufacturer's directions, an equal volume of 1× substrate solution containing 50 micromolar DEVD-R110 diluted in incubation buffer is added to each well. The 96-well plates are then incubated for 2 hours after which the plate is read in a fluorescence reader with an excitation filter at 485 nm and an emission filter at 535 nm. TNF-gamma-beta induces caspase production in a dose dependent fashion.

Antibodies generated against TNF-gamma-beta were tested for the ability to inhibit the TNF-gamma-beta induced caspase activation. Briefly, 24 micrograms/mL of each antibody (100× molar excess) was mixed with either 100 ng/mL of TNF-gamma-beta in medium (RPMI+1% FBS+20 micrograms/mL cyclohexamide) or in medium alone (RPMI+1% FBS+20 micrograms/mL cyclohexamide) in a total volume of 150 microliters. These solutions were then incubated for 1 hour at room temperature. The media containing TNF-gamma-beta+antibody or antibody alone solution were then added to the TF-1 cells and the caspase assay Was performed as described above. Using this assay, monoclonal antibodies 12D08, 14A03, 15E09, and 16H02 were identified as potent TNF-gamma-beta neutralizing antibodies.

Example 35

TR6 and DR3 Interact with TNF-Gamma-Beta

The premyeloid cell line TF-1 was stably transfected with SRE/SEAP (Signal Response Element/Secreted Alkaline Phosphatase) reporter plasmid that responds to the SRE signal transduction pathway. The TF1/SRE reporter cells were treated with TNF-gamma-beta at 200 ng/mL and showed activation response as recorded by the SEAP activity. This activity can be neutralized by TR6.fc fusion protein in a dose dependent manner. The TR6.Fc by itself, in contrast, showed no activity on the TF1/SRE reporter cells. The results demonstrate that 1) TF-1 is a target cell for TNF-gamma-beta ligand activity. 2) TR6 (International Publication Numbers WO98/30694 and WO00/52028) interacts with TNF-gamma-beta and inhibits its activity on TF-1 cells. TR6 has two splice forms, alpha and beta; both splice forms have been shown to interact with TNF-gamma-beta.

Similarly, the interaction of DR3 (International Publication Numbers WO97/33904 and WO/0064465) and TNF-gamma-beta can be demonstrated using TF-1/SRE reporter cells. The results indicate that DR3.fc interacts with TNF-gamma-beta, either by competing naturally expressed DR3 on TF-1 cells or forming inactive TNF-gamma-beta/DR3.fc complex, or both.

At least three additional pieces of evidence demonstrate an interaction between TNF-gamma-beta and DR3 and TR6. First, both TR6.Fc and DR3.Fc are able to inhibit TNF-gamma-beta activation of NFkB in 293T cells, whereas in the same experiment, TNFRI.Fc was not able to inhibit TNF-gamma-beta activation of NFkB in 293T cells. Secondly, both TR6.Fc and DR3.Fc can be used to immunoprecipitate TNF-gamma-beta. Thirdly, TR6.Fc proteins can be detected by FACS analysis to specifically bind cells transfected with TNF-gamma-beta.

Example 36

T Cell Proliferation and IFN-Gamma ELISA T Cell Proliferation Assay

The assay is performed as follows. PBMCs are purified from single donor whole blood by centrifugation through a histopaque gradient. PBMCs are cultured overnight in 10% RPMI and the following day non-adherent cells are collected and used for the proliferation assay. 96-well plates are pre-coated with either anti-CD3 or anti-CD3 and anti-CD28 and incubated overnight at 4 C. Plates are washed twice with PBS before use. TNF-gamma-beta protein at desired concentrations in 10% RPMI is added to the $2\times10^4$ cells/well in a final volume of 200 ul. 10 ng/ml recombinant human IL2 was used as a positive control. After 24 hours culture, samples are pulsed with 1 uCi/well 3H-thymidine. 26 hours after pulsing, cells are harvested and counted for 3H-thymidine.

IFNgamma ELISA:

The assay is performed as follows. Twenty-four well plates are coated with either 300 ng/ml or 600 ng/ml anti-CD3 and 5 ug/ml anti-CD28 (Pharmingen, San Diego, Calif.) in a final volume of 500 ul and incubated overnight at 4 C. Plates are washed twice with PBS before use. PBMC are isolated by Ficoll (LSM, ICN Biotechnologies, Aurora, Ohio) gradient centrifugation from human peripheral blood, and are cultured overnight in 10% FCS (Fetal Calf Serum, Biofluids, Rockville, Md.)/RPMI (Gibco BRL, Gaithersburg, Md.). The following day, the non adherent cells are collected, washed and used in the costimulation assay. The assay is performed in the pre-coated twenty-four well plate using $1\times10^5$ cells/well in a final volume of 900 ul. TNF-gamma-beta protein is added to the cultures. Recombinant human IL-2 (purchased from R & D Systems, Minneapolis, Minn.) at a final concentration of 10 ng/ml was used as a positive control. Controls and unknown samples are tested in duplicate. Supernatant samples (250 ul) are collected 2 days and 5 days after the beginning of the assay. The level of IFN gamma and IL-2 in culture supernatants is then measured by ELISA.

Results

TNF-gamma-beta treatment of PBMCs results in proliferation of T cells and a significant increase in IFN-gamma production compared to controls.

Example 37

TNF-Gamma-Beta Exacerbates an In-Vivo MLR Reaction

Acute graft-versus-host disease (aGVHD) is a major complication of allogeneic bone marrow transplantation (BMT), which is associated with a prolonged immune deficiency leading to life-threatening infections. The immunopathophysiology of GVHD is complex, and is considered to involve two phases. In the inductive phase, donor T lymphocytes recognize antigen expressed on recipient tissues resulting in alloactivation and proliferation of the allogeneic donor T cells. In the effector phase, inflammatory reactions may develop in specific host target tissues such as spleen, liver, intestine and skin that are characterized by mononuclear cell infiltration and histopathological damage. Some evidence suggests that GVHD-associated lymphoid hypoplasia and B cell dysfunction is dependent upon donor T cell-mediated Fas ligand function, but not perforin function: Parent-into-F1 mice is a representative model of an acute form of GVHD, that is caused by transfusion of C57BL/6 splenic T cells into (BALB/c×C57BL/6) F1 mice (CB6F1), and resulted in tissue damage of lymphoid, liver gastrointestinal tract or skin, and finally death. TNF-gamma-beta, a ligand of TNF superfamily, seems to be a T cell costimulator resulting in significant elevation of pro-inflammatory cytokine (INF-g and GM-CSF) secretion. In order to test the effect of TNF-gamma on T cell mediated alloactivation we co-administered TNF-gamma-beta protein along with C57BL/6 splenic T cells into CB6F1 mice and measured the course of the alloreaction via spleen weight and cytokine production among other parameters.

Briefly, CB6F1 mice were injected with $1.5 \times 10^8$ pooled spleen cells of C57BL/6 mice administered intravenously on day 0. TNF-gamma-beta, TL5 (a.k.a. AIM-II, another TNF family ligand used here as a control, or buffer was given intravenously at 3 mg/kg/day for 5 days (day 0 through day 4). All mice were sacrificed on day 5 for the purpose of collecting the spleen for weighting, and obtaining cells for cell proliferation and cytokine (IL-2, INF-gamma, GM-CSF, IL-12) production assays, as well as for FACS analysis.

Five days after parent splenocyte transfer, the alloactivation was observed in CB6F1 mice measured by splenomegaly, spontaneous splenocyte proliferation and cytokine production (buffer group vs. normal control). Treatment with TNF-gamma beta at 3 mg/kg/day, i.v. for 5 days resulted in a further significant enhancement of spleen weight ($p=0.001$ using ANOVA/T-test), the spontaneous splenocyte proliferation and cytokine (GM-CSF, INF-gamma) production when compared with the same parameters of buffer-treated control group; whereas TL5, showed no statistically significant difference from buffer group. In addition, neither TNF-gamma-beta nor TL5 show any significant effect on IL-12 and IL-2 production comparing with buffer group. This result suggests that human TNF-gamma is effective in vivo for modulating T cell-mediated immune response, and its effect on cytokine production may be selective.

Administration of TNF-gamma-beta protein to allografted mice exacerbates acute graft vs. host disease as measured by early sign of splenomegaly, spontaneous splenocyte proliferation and proinflammatory cytokine production suggesting that TNF-gamma-beta may play a pathogenic role in GVHD. Thus, antagonists of TNF-gamma-beta (e.g., neutralizing antibody against TNF-gamma or soluble DR3 or TR6 proteins such as Fc or albumin fusion proteins) might have therapeutic potential in treating patients with this and other T cell-mediated inflammatory processes and diseases, including, but not limited to, systemic lupus erythematosus, multiple sclerosis, arthritis, and delayed-type hypersensitivity reactions.

Example 38

TNF-Gamma-Beta is a Novel Ligand for DR3 and TR6-Alpha (DcR3) and Functions as a T Cell Costimulator Introduction Members of the TNF and TNFR superfamilies of proteins are involved in the regulation of many important biological processes, including development, organogenesis, innate and adaptive immunity (Locksley et al., Cell 104:487-501 (2001)). Interaction of TNF ligands such as TNF, Fas, LIGHT and BLyS with their cognate receptor (or receptors) has been shown to affect the immune responses, as they are able to activate signaling pathways that link them to the regulation of inflammation, apoptosis, homeostasis, host defense, and autoimmunity. The TNFR superfamily can be divided into two groups based on the presence of different domains in the intracellular portion of the receptor. One group contains a TRAF binding domain that enables them to couple to TRAFs (TNFR-associated factor); these in turn activate a signaling cascade that results in the activation of NF-κB and initiation of transcription. The other group of receptors is characterized by a 60 amino acid globular structure named Death Domain (DD). Historically death domain-containing receptors have been described as inducers of apoptosis via the activation of caspases. These receptors include TNFR1, DR3, DR4, DR5, DR6 and Fas. More recent evidence (Siegel et al., Nature Immunology 1:469-474 (2000) and references within) has shown that some members of this subgroup of receptors, such as Fas, also have the ability to positively affect T cell activation. A third group of receptors has also been described. The members of this group, that include DcR1, DcR2, OPG, and TNFR-6 alpha (also called DcR3, and hereinafter in this example referred to as "TR6"), have been named decoy receptors, as they lack a cytoplasmic domain and may act as inhibitors by competing with the signal transducing receptor for the ligand (Ashkenazi et al., Curr. Opin. Cell Biol. 11:255-260 (1999)). TR6, which exhibits closest homology to OPG, associates with high affinity to FasL and LIGHT, and inhibits FasL-induced apoptosis both in vitro and in vivo (Pitti et al., Nature 396:699-703 (1998), Yu, et al., J. Biol. Chem. 274: 13733-6 (1999); Connolly, et al., J. Pharmacol. Exp. Ther. 298:25-33 (2001)). Its role in down-regulating immune responses was strongly suggested by the observation that TR6 surpresses T-cell responses against alloantigen (Zhang et al., J. Clin. Invest. 107:1459-68 (2001)) and certain tumors overexpress TR6 (Pitti et al., Nature 396:699-703 (1998), Bai et al., Proc. natl. Acad. Sci. 97:1230-1235 (2000)).

DR3 (described in International Publication Numbers WO97/33904 and WO/0064465 which are herein incorporated by reference in their entireties) is a DD-containing receptor that shows highest homology to TNFR1 (Chinnaiyan et al., Science 274:990-2 (1996); Kitson et al., Nature 384:372-5 (1996), Marsters et al., Curr. Biol. 6:1669-76 (1996); Bodmer et al., Immunity 6:79-88 (1997); Screaton et al., Proc. Natl. Acad. Sci. 94:4615-19 (1997); Tan et al., Gene 204:35-46 (1997)). In contrast to TNFR1, which is ubiquitously expressed, DR3 appears to be mostly expressed by lymphocytes and is efficiently induced following T cell activation. TWEAK/Apo3L was previously shown to bind DR3 in vitro (Marsters et al., Curr. Biol. 8:525-528 (1998)). However, more recent work raised doubt about this interaction and showed that TWEAK was able to induce NF-κB and caspase activation in cells lacking DR3 (Schneider et al., Eur. J. Immunol. 29:1785-92 (1999); Kaptein et al., FEBS Letters 485:135-141 (2000)).

In this example, the characterization of the ligand, TNF-gamma-beta (also known as TL1β; described in International Publication Numbers: WO00/08139 and WO00/66608 which are herein incorporated by reference in their entireties), for both DR3 and TR6/DcR3 is described. TNF-gamma-beta is a longer variant of TNF-gamma-alpha (also known as VEGI and TL1; described in International Publication Numbers WO96/14328, WO99/23105, WO00/08139 and WO00/66608 which are herein incorporated by reference in their entireties), which was previously identified as an endothelial-derived factor that inhibited endothelial cell growth in vitro and tumor progression in vivo (Tan et al., Gene 204:35-46 (1997); Zhai et al., FASEB J. 13:181-9 (1999); Zhai et al., Int. J. Cancer 82:131-6 (1999); Yue et al., J. Biol. Chem. 274: 1479-86 (1999)). It was found that TNF-gamma-beta is the more abundant form than TNF-gamma-alpha and is upregulated by TNFα and IL-1α. U.S. Pat. No. 5,876,969.

As shown herein, the interaction between TNF-gamma-beta and DR3 in 293T cells and in the erythroleukemic line TF-1 results in activation of NF-κB and induction of caspase activity, respectively. TR6 is able to inhibit these activities by competing with DR3 for TNF-gamma-beta. More importantly, it was found that in vitro, TNF-gamma-beta functions specifically on activated T cells to promote survival and secretion of the proinflammatory cytokines IFNγ and GMCSF, and it markedly enhances acute graft-versus-host reactions in mice.

Results

TNF-Gamma-Beta is a Longer Variant of TNF-Gamma-Alpha, a Member of the TNF Superfamily of Ligands To identify novel TNF like molecules, a database of over three million human expressed sequence tag (EST) sequences was analyzed using the BLAST algorithm. Several EST clones with high homology to TNF like molecule 1, TNF-gamma-alpha (Tan et al., Gene 204:35-46 (1997); Zhai et al., FASEB J. 13:181-9 (1999); Yue et al., J. Biol. Chem 274: 1479-86 (1999)) were identified from endothelial cell cDNA libraries. Sequence analysis of these cDNA clones revealed a 2080 base pair (bp) insert encoding an open reading frame of 251 amino acids (aa) with two upstream in-frame stop codons. The predicted protein lacks a leader sequence but contains a hydrophobic transmembrane domain near the N-terminus, and a carboxyl domain that shares 20-30% sequence similarity with other TNF family members. Interestingly, the C-terminal 151-aa of this protein (residues 101-251) is identical to residues 24 to 174 of TNF-gamma-alpha, whereas the amino-terminal region shares no sequence similarity. The predicted extracellular receptor-interaction domain of TNF-gamma-betacontains two potential N-linked glycosylation sites and shows highest amino acid sequence identity to TNF (24.6%), followed by FasL (22.9%) and LTα (22.2%). A 337-bp stretch of the TNF-gamma-beta cDNA, containing most of the 5' untranslated region and the sequences encoding the first 70 amino acids of the TNF-gamma-beta protein, matches a genomic clone on human chromosome 9 (Genbank Accession: AL390240, clone RP11-428F18). Further analysis of the human genomic sequences reveals that TNF-gamma-alpha and TNF-gamma-beta are likely derived from the same gene. While TNF-gamma-beta is encoded by four putative exons, similar to most TNF-like molecules, TNF-gamma-alpha is encoded by only the last exon and the extended N-terminal intron region, and therefore lacks a putative transmembrane domain and the first conserved β-sheet Mouse and rat TNF-gamma-beta cDNAs isolated from normal kidney cDNAs each encode a 252-aa protein (SEQ ID NOS:31 and 32, respectively). The overall amino acid sequence homology between human and mouse, and human and rat TNF-gamma-beta proteins is 63.7% and 66.1%, respectively. Higher sequence homology was found in the predicted extracellular receptor-interaction domains, of which human and mouse share 71.8% and human and rat share 75.1% sequence identity. An 84.2% sequence identity is seen between the mouse and rat TNF-gamma-beta proteins.

Like most TNF ligands, TNF-gamma-beta exists as a membrane-bound protein and can also be processed into a soluble form when ectopically expressed. The N-terminal sequence of soluble TNF-gamma-beta protein purified from full-length TNF-gamma-beta transfected 293T cells was determined to be Leu 72.

TNF-Gamma-Beta is Predominantly Expressed by Endothelial Cells, a More Abundant Form than TNF-Gamma-Alpha, and is Inducible by TNF and IL-1α

To determine the expression pattern of TNF-gamma-beta, TNF-gamma-betaspecific primer and fluorescent probe were used for quantitative real-time polymerase chain reaction (TaqMan) and reverse transcriptase polymerase chain reaction (RT-PCR) (see Experimental Procedures below). TNF-gamma-beta is expressed predominantly by human endothelial cells, including the umbilical vein endothelial cells (HUVEC), the adult dermal microvascular endothelial cells (HMVEC-Ad), and uterus myometrial endothelial cells (Ut-MEC-Myo), with highest expression seen in HUVEC. A ~750 bp DNA fragment was readily amplified from these endothelial cells by RT-PCR, indicating the presence of full length TNF-gamma-beta transcripts. Very little expression was seen in human aortic endothelial cells (HAEC) or other human primary cells including adult dermal fibroblast (NHDF-Ad and HFL-1), aortic smooth muscle cells (AoSMC), skeletal muscle cells (SkMC), adult keratinocytes (NHEK-Ad), tonsillar B cells, T cells, NK cells, monocytes, or dendritic cells. Consistent with these results, TNF-gamma-beta RNA was detected in human kidney, prostate, stomach, and low levels were seen in intestine, lung, and thymus, but not in heart, brain, liver, spleen, or adrenal gland. No significant levels of TNF-gamma-beta mRNA in any of the cancer cell lines tested, including 293T, HeLa, Jurkat, Molt4, Raji, IM9, U937, Caco-2, SK-N-MC, HepG2, KS4-1, and GH4C were detected.

As the expression pattern of TNF-gamma-beta is very similar to that of TNF-gamma-alpha (Tan et al., Gene 204: 35-46 (1997); Zhai et al., FASEB J. 13:181-9 (1999)), the relative abundance of the two RNA species was analyzed using TNF-gamma-alpha and TNF-gamma-beta specific primers and fluorescence probes for conventional and quantitative RT-PCR. More TNF-gamma-beta mRNA was detected than that of TNF-gamma-alpha using both methods. The amount of TNF-gamma-beta mRNA is at least 15-fold higher than that of TNF-gamma-alpha in the same RNA samples. To determine if TNF-gamma-beta mRNA levels were inducible, HUVEC cells were stimulated with either TNF, IL-1α, PMA, bFGF or IFNγ PMA and IL-1α rapidly induced high levels of TNF-gamma-beta mRNA, with a peak in expression reached at 6 hours after treatment. TNF was also able to induce TNF-gamma-beta mRNA, but the time course of induction appeared to be delayed compared to PMA and IL-1α. In contrast, bFGF and IFNγ did not significantly affect the expression of TNF-gamma-beta. TNF-gamma-beta protein levels in the supernatants of activated HUVEC cells were analyzed by ELISA and a similar profile of induction was observed.

Identification of DR3 and TR6 as Receptors for TL1β

To identify the receptor for TNF-gamma-beta, we generated HEK293F stable transfectants expressing full length TNF-gamma-beta on the cell surface (confirmed by Taqman and flow cytometric analysis using TNF-gamma-beta monoclonal antibody). These cells were used to screen the Fc-fusion form of the extracellular domain of TNFR family members, including TNFR1, Fas, HveA, DR3, DR4, DR5, DR6, DcR1, DcR2, TR6, OPG, RANK, AITR, TACI, CD40, and OX40. DR3-Fc and TR6-Fc bound efficiently to cells expressing TNF-gamma-beta but not to vector control transfected cells. In contrast, HveA-Fc and all the other receptors tested did not bind to the TNF-gamma-beta expressing cells.

TR6 has been previously described as a decoy receptor (Pitti et al., Nature 396:699-703 (1998); Yu et al., J. Biol Chem. 274:13733-6 (1999)) capable of competing with Fas and HveA for binding of FasL and LIGHT, respectively. Whether TR6 could compete with DR3 for TNF-gamma-beta binding was tested. When a 2:1 molar ratio of a non-tagged form of TR6 and DR3-Fc were used, no binding of DR3-Fc was detected on TNF-gamma-beta expressing cells. These results demonstrated that both DR3 and TR6 can bind to membrane-bound form of the TNF-gamma-beta protein.

Whether TNF-gamma-beta protein could bind to membrane-bound form of the receptor, DR3 was tested. A FLAG-tagged soluble form of the TL1β (aa 72-251) protein was tested for binding of cells transiently transfected with different members of the TNFR family, including TNFR2, LTβ R, 4-1BB, CD27, CD30, BCMA, DR3, DR4, DR5, DR6, DcR1, DcR2, RANK, HveA, and AITR. Binding of FLAG-TL1β to cells expressing full length or DD-deleted DR3, but not to any of the other receptors tested, was consistently detected, demonstrating that TNF-gamma-beta interacts with membrane-associated DR3. The small shift (~30%) seen when full length DR3 was used is likely due to the presence of low DR3-expressing cells while DR3 overexpressed cells undergone apoptosis.

Coimmunoprecipitation studies were also performed to confirm that TNF-gamma-beta could specifically bind DR3 and TR6. Consistent with what we observed in FACS analysis, we found that DR3-Fc and TR6-Fc specifically interacted with FLAG-TNF-gamma-beta. In contrast, Fas-Fc or TACI-Fc could not immunoprecipitate FLAG-TNF-gamma-beta, but efficiently bound their known ligands, FLAG-FasL and FLAG-BlyS, respectively.

To verify that the TNF-gamma-beta binding to DR3 and TR6 was specific and exhibited characteristics that were similar to those observed with other TNF family members to their cognate receptors, a BIACORE™ analysis using a non-tagged TNF-gamma-beta(aa 72-251) protein purified from *E. coli* was perfomed. The kinetics of TNF-gamma-beta binding to DR3-Fc was determined using three different batches of the TNF-gamma-beta protein. The ka and kd values were found to be 6.39E+05 $Ms^{-1}$ and 4.13E-03$M^{-1}$, respectively. The average Kd value was 6.45±0.2 nM. TNF-gamma-beta was also examined for its ability to bind to several other TNF-related receptors (HveA, BCMA, TACI, and TR6). In addition to DR3, only TR6 was found to have significant and specific binding to TNF-gamma-beta. The ka and kd values were 1.04E+06 $Ms^{-1}$ and 1.9E-03 $M^{-1}$, respectively, which gives a Kd of 1.8 nM. The specificity of binding of TL1β to DR3-Fc and TR6-Fc were confirmed by the competition of TNF-gamma-beta binding in the presence of excess soluble receptor-Fc. These Kd values for binding of TNF-gamma-beta to DR3-Fc and TR6-Fc are comparable to those determined for other TNFR-ligand interactions.

Interaction of TL1β with DR3 Induces Activation of NF-κB

Previous reports have demonstrated that ectopic expression of DR3 results in the activation of the transcription factor NF-κB (Chinnaiyan et al., Science 274:990-2 (1996); Kitson et al., Nature 384:372-5 (1996), Marsters et al., Curr. Biol. 6:1669-76 (1996); Bodmer et al., Immunity 6:79-88 (1997)). TNF-gamma-beta induced signaling in a reconstituted system in 293T cells in which DR3 and a NF-κB-SEAP reporter were introduced by transient transfection was studied. To avoid spontaneous apoptosis or NF-κB activation accompanied with DR3 overexpression, a limited amount of DR3-expression DNA that by itself minimally activated these pathways was used. Under these conditions, cotransfection of cDNAs encoding full length or the soluble form of TNF-gamma-beta resulted in significant NF-κB activation. This signaling event was dependent on the ectopic expression of DR3 and the intactness of the DR3 death domain, as TNF-gamma-beta alone or in combination with a DD-deleted DR3 did not induce NF-κB activation in these cells. Cotransfection of DR3 with cDNAs encoding TNF-gamma-alpha (full length or N-terminal 24-aa truncated) failed to induce NF-κB activation. A similar induction of NF-κB activity was observed when increasing amounts of recombinant TL1β protein (aa 72-251, with or without FLAG tag) were added to DR3 expressing cells. This induction of NF-κB was specifically inhibited by the addition of excess amount of DR3-Fc or TR6-Fc, but not by the addition of Fas-Fc or TNFR1-Fc. These results demonstrated that TNF-gamma-beta is a signaling ligand for DR3 that induces NF-κB activation, and TR6 can specifically inhibit this event.

TL1κ Induces IL-2 Responsiveness and Cytokine Secretion from Activated T Cells

As DR3 expression is mostly restricted to the lymphocytes (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88(1997); Screaton et al., Proc. Natl. Acad. Sci. 94:4615-19 (1997); Tan et al., Gene 204:35-46 (1997)) and is upregulated upon T cell activation, we examined the biological activity of TNF-gamma-beta on T cells. Recombinant TNF-gamma-beta (aa 72-251) protein was tested for its ability to induce proliferation of resting or costimulated T cells (treated with amounts of anti-CD3 and anti-CD28 that are not sufficient to induce proliferation). In resting or costimulated T cells, no significant increase in proliferation over background was observed. Interestingly, cells that were previously treated with TNF-gamma-beta for 72 hours were able to proliferate significantly in the presence of IL-2 than cells without TNF-gamma-beta preincubation, indicating that TNF-gamma-beta increases the IL-2 responsiveness of costimulated T cells.

As enhanced IL-2 responsiveness has been associated with increased IL-2 receptor expression and altered cytokine secretion, it was of interest to assess these responses on costimulated T cells treated with TNF-gamma-beta. TNF-gamma-beta treatment indeed upregulated IL-2Rα (CD25) and IL-2Rβ (CD122) expression from these cells. The extent of the increase in IL-2 receptor expression is consistent with the moderate increase in IL-2 responsiveness compared with IL-2 itself. We next measured cytokine secretion from these cells and found that both IFNγ and GMCSF were significantly induced, whereas IL-2, IL-4, IL-10, or TNF were not. This effect was mostly dependent on the T cell coactivator CD28, as treatment of the cells with anti-CD3 and TNF-gamma-beta only minimally induced cytokine secretion. The effect that we observed on T cells was specifically mediated by TNF-gamma-beta, as addition of monoclonal neutralizing antibody to TL1β, or addition of DR3-Fc or TR6-Fc proteins was able to inhibit TNF-gamma-beta-mediated IFN γ secretion. TNF-gamma-beta was also tested on a variety of primary cells, including B cells, NK cells, and monocytes, but no significant activity was detected, suggesting a specific activity of TNF-gamma-beta on T cells.

TL1β Induces Caspase Activation in TF-1 Cells but not in T Cells

Overexpression of DR3 in cell lines induces capase activation (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88(1997)). We tested whether TL1β could induce caspase activation in primary T cells. Purified T cells were activated with PHA and incubated with recombinant TNF-gamma-beta or FasL in the presence or absence of cycloheximide (CHX). No induction of caspase activity was detected in TNF-gamma-beta treated T cells, but was readily measured when cells were triggered with FasL, suggesting that under this experimental condition, TNF-gamma-beta does not activate caspases in T cells (the assay we used detects activation of caspases 2, 3, 6, 7, 8, 9, and 10). Various cell lines for the expression of DR3 and found that the erythroleukimic cell line TF-1 expressed high levels of DR3 were then analyzed. The effect of recombinant TNF-gamma-beta protein on caspase activation in TF-1 cells was then measured. In the absence of cycloheximide, no significant increase in caspase activity was detected following TNF-gamma-beta treatment, while TNF-gamma-beta was able to efficiently induce caspase activation in the presence of cycloheximide. This effect was inhibited by either DR3-Fc or TR6-Fc protein but not by LIGHT-Fc. An anti-TNF-gamma-beta monoclonal antibody was also shown to completely inhibit this activity, confirming that the caspase activation was mediated by TNF-gamma-beta.

TL1β Promotes Splenocyte Alloactivation in Mice

To determine if the in vitro activities of TNF-gamma-beta could be reproduced in vivo, a mouse model of acute graft-versus-host-response (GVHR) was developed in which parental C57BL/6 splenocytes were injected intravenously into (BALB/c×C57 BL/6) F1 mice (CB6F1), and the recipient's immune responses were measured. Typical alloactivation results in increased splenic weight of the recipient mice and enhanced proliferation and cytokine production of the splenocytes cultured ex-vivo (Via, J. Immunol. 146:2603-9 (1991); Zhang et al., J. Clin. Invest. 107:1459-68 (2001)). The large number of T cells in the spleen and their expected upregulation of DR3 in response to alloactivation makes this an ideal model to assess the effect of TNF-gamma-beta on a defined in vivo immune response. Five day administration of 3 mg/kg of the recombinant TNF-gamma-beta protein markedly enhanced the graft-versus-host responses. The mean (n=4) weight of normal spleens obtained from naive CB6F1 mice was 0.091 g. Alloactivation resulted in a 2.5 fold increase in splenic weight (~0, 228 g). Treatment of allografted CB6F1 mice with recombinant TNF-gamma-beta protein (aa 72-251) further increased splenic weight about 50%, to a mean value of 0.349 g. TNF-gamma-beta treatment also significantly enhanced ex-vivo splenocyte expansion, and secretion of IFNγ and GMCSF. Thus, TNF-gamma-beta strongly enhances GVHR in vivo, and this effect is consistent with TNF-gamma-beta's in vitro activities.

Experimental Procedures

Cells, Constructs, and Other Reagents

All human cancer cell lines and normal lung fibroblast (HFL-1) were purchased from American Tissue Culture Collection. Human primary cells were purchased from Clonetics Corp. Cells were cultured as recommended. Human cDNA encoding the full length TNF-gamma-alpha, TNF-gamma-beta, DR3; the extracellular domain of TNF-gamma-alpha (aa 25-174), TNF-gamma-beta (aa 72-251), BlyS (aa 134-285), FasL (aa 130-281), and death domain truncated DR3 (DR3ADD, aa 1-345) were amplified by PCR and cloned into the mammalian expression vectors pC4 and/or pFLAGCMV1 (Sigma). The extracellular domain of human DR3 (aa 1-199), TACI (aa 1-159), HveA (aa 1-192), Fas (aa 1-169), and full length TR6 (aa 1-300), was each fused in-frame, at its C-terminus, to the Fc domain of human IgG1 and cloned into pC4. Rabbit polyclonal TNF-gamma-beta antibody was generated using recombinant TNF-gamma-beta (aa 72-251) protein and purified on a TNF-gamma-beta affinity column. Monoclonal antibodies were raised against recombinant TNF-gamma-beta as described (Kohler and Milstein, Nature 256:503-519 (1975)).

Cloning of Human, Mouse, and Rat TNF-Gamma-Beta cDNA

TNF-gamma-beta was identified by screening a human EST database for sequence homology with the extracellular domain of TNF, using the blastn and tblastn algorithms. The extracellular domain of the mouse and rat TNF-gamma-beta cDNA was isolated by PCR amplification from mouse or rat kidney Marathon-Ready cDNAs (Clontech) using human TNF-gamma-beta specific primers. The resulting sequences were then used to design mouse and rat TNF-gamma-beta specific primers to amplify the 5' and 3' ends of the cDNA using Marathon cDNA Amplification kit (Clontech). Each sequence was derived and confirmed from at least two independent PCR products.

Generation of TNF-Gamma-Beta Stable Cell line

HEK293F cells were transiently transfected with pcDNA3.1(+) (vector control) or pcDNA3.1(+) containing full length TNF-gamma-beta. Cells resistant to 0.5 mg/ml Genticin (Invitrogen) were selected and expanded. Expression of TNF-gamma-beta mRNA was confirmed by quantitative RT-PCR analysis and surface expression of TNF-gamma-beta protein confirmed by FACS analyses using TNF-gamma-beta monoclonal antibodies.

Quantitative Real-Time PCR (TaqMan) and RT-PCR Analysis

Total RNA was isolated from human cell lines and primary cells using TriZOL (Invitrogen). TaqMan was carried out in a 25 μl reaction containing 25 ng of total RNA, 0.6 μM each of gene-specific forward and reverse primers and 0.2 μM of gene-specific fluorescence probe. TNF-gamma-beta specific primers (forward: 5'-CACCTCTTAGAG CAGACG-GAGATAA-3' (SEQ ID NO:33), reverse: 5'-TTAAAGT-GCTGTGTGGGAGT TTGT -3' (SEQ ID NO:34), and probe: 5'-CCAAGGGCACACCTGACAGTTGTGA-3' (SEQ ID NO:35)) amplify an amplicon span nucleotide 257 to 340 of the TNF-gamma-beta cDNA (aa 86-114 of the protein), while TNF-gamma-alpha specific primers (forward: 5'-CAAAGTCTACAGTTTCCCAATGAGAA-3' (SEQ ID NO:36); reverse: 5'-GGGA ACTGATTTTTAAAGTGCT-GTGT-3' (SEQ ID NO:37); probe: 5'-TCCTCTTTCTTGT CTTTCCAGTTGTGAGACAAAC-3' (SEQ ID NO:38)) amplify nucleotide 17 to 113 of the TNF-gamma-alpha cDNA (aa 7-37 of the protein). Gene-specific PCR products were measured using an ABI PRISM 7700 Sequence Detection System following the manufacturer's instruction (PE Corp.). The relative mRNA level of TNF-gamma-beta was normalized to the 18S ribosomal RNA internal control in the same sample.

For RT-PCR analysis, 0.5 micrograms of total RNA was amplified with TNF-gamma-alpha (5'-GCAAAGTCTA-CAGTTTCCCAATGAGAAAATTAATCC-3'(SEQ ID NO:39)) or TNF-gamma-beta specific sense primer (5'-ATG-GCCGAGGATCTGGG ACTGAGC-3' (SEQ ID NO:40)) and an antisense primer (5'-CTATAGTAAGAAGGC TCCAAAGAAGGTTTTATCTTC-3' (SEQ ID NO:41)) using SuperScript One-Step RT-PCR System (Invitrogen). β-actin was used as internal control.

Transfection and NF-κB Reporter Assay 293T cells were transiently transfected using LipofectAMINE and PLUS reagents according to the manufacturer's instruction (Invitrogen). For reporter assays, 293T cells, at $5 \times 10^5$ cells/well, were seeded in 6-well plates and transfected with a total of 1 microgram of DNA. pC4 DNA was used as filler DNA. Conditioned supernatant was collected 24 hr post-transfection and assayed for secreted alkaline phosphatase (SEAP) activity using the Phospha-Light™ chemiluminescent reporter gene assay system (Tropix). pCMV-lacZ was used as internal control for transfection efficiency normalization.

Recombinant Protein Purification

FLAG fusion proteins were produced from 293T cells by transient transfection, and purified on anti-Flag M2 affinity columns (Sigma) according to manufacturer's instruction. Receptor proteins with or without Fc fusion were produced from Baculovirus or CHO stable cell lines as described (Zhang et al., J. Clin. Invest. 107:1459-68 (2001)). Recombinant, untagged TNF-gamma-beta protein (aa 72-251) was generated and purified from E. coli. Briefly, E. Coli cell extract was separated on a HQ-50 anion exchange column (Applied Biosystems) and eluted with a salt gradient. The 0.2 M NaCl elution was diluted and loaded on a HQ-50 column, and the flow through was collected, adjusted to 0.8 M ammonia sulfate and loaded on a Butyl-650s column (Toso Haus). The column was eluted with a 0.6M to 0 M ammonia sulfate gradient and the fractions containing TNF-gamma-beta protein were pooled and further purified by size exclusion on a Superdex-200 column (Pharmacia) in PBS. All recombinant proteins were confirmed by $NH_2$-terminal sequencing on a ABI-494 sequencer (Applied Biosystem). The endotoxin level of the purified protein was less than 10 EU/mg as measured on a LAL-5000E (Cape Cod Associates).

Flow Cytometry, Immunoprecipitation, and Western Blot Analysis

One million cells, in 0.1 ml of FACS buffer (PBS, 0.1% BSA, 0.1% $NaN_3$), were incubated with 0.1-1 microgram of protein or antibody at RT for 15 min. The cells were washed with 3 ml of FACS buffer, reacted with biotinylated primary antibody, and stained with PE-conjugated secondary antibody at RT for 15 min. Cells were then washed again, resuspended in 0.5 microgram/ml of propidium iodide, and live cells were gated and analyzed on a FACScan using the CellQuest software (BD Biosciences).

For coimmunoprecipiation studies, 2 micrograms each of purified TNFR-Fc proteins was incubated with 1 microgram of Flag-tagged TNF-gamma-beta, FasL or BlyS protein and 20 microliters of protein A-Sepharose beads in 0.5 ml of IP buffer (DMEM, 10% FCS, 0.1% Triton X-100) at 4° C. for 4 hr. The beads were then precipitated and washed extensively with PBST buffer (PBS, 0.5% Triton X-100) before boiled in SDS-sample buffer. Proteins were resolved on 4-20% Tris-Glycine gels (NOVEX), transferred to nitrocellulose membranes, and blotted with anti-Flag M2 monoclonal antibody (1 microgram/ml, Sigma) and horseradish peroxidase (HRP)-conjugated goat anti-mouse IgG antibody (0.5 microgram/ml).

BIACORE™ Analysis

Recombinant TNF-gamma-beta (from E. Coli) binding to various human TNF receptors was analyzed on a BIACORE™ 3000 instrument. TNFR-Fc were covalently immobilized to the BIACORE™ sensor chip (CM5 chip) via amine groups using N-ethyl-N'-(dimethylaminopropyl)carbodiimide/N-hydroxysuccinimide chemistry. A control receptor surface of identical density was prepared, BCMA-Fc, that was negative for TNF-gamma-beta binding and used for background subtraction. Eight different concentrations of TNF-gamma-beta (range: 3-370 nM) were flowed over the receptor-derivatized flow cells at 15 microliters/min for a total volume of 50 microliters. The amount of bound protein was determined during washing of the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 microliters of 10 mM glycine-HCl, pH 2.3. For kinetic analysis, the on and off rates were determined using the kinetic evaluation program in BIAevaluation 3 software using a 1:1 binding model and the global analysis method.

T cell Proliferation Assays.

Whole blood from human donors was separated by Ficoll (ICN Biotechnologies) gradient centrifugation and cells were cultured overnight in RPMI containing 10% FCS (Biofluids). T cells were separated using the MACS PanT separation kit (Milteny Biotech), the T cell purity achieved was usually higher that 90%. The cells were seeded on anti-CD3 (0.3 microgram/ml, Pharmingen) and anti-CD28 (5.0 microgram/ml) coated 96-well plates at $2 \times 10^4$/well, and were incubated with medium alone, 1 ng/ml of IL-2 (R & D Systems), or 100 ng/ml of TNF-gamma-beta (aa 72-251) at 37° C. After 72 hour in culture, the cells were either untreated or treated with 1 ng/ml of IL-2, and pulsed with 0.5 µCi of $^3$H-thymidine for another 24 hours and incorporation of $^3$H measured on a scintillation counter.

Cytokine ELISA Assays for Primary Cells $1 \times 10^5$ cells/ml of purified T cells were seeded in a 24-well tissue culture plate that had been coated with anti-CD3(0.3 microgram/ml) and anti-CD28 (5.0 microgram/ml) overnight at 4° C. Recombinant TNF-gamma-beta (aa72-251) protein (100 ng/ml) was added to cells and supernatants were collected 72 hours later. ELISA assay for IFNγ, GM-CSF, IL-2 IL-4, IL-10 and TNFα were performed using kits purchased from R & D Systems. Recombinant human IL-2 (5 ng/ml) was used as a positive control. All samples were tested in duplicate and results were expressed as an average of duplicate samples plus or minus error.

Caspase Assay

TF-1 cells or PHA-activated primary T cells were seeded at 75,000 cells/well in a black 96-well plate with clear bottom (Becton Dickinson) in RPMI Medium containing 1% fetal bovine serum (Biowhittaker). Cells were treated with TNF-gamma-beta (aa72-251, 100 ng/ml) in the presence or absence of cycloheximide (10 micrograms/ml). Caspase activity was measured directly in the wells by adding equal volume of a lysis buffer containing 25 µM DEVD-rodamine 110 (Roche Molecular Biochemicals), and allowed the reaction to proceed at 37 C for 1 to 2 hours. Release of rodamine 110 was monitored with a Wallac Victor2 fluorescence plate reader with excitation filter 485 nm and emission filter 535 nm.

For the inhibition studies using Fc-proteins or antibodies, the indicated amount of each protein was mixed with either medium or 100 ng/ml of TNF-gamma-beta in the presence or absence of cycloheximide. The reagents were incubated for 1 hour at RT to allow the formation of protein-TNF-gamma-beta complexes and then added to the cells. Caspase activity was measured as described above.

Murine Graft-Versus-Host Reaction

The F1 (CB6F1) of C57BL/6×BALB/c mice ($H-2^{bxd}$) were transfused intravenously with $1.5 \times 10^8$ spleen cells from C57BL/6 mice ($H-2^b$) on day 0. Recombinant TNF-gamma-beta (aa 72-251) protein or buffer alone was administered intravenously daily for 5 days at 3 mg/kg/day starting on the same day as the transfusion. The spleens of the recipient F1 mice were harvested on day 5, weighed and single cell suspensions prepared for in vitro assays.

Ex-Vivo Mouse Splenocyte ALAMAR BLUE™ and Cytokine Assays

Splenocytes from normal and the transfused F1 mice were cultured in triplicate in 96-well flat-bottomed plates ($4 \times 10^5$ cells/200 microliters/well) for 2-4 days. After removing 100 microliters of supernatant per well on the day of harvest, 10 microliters ALAMAR BLUE™ (Biosource) was added to each well and the cells cultured for additional 4 h. The cell number in each well was assessed according to $OD_{590\,nm}$ minus $OD_{530\,nm}$ background, using a CytoFluor apparatus (PerSeptive Biosystems). Cytokines in the culture supernatant were measured with commercial ELISA kits from Endogen or R & D Systems following manufacturer's instructions.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

Further, the Sequence Listing submitted herewith in both computer and paper forms are hereby incorporated by reference in their entireties. Additionally the specification and Sequence Listing of the following U.S. applications are herein incorporated by reference in their entirety: U.S. Provisional Application Ser. Nos.: 60/074,047, filed Feb. 9, 1998, 60/131,963, filed on Apr. 30, 1999; 60/132,227, filed May 3, 1999; and 60/134,067, filed May 13, 1999, 60/180,908, filed Feb. 8, 2000, 60/216,879, filed Jul. 7, 2000, and 60/278,449 filed Mar. 26, 2001; U.S. Nonprovisional application Ser. No.: 08/461,246, filed Jun. 5, 1995, Ser. No. 09/005,020, filed Jan. 9, 1998, 60/074,047, filed Feb. 9, 1998, Ser. No. 09/131,237, filed Aug. 7, 1998, Ser. No. 09/246,129, filed Feb. 8, 1999, Ser. No. 09/559,290, filed Apr. 27, 2000; and Ser. No. 09/560,921 filed Apr. 28, 2000 each of which is hereby incorporated by reference in its entirety; and PCT Application Serial Nos. PCT/US94/12880, filed Nov. 7, 1994, PCT/US99/02722, filed Feb. 8, 1999, PCT/US00/11689; each of which is hereby incorporated by reference in its entirety.

What is claimed is:

1. An isolated antibody or fragment thereof that specifically binds to a protein selected from the group consisting of:
   (a) a protein whose amino acid sequence consists of amino acid residues −27 to 147 of SEQ ID NO:2;
   (b) a protein whose amino acid sequence consists of amino acid residues −26 to 147 of SEQ ID NO:2;
   (c) a protein whose amino acid sequence consists of amino acid residues 1 to 147 of SEQ ID NO:2;
   (d) a protein whose amino acid sequence consists of amino acid residues 25 to 147 of SEQ ID NO:2;
   (e) a protein whose amino acid sequence consists of a portion of SEQ ID NO:2, wherein said portion is at least 30 contiguous amino acid residues in length;
   (f) a protein whose amino acid sequence consists of a portion of SEQ ID NO:2, wherein said portion is at least 50 contiguous amino acid residues in length;
   (g) a protein whose sequence consists of the amino acid sequence of the full-length polypeptide encoded by the cDNA contained in ATCC™ Deposit Number 75927;
   (h) a protein whose sequence consists of the amino acid sequence of the full-length polypeptide, excluding the N-terminal methionine residue, encoded by the cDNA contained in ATCC™ Deposit Number 75927; and
   (i) a protein whose sequence consists of the amino acid sequence of the extracellular domain of the polypeptide encoded by the cDNA contained in ATCC™ Deposit Number 75927.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 wherein said antibody or fragment thereof is monoclonal.

6. The antibody or fragment thereof of claim 1 wherein said protein bound by said antibody or fragment thereof is glycosylated.

7. The antibody or fragment thereof of claim 1 wherein said antibody or fragment thereof is human.

8. The antibody or fragment thereof of claim 1 which is selected from the group consisting of:
   (a) a chimeric antibody or fragment thereof;
   (b) a humanized antibody or fragment thereof;
   (c) a single chain antibody; and
   (d) a Fab fragment.

9. The antibody or fragment thereof of claim 1 which is labeled.

10. The antibody or fragment thereof of claim 1 wherein said antibody or fragment thereof specifically binds to said protein in a Western blot or an ELISA.

11. An isolated cell that produces the antibody or fragment thereof of claim 1.

12. A method of detecting a protein in a biological sample that is specifically bound by the antibody or fragment thereof of claim 1 comprising:
   (a) contacting the biological sample with the antibody or fragment thereof of claim 1; and
   (b) detecting the protein in the biological sample.

13. An isolated antibody or fragment thereof that specifically binds a tumor necrosis factor-gamma protein purified from a cell culture wherein said tumor necrosis factor-gamma protein is encoded by a polynucleotide encoding amino acids −27 to 147 of SEQ ID NO:2.

14. The antibody or fragment thereof of claim 13 wherein said antibody or fragment thereof is monoclonal.

15. The antibody or fragment thereof of claim 13 wherein said antibody or fragment thereof is polyclonal.

16. The antibody or fragment thereof of claim 13 wherein said antibody or fragment thereof is human.

17. The antibody or fragment thereof of claim 13 which is selected from the group consisting of:
   (a) a chimeric antibody or fragment thereof;
   (b) a humanized antibody or fragment thereof;
   (c) a single chain antibody; and
   (d) a Fab fragment.

18. The antibody or fragment thereof of claim 13 wherein said antibody or fragment thereof specifically binds to said protein in a Western blot or an ELISA.

19. The antibody or fragment thereof of claim 13 wherein the amino acid sequence of said tumor necrosis factor-gamma protein consists of amino acid residues −26 to 147 of SEQ ID NO:2.

20. The antibody or fragment thereof of claim 13 wherein the amino acid sequence of said tumor necrosis factor-gamma protein consists of amino acid residues 1 to 147 of SEQ ID NO:2.

* * * * *

SEQUENCE LISTING

```
<160> NUMBER OF SEQ ID NOS: 41

<210> SEQ ID NO 1
<211> LENGTH: 2442
<212> TYPE: DNA
<213> ORGANISM: Homo sapiens
<220> FEATURE:
<221> NAME/KEY: CDS
<222> LOCATION: (783)..(1304)
<220> FEATURE:
<221> NAME/KEY: sig_peptide
<222> LOCATION: (783)..(863)
<220> FEATURE:
<221> NAME/KEY: mat_peptide
<222> LOCATION: (864)..()
<220> FEATURE:
<221> NAME/KEY: misc_feature
<222> LOCATION: (2265)..(2265)
<223> OTHER INFORMATION: n equals a, t, g, or c
<220> FEATURE:
<221> NAME/KEY: misc_feature
<222> LOCATION: (2273)..(2273)
<223> OTHER INFORMATION: n equals a, t, g. or c
<220> FEATURE:
<221> NAME/KEY: misc_feature
<222> LOCATION: (2307)..(2307)
<223> OTHER INFORMATION: n equals a, t, g. or c
<220> FEATURE:
<221> NAME/KEY: misc_feature
<222> LOCATION: (2336)..(2336)
<223> OTHER INFORMATION: n equals a, t, g. or c
<220> FEATURE:
<221> NAME/KEY: misc_feature
<222> LOCATION: (2341)..(2341)
<223> OTHER INFORMATION: n equals a, t, g. or c
<220> FEATURE:
<221> NAME/KEY: misc_feature
<222> LOCATION: (2379)..(2379)
<223> OTHER INFORMATION: n equals a, t, g. or c

<400> SEQUENCE: 1
cccaatcaag agaaattcca tactatcacc agttggccga ctttccaagt ctagtgcaga      60
aatccaaggc acctcacacc tagagttcct atacctctga gactccagag gaaagaacaa     120
gacagtgcag aaggatatgt tagaacccac tgaaaaccta gaaggttgaa aaggaagcat     180
accctcctga cctataagaa aattttcagt ctgcagggg atatccttgt ggcccaagac      240
attggtgtta tcatttgact aagaggaaat tatttgtggt gagctctgag tgaggattag     300
gaccagggag atgccaagtt tctatcactt acctcatgcc tgtaagacaa gtgttttgtt     360
```

-continued

```
ccaattgatg aatggggaga aaacagttca gccaatcact tatgggcaca gaatggaatt    420
tgaagggtct ggtgcctgcc cttgtcatac gtaaacaaga gaggcatcga tgagttttat    480
ctgagtcatt tgggaaagga taattcttgc accaagccat tttcctaaac acagaagaat    540 aggggattc cttaaccttc attgttctcc aggatcatag gtctcaggat aaattaaaaa    600
ttttcaggtc agaccactca gtctcagaaa ggcaaagtaa tttgcccag gtcactagtc    660 caagatgtta ttctctttga acaaatgtgt atgtccagtc acatattctt cattcattcc    720
tccccaaagc agttttage tgttaggtat attcgatcac tttagtctat tttgaaaatg    780
```

| | | |
|---|---|---|
| at atg aga cgc ttt tta agc aaa gtc tac agt ttc cca atg aga aaa<br>   Met Arg Arg Phe Leu Ser Lys Val Tyr Ser Phe Pro Met Arg Lys<br>      -25                 -20                -15 | | 827 |
| tta atc ctc ttt ctt gtc ttt cca gtt gtg aga caa act ccc aca cag<br>Leu Ile Leu Phe Leu Val Phe Pro Val Val Arg Gln Thr Pro Thr Gln<br>     -10               -5                 -1  1 | | 875 |
| cac ttt aaa aat cag ttc cca gct ctg cac tgg gaa cat gaa cta ggc<br>His Phe Lys Asn Gln Phe Pro Ala Leu His Trp Glu His Glu Leu Gly<br>5                10                 15               20 | | 923 |
| ctg gcc ttc acc aag aac cga atg aac tat acc aac aaa ttc ctg ctg<br>Leu Ala Phe Thr Lys Asn Arg Met Asn Tyr Thr Asn Lys Phe Leu Leu<br>          25                30               35 | | 971 |
| atc cca gag tcg gga gac tac ttc att tac tcc cag gtc aca ttc cgt<br>Ile Pro Glu Ser Gly Asp Tyr Phe Ile Tyr Ser Gln Val Thr Phe Arg<br>      40                  45               50 | | 1019 |
| ggg atg acc tct gag tgc agt gaa atc aga caa gca ggc cga cca aac<br>Gly Met Thr Ser Glu Cys Ser Glu Ile Arg Gln Ala Gly Arg Pro Asn<br>     55                60               65 | | 1067 |
| aag cca gac tcc atc act gtg gtc atc acc aag gta aca gac agc tac<br>Lys Pro Asp Ser Ile Thr Val Val Ile Thr Lys Val Thr Asp Ser Tyr<br>70                75                 80 | | 1115 |
| cct gag cca acc cag ctc ctc atg ggg acc aag tct gta tgc gaa gta<br>Pro Glu Pro Thr Gln Leu Leu Met Gly Thr Lys Ser Val Cys Glu Val<br>85                90               95             100 | | 1163 |
| ggt agc aac tgg ttc cag ccc atc tac ctc gga gcc atg ttc tcc ttg<br>Gly Ser Asn Trp Phe Gln Pro Ile Tyr Leu Gly Ala Met Phe Ser Leu<br>             105              110            115 | | 1211 |
| caa gaa ggg gac aag cta atg gtg aac gtc agt gac atc tct ttg gtg<br>Gln Glu Gly Asp Lys Leu Met Val Asn Val Ser Asp Ile Ser Leu Val<br>         120              125              130 | | 1259 |
| gat tac aca aaa gaa gat aaa acc ttc ttt gga gcc ttc tta cta<br>Asp Tyr Thr Lys Glu Asp Lys Thr Phe Phe Gly Ala Phe Leu Leu<br>          135              140             145 | | 1304 |

```
taggaggaga gcaaatatca ttatatgaaa gtcctctgcc accgagttcc taattttctt    1364
tgttcaaatg taattataac caggggtttt cttggggccg ggagtagggg gcattccaca    1424
gggacaacgg tttagctatg aaatttgggg ccaaaatttc acacttcatg tgccttactg    1484
atgagagtac taactggaaa aaggctgaag agagcaaata tattattaag atgggttgga    1544
ggattggcga gtttctaaat attaagacac tgatcactaa atgaatggat gatctactcg    1604
ggtcaggatt gaaagagaaa tatttcaaca cctccctgct atacaatggt caccagtggt    1664
ccagttattg ttcaatttga tcataaattt gcttcaattc aggagctttg aaggaagtcc    1724
aaggaaagct ctagaaaaca gtataaactt tcagaggcaa aatccttcac caattttttcc    1784 acatactttc atgccttgcc taaaaaaat gaaagagag ttggtatgtc tcatgaatgt    1844
tcacacagaa ggagttggtt ttcatgtcat ctacagcata tgagaaaagc tacctttctt    1904
ttgattatgt acacagatat ctaaataagg aagtttgagt ttcacatgta tatcccaaat    1964
```

-continued

```
acaacagttg cttgtattca gtagagtttt cttgcccacc tattttgtgc tgggttctac    2024
cttaacccag aagacactat gaaaaacaag acagactcca ctcaaaattt atatgaacac    2084
cactagatac ttcctgatca acatcagtc aacatactct aaagaataac tccaagtctt    2144
ggccaggcgc agtggctcac acctgtaatc ccaacacttt gggaggccaa ggtgggtgga    2204
tcatctaagg ccgggagttc aagaccagcc tgaccaacgt ggagaaaccc catctctact    2264
naaaatacna aattagccgg gcgtggtagc gcatggctgt aancctggct actcaggagg    2324
ccgaggcaga anaattncctt gaactgggga ggcagaggtt gcggtgagcc cagancgcgc    2384
cattgcactc cagcctgggt aacaagagca aaactctgtc caaaaaaaaa aaaaaaaa    2442
```

<210> SEQ ID NO 2
<211> LENGTH: 174
<212> TYPE: PRT
<213> ORGANISM: Homo sapiens

<400> SEQUENCE: 2

```
Met Arg Arg Phe Leu Ser Lys Val Tyr Ser Phe Pro Met Arg Lys Leu
            -25                 -20                 -15

Ile Leu Phe Leu Val Phe Pro Val Val Arg Gln Thr Pro Thr Gln His
    -10                  -5                  -1   1                5

Phe Lys Asn Gln Phe Pro Ala Leu His Trp Glu His Glu Leu Gly Leu
                     10                  15                  20

Ala Phe Thr Lys Asn Arg Met Asn Tyr Thr Asn Lys Phe Leu Leu Ile
                 25                  30                  35

Pro Glu Ser Gly Asp Tyr Phe Ile Tyr Ser Gln Val Thr Phe Arg Gly
             40                  45                  50

Met Thr Ser Glu Cys Ser Glu Ile Arg Gln Ala Gly Arg Pro Asn Lys
         55                  60                  65

Pro Asp Ser Ile Thr Val Val Ile Thr Lys Val Thr Asp Ser Tyr Pro
70                   75                  80                  85

Glu Pro Thr Gln Leu Leu Met Gly Thr Lys Ser Val Cys Glu Val Gly
                 90                  95                  100

Ser Asn Trp Phe Gln Pro Ile Tyr Leu Gly Ala Met Phe Ser Leu Gln
             105                 110                 115

Glu Gly Asp Lys Leu Met Val Asn Val Ser Asp Ile Ser Leu Val Asp
         120                 125                 130

Tyr Thr Lys Glu Asp Lys Thr Phe Phe Gly Ala Phe Leu Leu
     135                 140                 145
```

<210> SEQ ID NO 3
<211> LENGTH: 233
<212> TYPE: PRT
<213> ORGANISM: Homo sapiens

<400> SEQUENCE: 3

```
Met Ser Thr Glu Ser Met Ile Arg Asp Val Glu Leu Ala Glu Glu Ala
1               5                  10                  15

Leu Pro Lys Lys Thr Gly Gly Pro Gln Gly Ser Arg Arg Cys Leu Phe
             20                  25                  30

Leu Ser Leu Phe Ser Phe Leu Ile Val Ala Gly Ala Thr Thr Leu Phe
         35                  40                  45

Cys Leu Leu His Phe Gly Val Ile Gly Pro Gln Arg Glu Glu Ser Pro
     50                  55                  60

Arg Asp Leu Ser Leu Ile Ser Pro Leu Ala Gln Ala Val Arg Ser Ser
65                   70                  75                  80
```

Ser Arg Thr Pro Ser Asp Lys Pro Val Ala His Val Ala Asn Pro
              85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 5

```
<211> LENGTH: 244
<212> TYPE: PRT
<213> ORGANISM: Homo sapiens

<400> SEQUENCE: 5

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
                35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly

<210> SEQ ID NO 6
<211> LENGTH: 278
<212> TYPE: PRT
<213> ORGANISM: Rattus norvegicus

<400> SEQUENCE: 6

Met Gln Gln Pro Val Asn Tyr Pro Cys Pro Gln Ile Tyr Trp Val Asp
1               5                   10                  15

Ser Ser Ala Thr Ser Pro Trp Ala Pro Pro Gly Ser Val Phe Ser Cys
            20                  25                  30

Pro Ser Ser Gly Pro Arg Gly Pro Gly Gln Arg Arg Pro Pro Pro Pro
        35                  40                  45

Pro Pro Pro Pro Ser Pro Leu Pro Pro Ser Gln Pro Pro Pro Leu
    50                  55                  60

Pro Pro Leu Ser Pro Leu Lys Lys Lys Asp Asn Ile Glu Leu Trp Leu
65                  70                  75                  80

Pro Val Ile Phe Phe Met Val Leu Val Ala Leu Val Gly Met Gly Leu
                85                  90                  95

Gly Met Tyr Gln Leu Phe His Leu Gln Lys Glu Leu Ala Glu Leu Arg
```

```
                    100                 105                 110
Glu Phe Thr Asn His Ser Leu Arg Val Ser Ser Phe Glu Lys Gln Ile
            115                 120                 125

Ala Asn Pro Ser Thr Pro Ser Glu Thr Lys Lys Pro Arg Ser Val Ala
        130                 135                 140

His Leu Thr Gly Asn Pro Arg Ser Arg Ser Ile Pro Leu Glu Trp Glu
145                 150                 155                 160

Asp Thr Tyr Gly Thr Ala Leu Ile Ser Gly Val Lys Tyr Lys Lys Gly
                165                 170                 175

Gly Leu Val Ile Asn Glu Ala Gly Leu Tyr Phe Val Tyr Ser Lys Val
            180                 185                 190

Tyr Phe Arg Gly Gln Ser Cys Asn Ser Gln Pro Leu Ser His Lys Val
        195                 200                 205

Tyr Met Arg Asn Phe Lys Tyr Pro Gly Asp Leu Val Leu Met Glu Glu
    210                 215                 220

Lys Lys Leu Asn Tyr Cys Thr Thr Gly Gln Ile Trp Ala His Ser Ser
225                 230                 235                 240

Tyr Leu Gly Ala Val Phe Asn Leu Thr Val Ala Asp His Leu Tyr Val
                245                 250                 255

Asn Ile Ser Gln Leu Ser Leu Ile Asn Phe Glu Glu Ser Lys Thr Phe
            260                 265                 270

Phe Gly Leu Tyr Lys Leu
        275

<210> SEQ ID NO 7
<211> LENGTH: 235
<212> TYPE: PRT
<213> ORGANISM: Homo sapiens

<400> SEQUENCE: 7

Met Ser Thr Glu Ser Met Ile Arg Asp Val Glu Leu Ala Glu Gly Pro
1               5                   10                  15

Leu Pro Lys Lys Ala Gly Gly Pro Gln Gly Ser Lys Arg Cys Leu Cys
            20                  25                  30

Leu Ser Leu Phe Ser Phe Leu Leu Val Ala Gly Ala Thr Thr Leu Phe
        35                  40                  45

Cys Leu Leu His Phe Arg Val Ile Gly Pro Gln Glu Glu Glu Gln Ser
    50                  55                  60

Pro Asn Asn Leu His Leu Val Asn Pro Val Ala Gln Met Val Thr Leu
65                  70                  75                  80

Arg Ser Ala Ser Arg Ala Leu Ser Asp Lys Pro Leu Ala His Val Val
                85                  90                  95

Ala Asn Pro Gln Val Glu Gly Gln Leu Gln Trp Leu Ser Gln Arg Ala
            100                 105                 110

Asn Ala Leu Leu Ala Asn Gly Met Lys Leu Thr Asp Asn Gln Leu Val
        115                 120                 125

Val Pro Ala Asp Gly Leu Tyr Leu Ile Tyr Ser Gln Val Leu Phe Ser
    130                 135                 140

Gly Gln Gly Cys Arg Ser Tyr Val Leu Leu Thr His Thr Val Ser Arg
145                 150                 155                 160

Phe Ala Val Ser Tyr Pro Asn Lys Val Asn Leu Leu Ser Ala Ile Lys
                165                 170                 175

Ser Pro Cys His Arg Glu Thr Pro Glu Glu Ala Glu Pro Met Ala Trp
            180                 185                 190

Tyr Glu Pro Ile Tyr Leu Gly Gly Val Phe Gln Leu Glu Lys Gly Asp
```

```
                195                 200                 205
Arg Leu Ser Thr Glu Val Asn Gln Pro Glu Tyr Leu Asp Leu Ala Glu
        210                 215                 220

Ser Gly Gln Val Tyr Phe Gly Ile Ile Ala Leu
225                 230                 235

<210> SEQ ID NO 8
<211> LENGTH: 434
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n equals a, t, g, or c
<220> FEATURE:
<221> NAME/KEY: misc_feature
<222> LOCATION: (19)..(19)
<223> OTHER INFORMATION: n equals a, t, g, or c
<220> FEATURE:
<221> NAME/KEY: misc_feature
<222> LOCATION: (133)..(133)
<223> OTHER INFORMATION: n equals a, t, g, or c
<220> FEATURE:
<221> NAME/KEY: misc_feature
<222> LOCATION: (388)..(388)
<223> OTHER INFORMATION: n equals a, t, g, or c
<220> FEATURE:
<221> NAME/KEY: misc_feature
<222> LOCATION: (424)..(424)
<223> OTHER INFORMATION: n equals a, t, g, or c

<400> SEQUENCE: 8
tctacacaag gtacngacng ctaccctgag ccaacccagc tcctcatggg gaccaagtct    60
gtatgcgaag taggtagcaa ctggttccag cccatctacc tcggagccat gttctccttg   120
caagaagggg acnagctaat ggtgaacgtc agtgacatct ctttggtgga ttacacaaaa   180
gaagataaaa ccttctttgg agccttctta ctataggagg agagcaaata tcattatatg   240
aaagtcctct gccaccgagt tcctaatttt ctttgttcaa atgtaattat aaccaggggt   300
tttcttgggg ccgggagtag ggggcattcc cacagggaca acggtttagc tatgaaattt   360 gggggggccca aaatttcaca acttcatngt tgcccttact tgatgagaag tacttaactt   420
gganaaaagg cttg                                                     434

<210> SEQ ID NO 9
<211> LENGTH: 493
<212> TYPE: DNA
<213> ORGANISM: Homo sapiens
<220> FEATURE:
<221> NAME/KEY: misc_feature
<222> LOCATION: (288)..(288)
<223> OTHER INFORMATION: n equals a, t, g, or c
<220> FEATURE:
<221> NAME/KEY: misc_feature
<222> LOCATION: (296)..(296)
<223> OTHER INFORMATION: n equals a, t, g, or c
<220> FEATURE:
<221> NAME/KEY: misc_feature
<222> LOCATION: (309)..(309)
<223> OTHER INFORMATION: n equals a, t, g, or c
<220> FEATURE:
<221> NAME/KEY: misc_feature
<222> LOCATION: (314)..(314)
<223> OTHER INFORMATION: n equals a, t, g, or c
<220> FEATURE:
<221> NAME/KEY: misc_feature
<222> LOCATION: (340)..(340)
<223> OTHER INFORMATION: n equals a, t, g, or c
<220> FEATURE:
<221> NAME/KEY: misc_feature
<222> LOCATION: (343)..(343)
```

```
<223> OTHER INFORMATION: n equals a, t, g, or c
<220> FEATURE:
<221> NAME/KEY: misc_feature
<222> LOCATION: (348)..(348)
<223> OTHER INFORMATION: n equals a, t, g, or c
<220> FEATURE:
<221> NAME/KEY: misc_feature
<222> LOCATION: (369)..(369)
<223> OTHER INFORMATION: n equals a, t, g, or c
<220> FEATURE:
<221> NAME/KEY: misc_feature
<222> LOCATION: (385)..(385)
<223> OTHER INFORMATION: n equals a, t, g, or c
<220> FEATURE:
<221> NAME/KEY: misc_feature
<222> LOCATION: (410)..(410)
<223> OTHER INFORMATION: n equals a, t, g, or c
<220> FEATURE:
<221> NAME/KEY: misc_feature
<222> LOCATION: (417)..(417)
<223> OTHER INFORMATION: n equals a, t, g, or c
<220> FEATURE:
<221> NAME/KEY: misc_feature
<222> LOCATION: (423)..(423)
<223> OTHER INFORMATION: n equals a, t, g, or c
<220> FEATURE:
<221> NAME/KEY: misc_feature
<222> LOCATION: (431)..(431)
<223> OTHER INFORMATION: n equals a, t, g, or c
<220> FEATURE:
<221> NAME/KEY: misc_feature
<222> LOCATION: (434)..(434)
<223> OTHER INFORMATION: n equals a, t, g, or c
<220> FEATURE:
<221> NAME/KEY: misc_feature
<222> LOCATION: (437)..(437)
<223> OTHER INFORMATION: n equals a, t, g, or c
<220> FEATURE:
<221> NAME/KEY: misc_feature
<222> LOCATION: (444)..(444)
<223> OTHER INFORMATION: n equals a, t, g, or c
<220> FEATURE:
<221> NAME/KEY: misc_feature
<222> LOCATION: (459)..(459)
<223> OTHER INFORMATION: n equals a, t, g, or c
<220> FEATURE:
<221> NAME/KEY: misc_feature
<222> LOCATION: (486)..(486)
<223> OTHER INFORMATION: n equals a, t, g, or c

<400> SEQUENCE: 9
aattcggcag agaaattcca tactatcacc agttggccaa ctttccaagt ctagtgcaga      60
aatccaaggc acctcacacc tagagttcct atacctctga gactccagag gaaagaacaa    120
gacagtgcag aaggatatgt tagaacccac tgaaaaccta gaaggttaaa aaggaagcat    180
accctcctga cctataagaa aatttttcagt ctgcagggggg atatccttgt ggcccaagac  240
attggtgtta tcatttgact aagaggaaat tatttgtggt gagctccnag tgaggnttag    300
ggaccaggng gtgnccaagt tctatcact tacctcatgn ctntaagnca agtgttttgt    360
tcccattgnt gatggggtta aaacnttcag ccatcacttt tggggcaagn atggggnttt    420
gangggttgg ngcnggnctt gtcntcgtaa acaggggnt tggtgggttt ttctgggtcc    480
ttgggnagga ctt                                                       493

<210> SEQ ID NO 10
<211> LENGTH: 380
<212> TYPE: DNA
<213> ORGANISM: Homo sapiens
<220> FEATURE:
<221> NAME/KEY: misc_feature
<222> LOCATION: (53)..(54)
<223> OTHER INFORMATION: n equals a, t, g, or c
<220> FEATURE:
```

<221> NAME/KEY: misc_feature
<222> LOCATION: (258)..(258)
<223> OTHER INFORMATION: n equals a, t, g, or c
<220> FEATURE:
<221> NAME/KEY: misc_feature
<222> LOCATION: (316)..(316)
<223> OTHER INFORMATION: n equals a, t, g, or c
<220> FEATURE:
<221> NAME/KEY: misc_feature
<222> LOCATION: (324)..(324)
<223> OTHER INFORMATION: n equals a, t, g, or c
<220> FEATURE:
<221> NAME/KEY: misc_feature
<222> LOCATION: (346)..(346)
<223> OTHER INFORMATION: n equals a, t, g, or c
<220> FEATURE:
<221> NAME/KEY: misc_feature
<222> LOCATION: (367)..(367)
<223> OTHER INFORMATION: n equals a, t, g, or c
<220> FEATURE:
<221> NAME/KEY: misc_feature
<222> LOCATION: (378)..(378)
<223> OTHER INFORMATION: n equals a, t, g, or c

<400> SEQUENCE: 10

```
ggcagaggtt caatttgatc ataaatttgc ttcaattcag gagctttgaa ggnngtccaa    60
ggaaagctct agaaaacagt ataaactttc agaggcaaaa tccttcacca attttttccac  120
atactttcat gccttgccta aaaaaaatga aaagagagtt ggtatgtctc atggaatgtt   180
cacacagaag gagttggttt tcatgtcatc tacagcatat gagaaaagct acctttcttt   240
tgattatgta cacaggtntc taaataagga agtatgagtt tcacatgtat attcaaaaat   300
acaacagttg cttgtnttca gttngggttt ttcttggccc acccanttt ggtgctgggg    360
gttctanctt taaccccnga                                                380
```

<210> SEQ ID NO 11
<211> LENGTH: 458
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n equals a, t, g, or c
<220> FEATURE:
<221> NAME/KEY: misc_feature
<222> LOCATION: (12)..(12)
<223> OTHER INFORMATION: n equals a, t, g, or c
<220> FEATURE:
<221> NAME/KEY: misc_feature
<222> LOCATION: (119)..(119)
<223> OTHER INFORMATION: n equals a, t, g, or c
<220> FEATURE:
<221> NAME/KEY: misc_feature
<222> LOCATION: (303)..(303)
<223> OTHER INFORMATION: n equals a, t, g, or c
<220> FEATURE:
<221> NAME/KEY: misc_feature
<222> LOCATION: (311)..(311)
<223> OTHER INFORMATION: n equals a, t, g, or c
<220> FEATURE:
<221> NAME/KEY: misc_feature
<222> LOCATION: (387)..(387)
<223> OTHER INFORMATION: n equals a, t, g, or c
<220> FEATURE:
<221> NAME/KEY: misc_feature
<222> LOCATION: (409)..(409)
<223> OTHER INFORMATION: n equals a, t, g, or c
<220> FEATURE:
<221> NAME/KEY: misc_feature
<222> LOCATION: (425)..(425)
<223> OTHER INFORMATION: n equals a, t, g, or c
<220> FEATURE:
<221> NAME/KEY: misc_feature
<222> LOCATION: (427)..(427)

```
<223> OTHER INFORMATION: n equals a, t, g, or c
<220> FEATURE:
<221> NAME/KEY: misc_feature
<222> LOCATION: (453)..(453)
<223> OTHER INFORMATION: n equals a, t, g, or c

<400> SEQUENCE: 11
ggcacagcng gnagtagggg gcattccaca gggacaacgg tttagctatg aaatttgggg    60
cccaaaattt cacacttcat gtgccttact gatgagagta ctaactggaa aaaggctgna   120
agagagcaaa tatattatta agatgggttg gaggattggc gagtttctaa atattaagac   180
actggatcac tgaaatgaat ggatgatcta ctcgggtcca ggattgaaag agaaatattt   240
caacaccttc ctgctataca atggtcacca gtggtccagt tattgttcca atttggatcc   300
atnaatttgc nttcaattcc aggagctttg gaaggaattc caaggaaagc tccaggaaaa   360
ccgtattaaa ctttccaggg gccaaantcc ttcaccaatt ttttccacna actttccagg   420
cctgncncaa aaaaatggaa agggagttgg tangtccc                           458

<210> SEQ ID NO 12
<211> LENGTH: 388
<212> TYPE: DNA
<213> ORGANISM: Homo sapiens
<220> FEATURE:
<221> NAME/KEY: misc_feature
<222> LOCATION: (11)..(12)
<223> OTHER INFORMATION: n equals a, t, g, or c
<220> FEATURE:
<221> NAME/KEY: misc_feature
<222> LOCATION: (46)..(46)
<223> OTHER INFORMATION: n equals a, t, g, or c
<220> FEATURE:
<221> NAME/KEY: misc_feature
<222> LOCATION: (50)..(50)
<223> OTHER INFORMATION: n equals a, t, g, or c
<220> FEATURE:
<221> NAME/KEY: misc_feature
<222> LOCATION: (81)..(81)
<223> OTHER INFORMATION: n equals a, t, g, or c
<220> FEATURE:
<221> NAME/KEY: misc_feature
<222> LOCATION: (138)..(138)
<223> OTHER INFORMATION: n equals a, t, g, or c
<220> FEATURE:
<221> NAME/KEY: misc_feature
<222> LOCATION: (155)..(155)
<223> OTHER INFORMATION: n equals a, t, g, or c
<220> FEATURE:
<221> NAME/KEY: misc_feature
<222> LOCATION: (182)..(182)
<223> OTHER INFORMATION: n equals a, t, g, or c
<220> FEATURE:
<221> NAME/KEY: misc_feature
<222> LOCATION: (188)..(188)
<223> OTHER INFORMATION: n equals a, t, g, or c
<220> FEATURE:
<221> NAME/KEY: misc_feature
<222> LOCATION: (269)..(269)
<223> OTHER INFORMATION: n equals a, t, g, or c
<220> FEATURE:
<221> NAME/KEY: misc_feature
<222> LOCATION: (317)..(317)
<223> OTHER INFORMATION: n equals a, t, g, or c
<220> FEATURE:
<221> NAME/KEY: misc_feature
<222> LOCATION: (322)..(322)
<223> OTHER INFORMATION: n equals a, t, g, or c
<220> FEATURE:
<221> NAME/KEY: misc_feature
<222> LOCATION: (358)..(358)
<223> OTHER INFORMATION: n equals a, t, g, or c
<220> FEATURE:
<221> NAME/KEY: misc_feature
<222> LOCATION: (363)..(363)
```

<223> OTHER INFORMATION: n equals a, t, g, or c
<220> FEATURE:
<221> NAME/KEY: misc_feature
<222> LOCATION: (375)..(375)
<223> OTHER INFORMATION: n equals a, t, g, or c

<400> SEQUENCE: 12

```
ctgcactggg nncatgaact aggcctggcc ttcaccaaga accgantgan ctataccaac    60
aaattcctgc tgatcccaga ntcgggagac tacttcattt actcccaggt cacattccgt   120
gggaatgaac ctctgaantg ccagtgaaaa tcagncaagc aggccgacca aacaagccag   180
antccatnca ctgtggtcat caccaaggta acagacagct accctgagcc aacccagctc   240
cttcatgggg accaagtttg tttgcgaant aggttagcaa ctggttccag cccattttac   300
cttgggggcc agttctnctt gncaagaagg ggacaagctt atggtggaac gttcatanca   360
tcnttttttgg gtggntttac acaaaagg                                     388
```

<210> SEQ ID NO 13
<211> LENGTH: 37
<212> TYPE: DNA
<213> ORGANISM: Artificial sequence
<220> FEATURE:
<223> OTHER INFORMATION: TNF-gamma 5' primer with BamHI restriction site

<400> SEQUENCE: 13

```
gcgcggatcc accatgagac gctttttaag caaagtc                             37
```

<210> SEQ ID NO 14
<211> LENGTH: 36
<212> TYPE: DNA
<213> ORGANISM: Artificial sequence
<220> FEATURE:
<223> OTHER INFORMATION: TNF-gamma 3' primer with XbaI restriction site

<400> SEQUENCE: 14

```
cgcgtctaga ctatagtaag aaggctccaa agaagg                              36
```

<210> SEQ ID NO 15
<211> LENGTH: 37
<212> TYPE: DNA
<213> ORGANISM: Artificial sequence
<220> FEATURE:
<223> OTHER INFORMATION: TNF-gamma 5' primer with BamHI restriction site

<400> SEQUENCE: 15

```
gcgcggatcc accatgagac gctttttaag caaagtc                             37
```

<210> SEQ ID NO 16
<211> LENGTH: 36
<212> TYPE: DNA
<213> ORGANISM: Artificial sequence
<220> FEATURE:
<223> OTHER INFORMATION: TNF-gamma 3' primer with XbaI restriction site

<400> SEQUENCE: 16

```
cgcgtctaga ctatagtaag aaggctccaa agaagg                              36
```

<210> SEQ ID NO 17
<211> LENGTH: 56
<212> TYPE: DNA
<213> ORGANISM: Artificial sequence
<220> FEATURE:
<223> OTHER INFORMATION: TNF-gamma 3' primer containing sequences
      complementary to XbaI site, translation stop codon and HA tag

<400> SEQUENCE: 17

```
cgctctagat caagcgtagt ctgggacgtc gtatggatag taagaaggct ccaaag        56

<210> SEQ ID NO 18
<211> LENGTH: 733
<212> TYPE: DNA
<213> ORGANISM: Homo sapiens

<400> SEQUENCE: 18
gggatccgga gcccaaatct tctgacaaaa ctcacacatg cccaccgtgc ccagcacctg     60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                      733

<210> SEQ ID NO 19
<211> LENGTH: 1116
<212> TYPE: DNA
<213> ORGANISM: Homo sapiens

<400> SEQUENCE: 19
atggccgagg atctgggact gagctttggg gaaacagcca gtgtggaaat gctgccagag     60
cacggcagct gcaggcccaa ggccaggagc agcagcgcac gctgggctct cacctgctgc   120
ctggtgttgc tccccttcct tgcaggactc accacatacc tgcttgtcag ccagctccgg   180
gcccagggag aggcctgtgt gcagttccag gctctaaaag acaggagtt tgcaccttca   240
catcagcaag tttatgcacc tcttagagca gacggagata agccaagggc acacctgaca   300
gttgtgagac aaactcccac acagcacttt aaaaatcagt tcccagctct gcactgggaa   360
catgaactag gcctggcctt caccaagaac cgaatgaact ataccaacaa attcctgctg   420
atcccagagt cggagactaa cttcattac tcccaggtca cattccgtgg gatgacctct   480
gagtgcagtg aaatcagaca agcaggccga ccaaacaagc cagactccat cactgtggtc   540
atcaccaagg taacagacag ctaccctgag ccaacccagc tcctcatggg gaccaagtct   600
gtatgcgaag taggtagcaa ctggttccag cccatctacc tcggagccat gttctccttg   660
caagaagggg acaagctaat ggtgaacgtc agtgacatct cttggtgga ttacacaaaa   720
gaagataaaa ccttcttgg agccttctta ctataggagg agagcaaata tcattatatg   780
aaagtcctct gccaccgagt tcctaatttt ctttgttcaa atgtaattat aaccaggggt   840
tttcttgggg ccgggagtag gggcattcca cagggacaac ggtttagcta tgaaatttgg   900
ggcccaaat ttcacacttc atgtgcctta ctgatgagag tactaactgg aaaaaggctg   960
aagagagcaa atatattatt aagatgggtt ggaggattgg cgagtttcta aatattaaga  1020
cactgatcac taaatgaatg gatgatctac tcgggtcagg attgaaagag aaatatttca  1080
```

```
acaccttcct gctatacaat ggtcaccagt ggtcca                              1116
```

<210> SEQ ID NO 20
<211> LENGTH: 251
<212> TYPE: PRT
<213> ORGANISM: Homo sapiens

<400> SEQUENCE: 20

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 21
<211> LENGTH: 434
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n equals a, t, g, or c
<220> FEATURE:
<221> NAME/KEY: misc_feature
<222> LOCATION: (19)..(19)
<223> OTHER INFORMATION: n equals a, t, g, or c
<220> FEATURE:
<221> NAME/KEY: misc_feature
<222> LOCATION: (133)..(133)
<223> OTHER INFORMATION: n equals a, t, g, or c
<220> FEATURE:
<221> NAME/KEY: misc_feature
<222> LOCATION: (388)..(388)
<223> OTHER INFORMATION: n equals a, t, g, or c
<220> FEATURE:
<221> NAME/KEY: misc_feature
<222> LOCATION: (424)..(424)
<223> OTHER INFORMATION: n equals a, t, g, or c

<400> SEQUENCE: 21

```
tctacacaag gtacngacng ctaccctgag ccaacccagc tcctcatggg gaccaagtct    60
gtatgcgaag taggtagcaa ctggttccag cccatctacc tcggagccat gttctccttg   120
caagaagggg acnagctaat ggtgaacgtc agtgacatct ctttggtgga ttacacaaaa   180
gaagataaaa ccttctttgg agccttctta ctataggagg agagcaaata tcattatatg   240
aaagtcctct gccaccgagt tcctaatttt ctttgttcaa atgtaattat aaccagggt    300 tttcttgggg ccgggagtag ggggcattcc cacagggaca acggtttagc tatgaaattt   360 gggggggccca aaatttcaca acttcatngt tgcccttact tgatgagaag tacttaactt   420
gganaaaagg cttg                                                     434
```

<210> SEQ ID NO 22
<211> LENGTH: 417
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n equals a, t, g, or c
<220> FEATURE:
<221> NAME/KEY: misc_feature
<222> LOCATION: (8)..(8)
<223> OTHER INFORMATION: n equals a, t, g, or c
<220> FEATURE:
<221> NAME/KEY: misc_feature
<222> LOCATION: (17)..(17)
<223> OTHER INFORMATION: n equals a, t, g, or c
<220> FEATURE:
<221> NAME/KEY: misc_feature
<222> LOCATION: (24)..(24)
<223> OTHER INFORMATION: n equals a, t, g, or c
<220> FEATURE:
<221> NAME/KEY: misc_feature
<222> LOCATION: (28)..(28)
<223> OTHER INFORMATION: n equals a, t, g, or c
<220> FEATURE:
<221> NAME/KEY: misc_feature
<222> LOCATION: (31)..(32)
<223> OTHER INFORMATION: n equals a, t, g, or c
<220> FEATURE:
<221> NAME/KEY: misc_feature
<222> LOCATION: (35)..(35)
<223> OTHER INFORMATION: n equals a, t, g, or c
<220> FEATURE:
<221> NAME/KEY: misc_feature
<222> LOCATION: (41)..(43)
<223> OTHER INFORMATION: n equals a, t, g, or c
<220> FEATURE:
<221> NAME/KEY: misc_feature
<222> LOCATION: (46)..(46)
<223> OTHER INFORMATION: n equals a, t, g, or c
<220> FEATURE:
<221> NAME/KEY: misc_feature
<222> LOCATION: (48)..(48)
<223> OTHER INFORMATION: n equals a, t, g, or c
<220> FEATURE:
<221> NAME/KEY: misc_feature
<222> LOCATION: (50)..(50)
<223> OTHER INFORMATION: n equals a, t, g, or c
<220> FEATURE:
<221> NAME/KEY: misc_feature
<222> LOCATION: (53)..(53)
<223> OTHER INFORMATION: n equals a, t, g, or c
<220> FEATURE:
<221> NAME/KEY: misc_feature
<222> LOCATION: (55)..(55)
<223> OTHER INFORMATION: n equals a, t, g, or c

```
<220> FEATURE:
<221> NAME/KEY: misc_feature
<222> LOCATION: (61)..(63)
<223> OTHER INFORMATION: n equals a, t, g, or c
<220> FEATURE:
<221> NAME/KEY: misc_feature
<222> LOCATION: (66)..(67)
<223> OTHER INFORMATION: n equals a, t, g, or c
<220> FEATURE:
<221> NAME/KEY: misc_feature
<222> LOCATION: (202)..(202)
<223> OTHER INFORMATION: n equals a, t, g, or c
<220> FEATURE:
<221> NAME/KEY: misc_feature
<222> LOCATION: (209)..(209)
<223> OTHER INFORMATION: n equals a, t, g, or c
<220> FEATURE:
<221> NAME/KEY: misc_feature
<222> LOCATION: (282)..(282)
<223> OTHER INFORMATION: n equals a, t, g, or c
<220> FEATURE:
<221> NAME/KEY: misc_feature
<222> LOCATION: (306)..(306)
<223> OTHER INFORMATION: n equals a, t, g, or c
<220> FEATURE:
<221> NAME/KEY: misc_feature
<222> LOCATION: (321)..(321)
<223> OTHER INFORMATION: n equals a, t, g, or c
<220> FEATURE:
<221> NAME/KEY: misc_feature
<222> LOCATION: (344)..(344)
<223> OTHER INFORMATION: n equals a, t, g, or c
<220> FEATURE:
<221> NAME/KEY: misc_feature
<222> LOCATION: (346)..(346)
<223> OTHER INFORMATION: n equals a, t, g, or c
<220> FEATURE:
<221> NAME/KEY: misc_feature
<222> LOCATION: (380)..(381)
<223> OTHER INFORMATION: n equals a, t, g, or c
<220> FEATURE:
<221> NAME/KEY: misc_feature
<222> LOCATION: (395)..(395)
<223> OTHER INFORMATION: n equals a, t, g, or c
<220> FEATURE:
<221> NAME/KEY: misc_feature
<222> LOCATION: (405)..(405)
<223> OTHER INFORMATION: n equals a, t, g, or c

<400> SEQUENCE: 22
attncggnac gagcagnggc atgnccgngg nnctnggact nnnctntngn gananagcca    60
nnnttnnaat gctgccagag cacggcagct gcaggcccaa ggccaggagc agcagcgcac   120
gctgggctct cacctgctgc ctggtgttgc tcccccttcct tgcaggactc accacatacc   180
tgcttgtcag ccagcttcgg gnccagggng aggcctgtgt gcagttccag ggtctaaaag   240
gacaggagtt tgcaccttca catcagcaag tttatgcacc tnttagagca gacggagata   300
agccangggg acaactgaca nttgtgagac aaattccaca cagnantttta aaatcagttt   360 ccagttttga atggggacan nattaggctg gcttnacaag accgntggat tttacag      417

<210> SEQ ID NO 23
<211> LENGTH: 388
<212> TYPE: DNA
<213> ORGANISM: Homo sapiens
<220> FEATURE:
<221> NAME/KEY: misc_feature
<222> LOCATION: (11)..(12)
<223> OTHER INFORMATION: n equals a, t, g, or c
<220> FEATURE:
<221> NAME/KEY: misc_feature
<222> LOCATION: (46)..(46)
<223> OTHER INFORMATION: n equals a, t, g, or c
<220> FEATURE:
<221> NAME/KEY: misc_feature
```

<222> LOCATION: (50)..(50)
<223> OTHER INFORMATION: n equals a, t, g, or c
<220> FEATURE:
<221> NAME/KEY: misc_feature
<222> LOCATION: (81)..(81)
<223> OTHER INFORMATION: n equals a, t, g, or c
<220> FEATURE:
<221> NAME/KEY: misc_feature
<222> LOCATION: (138)..(138)
<223> OTHER INFORMATION: n equals a, t, g, or c
<220> FEATURE:
<221> NAME/KEY: misc_feature
<222> LOCATION: (155)..(155)
<223> OTHER INFORMATION: n equals a, t, g, or c
<220> FEATURE:
<221> NAME/KEY: misc_feature
<222> LOCATION: (182)..(182)
<223> OTHER INFORMATION: n equals a, t, g, or c
<220> FEATURE:
<221> NAME/KEY: misc_feature
<222> LOCATION: (188)..(188)
<223> OTHER INFORMATION: n equals a, t, g, or c
<220> FEATURE:
<221> NAME/KEY: misc_feature
<222> LOCATION: (269)..(269)
<223> OTHER INFORMATION: n equals a, t, g, or c
<220> FEATURE:
<221> NAME/KEY: misc_feature
<222> LOCATION: (317)..(317)
<223> OTHER INFORMATION: n equals a, t, g, or c
<220> FEATURE:
<221> NAME/KEY: misc_feature
<222> LOCATION: (322)..(322)
<223> OTHER INFORMATION: n equals a, t, g, or c
<220> FEATURE:
<221> NAME/KEY: misc_feature
<222> LOCATION: (358)..(358)
<223> OTHER INFORMATION: n equals a, t, g, or c
<220> FEATURE:
<221> NAME/KEY: misc_feature
<222> LOCATION: (363)..(363)
<223> OTHER INFORMATION: n equals a, t, g, or c
<220> FEATURE:
<221> NAME/KEY: misc_feature
<222> LOCATION: (375)..(375)
<223> OTHER INFORMATION: n equals a, t, g, or c

<400> SEQUENCE: 23

```
ctgcactggg nncatgaact aggcctggcc ttcaccaaga accgantgan ctataccaac    60
aaattcctgc tgatcccaga ntcgggagac tacttcattt actccaggt cacattccgt   120
gggaatgaac ctctgaantg ccagtgaaaa tcagncaagc aggccgacca aacaagccag   180
antccatnca ctgtggtcat caccaaggta acagacagct accctgagcc aacccagctc   240
cttcatgggg accaagtttg tttgcgaant aggttagcaa ctggttccag cccatttac   300
cttgggggcc agttctnctt gncaagaagg ggacaagctt atggtggaac gttcatanca   360
tcntttttgg gtggntttac acaaaagg                                      388
```

<210> SEQ ID NO 24
<211> LENGTH: 458
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n equals a, t, g, or c
<220> FEATURE:
<221> NAME/KEY: misc_feature
<222> LOCATION: (12)..(12)
<223> OTHER INFORMATION: n equals a, t, g, or c
<220> FEATURE:
<221> NAME/KEY: misc_feature
<222> LOCATION: (119)..(119)
<223> OTHER INFORMATION: n equals a, t, g, or c

```
<220> FEATURE:
<221> NAME/KEY: misc_feature
<222> LOCATION: (303)..(303)
<223> OTHER INFORMATION: n equals a, t, g, or c
<220> FEATURE:
<221> NAME/KEY: misc_feature
<222> LOCATION: (311)..(311)
<223> OTHER INFORMATION: n equals a, t, g, or c
<220> FEATURE:
<221> NAME/KEY: misc_feature
<222> LOCATION: (387)..(387)
<223> OTHER INFORMATION: n equals a, t, g, or c
<220> FEATURE:
<221> NAME/KEY: misc_feature
<222> LOCATION: (409)..(409)
<223> OTHER INFORMATION: n equals a, t, g, or c
<220> FEATURE:
<221> NAME/KEY: misc_feature
<222> LOCATION: (425)..(425)
<223> OTHER INFORMATION: n equals a, t, g, or c
<220> FEATURE:
<221> NAME/KEY: misc_feature
<222> LOCATION: (427)..(427)
<223> OTHER INFORMATION: n equals a, t, g, or c
<220> FEATURE:
<221> NAME/KEY: misc_feature
<222> LOCATION: (453)..(453)
<223> OTHER INFORMATION: n equals a, t, g, or c

<400> SEQUENCE: 24
ggcacagcng gnagtagggg gcattccaca gggacaacgg tttagctatg aaatttgggg      60
cccaaaattt cacacttcat gtgccttact gatgagagta ctaactggaa aaaggctgna    120
agagagcaaa tatattatta agatgggttg gaggattggc gagtttctaa atattaagac    180
actggatcac tgaaatgaat ggatgatcta ctcgggtcca ggattgaaag agaaatattt    240
caacaccttc ctgctataca atggtcacca gtggtccagt tattgttcca atttggatcc    300
atnaatttgc nttcaattcc aggagctttg gaaggaattc caaggaaagc tccaggaaaa    360
ccgtattaaa ctttccaggg gccaaantcc ttcaccaatt ttttccacna actttccagg    420
cctgncncaa aaaaatggaa agggagttgg tangtccc                            458

<210> SEQ ID NO 25
<211> LENGTH: 546
<212> TYPE: DNA
<213> ORGANISM: Artificial sequence
<220> FEATURE:
<223> OTHER INFORMATION: Codon optimized form of TNF-gamma-beta

<400> SEQUENCE: 25
atgctgaaag gtcaagaatt cgcaccgtcc caccagcagg tttacgcacc gctgcgtgca     60
gacggtgata agccgcgtgc acacctgacc gttgtgcgcc agaccccgac ccagcacttc    120
aaaaaccagt tcccggctct gcactgggag cacgaactgg gcctggcctt caccaagaac    180
cgcatgaact acaccaacaa attcctgctg atcccggagt ctggtgacta cttcatctac    240
tcccaggtga ccttccgtgg tatgacctct gagtgctccg aaatccgtca ggcaggccgt    300
ccgaacaagc cggactccat caccgtggtg atcaccaaag tgaccgactc ttacccggag    360
ccgacccagc tgctgatggg taccaagtct gtttgcgaag ttggttccaa ctggttccag    420
ccgatctacc tcggtgccat gttctccctg caagagggcg acaaactgat ggtgaacgtg    480
tccgacatct ctctggtgga ttacaccaag gaagataaaa ccttcttcgg tgccttcctg    540
ctgtaa                                                               546

<210> SEQ ID NO 26
<211> LENGTH: 181
```

```
<212> TYPE: PRT
<213> ORGANISM: Artificial sequence
<220> FEATURE:
<223> OTHER INFORMATION: Translation product of codon optimized form
      of TNF-gamma-beta

<400> SEQUENCE: 26

Met Leu Lys Gly Gln Glu Phe Ala Pro Ser His Gln Gln Val Tyr Ala
1               5                   10                  15

Pro Leu Arg Ala Asp Gly Asp Lys Pro Arg Ala His Leu Thr Val Val
            20                  25                  30

Arg Gln Thr Pro Thr Gln His Phe Lys Asn Gln Phe Pro Ala Leu His
        35                  40                  45

Trp Glu His Glu Leu Gly Leu Ala Phe Thr Lys Asn Arg Met Asn Tyr
    50                  55                  60

Thr Asn Lys Phe Leu Leu Ile Pro Glu Ser Gly Asp Tyr Phe Ile Tyr
65                  70                  75                  80

Ser Gln Val Thr Phe Arg Gly Met Thr Ser Glu Cys Ser Glu Ile Arg
                85                  90                  95

Gln Ala Gly Arg Pro Asn Lys Pro Asp Ser Ile Thr Val Val Ile Thr
            100                 105                 110

Lys Val Thr Asp Ser Tyr Pro Glu Pro Thr Gln Leu Leu Met Gly Thr
        115                 120                 125

Lys Ser Val Cys Glu Val Gly Ser Asn Trp Phe Gln Pro Ile Tyr Leu
    130                 135                 140

Gly Ala Met Phe Ser Leu Gln Glu Gly Asp Lys Leu Met Val Asn Val
145                 150                 155                 160

Ser Asp Ile Ser Leu Val Asp Tyr Thr Lys Glu Asp Lys Thr Phe Phe
                165                 170                 175

Gly Ala Phe Leu Leu
            180

<210> SEQ ID NO 27
<211> LENGTH: 182
<212> TYPE: DNA
<213> ORGANISM: Artificial sequence
<220> FEATURE:
<223> OTHER INFORMATION: 5' primer useful for generating 5' portion of
      codon optimized form of TNF-gamma-beta

<400> SEQUENCE: 27
ggaattccat atgctgaaag gtcaagaatt cgcaccgtcc caccagcagg tttacgcacc      60
gctgcgtgca gacggtgata agccgcgtgc acacctgacc gttgtgcgcc agaccccgac     120
ccagcacttc aaaaaccagt tcccggctct gcactgggag cacgaactgg gcctggcctt     180
ca                                                                    182

<210> SEQ ID NO 28
<211> LENGTH: 179
<212> TYPE: DNA
<213> ORGANISM: Artificial sequence
<220> FEATURE:
<223> OTHER INFORMATION: 3' primer useful to generate 5' portion of
      codon optimized form of TNF-gamma-beta

<400> SEQUENCE: 28
atcaccacgg tgatggagtc cggcttgttc ggacggcctg cctgacggat tcggagcac       60 tcagaggtca taccacggaa ggtcacctgg gagtagatga agtagtcacc agactccggg     120
atcagcagga atttgttggt gtagttcatg cggttcttgg tgaaggccag gcccagttc     179
```

<210> SEQ ID NO 29
<211> LENGTH: 131
<212> TYPE: DNA
<213> ORGANISM: Artificial sequence
<220> FEATURE:
<223> OTHER INFORMATION: 5' primer useful to generate 3' portion of codon optimized form of TNF-gamma-beta

<400> SEQUENCE: 29

```
actccatcac cgtggtgatc accaaagtga ccgactctta cccggagccg acccagctgc      60
tgatgggtac caagtctgtt tgcgaagttg gttccaactg gttccagccg atctacctcg     120
gtgccatgtt c                                                          131
```

<210> SEQ ID NO 30
<211> LENGTH: 135
<212> TYPE: DNA
<213> ORGANISM: Artificial sequence
<220> FEATURE:
<223> OTHER INFORMATION: 3' primer useful to generate 3' portion of codon optimized form of TNF-gamma-beta

<400> SEQUENCE: 30

```
cgctctagat tattacagca ggaaggcacc gaagaaggtt ttatcttcct tggtgtaatc      60
caccagagag atgtcggaca cgttcaccat cagtttgtcg ccctcttgca gggagaacat     120
ggcaccgagg tagat                                                      135
```

<210> SEQ ID NO 31
<211> LENGTH: 252
<212> TYPE: PRT
<213> ORGANISM: Mus musculus

<400> SEQUENCE: 31

```
Met Ala Glu Glu Leu Gly Leu Gly Phe Gly Glu Gly Val Pro Val Glu
1               5                   10                  15

Val Leu Pro Glu Gly Cys Arg His Arg Pro Glu Ala Arg Ala Gly Leu
            20                  25                  30

Ala Ala Arg Ser Lys Ala Cys Leu Ala Leu Thr Cys Cys Leu Leu Ser
        35                  40                  45

Phe Pro Ile Leu Ala Gly Leu Ser Thr Leu Leu Met Ala Gly Gln Leu
    50                  55                  60

Arg Val Pro Gly Lys Asp Cys Met Leu Arg Ala Ile Thr Glu Glu Arg
65                  70                  75                  80

Ser Glu Pro Ser Pro Gln Gln Val Tyr Ser Pro Pro Arg Gly Lys Pro
                85                  90                  95

Arg Ala His Leu Thr Ile Lys Lys Gln Thr Pro Ala Pro His Leu Lys
            100                 105                 110

Asn Gln Leu Ser Ala Leu His Trp Glu His Asp Leu Gly Met Ala Phe
        115                 120                 125

Thr Lys Asn Gly Met Lys Tyr Ile Asn Lys Ser Leu Val Ile Pro Glu
    130                 135                 140

Ser Gly Asp Tyr Phe Ile Tyr Ser Gln Ile Thr Phe Arg Gly Thr Thr
145                 150                 155                 160

Ser Val Cys Gly Asp Ile Ser Arg Gly Arg Arg Pro Asn Lys Pro Asp
                165                 170                 175

Ser Ile Thr Val Val Ile Thr Lys Val Ala Asp Ser Tyr Pro Glu Pro
            180                 185                 190

Ala Arg Leu Leu Thr Gly Ser Lys Ser Val Cys Glu Ile Ser Asn Asn
        195                 200                 205
```

```
Trp Phe Gln Ser Leu Tyr Leu Gly Ala Met Phe Ser Leu Glu Glu Gly
    210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Leu
                245                 250

<210> SEQ ID NO 32
<211> LENGTH: 252
<212> TYPE: PRT
<213> ORGANISM: Rattus norvegicus

<400> SEQUENCE: 32

Met Ala Glu Glu Leu Gly Leu Gly Phe Gly Glu Ala Val Pro Val Glu
1               5                   10                  15

Met Leu Pro Glu Gly Cys Arg His Arg Arg Glu Ala Arg Thr Gly Leu
                20                  25                  30

Ala Ala Arg Ser Lys Ala Cys Leu Ala Leu Thr Cys Cys Leu Leu Ser
            35                  40                  45

Phe Pro Ile Leu Ala Gly Leu Ser Thr Leu Leu Met Thr Gly Gln Leu
50                  55                  60

Arg Ile Pro Gly Lys Asp Cys Met Phe Pro Thr Val Thr Glu Arg
65                  70                  75                  80

Ser Ala Pro Ser Ala Gln Pro Val Tyr Thr Pro Ser Arg Asp Lys Pro
                85                  90                  95

Lys Ala His Leu Thr Ile Met Arg Gln Thr Pro Val Pro His Leu Lys
            100                 105                 110

Asn Glu Leu Ala Ala Leu His Trp Glu Asn Asn Leu Gly Met Ala Phe
        115                 120                 125

Thr Lys Asn Arg Met Asn Tyr Thr Asn Lys Phe Leu Val Ile Pro Glu
    130                 135                 140

Ser Gly Asp Tyr Phe Ile Tyr Ser Gln Ile Thr Phe Arg Gly Thr Thr
145                 150                 155                 160

Ser Glu Cys Gly Asp Ile Ser Arg Val Arg Arg Pro Lys Lys Pro Asp
                165                 170                 175

Ser Ile Thr Val Val Ile Thr Lys Val Ala Asp Ser Tyr Pro Glu Pro
            180                 185                 190

Ala His Leu Leu Thr Gly Thr Lys Ser Val Cys Glu Ile Ser Ser Asn
        195                 200                 205

Trp Phe Gln Pro Ile Tyr Leu Gly Ala Met Phe Ser Leu Glu Glu Gly
    210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Ile
                245                 250

<210> SEQ ID NO 33
<211> LENGTH: 25
<212> TYPE: DNA
<213> ORGANISM: Artificial sequence
<220> FEATURE:
<223> OTHER INFORMATION: Forard TNF-gamma-beta primer useful to amplify
      nucleotides encoding amino acids 86-114 of TNF-gamma-beta protein

<400> SEQUENCE: 33
cacctcttag agcagacgga gataa                                       25
```

```
<210> SEQ ID NO 34
<211> LENGTH: 24
<212> TYPE: DNA
<213> ORGANISM: Artificial sequence
<220> FEATURE:
<223> OTHER INFORMATION: Reverse TNF-gamma-beta primer useful to amplify
      nucleotides encoding amino acids 86-114 of TNF-gamma-beta protein

<400> SEQUENCE: 34
ttaaagtgct gtgtgggagt ttgt                                           24

<210> SEQ ID NO 35
<211> LENGTH: 25
<212> TYPE: DNA
<213> ORGANISM: Artificial sequence
<220> FEATURE:
<223> OTHER INFORMATION: Probe that hybridizes to TNF-gamma-beta cDNA

<400> SEQUENCE: 35
ccaagggcac acctgacagt tgtga                                          25

<210> SEQ ID NO 36
<211> LENGTH: 26
<212> TYPE: DNA
<213> ORGANISM: Artificial sequence
<220> FEATURE:
<223> OTHER INFORMATION: Forward TNF-gamma-alpha primer useful to
      amplify nucleotides encoding amino acids 7-37 of TNF-gamma-alpha
      protein

<400> SEQUENCE: 36
caaagtctac agtttcccaa tgagaa                                         26

<210> SEQ ID NO 37
<211> LENGTH: 26
<212> TYPE: DNA
<213> ORGANISM: Artificial sequence
<220> FEATURE:
<223> OTHER INFORMATION: Forward TNF-gamma-alpha primer useful to
      amplify nucleotides encoding amino acids 7-37 of TNF-gamma-alpha
      protein

<400> SEQUENCE: 37
gggaactgat ttttaaagtg ctgtgt                                         26

<210> SEQ ID NO 38
<211> LENGTH: 34
<212> TYPE: DNA
<213> ORGANISM: Artificial sequence
<220> FEATURE:
<223> OTHER INFORMATION: Probe that hybridizes to TNF-gamma-alpha cDNA

<400> SEQUENCE: 38
tcctctttct tgtctttcca gttgtgagac aaac                                34

<210> SEQ ID NO 39
<211> LENGTH: 36
<212> TYPE: DNA
<213> ORGANISM: Artificial sequence
<220> FEATURE:
<223> OTHER INFORMATION: Forward TNF-gamma-alpha primer

<400> SEQUENCE: 39
gcaaagtcta cagtttccca atgagaaaat taatcc                              36

<210> SEQ ID NO 40
<211> LENGTH: 24
<212> TYPE: DNA
```

```
<213> ORGANISM: Artificial sequence
<220> FEATURE:
<223> OTHER INFORMATION: Forward TNF-gamma-beta primer

<400> SEQUENCE: 40
atggccgagg atctgggact gagc                                          24

<210> SEQ ID NO 41
<211> LENGTH: 36
<212> TYPE: DNA
<213> ORGANISM: Artificial sequence
<220> FEATURE:
<223> OTHER INFORMATION: Reverse TNF-gamma-alpha/beta primer

<400> SEQUENCE: 41
ctatagtaag aaggctccaa agaaggtttt atcttc                             36
```